(12) United States Patent
Neelam et al.

(10) Patent No.: US 6,919,191 B2
(45) Date of Patent: Jul. 19, 2005

(54) ISOLATED HUMAN KINASE PROTEINS, NUCLEIC ACID MOLECULES ENCODING HUMAN KINASE PROTEINS, AND USES THEREOF

(75) Inventors: Beena Neelam, Gaithersburg, MD (US); Natalia Milshina, Germantown, MD (US); Chunhua Yan, Boyds, MD (US); Valentina DiFrancesco, Rockville, MD (US); Ellen M. Beasley, Darnestown, MD (US); Karen A. Ketchum, Germantown, MD (US)

(73) Assignee: Applera Corporation, Norwalk, CT (US)

( * ) Notice: Subject to any disclaimer, the term of this patent is extended or adjusted under 35 U.S.C. 154(b) by 353 days.

(21) Appl. No.: 10/283,247

(22) Filed: Oct. 30, 2002

(65) Prior Publication Data

US 2003/0119037 A1 Jun. 26, 2003

Related U.S. Application Data

(60) Provisional application No. 60/330,756, filed on Oct. 30, 2001.

(51) Int. Cl.[7] ......................... C12N 9/12; C12N 15/00; C12N 5/00; C12N 1/20; C12Q 1/68
(52) U.S. Cl. ...................... 435/194; 435/6; 435/252.3; 435/320.1; 435/325; 536/23.2
(58) Field of Search .................. 435/194, 6, 252.3, 435/320.1, 325; 536/23.2

(56) References Cited

U.S. PATENT DOCUMENTS 6,455,292 B1  9/2002  Shu et al.

OTHER PUBLICATIONS

Results of BLAST search of Seq Id No:2 against Derwent (FastAlert and GeneSeqP) and NCBI (pataa) protein patent databases on Mar. 3, 2004,(50 pages).

Results of BLAST search of Seq Id No:2 against Genbank "nr" protein patent databases on Mar. 3, 2004 (12 pages).

Results of BLAST search of Seq Id No:5 against Derwent (FastAlert and GeneSeqP) and NCBI (pataa) protein patent databases on Mar. 3, 2004 (51 pages).

Results of BLAST search of Seq Id No:5 against Genbank "nr" protein patent database on Mar. 3, 2004 (12 pages).

Stanchi et al. "Characterization of 16 Novel Genes Showing High Similarity to Yeast Sequences." Database SPTREMBL, No. 060843. Aug. 1998.

International Search report dated Jun. 6, 2003.

BLAST alignment of Seq Id No:2 against Derwent and NCBI protein databases, pp. 1–37 (most relevant pages = pp. 1–4), Jun. 29, 2000.

*Primary Examiner*—Maryam Monshipouri
(74) *Attorney, Agent, or Firm*—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

16 Claims, 79 Drawing Sheets

SPLICE FORM 1:

```
   1 ATGACATCGA CGGGGAAGGA CGGCGGCGCG CAGCACGCGC AGTATGTTGG
  51 GCCCTACCGG CTGGAGAAGA CGCTGGGCAA GGGGCAGACA GGTCTGGTGA
 101 AGCTGGGGGT TCACTGCGTC ACCTGCCAGA AGGTGGCCAT CAAGATCGTC
 151 AACCGTGAGA AGCTCAGCGA GTCGGTGCTG ATGAAGGTGG AGCGGGAGAT
 201 CGCGATCCTG AAGCTCATTG AGCACCCCCA CGTCCTAAAG CTGCACGACG
 251 TTTATGAAAA CAAAAAATAT TTGTACCTGG TGCTAGAACA CGTGTCAGGT
 301 GGTGAGCTCT TCGACTACCT GGTGAAGAAG GGGAGGCTGA CGCCTAAGGA
 351 GGCTCGGAAG TTCTTCCGGC AGATCATCTC TGCGCTGGAC TTCTGCCACA
 401 GCCACTCCAT ATGCCACAGG GATCTGAAAC TGAAAACCT CCTGCTGGAC
 451 GAGAAGAACA ACATCCGCAT CGCAGACTTT GGCATGGCGT CCCTGCAGGT
 501 TGGCGACAGC CTGTTGGAGA CCAGCTGTGG GTCCCCCCAC TACGCCTGCC
 551 CCGAGGTGAT CCGGGGGGAG AAGTATGACG GCCGGAAGGC GGACGTGTGG
 601 AGCTGCGGCG TCATCCTGTT CGCCTTGCTG GTGGGGGCTC TGCCCTTCGA
 651 CGATGACAAC TTGCGACAGC TGCTGGAGAA GGTGAAGCGG GGCGTGTTCC
 701 ACATGCCGCA CTTTATCCCG CCCGACTGCC AGAGTCTGCT ACGGGGCATG
 751 ATCGAGGTGG ACGCCGCACG CCGCCTCACG CTAGAGCACA TTCAGAAACA
 801 CATATGGTAT ATAGGGGGCA AGAATGAGCC CGAACCAGAG CAGCCCATTC
 851 CTCGCAAGGT GCAGATCCGC TCGCTGCCCA GCCTGGAGGA CATCGACCCC
 901 GACGTGCTGG ACAGCATGCA CTCACTGGGC TGCTTCCGAG ACCGCAACAA
 951 GCTGCTGCAG GACCTGCTGT CCGAGGAGGA GAACCAGGAG AAGATGATTT
1001 ACTTCCTCCT CCTGGACCGG AAAGAAAGGT ACCCGAGCCA GGAGGATGAG
1051 GACCTGCCCC CCCGGAACGA GATAGACCCT CCCCGGAAGC GTGTGGACTC
1101 CCCGATGCTG AACCGGCACG GCAAGCGGCG GCCAGAACGC AAATCCATGG
1151 AGGTGCTCAG CGTGACGGAC GGCGGCTCCC CGGTGCCTGC GCGGCGGGCC
1201 ATTGAGATGG CCCAGCACGG CCAGAGGTCT CGGTCCATCA GCGGTGCCTC
1251 CTCAGGCCTT TCCACCAGCC CACTCAGCAG CCCCCGGGTG ACCCCTCACC
1301 CCTCACCAAG GGGCAGTCCC CTCCCCACCC CAAGGGGAC ACCTGTCCAC
1351 ACGCCAAAGG AGAGCCCGGC TGGCACGCCC AACCCCACGC CCCCGTCCAG
1401 CCCCAGCGTC GGAGGGGTGC CCTGGAGGGC GCGGCTCAAC TCCATCAAGA
1451 ACAGCTTTCT GGGCTCACCC CGCTTCCACC GCCGGAAACT GCAAGTTCCG
1501 ACGCCGGAGG AGATGTCCAA CCTGACACCA GAGTCGTCCC CAGAGCTGGC
1551 GAAGAAGTCC TGGTTTGGGA ACTTCATCAG CCTGGAGAAG GAGGAGCAGA
1601 TCTTCGTGGT CATCAAAGAC AAACCTCTGA GCTCCATCAA GGCTGACATC
1651 GTGCACGCCT TCCTGTCGAT TCCCAGTCTC AGCCACAGCG TCATCTCCCA
1701 AACGAGCTTC CGGGCCGAGT ACAAGGCCAC GGGGGGGCCA GCCGTGTTCC
1751 AGAAGCCGGT CAAGTTCCAG GTTGATATCA CCTACACGGA GGGTGGGGAG
1801 GCGCAGAAGG AGAACGGCAT CTACTCCGTC ACCTTCACCC TGCTCTCAGG
1851 CCCCAGCCGT CGCTTCAAGA GGGTGGTGGA GACCATCCAG GCCCAGCTGC
1901 TGAGCACACA CGACCCGCCT GCGGCCCAGC ACTTGTCAGA ACCCCCCCCA
1951 CCAGCGCCAG GACTAAGCTG GGGTGCTGGG CTTAAGGGCC AGAAGGTGGC
2001 CACCAGCTAC GAGAGTAGCC TCTGA  (SEQ ID NO:1)
```

FEATURES:
Start Codon: 1
Stop Codon: 2023

Homologous proteins:
Top 10 BLAST Hits

|  | Score | E |
|---|---|---|
| CRA|225000041315817 /altid=gi|18098147 /def=emb|CAD20436.1| (AX... | 1376 | 0.0 |

FIGURE 1A

```
CRA|222000005909801 /dataset=GENESEQ /org=Homo sapiens /taxon=9...    1376  0.0
CRA|225000043542817 /dataset=FastAlert /length=668 /altid=Derwe...    1321  0.0
CRA|225000043542817 /dataset=FastAlert /length=668 /altid=Derwe...    1321  0.0
CRA|1000686812371  /dataset=FastAlert /length=603 /altid=Derwent...   1236  0.0
CRA|225000043542819 /dataset=FastAlert /length=608 /altid=Derwe...    1200  0.0
CRA|225000045828654 /dataset=FastAlert /length=585 /altid=Derwe...    1138  0.0
CRA|61000076490969 /dataset=GENESEQ /org=Homo sapiens /taxon=96...    1070  0.0
CRA|61000076490969 /dataset=GENESEQ /org=Homo sapiens /taxon=96...    1070  0.0
CRA|89000000228063 /dataset=GENESEQ /org=Drosophila melanogaste...     582  e-165
```

EXPRESSION INFORMATION FOR MODULATORY USE:
Blast hits to dbEST:

| CRA Number | gi Number | Score | Expect |
|---|---|---|---|
| CRA|58000099122436 | gi|12801507 | 1507 bits (760) | 0.0 |
| CRA|153000112875419 | gi|13289073 | 1296 bits (654) | 0.0 |
| CRA|224000004431285 | gi|15937305 | 1170 bits (590) | 0.0 |
| CRA|11000545189179 | gi|9122058 | 1100 bits (555) | 0.0 |
| CRA|11000545267820 | gi|9129619 | 1013 bits (511) | 0.0 |
| CRA|39000074597310 | gi|11129830 | 1003 bits (506) | 0.0 |
| CRA|225000015089021 | gi|18515671 | 807 bits (407) | 0.0 |
| CRA|224000005498364 | gi|16180845 | 785 bits (396) | 0.0 |
| CRA|161000128842328 | gi|11614384 | 779 bits (393) | 0.0 |
| CRA|147000029593005 | gi|11289261 | 684 bits (345) | 0.0 |
| CRA|225000016183098 | gi|19038706 | 638 bits (322) | 1e-180 |
| CRA|165000106358355 | gi|12616009 | 613 bits (309) | 1e-172 |
| CRA|225000015232871 | gi|18524476 | 565 bits (285) | 1e-158 |
| CRA|196000006616072 | gi|12119811 | 424 bits (214) | 1e-116 |
| CRA|148000005490112 | gi|8751899 | 371 bits (187) | 1e-100 |
| CRA|11000545356609 | gi|9137935 | 343 bits (173) | 2e-91 | library source:

| gi Number | Organ | Tissue Type |
|---|---|---|
| gi|12801507 | Fetal brain | |
| gi|13289073 | eye | retinoblastoma |
| gi|15937305 | brain | medulla |
| gi|9122058 | eye | retinoblastoma |
| gi|9129619 | eye | retinoblastoma |
| gi|11129830 | | pooled germ cell tumors |
| gi|18515671 | eye | retinoblastoma |
| gi|16180845 | brain | |
| gi|11614384 | brain | anaplastic oligodendroglioma with 1p/19q loss |
| gi|11289261 | brain | glioblastoma with EGFR amplification |
| gi|19038706 | eye | fetal eyes, lens, eye anterior segment, optic nerve, retina, Retina Foveal and Macular, RPE and Chor |
| gi|12616009 | liver | adenocarcinoma, cell line |
| gi|18524476 | eye | retinoblastoma |
| gi|12119811 | epid_tumor | |
| gi|8751899 | lung | small cell carcinoma |
| gi|9137935 | lung | small cell carcinoma |

FIGURE 1B

SPLICE FORM 2:

```
   1 ATGAAGGTGG AGCGGGAGAT CGCGATCCTG AAGCTCATTG AGCACCCCCA
  51 CGTCCTAAAG CTGCACGACG TTTATGAAAA CAAAAAATAT TTGTACCTGG
 101 TGCTAGAACA CGTGTCAGGT GGTGAGCTCT TCGACTACCT GGTGAAGAAG
 151 GGGAGGCTGA CGCCTAAGGA GGCTCGGAAG TTCTTCCGGC AGATCATCTC
 201 TGCCGCTGGAC TTCTGCCACA GCCACTCCAT ATGCACAGG GATCTGAAAC
 251 CTGAAAACCT CCTGCTGGAC GAGAAGAACA ACATCCGCAT CGCAGACTTT
 301 GGCATGGCGT CCCTGCAGGT TGGCGACAGC CTGTTGGAGA CCAGCTGTGG
 351 GTCCCCCCAC TACGCCTGCC CCGAGGTGAT CCGGGGGGAG AAGTATGACG
 401 GCCGGAAGGC GGACGTGTGG AGCTGCGGCG TCATCCTGTT CGCCTTGCTG
 451 GTGGGGGCTC TGCCCTTCGA CGATGACAAC TTGCGACAGC TGCTGGAGAA
 501 GGTGAAGCGG GGCGTGTTCC ACATGCCGCA CTTTATCCCG CCCGACTGCC
 551 AGAGTCTGCT ACGGGGCATG ATCGAGGTGG ACGCCGCACG CCGCCTCACG
 601 CTAGAGCACA TTCAGAAACA CATATGGTAT ATAGGGGGCA AGAATGAGCC
 651 CGAACCAGAG CAGCCCATTC CTCGCAAGGT GCAGATCCGC TCGCTGCCCA
 701 GCCTGGAGGA CATCGACCCC GACGTGCTGG ACAGCATGCA CTCACTGGGC
 751 TGCTTCCGAG ACCGCAACAA GCTGCTGCAG GACCTGCTGT CCGAGGAGGA
 801 GAACCAGGAG AAGATGATTT ACTTCCTCCT CCTGGACCGG AAAGAAAGGT
 851 ACCCGAGCCA GGAGGATGAG GACCTGCCCC CCCGGAACGA GATAGACCCT
 901 CCCCGGAAGC GTGTGGACTC CCCGATGCTG AACCGGCACG GCAAGCGGCG
 951 GCCAGAACGC AAATCCATGG AGGTGCTCAG CGTGACGGAC GGCGGCTCCC
1001 CGGTGCCTGC GCGGCGGGCC ATTGAGATGG CCCAGCACGG CCAGAGTAAA
1051 GCAATGTTCA GTAAAAGCCT GGATATCGCT GAGGCCCATC CCCAATTCAG
1101 CAAAGAAGAC AGGTCTCGGT CCATCAGCGG TGCCTCCTCA GGCCTTTCCA
1151 CCAGCCCACT CAGCAGCCCC CGGGTGACCC CTCACCCCTC ACCAAGGGGC
1201 AGTCCCCTCC CCACCCCCAA GGGGACACCT GTCCACACGC CAAAGGAGAG
1251 CCCGGCTGGC ACGCCCAACC CCACGCCCCC GTCCAGCCCC AGCGTCGGAG
1301 GGGTGCCCTG GAGGGCGCGG CTCAACTCCA TCAAGAACAG CTTTCTGGGC
1351 TCACCCCGCT TCCACCGCCG GAAACTGCAA GTTCCGACGC CGGAGGAGAT
1401 GTCCAACCTG ACACCAGAGT CGTCCCCAGA GCTGGCGAAG AAGTCCTGGT
1451 TTGGGAACTT CATCAGCCTG GAGAAGGAGG AGCAGATCTT CGTGGTCATC
1501 AAAGACAAAC CTCTGAGCTC CATCAAGGCT GACATCGTGC ACGCCTTCCT
1551 GTCGATTCCC AGTCTCAGCC ACAGCGTCAT CTCCCAAACG AGCTTCCGGG
1601 CCGAGTACAA GGCCACGGGG GGGCCAGCCG TGTTCCAGAA GCCGGTCAAG
1651 TTCCAGGTTG ATATCACCTA CACGGAGGGT GGGGAGGCGC AGAAGGAGAA
1701 CGGCATCTAC TCCGTCACCT TCACCCTGCT CTCAGGCCCC AGCCGTCGCT
1751 TCAAGAGGGT GGTGGAGACC ATCCAGGCCC AGCTGCTGAG CACACACGAC
1801 CCGCCTGCGG CCCAGCACTT GTCAGAACCC CCCCCACCAG CGCCAGGACT
1851 AAGCTGGGGT GCTGGGCTTA AGGGCCAGAA GGTGGCCACC AGCTACGAGA
1901 GTAGCCTCTG A (SEQ ID NO:4)
```

FEATURES:
Start Codon: 1
Stop Codon: 1909

Homologous proteins:
Top 10 BLAST Hits

```
                                                                  Score    E
CRA|225000041315817 /altid=gi|18098147 /def=emb|CAD20436.1| (AX... 1243   0.0
CRA|222000005909801 /dataset=GENESEQ /org=Homo sapiens /taxon=9... 1243   0.0
CRA|1000686812371 /dataset=FastAlert /length=603 /altid=Derwent... 1224   0.0
```

FIGURE 1C

```
CRA|225000043542819 /dataset=FastAlert /length=608 /altid=Derwe...  1187  0.0
CRA|225000043542817 /dataset=FastAlert /length=668 /altid=Derwe...  1187  0.0
CRA|225000043542817 /dataset=FastAlert /length=668 /altid=Derwe...  1187  0.0
CRA|225000045828654 /dataset=FastAlert /length=585 /altid=Derwe...  1125  0.0
CRA|61000076490969 /dataset=GENESEQ /org=Homo sapiens /taxon=96...   964  0.0
CRA|61000076490969 /dataset=GENESEQ /org=Homo sapiens /taxon=96...   964  0.0
CRA|89000000228063 /dataset=GENESEQ /org=Drosophila melanogaste...   657  0.0
```

EXPRESSION INFORMATION:
Blast hits to dbEST:

| CRA Number | gi Number | Score | Expect |
|---|---|---|---|
| CRA|153000112875419 | gi|13289073 | 1296 bits (654) | 0.0 |
| CRA|224000004431285 | gi|15937305 | 1170 bits (590) | 0.0 |
| CRA|58000099122436 | gi|12801507 | 1166 bits (588) | 0.0 |
| CRA|11000545189179 | gi|9122058 | 1100 bits (555) | 0.0 |
| CRA|11000545267820 | gi|9129619 | 1013 bits (511) | 0.0 |
| CRA|39000074597310 | gi|11129830 | 1003 bits (506) | 0.0 |
| CRA|224000005498364 | gi|16180845 | 785 bits (396) | 0.0 |
| CRA|161000128842328 | gi|11614384 | 779 bits (393) | 0.0 |
| CRA|225000015089021 | gi|18515671 | 771 bits (389) | 0.0 |
| CRA|147000029593005 | gi|11289261 | 684 bits (345) | 0.0 |
| CRA|225000016183098 | gi|19038706 | 638 bits (322) | 1e-180 |
| CRA|165000106358355 | gi|12616009 | 613 bits (309) | 1e-172 |
| CRA|225000015232871 | gi|18524476 | 565 bits (285) | 1e-158 |
| CRA|196000006616072 | gi|12119811 | 424 bits (214) | 1e-116 |
| CRA|148000005490112 | gi|8751899 | 371 bits (187) | 1e-100 |
| CRA|11000545356609 | gi|9137935 | 343 bits (173) | 2e-91 | library source:

| gi Number | Organ | Tissue Type |
|---|---|---|
| gi|13289073 | eye | retinoblastoma |
| gi|15937305 | brain | medulla |
| gi|12801507 | Fetal brain | |
| gi|9122058 | eye | retinoblastoma |
| gi|9129619 | eye | retinoblastoma |
| gi|11129830 | | pooled germ cell tumors |
| gi|16180845 | brain | |
| gi|11614384 | brain | anaplastic oligodendroglioma with 1p/19q loss |
| gi|18515671 | eye | retinoblastoma |
| gi|11289261 | brain | glioblastoma with EGFR amplification |
| gi|19038706 | eye optic nerve, retina, Retina Foveal | fetal eyes, lens, eye anterior segment, and Macular, RPE and Chor |
| gi|12616009 | liver | adenocarcinoma, cell line |
| gi|18524476 | eye | retinoblastoma |
| gi|12119811 | epid_tumor | |
| gi|8751899 | lung | small cell carcinoma |
| gi|9137935 | lung | small cell carcinoma |

FIGURE 1D

SPLICE FORM 1:

```
  1 MTSTGKDGGA QHAQYVGPYR LEKTLGKGQT GLVKLGVHCV TCQKVAIKIV
 51 NREKLSESVL MKVEREIAIL KLIEHPHVLK LHDVYENKKY LYLVLEHVSG
101 GELFDYLVKK GRLTPKEARK FFRQIISALD FCHSHSICHR DLKPENLLLD
151 EKNNIRIADF GMASLQVGDS LLETSCGSPH YACPEVIRGE KYDGRKADVW
201 SCGVILFALL VGALPFDDDN LRQLLEKVKR GVFHMPHFIP PDCQSLLRGM
251 IEVDAARRLT LEHIQKHIWY IGGKNEPEPE QPIPRKVQIR SLPSLEDIDP
301 DVLDSMHSLG CFRDRNKLLQ DLLSEEENQE KMIYFLLLDR KERYPSQEDE
351 DLPPRNEIDP PRKRVDSPML NRHGKRRPER KSMEVLSVTD GGSPVPARRA
401 IEMAQHGQRS RSISGASSGL STSPLSSPRV TPHPSPRGSP LPTPKGTPVH
451 TPKESPAGTP NPTPPSSPSV GGVPWRARLN SIKNSFLGSP RFHRRKLQVP
501 TPEEMSNLTP ESSPELAKKS WFGNFISLEK EEQIFVVIKD KPLSSIKADI
551 VHAFLSIPSL SHSVISQTSF RAEYKATGGP AVFQKPVKFQ VDITYTEGGE
601 AQKENGIYSV TFTLLSGPSR RFKRVVETIQ AQLLSTHDPP AAQHLSEPPP
651 PAPGLSWGAG LKGQKVATSY ESSL  (SEQ ID NO:2)
```

FEATURES:
Functional domains and key regions:
Prosite results:
PDOC00004 PS00004 CAMP_PHOSPHO_SITE
cAMP- and cGMP-dependent protein kinase phosphorylation site
        257-260      RRLT PDOC00005 PS00005 PKC_PHOSPHO_SITE
Protein kinase C phosphorylation site
Number of matches: 11

| | | |
|---|---|---|
| 1 | 4-6 | TGK |
| 2 | 114-116 | TPK |
| 3 | 427-429 | SPR |
| 4 | 435-437 | SPR |
| 5 | 443-445 | TPK |
| 6 | 451-453 | TPK |
| 7 | 481-483 | SIK |
| 8 | 489-491 | SPR |
| 9 | 545-547 | SIK |
| 10 | 569-571 | SFR |
| 11 | 619-621 | SRR |

PDOC00006 PS00006 CK2_PHOSPHO_SITE
Casein kinase II phosphorylation site
Number of matches: 15

| | | |
|---|---|---|
| 1 | 4-7 | TGKD |
| 2 | 99-102 | SGGE |
| 3 | 114-117 | TPKE |
| 4 | 127-130 | SALD |
| 5 | 170-173 | SLLE |
| 6 | 294-297 | SLED |
| 7 | 324-327 | SEEE |
| 8 | 346-349 | SQED |
| 9 | 387-390 | SVTD |
| 10 | 451-454 | TPKE |
| 11 | 501-504 | TPEE |

FIGURE 2A

```
12    512-515    SSPE
13    594-597    TYTE
14    635-638    STHD
15    668-671    TSYE
```

PDOC00007 PS00007 TYR_PHOSPHO_SITE
Tyrosine kinase phosphorylation site
```
        588-595    KFQVDITY
```

PDOC00008 PS00008 MYRISTYL
N-myristoylation site
Number of matches: 5
```
    1    9-14       GAQHAQ
    2    415-420    GASSGL
    3    523-528    GNFISL
    4    654-659    GLSWGA
    5    663-668    GQKVAT
```

PDOC00009 PS00009 AMIDATION
Amidation site
Number of matches: 2
```
    1    193-196    DGRK
    2    373-376    HGKR
```

PDOC00100 PS00107 PROTEIN_KINASE_ATP
Protein kinases ATP-binding region signature
```
        25-48    LGKGQTGLVKLGVHCVTCQKVAIK
```

PDOC00100 PS00108 PROTEIN_KINASE_ST
Serine/Threonine protein kinases active-site signature
```
        137-149    ICHRDLKPENLLL
```

Membrane spanning structure and domains:

| Helix | Begin | End | Score | Certainty |
|---|---|---|---|---|
| 1 | 197 | 217 | 1.817 | Certain |
| 2 | 550 | 570 | 1.051 | Certain |

FIGURE 2B

BLAST Alignment to Top Hits:
>CRA|225000041315817 /altid=gi|18098147 /def=emb|CAD20436.1|
    (AX327993) unnamed protein product [Homo sapiens]
    /org=Homo sapiens /taxon=9606 /div=PRI /dataset=pataa
    /length=674
    Length = 674

Score = 1376 bits (3523), Expect = 0.0
Identities = 673/674 (99%), Positives = 673/674 (99%)

```
Query:   1  MTSTGKDGGAQHAQYVGPYRLEKTLGKGQTGLVKLGVHCVTCQKVAIKIVNREKLSESVL  60
            MTSTGKDGGAQHAQYVGPYRLEKTLGKGQTGLVKLGVHCVTCQKVAIKIVNREKLSESVL
Sbjct:   1  MTSTGKDGGAQHAQYVGPYRLEKTLGKGQTGLVKLGVHCVTCQKVAIKIVNREKLSESVL  60

Query:  61  MKVEREIAILKLIEHPHVLKLHDVYENKKYLYLVLEHVSGGELFDYLVKKGRLTPKEARK  120
            MKVEREIAILKLIEHPHVLKLHDVYENKKYLYLVLEHVSGGELFDYLVKKGRLTPKEARK
Sbjct:  61  MKVEREIAILKLIEHPHVLKLHDVYENKKYLYLVLEHVSGGELFDYLVKKGRLTPKEARK  120

Query: 121  FFRQIISALDFCHSHSICHRDLKPENLLLDEKNNIRIADFGMASLQVGDSLLETSCGSPH  180
            FFRQIISALDFCHSHSICHRDLKPENLLLDEKNNIRIADFGMASLQVGDSLLETSCGSPH
Sbjct: 121  FFRQIISALDFCHSHSICHRDLKPENLLLDEKNNIRIADFGMASLQVGDSLLETSCGSPH  180

Query: 181  YACPEVIRGEKYDGRKADVWSCGVILFALLVGALPFDDDNLRQLLEKVKRGVFHMPHFIP  240
            YACPEVIRGEKYDGRKADVWSCGVILFALLVGALPFDDDNLRQLLEKVKRGVFHMPHFIP
Sbjct: 181  YACPEVIRGEKYDGRKADVWSCGVILFALLVGALPFDDDNLRQLLEKVKRGVFHMPHFIP  240

Query: 241  PDCQSLLRGMIEVDAARRLTLEHIQKHIWYIGGKNEPEPEQPIPRKVQIRSLPSLEDIDP  300
            PDCQSLLRGM EVDAARRLTLEHIQKHIWYIGGKNEPEPEQPIPRKVQIRSLPSLEDIDP
Sbjct: 241  PDCQSLLRGMSEVDAARRLTLEHIQKHIWYIGGKNEPEPEQPIPRKVQIRSLPSLEDIDP  300

Query: 301  DVLDSMHSLGCFRDRNKLLQDLLSEEENQEKMIYFLLLDRKERYPSQEDEDLPPRNEIDP  360
            DVLDSMHSLGCFRDRNKLLQDLLSEEENQEKMIYFLLLDRKERYPSQEDEDLPPRNEIDP
Sbjct: 301  DVLDSMHSLGCFRDRNKLLQDLLSEEENQEKMIYFLLLDRKERYPSQEDEDLPPRNEIDP  360

Query: 361  PRKRVDSPMLNRHGKRRPERKSMEVLSVTDGGSPVPARRAIEMAQHGQRSRSISGASSGL  420
            PRKRVDSPMLNRHGKRRPERKSMEVLSVTDGGSPVPARRAIEMAQHGQRSRSISGASSGL
Sbjct: 361  PRKRVDSPMLNRHGKRRPERKSMEVLSVTDGGSPVPARRAIEMAQHGQRSRSISGASSGL  420

Query: 421  STSPLSSPRVTPHPSPRGSPLPTPKGTPVHTPKESPAGTPNPTPPSSPSVGGVPWRARLN  480
            STSPLSSPRVTPHPSPRGSPLPTPKGTPVHTPKESPAGTPNPTPPSSPSVGGVPWRARLN
Sbjct: 421  STSPLSSPRVTPHPSPRGSPLPTPKGTPVHTPKESPAGTPNPTPPSSPSVGGVPWRARLN  480

Query: 481  SIKNSFLGSPRFHRRKLQVPTPEEMSNLTPESSPELAKKSWFGNFISLEKEEQIFVVIKD  540
            SIKNSFLGSPRFHRRKLQVPTPEEMSNLTPESSPELAKKSWFGNFISLEKEEQIFVVIKD
Sbjct: 481  SIKNSFLGSPRFHRRKLQVPTPEEMSNLTPESSPELAKKSWFGNFISLEKEEQIFVVIKD  540

Query: 541  KPLSSIKADIVHAFLSIPSLSHSVISQTSFRAEYKATGGPAVFQKPVKFQVDITYTEGGE  600
            KPLSSIKADIVHAFLSIPSLSHSVISQTSFRAEYKATGGPAVFQKPVKFQVDITYTEGGE
Sbjct: 541  KPLSSIKADIVHAFLSIPSLSHSVISQTSFRAEYKATGGPAVFQKPVKFQVDITYTEGGE  600

Query: 601  AQKENGIYSVTFTLLSGPSRRFKRVVETIQAQLLSTHDPPAAQHLSEPPPPAPGLSWGAG  660
            AQKENGIYSVTFTLLSGPSRRFKRVVETIQAQLLSTHDPPAAQHLSEPPPPAPGLSWGAG
Sbjct: 601  AQKENGIYSVTFTLLSGPSRRFKRVVETIQAQLLSTHDPPAAQHLSEPPPPAPGLSWGAG  660
```

FIGURE 2C

```
Query: 661  LKGQKVATSYESSL  674
             LKGQKVATSYESSL
Sbjct: 661  LKGQKVATSYESSL  674   (SEQ ID NO:7)

>CRA|222000005909801 /dataset=GENESEQ /org=Homo sapiens /taxon=9606
              /mol_type=aa /date=19-FEB-02 /length=674
              /altid=derwent_ac|AAM47830 /altid=derwent_id|AAM47830
              /def=Human protein kinase 2246 SEQ ID NO 2
              /patent=WO200181588-A2 /pat_section=Claim
          Length = 674

Score = 1376 bits (3523), Expect = 0.0
 Identities = 673/674 (99%), Positives = 673/674 (99%)

Query:   1  MTSTGKDGGAQHAQYVGPYRLEKTLGKGQTGLVKLGVHCVTCQKVAIKIVNREKLSESVL   60
            MTSTGKDGGAQHAQYVGPYRLEKTLGKGQTGLVKLGVHCVTCQKVAIKIVNREKLSESVL
Sbjct:   1  MTSTGKDGGAQHAQYVGPYRLEKTLGKGQTGLVKLGVHCVTCQKVAIKIVNREKLSESVL   60

Query:  61  MKVEREIAILKLIEHPHVLKLHDVYENKKYLYLVLEHVSGGELFDYLVKKGRLTPKEARK  120
            MKVEREIAILKLIEHPHVLKLHDVYENKKYLYLVLEHVSGGELFDYLVKKGRLTPKEARK
Sbjct:  61  MKVEREIAILKLIEHPHVLKLHDVYENKKYLYLVLEHVSGGELFDYLVKKGRLTPKEARK  120

Query: 121  FFRQIISALDFCHSHSICHRDLKPENLLLDEKNNIRIADFGMASLQVGDSLLETSCGSPH  180
            FFRQIISALDFCHSHSICHRDLKPENLLLDEKNNIRIADFGMASLQVGDSLLETSCGSPH
Sbjct: 121  FFRQIISALDFCHSHSICHRDLKPENLLLDEKNNIRIADFGMASLQVGDSLLETSCGSPH  180

Query: 181  YACPEVIRGEKYDGRKADVWSCGVILFALLVGALPFDDDNLRQLLEKVKRGVFHMPHFIP  240
            YACPEVIRGEKYDGRKADVWSCGVILFALLVGALPFDDDNLRQLLEKVKRGVFHMPHFIP
Sbjct: 181  YACPEVIRGEKYDGRKADVWSCGVILFALLVGALPFDDDNLRQLLEKVKRGVFHMPHFIP  240

Query: 241  PDCQSLLRGMIEVDAARRLTLEHIQKHIWYIGGKNEPEPEQPIPRKVQIRSLPSLEDIDP  300
            PDCQSLLRGM EVDAARRLTLEHIQKHIWYIGGKNEPEPEQPIPRKVQIRSLPSLEDIDP
Sbjct: 241  PDCQSLLRGMSEVDAARRLTLEHIQKHIWYIGGKNEPEPEQPIPRKVQIRSLPSLEDIDP  300

Query: 301  DVLDSMHSLGCFRDRNKLLQDLLSEEENQEKMIYFLLLDRKERYPSQEDEDLPPRNEIDP  360
            DVLDSMHSLGCFRDRNKLLQDLLSEEENQEKMIYFLLLDRKERYPSQEDEDLPPRNEIDP
Sbjct: 301  DVLDSMHSLGCFRDRNKLLQDLLSEEENQEKMIYFLLLDRKERYPSQEDEDLPPRNEIDP  360

Query: 361  PRKRVDSPMLNRHGKRRPERKSMEVLSVTDGGSPVPARRAIEMAQHGQRSRSISGASSGL  420
            PRKRVDSPMLNRHGKRRPERKSMEVLSVTDGGSPVPARRAIEMAQHGQRSRSISGASSGL
Sbjct: 361  PRKRVDSPMLNRHGKRRPERKSMEVLSVTDGGSPVPARRAIEMAQHGQRSRSISGASSGL  420

Query: 421  STSPLSSPRVTPHPSPRGSPLPTPKGTPVHTPKESPAGTPNPTPPSSPSVGGVPWRARLN  480
            STSPLSSPRVTPHPSPRGSPLPTPKGTPVHTPKESPAGTPNPTPPSSPSVGGVPWRARLN
Sbjct: 421  STSPLSSPRVTPHPSPRGSPLPTPKGTPVHTPKESPAGTPNPTPPSSPSVGGVPWRARLN  480

Query: 481  SIKNSFLGSPRFHRRKLQVPTPEEMSNLTPESSPELAKKSWFGNFISLEKEEQIFVVIKD  540
            SIKNSFLGSPRFHRRKLQVPTPEEMSNLTPESSPELAKKSWFGNFISLEKEEQIFVVIKD
Sbjct: 481  SIKNSFLGSPRFHRRKLQVPTPEEMSNLTPESSPELAKKSWFGNFISLEKEEQIFVVIKD  540

Query: 541  KPLSSIKADIVHAFLSIPSLSHSVISQTSFRAEYKATGGPAVFQKPVKFQVDITYTEGGE  600
```

FIGURE 2D

```
         KPLSSIKADIVHAFLSIPSLSHSVISQTSFRAEYKATGGPAVFQKPVKFQVDITYTEGGE
Sbjct: 541 KPLSSIKADIVHAFLSIPSLSHSVISQTSFRAEYKATGGPAVFQKPVKFQVDITYTEGGE 600

Query: 601 AQKENGIYSVTFTLLSGPSRRFKRVVETIQAQLLSTHDPPAAQHLSEPPPPAPGLSWGAG 660
           AQKENGIYSVTFTLLSGPSRRFKRVVETIQAQLLSTHDPPAAQHLSEPPPPAPGLSWGAG
Sbjct: 601 AQKENGIYSVTFTLLSGPSRRFKRVVETIQAQLLSTHDPPAAQHLSEPPPPAPGLSWGAG 660

Query: 661 LKGQKVATSYESSL 674
           LKGQKVATSYESSL
Sbjct: 661 LKGQKVATSYESSL 674    (SEQ ID NO:8)

Hmmer search results (Pfam):
Scores for sequence family classification (score includes all domains):
Model    Description                                  Score    E-value    N
PF00069  Eukaryotic protein kinase domain             322.6    8.8e-94    1

SPLICE FORM 2:

1 MKVEREIAIL KLIEHPHVLK LHDVYENKKY LYLVLEHVSG GELFDYLVKK
 51 GRLTPKEARK FFRQIISALD FCHSHSICHR DLKPENLLLD EKNNIRIADF
101 GMASLQVGDS LLETSCGSPH YACPEVIRGE KYDGRKADVW SCGVILFALL
151 VGALPFDDDN LRQLLEKVKR GVFHMPHFIP PDCQSLLRGM IEVDAARRLT
201 LEHIQKHIWY IGGKNEPEPE QPIPRKVQIR SLPSLEDIDP DVLDSMHSLG
251 CFRDRNKLLQ DLLSEEENQE KMIYFLLLDR KERYPSQEDE DLPPRNEIDP
301 PRKRVDSPML NRHGKRRPER KSMEVLSVTD GGSPVPARRA IEMAQHGQSK
351 AMFSKSLDIA EAHPQFSKED RSRSISGASS GLSTSPLSSP RVTPHPSPRG
401 SPLPTPKGTP VHTPKESPAG TPNPTPPSSP SVGGVPWRAR LNSIKNSFLG
451 SPRFHRRKLQ VPTPEEMSNL TPESSPELAK KSWFGNFISL EKEEQIFVVI
501 KDKPLSSIKA DIVHAFLSIP SLSHSVISQT SFRAEYKATG GPAVFQKPVK
551 FQVDITYTEG GEAQKENGIY SVTFTLLSGP SRRFKRVVET IQAQLLSTHD
601 PPAAQHLSEP PPPAPGLSWG AGLKGQKVAT SYESSL    (SEQ ID NO:5)

FEATURES:
Functional domains and key regions:
Prosite results:
PDOC00004 PS00004 CAMP_PHOSPHO_SITE
cAMP- and cGMP-dependent protein kinase phosphorylation site
          197-200         RRLT PDOC00005 PS00005 PKC_PHOSPHO_SITE
Protein kinase C phosphorylation site
Number of matches: 10
       1     54-56    TPK
       2    389-391   SPR
       3    397-399   SPR
       4    405-407   TPK
       5    413-415   TPK
       6    443-445   SIK
       7    451-453   SPR
       8    507-509   SIK
```

FIGURE 2E

```
         9    531-533    SFR
        10    581-583    SRR
```

PDOC00006 PS00006 CK2_PHOSPHO_SITE
Casein kinase II phosphorylation site
Number of matches: 15
```
         1    39-42    SGGE
         2    54-57    TPKE
         3    67-70    SALD
         4    110-113  SLLE
         5    234-237  SLED
         6    264-267  SEEE
         7    286-289  SQED
         8    327-330  SVTD
         9    367-370  SKED
        10    413-416  TPKE
        11    463-466  TPEE
        12    474-477  SSPE
        13    556-559  TYTE
        14    597-600  STHD
        15    630-633  TSYE
```

PDOC00007 PS00007 TYR_PHOSPHO_SITE
Tyrosine kinase phosphorylation site
```
              550-557    KFQVDITY
```

PDOC00008 PS00008 MYRISTYL
N-myristoylation site
Number of matches: 5
```
         1    347-352    GQSKAM
         2    377-382    GASSGL
         3    485-490    GNFISL
         4    616-621    GLSWGA
         5    625-630    GQKVAT
```

PDOC00009 PS00009 AMIDATION
Amidation site
Number of matches: 2
```
         1    133-136    DGRK
         2    313-316    HGKR
```

PDOC00100 PS00108 PROTEIN_KINASE_ST
Serine/Threonine protein kinases active-site signature
```
              77-89    ICHRDLKPENLLL
```

Membrane spanning structure and domains:

| Helix | Begin | End | Score | Certainty |
|---|---|---|---|---|
| 1 | 137 | 157 | 1.817 | Certain |
| 2 | 512 | 532 | 1.051 | Certain |

FIGURE 2F

Alignment to top blast hits:
>CRA|225000041315817 /altid=gi|18098147 /def=emb|CAD20436.1|
       (AX327993) unnamed protein product [Homo sapiens]
       /org=Homo sapiens /taxon=9606 /div=PRI /dataset=pataa
       /length=674
       Length = 674

Score = 1243 bits (3181), Expect = 0.0
 Identities = 613/636 (96%), Positives = 613/636 (96%), Gaps = 22/636 (3%)

```
Query:   1   MKVEREIAILKLIEHPHVLKLHDVYENKKYLYLVLEHVSGGELFDYLVKKGRLTPKEARK   60
             MKVEREIAILKLIEHPHVLKLHDVYENKKYLYLVLEHVSGGELFDYLVKKGRLTPKEARK
Sbjct:  61   MKVEREIAILKLIEHPHVLKLHDVYENKKYLYLVLEHVSGGELFDYLVKKGRLTPKEARK  120

Query:  61   FFRQIISALDFCHSHSICHRDLKPENLLLDEKNNIRIADFGMASLQVGDSLLETSCGSPH  120
             FFRQIISALDFCHSHSICHRDLKPENLLLDEKNNIRIADFGMASLQVGDSLLETSCGSPH
Sbjct: 121   FFRQIISALDFCHSHSICHRDLKPENLLLDEKNNIRIADFGMASLQVGDSLLETSCGSPH  180

Query: 121   YACPEVIRGEKYDGRKADVWSCGVILFALLVGALPFDDDNLRQLLEKVKRGVFHMPHFIP  180
             YACPEVIRGEKYDGRKADVWSCGVILFALLVGALPFDDDNLRQLLEKVKRGVFHMPHFIP
Sbjct: 181   YACPEVIRGEKYDGRKADVWSCGVILFALLVGALPFDDDNLRQLLEKVKRGVFHMPHFIP  240

Query: 181   PDCQSLLRGMIEVDAARRLTLEHIQKHIWYIGGKNEPEPEQPIPRKVQIRSLPSLEDIDP  240
             PDCQSLLRGM EVDAARRLTLEHIQKHIWYIGGKNEPEPEQPIPRKVQIRSLPSLEDIDP
Sbjct: 241   PDCQSLLRGMSEVDAARRLTLEHIQKHIWYIGGKNEPEPEQPIPRKVQIRSLPSLEDIDP  300

Query: 241   DVLDSMHSLGCFRDRNKLLQDLLSEEENQEKMIYFLLLDRKERYPSQEDEDLPPRNEIDP  300
             DVLDSMHSLGCFRDRNKLLQDLLSEEENQEKMIYFLLLDRKERYPSQEDEDLPPRNEIDP
Sbjct: 301   DVLDSMHSLGCFRDRNKLLQDLLSEEENQEKMIYFLLLDRKERYPSQEDEDLPPRNEIDP  360

Query: 301   PRKRVDSPMLNRHGKRRPERKSMEVLSVTDGGSPVPARRAIEMAQHGQSKAMFSKSLDIA  360
             PRKRVDSPMLNRHGKRRPERKSMEVLSVTDGGSPVPARRAIEMAQHGQ
Sbjct: 361   PRKRVDSPMLNRHGKRRPERKSMEVLSVTDGGSPVPARRAIEMAQHGQ-----------  408

Query: 361   EAHPQFSKEDRSRSISGASSGLSTSPLSSPRVTPHPSPRGSPLPTPKGTPVHTPKESPAG  420
                       RSRSISGASSGLSTSPLSSPRVTPHPSPRGSPLPTPKGTPVHTPKESPAG
Sbjct: 409   ----------RSRSISGASSGLSTSPLSSPRVTPHPSPRGSPLPTPKGTPVHTPKESPAG  458

Query: 421   TPNPTPPSSPSVGGVPWRARLNSIKNSFLGSPRFHRRKLQVPTPEEMSNLTPESSPELAK  480
             TPNPTPPSSPSVGGVPWRARLNSIKNSFLGSPRFHRRKLQVPTPEEMSNLTPESSPELAK
Sbjct: 459   TPNPTPPSSPSVGGVPWRARLNSIKNSFLGSPRFHRRKLQVPTPEEMSNLTPESSPELAK  518

Query: 481   KSWFGNFISLEKEEQIFVVIKDKPLSSIKADIVHAFLSIPSLSHSVISQTSFRAEYKATG  540
             KSWFGNFISLEKEEQIFVVIKDKPLSSIKADIVHAFLSIPSLSHSVISQTSFRAEYKATG
Sbjct: 519   KSWFGNFISLEKEEQIFVVIKDKPLSSIKADIVHAFLSIPSLSHSVISQTSFRAEYKATG  578

Query: 541   GPAVFQKPVKFQVDITYTEGGEAQKENGIYSVTFTLLSGPSRRFKRVVETIQAQLLSTHD  600
             GPAVFQKPVKFQVDITYTEGGEAQKENGIYSVTFTLLSGPSRRFKRVVETIQAQLLSTHD
Sbjct: 579   GPAVFQKPVKFQVDITYTEGGEAQKENGIYSVTFTLLSGPSRRFKRVVETIQAQLLSTHD  638

Query: 601   PPAAQHLSEPPPPAPGLSWGAGLKGQKVATSYESSL  636
             PPAAQHLSEPPPPAPGLSWGAGLKGQKVATSYESSL
Sbjct: 639   PPAAQHLSEPPPPAPGLSWGAGLKGQKVATSYESSL  674    (SEQ ID NO:9)
```

FIGURE 2G

```
>CRA|222000005909801 /dataset=GENESEQ /org=Homo sapiens /taxon=9606
         /mol_type=aa /date=19-FEB-02 /length=674
         /altid=derwent_ac|AAM47830 /altid=derwent_id|AAM47830
         /def=Human protein kinase 2246 SEQ ID NO 2
         /patent=WO200181588-A2 /pat_section=Claim
         Length = 674

Score = 1243 bits (3181), Expect = 0.0
 Identities = 613/636 (96%), Positives = 613/636 (96%), Gaps = 22/636 (3%)

Query: 1    MKVEREIAILKLIEHPHVLKLHDVYENKKYLYLVLEHVSGGELFDYLVKKGRLTPKEARK  60
            MKVEREIAILKLIEHPHVLKLHDVYENKKYLYLVLEHVSGGELFDYLVKKGRLTPKEARK
Sbjct: 61   MKVEREIAILKLIEHPHVLKLHDVYENKKYLYLVLEHVSGGELFDYLVKKGRLTPKEARK  120

Query: 61   FFRQIISALDFCHSHSICHRDLKPENLLLDEKNNIRIADFGMASLQVGDSLLETSCGSPH  120
            FFRQIISALDFCHSHSICHRDLKPENLLLDEKNNIRIADFGMASLQVGDSLLETSCGSPH
Sbjct: 121  FFRQIISALDFCHSHSICHRDLKPENLLLDEKNNIRIADFGMASLQVGDSLLETSCGSPH  180

Query: 121  YACPEVIRGEKYDGRKADVWSCGVILFALLVGALPFDDDNLRQLLEKVKRGVFHMPHFIP  180
            YACPEVIRGEKYDGRKADVWSCGVILFALLVGALPFDDDNLRQLLEKVKRGVFHMPHFIP
Sbjct: 181  YACPEVIRGEKYDGRKADVWSCGVILFALLVGALPFDDDNLRQLLEKVKRGVFHMPHFIP  240

Query: 181  PDCQSLLRGMIEVDAARRLTLEHIQKHIWYIGGKNEPEPEQPIPRKVQIRSLPSLEDIDP  240
            PDCQSLLRGM EVDAARRLTLEHIQKHIWYIGGKNEPEPEQPIPRKVQIRSLPSLEDIDP
Sbjct: 241  PDCQSLLRGMSEVDAARRLTLEHIQKHIWYIGGKNEPEPEQPIPRKVQIRSLPSLEDIDP  300

Query: 241  DVLDSMHSLGCFRDRNKLLQDLLSEEENQEKMIYFLLLDRKERYPSQEDEDLPPRNEIDP  300
            DVLDSMHSLGCFRDRNKLLQDLLSEEENQEKMIYFLLLDRKERYPSQEDEDLPPRNEIDP
Sbjct: 301  DVLDSMHSLGCFRDRNKLLQDLLSEEENQEKMIYFLLLDRKERYPSQEDEDLPPRNEIDP  360

Query: 301  PRKRVDSPMLNRHGKRRPERKSMEVLSVTDGGSPVPARRAIEMAQHGQSKAMFSKSLDIA  360
            PRKRVDSPMLNRHGKRRPERKSMEVLSVTDGGSPVPARRAIEMAQHGQ
Sbjct: 361  PRKRVDSPMLNRHGKRRPERKSMEVLSVTDGGSPVPARRAIEMAQHGQ------------  408

Query: 361  EAHPQFSKEDRSRSISGASSGLSTSPLSSPRVTPHPSPRGSPLPTPKGTPVHTPKESPAG  420
                      RSRSISGASSGLSTSPLSSPRVTPHPSPRGSPLPTPKGTPVHTPKESPAG
Sbjct: 409  ----------RSRSISGASSGLSTSPLSSPRVTPHPSPRGSPLPTPKGTPVHTPKESPAG  458

Query: 421  TPNPTPPSSPSVGGVPWRARLNSIKNSFLGSPRFHRRKLQVPTPEEMSNLTPESSPELAK  480
            TPNPTPPSSPSVGGVPWRARLNSIKNSFLGSPRFHRRKLQVPTPEEMSNLTPESSPELAK
Sbjct: 459  TPNPTPPSSPSVGGVPWRARLNSIKNSFLGSPRFHRRKLQVPTPEEMSNLTPESSPELAK  518

Query: 481  KSWFGNFISLEKEEQIFVVIKDKPLSSIKADIVHAFLSIPSLSHSVISQTSFRAEYKATG  540
            KSWFGNFISLEKEEQIFVVIKDKPLSSIKADIVHAFLSIPSLSHSVISQTSFRAEYKATG
Sbjct: 519  KSWFGNFISLEKEEQIFVVIKDKPLSSIKADIVHAFLSIPSLSHSVISQTSFRAEYKATG  578

Query: 541  GPAVFQKPVKFQVDITYTEGGEAQKENGIYSVTFTLLSGPSRRFKRVVETIQAQLLSTHD  600
            GPAVFQKPVKFQVDITYTEGGEAQKENGIYSVTFTLLSGPSRRFKRVVETIQAQLLSTHD
Sbjct: 579  GPAVFQKPVKFQVDITYTEGGEAQKENGIYSVTFTLLSGPSRRFKRVVETIQAQLLSTHD  638

Query: 601  PPAAQHLSEPPPPAPGLSWGAGLKGQKVATSYESSL 636
```

FIGURE 2H

```
                PPAAQHLSEPPPPAPGLSWGAGLKGQKVATSYESSL
    Sbjct: 639 PPAAQHLSEPPPPAPGLSWGAGLKGQKVATSYESSL 674  (SEQ ID NO:10)

Hmmer search results (Pfam):
Scores for sequence family classification (score includes all domains):
Model    Description                                    Score    E-value   N
pkinase  Protein kinase domain                          273.6    2.5e-78   1
Cnd1     Non-SMC condensin subunit, XCAP-D2/Cnd1          1.1        6.7   1

Parsed for domains:
Model    Domain  seq-f seq-t    hmm-f hmm-t     score  E-value
Cnd1       1/1     151   166 ..  1238  1253 .]    1.1      6.7
pkinase    1/1       3   210 ..    45   294 .]  273.6  2.5e-78
```

FIGURE 2I

GENOMIC INFORMATION BASED ON SPLICE FORM 1:

```
   1 GGATGTCACA AAGGTGCGTC TGACTCTGCT GCAGCCTGGG AGGCCAGGTG
  51 ACCATGGCAG CAGAGAGAGG GCATCTCAGG TCAAGTGCCC CTGCCCTCTG
 101 GCTGTGGCCT GACGCCCTCT CCTGGTCTCC TGCACACCCT CGGCCTCTGT
 151 TGGCACCTGG ACCAGACCAC TCCCAGTCAG CCTCCAGCCA GACCTCACTG
 201 CTTGACAGTT TCTCCAGCTG GAGGTCCCAG TCTACATTCA GCTAAAAATG
 251 TCTGCTGTCC CCACTCACAG CAGCAGCAGC GGGGGAAAGG GGAGTGCCCT
 301 CTGCCTCTGT CCCATGCTCT CAGCCCCCCT CCCCTGCCCC CACTGGTGGG
 351 GCCCTGATTG CTCATGCTCA GAGGCCCCAG AATTGGGTAG GGAGGACCCT
 401 TAGTCCACAG CATTTGAAGG GAAGCAGGGC GGGCGGGTGC AGGCCGAGAG
 451 TGGACAGGTG CTTTGGGGCC CACTCCCCTT CCCCAGCTGG AAATACAGAC
 501 AGCCCAAAGA GCAGGAGGGC GCACTGGGAA GACCCCGCAG TTTCCTGAGC
 551 TCATACGGGC TTACCAGCGT GGGGAGCGGA CCACGGTCAG CAGCAGTGTG
 601 TGGCAGAGCC CGCAGGGGAA ACGTTGCCCG CAGACCATAC ACGGGCAAGA
 651 TCTGGGACCC CCACTTCTGC AGCGTTCCGG GTCTCCCTCA CCTCTCCCCT
 701 CCCACCACCT TCTGCAGCAC GGGCTTAAGG AAATACCAGT GTTTTTCTGC
 751 AAAGAAACAG AGGGTCCGTC CAGGTCTGGC TGCCTCTTCG GCTGCCTGTG
 801 TTTAGACCTC CAAAGGCTGC TCCCGGCAAC CCCTGCCCAG CTGCTCAACC
 851 TGAAAGAGGG GTCGGTAGCA AGGGCCGGGA GGCGCCAGGG CGCTGCGGCC
 901 GGATCCCAGG TGAGTTCCTT GACTCCGCGC CGCGCAGCTC ACTGTGGCAT
 951 AACTGGGAAA ACCGCCGCTT CTCCCTCGGG AGCGGAGGCG GAGGGCCACG
1001 TCCTCCCTGG GGGTGCACAA TCTCTGCTTG GACAACGCCC GCGTGCAGTA
1051 GCCCCACAGA CTCCCATGCA GCCCCCCCGC CACGTGTGCC GCATCCGCGC
1101 CCTGCATGCA ACACCCGCCC CCTCCAGCGC AGCATGCCCC TCGCTGGCGT
1151 GCAGCACCCC CCATGTGTGC AGCACCCCTG CCCCGAATAC AGCACCTCTC
1201 CCCAGTACAG CACTCCCGCC CCGCATGCAA CACTCGCCCC CCTCCAGGGC
1251 AGCATCCCCA TCCCCCGCGC GTGCAGCACC CCCTCGAGGG GCGGGAAACT
1301 CTTTGGGACA CCCGGGGTCA CGCCCTGCAG GGTAAAACCC CCGTCCAGGG
1351 CAGCCATCTG CACCCCCTCG CCATGGGCCC ACTGCCTGCT CCGTCCCGGG
1401 ATGCGCCTTA ATGGCGGGTC GGGCGGCAGC GGGAGCTCTG CTGCCTGGTG
1451 GGACCGGACG TGGCAGCCGG CGGGCTGGAG GCTCCCAGGT CCCGGCCTCG
1501 CCCTGGCCTC GCCTCGCCCC CTAGAGTCTC CCCGAGCGCT CGTAGCGGCG
1551 GGGCGGGGTG GGGAGGCGCT GATTGGCCGG CGCGGGCACC GCTTGCCGCC
1601 GCCACGGCAT CCCGCTGCGT TCGTACAGGC TCGTGTCGAC TCGGCTCCGT
1651 TGCGCGGCCC GGCTCGGCTC CCCTCAGCTG CGCTCGACTC CGCTGTTCGG
1701 CTCGGCTGTT CGGCTTGGCT ACAGGGCTCG GCTGTTCGGC TTGGCTACAT
1751 GGCTCGGCTG CGCGGCTCGG CTCTGTTCGG CTCGGCTCGG CTGCTGGGCT
1801 CGGCTGTTCG GCTCAGCTGC GCGGCTCGGC TCGTCTCGGC TCTGTTCGGC
1851 TCGGCTCGGC TGCTGGGCTC GGCTGTTCGG CTCAGCTGCA CGGCTCGGCT
1901 CGGCTCGGCT CGGCTCGGCT GCGCGGCCGC TGACGGGCGT GCGCTGGGGG
1951 CGCGGGGCGC GGGGCGCGGG CCTCGGCGGC GGCGGCGGCG GCGGCGGCGG
2001 AAGCCAGGTG CCCCCGCCCG CCCTGTCCTC TCGACGAGGC GGAGGCGTCG
2051 CCGCGGGCCA GGCCTCGGAC TGCCGCGTCG GAGTGGACGC GGGGGGCGGC
2101 GGCGCGGGCG GACGCGGGCG GCGCGAAGCA GCGGGGCCCG CGGGGGCGCC
2151 CCGGCCGGGT CGGCGCGGAC GGCACTCGGC GGACGCGGGC GGACGCTGGG
2201 CGGCCCCTCC CTGCCCGCGC GCCCGGGCGC CCCTGGCCGG CGCTGGGCCC
2251 CAGAGCGATG ACATCGACGG GGAAGGACGG CGGCGCGCAG CACGCGCAGT
2301 ATGTTGGGCC CTACCGGCTG GAGAAGACGC TGGGCAAGGG GCAGACAGGT
2351 GCGTGCGGCC GGGGCGGGGA CCGGGGCCGG GGAGGCCGCG CTGGCAGCGC
2401 GCTGGGTGGG GGGCGCCCGA GGGAGGCCCC GGCCGCGAAG CCGCAGGCCC
2451 GGCCCGGGCC CCGGCCGCGA ACAATGGGCG GCCCGTGCGC CCCCGTCCGC
2501 TCGTGCGCCC CGGTTCCGCC GCGGATCCCG CAGGCCGCTT GGCTGCGGTC
```

FIGURE 3-1

```
2551 GGCCGGGCGC GGCCCAAGGA CACGCGGCGC GGCGCGGGGC GCGCAGGCGG
2601 ACAGGGGCGC ACGGGACGGC GCCCCTCGGG CCCCGCTGCA GGTGCGCGGC
2651 CCGGGCCGCA TTGTGCGCCC CAGCGACCGG GCCCATTGTG CCGCGGGAGG
2701 AGGGGGCCGC GCGGGCGCCC ATCTGCCGTC TGCCGCGGCC GCGCTAATAG
2751 GCGTGCTGCC CGAGCAGCTG CGCCCCCGGC GGGACTCCCA CCTCCGCGCG
2801 CCGGCCACCG GGGCCTCCGG GCAGGCCCGA TCTCCCTCCG CGGTGGGGGC
2851 GGGAGAGTGC GGGGACCTGC AGAGGGCTGG ACAGCGCCTT GCGCTGCTCC
2901 GGCTCGGGCT CGGGCGGGCG GAGCGTCTGT GACCTGCATT CCCACGGGGC
2951 AGGGAGAGGC CATTGGTGCT GGGACCAGAA GTGCGTGGGA CCTGACCCGT
3001 GGAGCAGCCC CGCGGCCTGC CGGTGGAGGG GGCTTCCCGG TGGGGCCTGG
3051 CTGTCATTCT AGGGAACAGG CCGGGTCCCT GCGGGGCCGA ACCCAGGCCA
3101 GAGGCAACCC AGCTACCCTC GCATGTGGCC AACTCTCCCC GGCCCGCTGG
3151 GTTTGGCTAG CCCTTCATCT GGTCAGGCAC ATTCACAGAG TCGCCTTTGT
3201 GGAGGCTGGG GCTCAGCCAT TTTCTTTCTT CTCTCAGGAC CGGCCTGTCT
3251 CTTGGTGTCC CCGAGGTCCC ACGGCACTGC CTCTCCCTTC CAATCCGAGA
3301 AGTTCCTTAG ACCCGGGCGG GCAGGGGTGG AGGGAAGGAG GAGGAGAGCG
3351 CTGGTGCAGG GTGGAGGCTC AGCCCCTCAC GGCTGCACAG AGGAGGAGCT
3401 GGGAGGTGGC GTTGGGGAAA GAAAGTGGGC CAGGCCCAGG CTCTTGGGGG
3451 AGGGCCGTGG CTGTGATGTA ACTACGGCAG AGCTGCAGGA AGGGGTTTAG
3501 ACTGAGGGGT TCAGGGGAGC TGCCTCACCT TGGGTGCACA GCCTTCCGCC
3551 ACCCGCCACG GCACGGAAGG GCCCCTGGCC ACAGGGCAGG GCCTGGGCAG
3601 GTGGGGTGGT GCAGCCTGGG TTGGAGAAGG AGGTGGCATT CAGCCCATGT
3651 CACCTGAGTT CAAAATTCTC GTCTTTCCCG GAAAGAAAAA CTAGTGTGTG
3701 AAATCCGTGG TGAAGGAGGG GCCCAGGGCA GCAGGATGCA GGAGTCAGTG
3751 AGATAATCCA ATTACGGTCC CAATAAAATG TTATTATAAG GAAACATCCG
3801 TGTGTAAATG AAGCACGAT GAGTTATGTG CTGTGCGCGG CCTCGGTGGG
3851 TAGGGGCTGG TCTCCACTCT TCATGGCATT CTGCTGGCGG CAGTTAATTA
3901 CGGGAGGTTT CCACTGTAAT TAACAGTAAT GAATACAAAA GGATGGGCTG
3951 TGTGTGTCTA CAACGTGCTG AGAGAGATAT TTAGAAAACA GCTCGAGGGG
4001 GGGCACAAAG CGGCCCCTCT CTCCCGAGTT ATGACGGGCA GAGCGCAAGC
4051 GTGTCACCGG GAGGGCCCTG GAGAAGGCCA CCATTTCTGT GCGTCTTCTG
4101 TTGCTGCTGC TGAAGGGTCA CCAGGAGTTG GGTGGACATG GGGCCTGGAG
4151 TGTGTGTGCT GGGCCACTTG GCACCAGATG CCAGGAGAGC TGCCAGGTCC
4201 CAAGCTCAAG AGGGAGATAG GCTTCCTGCC AGGAGACCTC CGTGGGAGAA
4251 CGGGAGGCTG GGCTTCTGGC CGCCACCACC CGAGGACGAT CTGATCCTGC
4301 CGTTGAGAAC GCTTCTCCTT CCAGGGACCT GGCCACAGGG GAGCTGTGGA
4351 GGCCTTGCTT GGGGGGCCAT TGGTGTGGAC GCGACTCCAG CCCCTTCCCC
4401 GTGTCTGTGG CTGGCAGCTT TGTTTGGCCC TCTCTGTTCA TCTCTCTCAG
4451 CCTGAGACCT TGGAAGGAGG AGCTGCTCGA CTTGAGGTGG CCACTGAGAG
4501 GGAGGTGGTC AGTGGCAGTG GCAGTGAGCC TTGTGGTGCC ACGAGAGCCC
4551 TTCCACCCAG CTGACCCAAG CTGGGGCCTG CTGGACGGTG GGCCAAAGAT
4601 GTGGTCCGAA ACCTGCCCTT GGGGAGTCTG GCCGTGTGGG GAGGGGAGAC
4651 CACGCAGCAC CCCCACCGGG GCCTGGAGGA CGCCCTTCTA GACGCCGCAG
4701 GGTCCGGTCG GCTGTCTTCT TCTGCCTTTC AGCGTGAGCG CTGCATGGTC
4751 TCACCTGTAC GGCACCTGCC TGTCTTGTTG GGTCTGTGCG TCCTGCAGGG
4801 CCAGTGTGGC TGTAGGGTCG TCCTTCTGCA TGGGCGTCC TCTGCACAGC
4851 TCCCCTCGGT GGCTGTGGGG GTTGCCTTCA GTGGTCTCAC TGCCGGTGCC
4901 AGGCACCAGG TGAAGCCGTC AGAGCACTGA GCATCTGTGG AAGCCTCCTC
4951 GCCGGCTGCT TGGTGGTTTC TGGCCAAGAC TTAGGGGGAT GTAGGCTGGG
5001 GTTGGGGTGG GAACCCACCT GCAAAGGTGC TGCCTTAGCT TTTCTTGGGG
5051 CTGAGAAAGG CTTGTGTAGC CTCATCTGAG CTTGACCCCT GCAGAGATGC
5101 CGAGACACAG TCCCTGCCAG CAAGGGCAAC CATGGAGGTT GGAGGGCGCA
5151 GACACTCCGA GTTGGAGCAT GCAGGTCCAG GAGGGTGTGT GGCACGGGCT
```

FIGURE 3-2

```
5201 GGGTGGCTTT TGTCCCTGCG CGCCTTTGTC CCTGTGCCCC ATCAGTACGT
5251 GGAGCAGGGC ACCTTCTTGC CCAAACCTCG GCTTAGCTCC TGAAATCTGG
5301 GAGGCCTGGG AGGGCCCTGT GGGAGGAGCT GGAGAACCTC GGGCCCTTGG
5351 AGCTGTTCTT GGGGGCAGGC GGGTGGGCTG CATGGGACGA TGAGGGGCCT
5401 GCCTTCGGGA ATCCTCTGTC TGGGGGGCGG GAGAAAGGAA TAATGGCCGC
5451 GATAGGGCTC CCTGCGAGGG AACGAAGGAG CTAGGATGAG GGGCTGCCCT
5501 GCAGCTCACC TGGCAGTGTT CACCTGCTGT GGCGTGGGGG AGGGACCTAG
5551 GCTGCCAGGG ACCTGGGGCC GCCCCTCCAT GTTCTCAATG GCCTTTAGGA
5601 AGGTTGAGCC CTGGTGGCTG CCAGGGTGGA GAGGGGTCCT GGGATGGGAG
5651 GAGTCATTGA AGATGGAACA GGTGAGGGGA GGGAGAGCCT GTGCCTGGGA
5701 GACCCTGGGG GTGACCCCAG GCCCAGAAGC TGGAGGCAGA TGTGGAGGGG
5751 AAGGAAGCTG GTCTGAGATG GGGTCTGTTT AGAAAGTTGA GCAGGACGGG
5801 CAGCGATGGG CTGTGGTGTG CAGGTCCCTG GAGATGGGCC ATGGAGATGG
5851 GTCCTGGAGA TGGGTCCTGG AGATGGGCCC CTGGAGATGG CCATGGAGA
5901 TGGGTCCTGG AGATGGGCCC CTGGAGATGG CCATGGAGG TGGGTCCTGG
5951 AGATGGGTCC TGGAGATGGG CCATGGAGAT GGGTCCCTGG AGATGGGCCC
6001 CTGGAGATGG GCCATGGAGA TGGGTCCTGG AGATGGGTCC TGGAGATGGG
6051 CCATGGAGAT GGGCCATGGA GATGGGCCAT GGAGATGGGT CCCTGGAGAT
6101 GGGCCCCTGG AGATGGGCCA TGGAGATGGG CCATGGAGAT GGCTCCCTGA
6151 GATGGGCCAT GCAGATGCGT CCTGGAGATG GCCATGGAG ATGGGTCCTG
6201 GAGATGGGTC CTGGAGATGG GCCCTGGAGA TGGGCATGGA GATGGGTCCT
6251 GGAGATGGGT CCTGGAGATG GGCCATGGAG ATGGGTCCTG GAGATGGGCC
6301 ATGGAGATGG GTCCTGGAGA TGGGTCCTGG AGATGGGCCA TGGAGATGGG
6351 TCCTGGAGAT GGGTCCCTGG AGATGGGTCC TGGAGATGGG TCCTGGAGAT
6401 GGGTCCCTGG AGATGGGCCA TGGAGATGGG TCCTGGAGAT GGGTCCTGGA
6451 GATGGGCCCC TGGAGATGGG CCATGGAGAT GGGTCCTGGA GATGGGTCCT
6501 GGAGATGGGC CATGGAGATG GGTCCTGGAG ATGGGTCCTG GAGATGGGCC
6551 CCTGGAGATG GGCCATGGAG ATGGGTCCTG GAGGTGGGTC CTGGAGATGG
6601 GCCATGGAGA TGGGTCCTGG AGATGGGTCC TGGAGATGGG TCCTGGAGAT
6651 GGGCCCCTGG AGATGGGCCA TGGAGATGGG TCCTGGAGAT GGGCCCCTGG
6701 AGATGGGCTG TGCAGGGCTG AGCCCGGAGA GCGCATGGGT AGACAGGACC
6751 CGGCAGCCTC CCCAGCCATG AAGGTGAAGG TGGACTCAGC GTGGGGTGTC
6801 TGCTGCGAGA CCCCAGGAAT TCTGTGGCCT TCCCCACATC AGGCCCTGGC
6851 CATCTGACCC CAGCTGTTTT GTCAGGGCAG CAGCAGCCTG GGGCTGGACT
6901 GAACCCCTCA TCTGCCCTGC ACGGGGTTTC TACAAGCTGA GGTCTCAGGA
6951 CGCTGTTCTC AGGGGCGCCG TGCACAGAGC CCGGGGAGCC AGCATGGTGG
7001 GTAGCCCTCC CATCTGAAGT CTCCCTGGCC CCCTGAAGTC CTGGAAAGG
7051 CCCATTTGGT GTCGCTGGGC GCCATGTCAG TGACTGCGCC AGGGTGGAGG
7101 CCTCAAGATG CTGCCCCTGG CGTCTTCCTG CCCTGCATGC CCTCCACAGG
7151 GAGCCCCCTT TCCAGCTGAG AGCTGGCCTT GAGTGTCCCT GTCAGGGCCC
7201 TTGGCACAGA GGTTCCGGGT GGTGAGGACG GCAGTTCCCC TAGGCGGGGG
7251 CGGGAGGGTC GTTGGAGGCG GGAGCCCTAG GCCCTTGTCC TGTCCCCACC
7301 CACTGTGGCC CTGGGCACCT CAGGTGTGTG TGTCCCTGTT GACGTGGGTC
7351 TCCCTGCCTT GTCACTGGCA ATGGCTGGAA AAGACACGCT GGGCAGAGGG
7401 CACCGCCCGG CCCTGATCGT GCTGGCCGTG CTGGCCCTGC TCTGCTGAGG
7451 TGCGTGCACG CCGTGGATTT CCTGGATGTG GAAGCCTCAA GGCCAGGCTG
7501 TGCCCCCTCC CCCAGCTGTG CCAGGGAGGG CTTTCCAGAG TCACCGTGGC
7551 TGGCTGCTGC CCCGCCTGCT CCACCATCTG CCCGAGCAGG GAGTTGTGTC
7601 CAGAACCACT GGGGAATGCA GGGCCTGGGC TGTGATGTGA GGTTGGCCTC
7651 TAGGCTTCAA GGGGATCTGT TTCTGGCAAA TCTCACGCAG GCCCAGCTGG
7701 AGCTACTATC AAGGGCCGTG GCTCCTGCCC ACGACCCAAG CTCCAGGGCC
7751 TCTGGGTCCC CACCATCGTT GGCTGCCGAG GTGGCCAGGT CCCTTCCTTG
7801 CTCTGAGGGT GGCTGGGAGT GTCTTAAGGT TGTCGCTGTG CCAGGTGTGT
```

FIGURE 3-3

```
7851 GTGGACCCCT GCGTCCCCCG CTCCTCGTCT CTCTTCCCTT CCACCCACGT
7901 CCCCCACTCC TGGTCCCTCT TCCCTTCCAC CCACGTCCCC CACTCCTGGT
7951 CCCTCTTCCC TTCCACCCAC GTCCCCCACT CCTGGTCCCT CTTCCCTTAC
8001 AGCCGCCTCG AGGACTGCAT GGGGCCAGCA AGGCCTGTAC CCCAGGACAC
8051 CAGAGTTGCT CGGACCGGCT CCCGGACCTG GGCCTAAGCG AGCTCTCCTG
8101 GTTCTCACTC CCGAGTCTGC GGAGTGACCC CGGGCCCTCT CATCATGGCC
8151 TCACCCTGCT CCGGCGCTCT GGGTGCTTTG AAGCAGACAG GAGACCCCCT
8201 CCAGGCTGGC CCGAGGGCAG GTCAGACCCC AGTCCCTGGG AACAGCCTGA
8251 GTGGGCTGTG CCTCCCCGTC GGCCACTGGC GCTCAGGAGG AGCCGTCGGG
8301 AAGGCCCCTT TGCCATCACC TGGTGGCGCT TGCTTGAGGG CTTCTGTGCC
8351 TTCCAGTCCT CACTGGGCAC AGACTAGCTT CTTTGGGCAC CTGGGGAGGG
8401 TCAGGCTGTC TCTGAAGTCA GCAGCCCTGC TGGGCAGCCG GCACCAGGAG
8451 AGGAGGCGGG CTGGTCCCCG TGACTGCCGG CCGCCGGCAT CCACCTATGT
8501 GGGGCTGTGC CTAGATGGTG GCACTGTGGG GCATCACTGT GCAGTTCTGG
8551 GCCCTGCCCT CAGCTCTGGA CAGCCCACCT GGACCCTGGC CCCTCGGAAG
8601 TGGAAGGACT GGGACCCTCAG GGCCCCTGAG TGTAGAATGG GGTTTCCCTG
8651 AAGCTTGTGC GAGGTTCCAA TGGCTGGAAA CACCGTACCG CGCAGGAGGA
8701 CGGCAGACCA GCATCTGTCA GGCCCCTTGG GGCTCACATG GCTGGTCCTC
8751 TGTGCTGCCC TGTGCTCTGC AGGAAGTTAA CGGCACCCTG CCACCTCCTC
8801 TGTGCAGGGC AGCCCCGCTT TCACCTGTAG GGCTGGTGCC TGTGTCAGGC
8851 CCAAGCCCCA GGTCCTAGCC TAGGCTGACC AAGCGGCCTG CAGATCTCCC
8901 TGAGGCCTCA CCCCGGGGAT GTCCGCCGGG CCAGGCTGCC CTGAGCCAGC
8951 TGCCTGGGGC TCTGGACAAG ATGGAGGCTG GGCTGGGCA GAGGCTGCAG
9001 GGACAAAGCA CGGATTGTGC CAAGCCGGCT GCCTTTCAGG GCCCGGCCTG
9051 CCAGGTCCAG GCCTTGTTCT ACCGCCTCTG AGGGGCCAGT GTTCTGGGCC
9101 CAGCAGCTGG GAGCCAGGCC CCACCCACAG AGCAGTGCTC CCGAAAGTCC
9151 TGCTGTTAAA GAGAAACTCC TCGTTTTCCT GGACGCCTCC AGCTTCCCAG
9201 GCTCGTTCTG CCTTCAGTCC CGGGGCCCAC GGAGGCCGTG GCTGCCCTAC
9251 GCTGCTTTGC CCCAGGGGCC TGGGCTGCAG GCTGGGCCTG GCTTCCTCCC
9301 CGAACCCTGG AGAGTGACAG CACCACCCCC AGTGGATGGC AAGGTCCCAT
9351 CGGTTGGCAT GTGTCTCTCT GGGCACCATG CTCCTCGTTG GGTGCCACGT
9401 CCTTGGGCTG AGCTTGGGTC CTGTCTGCCC TGGGGTACC ATCCTATGAG
9451 GACAGAGCTG CCTTTCCTGG GTGGCCATGG CAGCCTCATG GCACTGGCTG
9501 AGGGGAATGG ACACTTCTGG GATGGAGCTG GGCTGGGGTG GGGCTGGGTA
9551 GGGCCAGTGG GAGTTCTGGG CACCTTGGCC TGAGGGGAT GGGGGTGCCC
9601 AGGGCATTCA CGCCATCACT GCCCACTTGG CTTAAGCTGG AGCCCAGGGC
9651 CCTGGAGGGC AGGCTGGCCT TCCCGGCCCC GGGCAGAGGT GGGAGGGCGC
9701 CTGGACGGCT GCCTGCATGA TCCCCGTGAT ACAGCGGGGA TGGCTGCACG
9751 TCGGGCTGAG TCCAGCTGTG GGTGGTTTGC GGGGCACAG GGAGCCTGCC
9801 TGGCCAGGAA TGTGGCCTCT GCGGGTGTCT TGGCCTGGGA GCCCCCGGGG
9851 AACCCTTTGT ATGGGAGAAG GGGTCGGGAT AGGGGCTGGG GGGCAGTGCC
9901 TGGTGGCCCT CCATGCTGAG GGAAAGCCCC TCTTCACAGC TAGCATCGGG
9951 CCTCGTGTCC TCAGCACCCT GAATCAGCTG CAGGGCTAGC TGCTGCCTGA
10001 GCTGCCTGGT TGGGGCTGGC CTGGGCCCCT GATTGGCTGC TTCCCTGGGC
10051 GGGGGTGACG TTGCTGCCCT GGGTCCGAGA GTTATCTTGT GCGGACAGAG
10101 GTAATAGGTG TGGTACCCGC CCCGGGAAGG GTGGTGGCCA GGGTGGCCAT
10151 GTCAGGCGCC TTGGCCCTGC CCCCTGGGGA TACAGGGGGT GGAGAGGCAG
10201 CCCCAAAGCT GGGTTCTCAG AGACCTGGGG TGGCCAGATG GGGGCTCATT
10251 CAGCTGCCCC CTGTGCAGCC CCTTGGTGCC ATTAACTTTC TGCAGAGCGC
10301 AGGGCAGCAC AGAGGGCCAG CCAGGCCAGG GGGCCAGAGG TTCCCCTCCC
10351 ACACAAGCTC CGAGGTGTCC AGACAGGAGG CGGTGGCCCC AGTCCGCATA
10401 GGCCTTTCTC CAGGGCAGCC CTTTCCCCAG GGTTAGGCTG CAGGCCCTGC
10451 CGGTGTGGCT TCAGGAGTCC TGGTCCCCGC ACTCAAGCTT CCCTCCTGCT
```

FIGURE 3-4

```
10501 CATCTGTGAT GGGGCCTGGG TGTACCCAGG TCCTTGGTAG GCGCCAGGAG
10551 ATGTGTGGGG CCCCCTGGAG CCTGGAGCCC CCCCAGCCCC TCCGCTTATC
10601 TTTGGTGTCT GGGGCGGAGA CTGGCCCTTG GCACCCGCGG CCGTCCCTGG
10651 CTTTCGTCCT GCGCCGTCCT GGGTCTTTGG GTCCCTCTGC CAGCCCCGTG
10701 GTGACTTCTT GCACACAGGG TTTGCAGGGG GGCTGCGGAA TGACTCCGTC
10751 CCTTCCACAG CACACGGGCA CCTCCAGCCA GGAAGGAGCT GGGCAGGCAG
10801 CCCCGCCCCA GGCCAGAGCC ACAGAGCCGT TGTGACTGGG GGTCTCTGGC
10851 CAGGACGTTC CTGTGCTGTC TGTTGTGGGC AGGCCCCCCA GGGCAGGGCC
10901 ACCTCCAGGG TACTTGGTTC CAGACGCTGG CTGAGTGGTC ACTTGTGTCC
10951 ACACCGCAGT TTCCCTATCT GTGAAGTGGC TTGGATAGGA TGGTGGGGTG
11001 GTGCCAGGGG GTTGCTCTTG CCGGGACTGA GCCCAGGGCC TGGCCCTGCC
11051 ACTGGGGCCA GCGTCAGCCT CAGGACAGCC GAGGAGGGGA GATGGCTTGT
11101 GGGCCAGGAT GCCCGAGGGT GGGGAGAAGC AGCTCAGATG GCGTCACTGT
11151 GTTGCCTTCC CCCAGCCGAT GGGATTTTTG TGGAGCTCTC TCTGCTGGGG
11201 ACAATGAGAG GGGAGCCGTG AGCCGTGATA GGGATTGTGG CAAGGCCGGG
11251 CTGGTCAGCT GGGGATGCCA GGGCCGCACA GTCCCTCGGG GCTCAAACTG
11301 GCAGCTGTCC CCCCAGGGCT CTGGGCTGGT GAGGAGCTTG TCCTGCCCGT
11351 CCCTCTGCTG CCACAGTAAC CCCGGACACA TCCCATGTCA TCTGCTGTGG
11401 CCCTGCCTTC TGCCGGGTGG ACATGGGGGA TTTGGGGTAC AGGGAAGCAG
11451 TGAGTTCTGG GCCGACCAAA TTCCCCGGTG CCGTCGGGCC CAGCCTCCTT
11501 CTTCCTTGGC ACCCTGGGGT GTGTCGTGGC TGAGCCCCAG CTCTGTGGTT
11551 CCCGAGGCTT TTCTGGGATG GAGGCCTCGC TCCGGGTCCT GGTGTTTTCA
11601 CATGGGAGCA GAGGAGAGTG CCCCAAGCCT GGCGAGCACC GCCTGTAGCC
11651 GCCAGCAACA CCCCCCACCT CCGTTACGCA GGAATAGTCC CAGCCACCAT
11701 TTATTGTAAA CATTTGGTCT GCACATATAA CAGAGAAACT CTTGAAAACC
11751 AAAGGGCCGT TATCACCCTG AGAAATTAGC ACTGATTTCT AGAAACTGGC
11801 AGGAAGCCAG TCGGATGCTG GGATTTTAAC TTTAAAAGAA CATTTCCCAG
11851 GCCTGGGCCT CCGCCGCCAG CCCAGTCTCC CTGCAGGAGG GAGTGGGCAG
11901 GCGCTGGGCT CTGCGTGGGG CCGTGGACTC AGTCTCCCGC CCCCTCCATG
11951 GCTGGGGGCT GTTCCCAGGG GCCCTAAGCC TCAGCTTTCC CCGGAGGCCC
12001 GGGCATGGGG TGGGCCTGGG CTCTGCATCT CTCAGAAGTT TCCAGGTGAT
12051 GCTGACGCTG GTTGGGGGAC CCCACTTGGA GAGCTGGGGT GGCGGTGGCC
12101 TCCTCTTCCA TAACCCCTGA CCCTGGGCGG TGGCCTCCTC TTCCATAACC
12151 CCTGACCCTG GGCAGTGACC GCCTCTTCCA TAACCCCTGA CCCTGTATAG
12201 CGGCCGTGGG TACTGTCTTC CACCCGTCCA CATCCTTCCT GGGCACCGAA
12251 CACTGCCAGC ACCAAGCCAG GCACGGGGCC AGCAAAATGC CCTGCCCGCC
12301 TGGGGACACA CATGCTGGAA CGTTCACTGT GTGTCACACA CGTGCAGGTG
12351 GTCTCGGGGG GCAGATGCCA CATGGGAGGA ATGGGCCCCT GTCAGCTGTG
12401 TTCTCCATTG TGGTCGGGGG TGGGGCAGG TAGTGGAGGA CCTGCCGGCT
12451 CTGCCTGGGC CCTGCGGCCA CCCACCCCGG ACACTGTGGC ACTGGGAGGG
12501 GTGCAGATGA GGAGCCGGTC CAGGGCTAGG GCCCTTCCTG TCTAGCCATG
12551 GCCCTCCCCA GGCTCCTCGT GGTGCTGGGA CCCTGTGGCG TCTGCTCCTC
12601 TGCCCAGTG GCTGTCGGCG GCGGGGCCGT GTGACCCTCC TTCCTTCCAT
12651 CCCTGCTGGT GCATGCCCAG CTCCCAGCCT GGCCTCAATG CGGGGCATGA
12701 GGGCTCATTT CATTCAGGCC ACATGAGTGT CAGGACAGCC ACCGTTGGGC
12751 ATCAGGGAGG ACCAGCAGAC AGAATAGTGG TGGAGCCGGT CACAGAGCTG
12801 CACGGGGCAG GGTGGAGCCG GTCACAGAGC TGCATGGGGC AGGGGACGCC
12851 CTGCCCACTC CGCAGGCCTC TAGGCTCCCG TCTTCACAGA GTTCTCCTGC
12901 TGAGGCACCT GGCCTGTGTC CTCAGCACAT GCCCCGGCA TCACACCTCA
12951 CCCGTGAGCA ACTGATGCAC GGCTACCCTC GCGGGTCTGT ATTTTGGGAT
13001 TTCCTGCCAG TGTCTGTGAG TCGGGGCTCA CGCCCGGGGT GCGGGTGCCC
13051 TCCTGGAAGT GTCTGTGTCT CATAGTGAGT CTGTCTGCCT GGGATTGTCA
13101 CAACCTGGAA GAATAGGTCG CTCTTCCAGT CCCCCACCTT CCTGCACGGT
```

FIGURE 3-5

```
13151 CCAGGGTCGC TCAGGAGCCC CTGGGACCAG GGCCAGCATA CCCTGGAGTA
13201 TGTTCCTGGA GCCAGGGAAC ATCACTCCTG GGCCAGCAGC CCCACCTCCT
13251 GCAGGCTGCA CCGAGCCCCT TCGGGCCCAT GCCAACCGCC GGTGCAGCCT
13301 CTGCCCGTCC TCTCTGGTCT CCAGGGAAGG CGGCAGCAGC CGTGGGTGGT
13351 ATGGAAGCCC CTGCTCTGCT GCGTCGTGCC AGAGCGGACT GTGGGGACAC
13401 AGCAGGGAGT TTGCCGACTT TGAGGAGGAG GAAAGGACCT TATGCCCTGT
13451 TCGGGAGGCG GAGAGGCCCT CAGGGAGCTG TCCAGCACCA GCCGTGCTGA
13501 AGTCTGCAGC TTCCTCCTCC CGCGAGGGCG CCTGCCTTGG CGCTGGGTCC
13551 TCACAGCCCA GCTGCAGCTG GAAAGAAGCT ATGTGAGGGC CGGTGATTTT
13601 TGGCAAGATC CCAAACCTGT CGTCAGCTGT GGGTCTCTGG TTCTGTGCTG
13651 AGGAGGGGCA GGAGGAAACC AGATGTGTTC GGTGCCTCCT GCTGGCCAGT
13701 CCCCCAGCCC TGGGCCCTGA GCAGACCCAC AGGACCCACC CCTCGTGCCC
13751 CGCCAGGGCC TCTCTGTCTT TAACTTACAG GGGAGAGGGA GGGCCAGGGC
13801 CCCGCAGAGC TGAGGGTGCC CCTGCGTGTG GGTGCCGGAG AGCAGGCATG
13851 GAGCAGCCTG GGGAAGGCTG GGGGGCCTGA CCTTGCGCTC TCCAGAGGCG
13901 GTGGGTGTCG GGGCTCCCCG GGGCGGGGCA GGCACAGCAG GCTGTGGTGG
13951 GGTCTGATCC ATGTCCCCTG GAGCGCACTC CTGGGAGCCC TTTGTGACAG
14001 ACTCCTCCAA GTCACCTTGT TTCAGGGCTC ATGTGGCCTA AGGGTAGGTT
14051 AGTTGCAGGA GTTTGAGAAG GTGGCCTTGG GGGTGGATGG TCATGGGCAG
14101 AGGAGCTACT GCCGCAAACT CAGCTCCAAG CTGCCTCCAC CTGAACCTTG
14151 TCCGTGCCTG AGCCCCGCCT CCGGGGAGGA GCATCGCAAA GGATGGGTGG
14201 TGCTGCGTGT AACCCTCTGG CTGCCCCACC CTTCTCCGGG GACTTGCCCC
14251 TCAGGCCAGC CCAGCCAGCC CTCCACACTC CTCCTGGGGG GTGAGGGGCA
14301 GCGTCTCCCT GGAGCTCCCC ACACACAGGA GAGGGTTCTC TAGGGCCTCA
14351 TCTGATCCTG CCTGGGCACT GGCAGAGGGC CAGGACTCAG GAGGCCAGGA
14401 CAGAAAAGGC CACTGAGGCC CACAGCCCCT CACTCAGGGA CACAGGGTCT
14451 CCTGCCAAAG GCAGAGGGAG TGGAGTGGGG GCAGCTGACA CACGGGGAGG
14501 GAACAGGCCC CCAGCAGAGG AGGCGGGAGC GGCGCTGAGC TCGGCAGAGT
14551 GAGGGGCTGT GACTGCCTCT GAGGAGATGG AGGGCTCGGA TCTGCTTGGA
14601 GGTTTGTTGA CCCTAAACCC CAAATCCCCG GGGATTTGTG ACTCATCGTA
14651 AAGTGCACAG ATGAGCGCCC TCTCCAGCAA AAGCCAGAGC CGCCGAGGGC
14701 GTTTGCAGAT GGCGTGGGTG GGAGGACGGG CGGGGCCCCC CAGGGCCACC
14751 ACGGGGTAGG TGCCTGGCTG CAGACCTCTG CCCGCCTCT CACCCATGGG
14801 GTGTTGAGTC CCCCATTCCA CAGCTCAACT GTGGGGTCAG CTGGCTTGGG
14851 GCCTTATCCT CGGGGGGCCT GTGTCACGCT ACCCTTCCCC TGGGGCAGTG
14901 CCCTTGTCAC TGCCTGCTGT GACCGGACTG GCCAGCCTTG TCTGCTGGAG
14951 GGAACGTGGC AGTTGTCCCC CAGCCCAGGA TGGAGGCTGC TGTGCGTGGC
15001 AGAGCACGTG AGGCAGCCAC CCCTCACCGC AGGCCACAGC GTCACTGGCT
15051 CACCGGTCAC TGTGGGGTCC TCCCCACCAG GGCTACCCTG CTGGTGCCCC
15101 TGCTGGTGCT GGGGTTGGAG CTGAAGGCTG CTCTTGGGCC TGGGGGCCCT
15151 GCGCTCCTGG TCTCAGCCCC CTCTCTGCTC CTTCCACTCA GGAGGCCACG
15201 AAACCCGCAG GCTCATGGGA TGGGCAGGGG CTGCGGAGGA GGGGCCCAGG
15251 CGGTTGGAGC TGGCTGTTTG GTGTGAAAGG GGGATAACTG ATACCCCACC
15301 TCTGACGGTG TGTCCTGAGC TCCCATCACC CCAGTTCAGT GGTGTCTGAC
15351 AGCCCCCTTA GGTCCCTCAC CTGCTGGTGA CAGTCCTGTT GTGGCACCTG
15401 GTGCACTGAT GGTCGCCTGT GGACCCCCAT GCTGGTGAGA CAGAAGTGGG
15451 CTCTGTTCTG GGCTCTGTGG CTCCTGGTGG CGTTGGATAA ACCAAGCCCC
15501 CACAGGGCCT GTGCAGAGAG TGACCTGGAA GTGTCCTGGC TTCTCTGGGG
15551 GAAACACGTT GAGCGCTTCC CCACGTGGGG AGGCGGCCGG GCTCCAGGCC
15601 CCACTGCCCA ACTTGGGACG GTGGCATCAC GGGAGTTGGG ATGGGAGGCG
15651 GGCGGTGGGC CTGGTCAGAT GGGGCGAATG GGGTGAGCCT GGCCTGGAGT
15701 TGTACCCAAG CCCCTGCCCC TCTCCTGGGC TTCGCTCTTT GACCAGTGAA
15751 GTGTGAGCAG AGTTCACATC TGTCTGGGTG AAAGCTTCCA GAGCCAGCAC
```

FIGURE 3-6

```
15801 CCTCTCCACT GTCCCACAGA AGCTGGTGTG GGCACACAGC ACCTCCAGCC
15851 TGGCCCTGGG AGGTTGGAGA CTCAGCCCTG CGGCCACCCT TTGATTGCTG
15901 CCTGCCCCAG CTGCCCGCAA TCTGGGTGCG CGGAGCTGTG TCCCTGCCCA
15951 GGGCCTCACT CCTCTGTGTT CCCCTCCTGT CTCTGGGCCC CGTGTCCTTG
16001 ATGCTGCCCC TTTTCCTGAC CCTGCTCTCC TATCACGTCC CCTCTTCAGG
16051 GGAGTGGCCA CGGGAGGAGG CCGTCGTCCC AGCCAGCCCT CCGCCTGCCT
16101 CAGCCTCCCA GGGCAGACGT CCCTTTGGCC GAGAGTTGCA CCTGCCTCTG
16151 ATCCTTGCCC TTGCTCTGTC TTCCCCTCCG TCCCTGTCCC AGCACCCAGA
16201 GGAGGTTGGG GTGGGGAAAG GTCCTCGGGG GAGACCATCT GCACGGCCCC
16251 TCCCTGGATG CCACAGAGCA CCAGCCTTGG GAGGGCAGAG GGGGCGCCCC
16301 GGAGGTGGAT GCCCTGCCCT GGTTCCTGAT GTGGCCCCTG CCTCTAAGAC
16351 CACAAGGCAC TCAGGGACAG ATGCTAATGT TTGGGAGGGT AGGAGCAACG
16401 GGCGTGGGCT TGCAGCCCCT GCCTCTCCCC TCTCTGCCCT TCCCGCAAGC
16451 CGCCCGCTAC CCACTGCCCA CTAAGCAGCT CTATTCTTAC CGCGCCCTGG
16501 AGATTACTGC TGCGACGGCT CCTCTGGGAC AGGCAGGCTC GCCGGGCTGG
16551 GGGCAGGGCT CAGCACTCCC GCTCTGTGGG AGGGTGGCCG CAGGGCCCTG
16601 CGTGGAGTCC CTCCCCAGCC CTCGCTGCCC CTGTGTCCTG ACACAAGGCC
16651 CCCAAGGTGT GGCAGGCAGG CGGGCGTGCA GGCCTCTGTC TCTGGTGGTC
16701 TAGGGGGTGG GGGTGGCTCT CTGAGGGGTG TGGGCCTCCA TCTCTGGTGG
16751 TCTAGGGGGT TGTAGGGGGG CTCTCTGAGG GGTGTGGGCC TCCATCTCTG
16801 GTGGTCTAGG GGGTTGTAGG GGGGCTCTCT GAGGGGCCTG AGCAGCCTCC
16851 AGCCCCTCCC CAGGGAGGTC AGTCACCCTG GGAGGGGGTT GGGAGCGGCC
16901 CGGGCCAGGC TGCCTCATCC ACAGCCCTGG GCCAGTCAGT GGGGCAGGGA
16951 ATGTGGACAC TGCCCTCCTA GCCCTCTGCC TGGGATCCTC TACGTCTCCC
17001 CACTTGGGAC AGGAGCTGAC GTTGCTCCTG GAGCCCTGCG TGCCAGCTGG
17051 GGTGGGAGGT GTGTGCGTCT GTGTATGTGT GTGTGGTGTG TCTGCATATG
17101 CAGGTGTGTG TGTGCGTGCC CACCTGTGTG TGCAGGTGCC AGCCTTGCCC
17151 AGCCTTCCCC CTGTGGCTCG TGAAGCTCAG GATGGCTGGG GGAGCTGGTG
17201 GCAGCCCCAC TGCATGATAG TTGAGAAGTT GGGATCCTAG GGCTTGCCTG
17251 CAGCCAGCAC CCCACAGTTA CAGGCAGCGA GCTGCCAGCC CCAGCCCCTT
17301 CCTCTAGGAA AACATGCCCT GTCCTGCCCA GGGGTCTGGG ATGGGGGACC
17351 GACCAGCGGC GCCAGCTACC CCCAAGGGCA CAGGCTTGGC CGTTGACCTT
17401 TGCTCCCCAG CTTTGAGGAC CCAGGGTTGA GCCAGGAAGA TGGGGTGCGG
17451 AGCTCTTGGG CTCAGGGCAG CCTAAAGATT GTGCTCTGTG CCGAGGTGGG
17501 GAGGTCCGTC CTTTCCTGAG TGTGGCCCCA GCCAGCAGCC CGCATCTCCA
17551 GCGCTCGGTC CTTCCTGCCT ACCTGCGTGG CAGTGACCCC ATCCAGCCCC
17601 TGCTCCTTGG CCCCGCAGGC CCCACACCCC TTGCCGAGTG ATTGGCCCAG
17651 CCCCAGGCGC CCCTTCTGTC CACGTCAGAC GCTGGTCTGC ACCTGTGCCA
17701 TTCCATCCCC AGCCTTCCCA GACCCCCACA AGCCCCCACA GGCTCCTAAA
17751 CCCACCCAAG ATACGGAGAC AGGAACCTCC CAACTCTGTC CCAGCTCCTC
17801 ACACTGTTTG TTGCCCGCTC CCCTGCCGAG GTCAGGGTGT CCCTCGGCCA
17851 GCGGCTCCTC CTGCCCAGCC TTCCCCTCCT CCTGCCTGGC CTTCCTCTCC
17901 CTGCCCAGCC GCCAGAGGTC CCTTCTTAGG AGATAAACTG GGCCGGGCGC
17951 AGTGGCTCAC GCCTGTAATC CCAGCACTTT GGGAGGCCAA GGCTGCCAAG
18001 GTCAGGAGAT GGAGACCATC CTGGCTAACA CGGTGAAACC CCATCTCTAC
18051 TAAAAATACA AAACAAAACA AAAATTAGCC GGGCATGGTG GTGGGTGCCT
18101 GTAGTTCCAG CTACTGGGGA GGCTGAGGCG GGAGAATGGC ATGAACCCGG
18151 GAGGCGGAGC TTGCAGTGAG CTGAGATCAC GCCACTGCAC TCCAGCCTGG
18201 GTGATAGAGC AAGACTCTGT CTCAATAAAA AGATAAACTG AGCCACACCT
18251 GGGCTGTCCC TGCCACTCAG GACCCCAGAG AGCTCAGCAA ATTGCATGGG
18301 GGGCGAGCGG AGCTGGTATT TGGCAACACA GGAGGGCGGG GGCCCAAACC
18351 CCTGCAGAGG ATGCCAGCAA GCCCCAGGCT CTCAGGATGG GCCACACGGA
18401 GCTGGCATGA GGAGGCCTGC AGAGGCCAGG ACAGCTGTGT GTCCAGCACT
```

FIGURE 3-7

```
18451 CGGCCGCCTG CTGGCTGTGC TGCTGGAGGG TGCGGGGGTG GGCCTGTCGC
18501 TGGGCCACAT CCCAGGGCCT GTGGTGGGGC TGGCAGGGTG TCAGCCTGCA
18551 GCTTGGAAAA GAGGAGCCCA GGCATCTGCT CCCTCCACGA GGTACACGCA
18601 TGTGTGTGCA TGTCCATGTG CAGGTTTGTG TGCGCCTGCA TATCTGTGTG
18651 TCTGTGTGCG TGTGTGTGTG TGGTGCGTCT GCATGTGCAG GTGTGTGCGT
18701 GCGTGCCTGC CTGTGCGTGC AAACGTGTGT GCGCATGTGT GTGGTCTGTG
18751 CATCCTTGTC TGCCTGCACC TAGGATGACA GGCGGAGGCT CCTAGGGTTT
18801 CCCAGGGAAG GGGGTCCCAA CGTCACCACA GCGACTTGT AGCCATTCCC
18851 TGGGCTGCCG AGGGTGGGGC CTGGCAGGTG CAGAGCGGAG GGAGCTGCAG
18901 GCCCTGGAGG AGGCTGCTGT GGTGGCTGTG GTGTCTGCGT GGGTCCCCCA
18951 CATCTGATGT CTCCTTCCCA CCCCTGCCCT CTCTGAGCTT GGTGTGGGTC
19001 ACCGGCTCTG ACTGGCTCCC GCTGGCCACC TCTGCTGTGT CCACGACAGC
19051 CCCACTGCCT GCAGAGGGCC CTGCTGCCCC CTATGCCCTC TGGCAACACC
19101 GTGGTGTCCC CACAGGAAGT AGGTTCCTGG CCCCACAGAG TCCACTTGGG
19151 GGGCTTCTCA CATCGGACCC TTGGCCACAG TGCCACCCGT CTTCCTGCAC
19201 GGGCCTCCCC TCCGAGGCCC TTGTTCCTGC CGCCTGCCCT GCATGACCTT
19251 CAAGGAAATT GCTGACCCCC AGGAGACCCC TTCCTTCATG GGGTGCCTCA
19301 GACCCCACCT CTGCAGGGGT TCTAGCAGCC TGGTTCTAGC AGCTCTGCAG
19351 GGGTTCTAGA CCCTCTAGGG GCCTCGACGC AGCCCCTAAA CTAGGACACT
19401 AGCTTCAGAG ACTGAATCAC CAAATAGTTA CAGGATTCAA TCAAAATGTT
19451 TCATCGGGCT AATCTTTCAA TATTGAATTG TGAAAACCAG TTAATAGAAG
19501 TCTAACGTGA TCAACTGGCT CCGCTGGGAT TGGGTCCCGC CGCCTCCAGG
19551 CAGGTGCCAC CTCCAGGAGG GCTTTCCCAG AGTGTGGGGC GGGCCCGGCA
19601 GGGAGGGGCT GTTTGCTGCT CCATTTGCCC AGTGTGCCCT CAGATCCACA
19651 GCCTCAGGGC ACCTGTGCCC TCCAGGGAAG GCCGCCTGGG TCTCCTGCCC
19701 ACCCTGGAGC TGAGCCCACC TGCCCTGCAG CTAGAGGGGG CAGGGGCTGC
19751 CTGGGCACCT CCTCCATCAC CTCCTGGTGG AGGGGTTCCT GGTCCCAGGT
19801 CCTTCCACTC CAGAATCCAC CTTTGAGCCC CATACTCTCT GCAGCCCATC
19851 CTCTGGCCTC CCTGGGGCAA ACTGTGAGGC TTATGGCGTG GGGAGCACAG
19901 GCGGGCCTGG CCTCGGGCCC CAGCCTCCCT CCGCCTGTTC CTAGAGCCCA
19951 CAGTTCCACT GCTGGAGCTT TCTCTTGGCC ACCTGACCAG TTCCCCTCCC
20001 TGTGTCCAGC AGTCCTCTGC AGTCCCACAC TCATGCCCCA GGAATCCATC
20051 CAGCTCCTGC TGATCCTCTC ATAGCCCCTG GCTTTGGGGA GGGTGGAGTC
20101 CAGGGTCCCA GGTCACCATC CACCTTAGAA GTCCAGCGTC CAGCCCCAGG
20151 GCAGCAGCCA CGGGAGAACT GGGGAGAAGG CTGTATGGGG TGGGGGTCTT
20201 CACACAGCGG CCACCAGGCT GGGGGTATCC TGAGGTCAAA GCCTGTGCCA
20251 CGTCCCCCCA TCTTCCCAGG AGACACCTGA GTGCTATGGC CACTCCTTGT
20301 CAGGTCCAGG GCCTGGACCC TCAAGGACAC CCCTGTGGCT GCCATCCTGA
20351 CAGGCGGAAT TCATCGCAGA CCCTCAACCT GATGGCACAG GTCAGGGTTC
20401 ACGTCGGAAC CCTCCCCGCT GGTCCTTACT AGATCTGAGA GTGAGTCAGG
20451 TGGGGTGTGT GTGTGTGCAC ATCTGCCTGT GCAGGGGTAT GTGTGTGCAC
20501 GTCTGCCTGT GCAGGGGTGT GTGTGTGTTT GTGCAAGGGT GTGTGTTTGC
20551 CTGTGCTGGT GTGTGTGTGT GTGTGTGTGT GTGGCTGTGC TGGGGTGTGT
20601 GTGCATATCT GCCTGTACAG GGGTGTGTAT GTCTGCCTTA TGGAGGTTTA
20651 TGTGTGTCTG CCTGTGCAAG GGTGTGTGTG TGTATGTATC TGTATACAGG
20701 TGTTTGCCTG TGCAGGTGTG TGTGTGTGT GTGTATGTC TGTGCAGGGG
20751 TGTGCATATG TGTCTGCCTA TGCAGGGATG TATGTGTGTC TGCCTGTACA
20801 GGGGTGTGTG TGTATGTGTG TGCCTGTGTA AGGGTGTGTG TACACACATC
20851 TGTGTGTGCC GTCTGACCCT GGAGGCATGG GCCTGGCTTT CCTCAGGGCC
20901 TGCATTTCCC TCTCTGTTTC TCTGCCCCGC CCAGCCATC CCCTTCACCC
20951 CTTGCAGCCT GGAGCTGGGG GAGTCAGGGA GAGGCTGGGG CTGCAGACGG
21001 GGCAGCTGGC ATCCTCATGC TCCCGTGCCC GCCTCTTCTC CCTGTGCTCA
21051 GTCGTGCTGC TTGGGCCGTG GGAGTGGAGC TCCTTCGCAC AGGTGTTAGT
```

FIGURE 3-8

```
21101 CATCTGTGTT TCCTTAGCGA TTTACCTGTC CTTGGCTCAT TTAAAACAGT
21151 TGGAGTGTTG GTGGTTTTGT AACGAACTGG TCAGAGCACC TTCCGTGAGA
21201 AGGGCCTTTT CCCCCAGTTC ACCGGGGCTC CCCTGCTCAG GGTGTGCCGG
21251 GGGCTTTGAG TCACTTCTGT GTCTCCTTGG AGGCTGTGTG GCGTCCGTGG
21301 AAGTTGGCGT CTGTGCGGTG TGGTTCTGTT TATGGGTGTT GTAGAGAAGG
21351 CGCCGTCCAG AGACAGAGCC ACTGCTGAGG TGGGTGGGGG GTGTATGAAG
21401 GGCACAAGGA CGCTTTGGGG GTGTCAGGTA TGACGGCCCT CAGGTCATGG
21451 TTTCACACGC GTGTGCTTTA AATGCGTGCT GGCTGTCACG TGTCAGTCGT
21501 GCCTCCACAG AGCTTCAGGA ACCACCGAGA TGGGGAGCCT GCCGGAGACA
21551 CAGGTTTTCT GAGCGCACCA GCGGCTCCAA AAGCAGAGGG AAGAGCCCTG
21601 CGTGCAGGTG GGGCGCTCAT GGCGTCGGCC TCGCAGAGCG GTGACGGACA
21651 CAGAGTCCGT GTTTGGGGGG GTTTGGGACG TCGGCCTCGC AGAGCGGTGA
21701 CGGTCGCAGA GTCTGTGTTT TGGGGGGTTT GTGACGAGTC CGTGTTTGGG
21751 GGGGTTTGTG ACGTCGGCCT CGCAGAGCGG TGACGGTCGC AGAGTCTGTG
21801 TTTTGGGGGG TTTGTGACGA GTCTGTGTTT GGGGGGGTTT GTGACGTCGG
21851 CCTCGCAGAG CGGTGACGGT CGCAGAGTCT GTGTTTTGGG GGGTTTGTGA
21901 CGAGTTCGTG TTTGGGGGGG TTTGTGACGT CGGCCTCGCA GAGTGGTGAC
21951 GGACACAGAG TCCGTGTTTG GGGGGTTTG TGACGTCGGC CTCGCAGAGC
22001 GGTGACAGTT GCAGAGTCCG TGTTTGGGGG GGTTTGTGAC GTCGGCCTCG
22051 CAGAGCGGTG ACAGTTGCAG AGTCCGTGTT TGGGGGGGTT TGTGACGTCG
22101 GCCTCGCAGA GCGGTGACGG TCGCAGAGTC CGTGTTTGGG GGGGTTTGTG
22151 ACGTCGGCCT CGCAGAGCGG TGACAGTTGC AGAGTCCGTG TTTGGGGGCG
22201 CCGTGAAAGC ACCCAGCGTA GTCATGCTGC TGTGTGCGAT GGGTGCTGGG
22251 CCCGCAGACT TCGGTGCTTC AAAGGCCTCA CTGCTGAGCA CGAGACGCCG
22301 CTTTTGATGT CGTCAGGCTC TCTGGTCCCC GGGAGTGGAC TCGGGGCTC
22351 CGAGTGCAGG GCTCACACTG TGTCTTTGAG GGCTGGTCAC CCACCCAGGC
22401 ACACCTGTGG CCCTGAGTCA GCACTGCCTG ACGCCCACCC TCAGGAGCCC
22451 CCGCCTGCCT AGGGTGGGAC CATGGGGGAG GCTGGTCCTC CATTCTCAGG
22501 GGCTGGGGGA CACCCCTTCT GGTTGAGAAG GCCACAGGTG GCCCCCCCGC
22551 CACCCGGCAG GCACAGCAGG GCACCACCGA GACCACTGTG GCCTGAGGAG
22601 GAGCTTCAGC AGCCACTTGG TAGGAGGGCC TTCGACGGCC CTTTTGTGCA
22651 GAAGGTGGGT GTTCCCCAGT CTCAGAGGCC AGGGCCCTTG CTGGCTGGGG
22701 TGGGGGCTCC AGCCCAGGGC CCCGCTGAGG GGGGCAGGAG CAGGGGCGGA
22751 GAGAACAGCC GTGCGTCTGC CTTTTCTGCT CCCATCACCA TGGCAACAGA
22801 TGGAGATTTG GCAGGAAGGA GGAGGGGGCG GGCTTTGGAG GAGGCAGCCC
22851 AGGTTTGGAG ACCAGCTGGG GATCCTCAGG GGCCTAGGGT GGGGGCTCCA
22901 GTCTCAGGCT GGCTAGTTCC TCCTTCCTGG TCACTGAGCC AGCCTTGCTG
22951 AGGGGAGAGC GGGTTCTGGA CGTGCTCTGA GCTTCCTTCC TCACAGCCTT
23001 GCTCCTGGGC CAGATCAGCA GGAAAGCAGC CAGTGCCCCG CCATGGCCTG
23051 CCCGGGTGGG GTCCTGAAGC TGGGGCCGGA GCAGGGGGCA CAGTTCTGCC
23101 CCATCTGGCC CTAGTTTGGG GAGGGAGCCT GGTAGGGCAC CAGCCTCACC
23151 CCATGAGCCC TGAGGGCCAC CCCAGCCGAT GGGCACGTCC CCGCCGGCCC
23201 TGCATCTGTC CTTCCTCCCT CTGCTCCCCA AGAGAGCCCA GGTCTGGCCC
23251 AGCGGTGGGC AGGGGAGGGG CCGCACATCA CAGAGTGCCA GCTGGCCACA
23301 CTCCCGGCCC ACAGCTGCTC CAGCCGCACC TCCACCTTCC TCAAGGCCAG
23351 ACCTGGCTCT GCCTGCAGCC CAGCCCAGCA GGTGCGTGCC ACGCTCCCTG
23401 GCTGGCCAGG GCCCCTCGAG GGAGGAGTGT GTTCATGTGT GAGGGATGCA
23451 GCCCCCACGG CAGGGACGGG GGACCTCGCC AGCACTGGTG GGCTGCACCT
23501 GCTGGGAGGG CCAGCTGTGC GGGTTCCTAC GCTGGCGCTG CCTGCCCCTA
23551 TGTGGAGAGG CGCCTGCCCC TATGTGGAGA GGCTCCTGCC CACTGGCCCG
23601 GCCTGGCATC CGGGCCCTCA TCTTGCCCTC CCAAAAAGAG CTCTGCCCCC
23651 TGTGCTGCCC CATCCTGTGG GGAACGTGGC CTTGGTCACC AGCCTTAACA
23701 GCAGTCCTGC GGTGGGTGGA GTCTCAGCTG CGCCGCCCCG TCCTGCGGTG
```

FIGURE 3-9

```
23751 GGTGGAGTCT CAGCTGCGCC GCCCCGTCCT GCGGTGGGTG GAGTCTCAGC
23801 TGCGCCGCCC CGTCCTGCGG TGGGTGGAGT CTCAGCTGCG CCGCCCCGTC
23851 CTGCGGTGGG TGGAGTCCCA GCTGCGCCGC CCCGTCCTGC GGTGGGTGGA
23901 GTCTCAGCTG CGCCGCCCCG TCCTGCGGTG GGTGGAGTCT CAGCTGTGCT
23951 GCCCCGTCCT GTGATTGGTG AACTCTGAGC TGTGCTGCTC TGTCCTCTCT
24001 GGTCTGTGAA GTCTGAGCTG TTTGGTAGGC GGGGCCGAGG GAGCAGGCGC
24051 CCTCAGAAAA TGCGAGACAG GGTCGGGTTG CGGGGAGGGC GTCCAGTGGT
24101 GGGAGGGGCC CAGCAGAGCT GAGGTTTCTG TGGAAAACC TTTACTGAGC
24151 CAGGGACAGT GGCTGGGGGG TCAGATAAGG CAGCCCCAGC CCAGAGGGGA
24201 TCCTCCTGCC TGCTGGGAGT GGGCAACGGT GCCCTGGCTG CACAGATCAA
24251 CCCAGGCCCG TTGGATCACT AGCCCTGGCC GCACACAGCA ACCCCGCGTC
24301 CCAGGCAACC CTGCGTCCCA GGCCCGTCGG GTCTCTGGCC CAGGGCACAG
24351 TAGTGGCAGT CACTCACATG GGACGGGACC GCCCATGGCC TCCCACCGTG
24401 CACGCCCTTT CTGACTGCTG TAGGCCTGAG GGGTGGATGG GCGGGGCTCA
24451 CTGCAGGCGC TGCCCCCGGC ACCCCAGGCC CTGGCCTCCT TCTTCCCATG
24501 TTAGGAGCCT GCGTTCAGAA CCCGCATTCC TGGGGAGGAT GGGGCTGGGC
24551 AGGGACTGGG GTGGGTCTCT CCCCATCTCA TGGCACCAGC TCAGACCTAA
24601 GCCAGGATCT CTGACTGGAG CCAGCCAGAT GTCCAGCTGC CATGAGCTCC
24651 CCTGGGGGCT TCTGCCTCCC AGACGGCCCC TGGGACGGC CCCTCGGGAC
24701 ACCCCCTCAG GTGTGGTGTG CCCTGACCCC ACTGTCCACT GGGGTCAGCC
24751 CAGGAGACCC TCCCTCTGGC CCACCCCTCC CACCCCTGCA GCCCCTTGCA
24801 GGGGCCACGG GGAGACTCAC AGAGGCAGTG CCCCAGGACC ATGGTAGGAG
24851 ACTCATCCTT CTTGGAGGCC AGAGGCTTCT GCAGGGCCTG AGCTGTCTCT
24901 GTCCAGCCCC GAGGGCCCTG GCAGTGGTAT CTCTGCAGGT GGAGGGGCCC
24951 TGTGCCCAGG CTGTGCCCTG ACCTTCTGCC CTGGGAGCCC TACAGCCCAC
25001 ATGGGCCCTG GCATCCAGCT CCCCAGTAGA ACTTCCCCAA GCCAGGAAGG
25051 AAGTGGTCAT GGGCGTCTGG GGTCTGTGTG CCTGGAGCTG GGCCATGTGG
25101 CCTGGGCTCC CTGCACTGCC CACCACCCAC TGACCCTGAC AACACAGGTC
25151 CATGGCGGGG CCTGGGCAGA ACGGGGGAAC CAAAAGGAGG GGCCTGAGCT
25201 GAGCCTGGGG TGGTGGGGCC TGGCACCCCC ACTCCATCAG CCCCTCCTGC
25251 CATCTCTGGG GGCATCAGTG GCCCCAGAGC CAAGGAGCAG CCCCAGGGGC
25301 TGGAGCTCAG GTGAGGTCGG GTGGGTAAGG GGCTGCTGCT GCACAGTGGT
25351 GGGCAGCCAC AGCGCCCAGC TCCGCCTTCC GCCCCGAGGA AAATGGGCTG
25401 CCTCCCACAC TGGACACACA GCGCCAGCCA CTTCCTCACA CGGTTTACTG
25451 TAGCCAGACT TGGAAATAGT CATGTGATCC CCAGGGATAT ATAACTGCGT
25501 TTTCTCCATC TGTGCTTAGT TTAAAAACAA TTGTTCATTA ATTTAAAAGG
25551 AAGAGTTTAC CTTCAAACAT AAAGATATTC AAATTAAAGA TACTCAAATT
25601 TTTCTGTATG AACTAGGATT TGTGCTGGTC AAAAATACCA CACCCCAAAG
25651 TTGCCATTGT CCCGTTGTTT AAAATTCTAT GTGCAAATAG AATCTCCAGA
25701 GGCCGGGCAG GAGGAGGACG GCCTGGGAGT GTCCAGGCTG CTTCTCCGCC
25751 TGGAAAGCTG TCTCCATGCC CCTGTGGCAG TTTGAGGCTG GGGATGCCAC
25801 TGCCCCACAG TGTGCTCCGG GGATCTCAGG GCGCTAGGAA CTTCCCTCTG
25851 TAGAGAGTTG GCATCACTGG GATCCCAGGA TGAACTTATG TGTGGAATGC
25901 GGTGTTCATT AGAAGCTAAG GAGCCTCAGA GTATGCTAAG GTGCAGCTTC
25951 AAAGGCAGCA ATTGTTTGGA ACTTAGGCCA AGGAAGATTT GTGTTTTGGA
26001 AATGGCATGT ATTTTATCAC TGACATTGTT TAGTGTAGGG TGATAAAAAG
26051 TAGACTGAAT TTTTTTAATT AAAATGAAAT TCGCATAATA TAAAATTAAC
26101 CATACAATTC AGGGACGGTT AGCGCATTCA CGGTGCTACG CGGCCACCAC
26151 TGTCTAGTTC CAGAATGTTC CACCCCAAGG GACCCTGCGC CACACGTTCT
26201 CTTGCCCCTC CTCCATCCGT GGGAGCGTGG CCTGCCTTCC GTTTCTGGAC
26251 GTGTCACAGA CACTGGTCCC ATGCTGTGCG TCCCTCTGCG TCTGGCTTCC
26301 TTCACACAGC AGAATGTACT CAGGGCCATC CCTGTTGTCA TCCCTGTTGG
26351 GGTTTCCTTC CTTTTGAGGC TGAACACACT TACCTGTGTG GACAGACCAC
```

FIGURE 3-10

```
26401 GTTGTTCGCC TATCATCTGC CGTGGACATG TGGCTGCTTC CACCTTGTGG
26451 CTCTCAGGAG TGGCGCGCTG TGGACGTGTG TGTGAGTACC CACGTGGGTC
26501 CCTGAGCTCA GTTCCTGGGA GCATAGACCT CAGAGTGGTA ATTCTGTCTT
26551 TACCTTTTTT TTTTTTTTTT TTTTGAGATG GAGTCTCGCT CTGTTGCCCA
26601 GGATGGAGTG CAGTGGCGTG ATCTCGGCTC ACTGCAAGCT CCGCCTCCAG
26651 GGTTCACACC ATTCTCTTGC CTCAGCCTCC TGAGTAGCTG GGACTACAGG
26701 CGCTCACCAC CACGCCTGGC TAATTTTTTG TATTTTTAGT AGAGAGGGGG
26751 TTTCACCATG TTAGCCAGGA TGGTCTTGAT CTCCTGACCT CATGATCCGC
26801 CCGTCTGGGC CTCCCAAAGT GCTGGGATTA CAGGCATGAG CCACTGCGCC
26851 TGGCCCTGTC TTTACCTTTT TAAAAAAATT AGTTCATTTA TTTTTCTGAG
26901 ACAGGGTCTC ACTCTGTTGT CCAGCTGGAG TGCAGCGATT TGATTCTGGC
26951 TCACTGCAGC CTTGGCCTCC CAACATGCTA AGATTACAGG CTTGAGCCAC
27001 TGCACCTGGC TTGTGTTTAA CTTTGAGGAG CTGCCAGACT TTCTCATTGG
27051 ACCCAGTTTT AGTCAGCCTC ATTTGGGTTT TTTAAGGCCC CACAGAAAAG
27101 GCAGCCCTGG TCCCTGCTGG ATAGCTGGCA CCCCTGCCTG CCCGGGGCCT
27151 GCTCTGCCCC CTTGGGTCCC TCACTTTCCT TCATAGAATT CACTGGCTTG
27201 GAGGAACCCA TTACCTGCTC ACTGCCCACA CGGTGGTCCC AGCAGAGGAC
27251 TTGGAGCGGC TGCCCCTTCT GTTGCACGGG CTCCACCACG GCCTCCTCGG
27301 CCACTGTCCC CTGGGAGGGC AGCTGTGGTA AAGGCCGGAG CTCCCAGCTT
27351 TGGGCAGGTG AGTGCCCCTG GCAGTTCTTT TCTGTGATGT AGGTTTTTCA
27401 GACTGGGAAA AGTTGAGAGT TTCAAAGTCC ATTGCCAGTG GGAACTGGAA
27451 CCAGGCAAGC TGAACCAAGT TCATTAGTGC TCTTGGCAAC CTCAGGGCTC
27501 ACCTGGTGCA CGGGGACCTT TGCAATGGCC AGGGCCTGGG GCCACCCGAG
27551 CTAGGGCAAG GGGAGGGGGA GGGATGTGTT TATAAAATTT CTGTTTTAAT
27601 TTCAAGTACA GTAATGTTGG TGGATAGAAA CACACAAACC ACAGCACTTT
27651 GATTTTGTCA GTAACTCTTA AGAGTACGGA GGGTCCTGAG GCTGGGGGGT
27701 CTCGTGGGCA CAGAGTATGA TGCCTGTGAG GACGTCCTTC CAGCCACACA
27751 GCCCGTGGAC TGCAGCATTG AGTGTTCTAT TTCCTGGGTG TCACGTCCGC
27801 AAAATCCGCT GTTTTGCAGG GTCAGTCTTC GAGAAATGCT CTTGTAAGAA
27851 CAGGTTTTTA GGCTCATGTG CCCCCTTCCC AGTGCCCGTC ACCTCTCCCT
27901 GAGGCTGTGG CCTGGGCTCA CCTCCCTCGG ACCAAGGGC TTCCCACACG
27951 TCTGTGTCCA ACACGTTCCC CCGGCTTTCA TTTAACTACC GGCGGCTGTA
28001 TTTAGCCTCA GTTTTGGAGG ATACTTTTGC TGAATGTAGA ATTCTGGGTT
28051 TCCTTTGAGT GCTTAGCAGG TGCTACACCA TGGTCCTCTG CTGGTGAGAG
28101 GCAGCCACCA CTGAGGCCCT GGGTATGATG TGTGTCTCTG GCTGCTTTTG
28151 AGGTTTTCTT TTTATCCTTC GGTTTTGTGT GTTTCGCAGT GACCCACCTT
28201 GGTGTGTTCC TCCAGGTGTC TGTCCTGCTT GAGGTTCAGT GAGCCCCGTG
28251 GATCCACGGG CTGATGTATT TAGTACATTT GGGGAAATTC TTCATTGTTC
28301 TCTCTTAAAA TGTGGCCTCT TCAGCCAGGC GCGGTGGCTC ATGCCTGTAA
28351 TCCCAACACT TTGGGAGGTC AAGGAGGGCG GATCACGAGG TCAGGCGTTC
28401 GAGACCAGCC TGGCCAACAT GGTGAAACCC CATCTCTACT AAAAATACAA
28451 AAATTAGCCA GGTGTAGTGG CAGGCACCTG TAATCCCAGC CACTCGGGAG
28501 GCTGAGGCAG GAGAATTGCT TGAGCCTGGG AGGTGGAGTT TGCGGTGAGC
28551 TGAGATTGCA CCACTGCACT CCACACTGGG GGATAAAGCG AGACTCCATC
28601 TCAGAAAAAA ATAAAAATAA AATGCGCCCT TTTCCCTATT TGCTCTTTCC
28651 TGTATTGAGG GACTCTGGGA ACAAGTGCCT TAGACTATGA GGGGGCTCCA
28701 TAGGCACCTG ACATGCTGTG AGGTCTCCAC CTCCCTTTTT TGCTTTGGTG
28751 CTTGTCAGGA TAGTTTCTGC TGGCTGGTCA TTGAGGTCAC TGTTCTTCTA
28801 TTGTACCCAC GCTGCTGTTC AGCCAATCCA CTGAATTAAT TTCGTTCATC
28851 TTTTTCTCCA ATGAAATATA TATATGTGTG ATATTATCTT ATCCTTTTCT
28901 GAAAATTCTA GCATTTAGAT CACCTGTGTC CTGCTTCTGT TGGCTGTTTC
28951 TTCTCTTGAG AGTGGGTCAC ACTGTGTCCT GCTTCTGTGG GCTGTTTCTT
29001 CTCTTGAGAG TGGGTCACAC TGTGTCCTGC TTCTGTTGGC TGTTTCTTCT
```

FIGURE 3-11

```
29051 CTTGAGAGTG GGTCACCTGT GTCCTGCTTC TGTTGGCTGT TTCTTCTCTT
29101 GAGAGTGGGT CACACTGTGT CCTGCTTCTG TTGGCTGTTT CTTCTCTTGA
29151 GAGTGGGTCA CACTGTGTCC TGCTTCTGTT GGCTGTTTCT TCTCTTGAGA
29201 GTGGGTCACA CTGTGTCCTG CTTCTGTTGG CTGTTTCTTC TCTTGAGAGT
29251 GGGTCACACT GTGTCCTGCT TCTGTTGGCT GTTTCTTCTC TTGAGAGTGG
29301 GTCACCTGTG TCCTGCTTCT GTGGGCTGTT TCTTCTCTTG AGAGTGGGTC
29351 ACCTGTGTCC TGCTTCTGTG GGCTGTTTCT TCTCTTGAGA GTGGGTCACA
29401 CTGTGTCCTG CTTCTGTTGG CAGTTTCTTC TCTTGAGAGT GGTTCTCCTG
29451 TGTCCTGCTT CTGTTGGCTG TTTCTTCTCT TGAGAGTGGG TCACCTGTGT
29501 CCTGCTTCTG TTGGCAGTTT CTTCTCTTGA GAGTGGTTCT CCTGTGTCCT
29551 GCTTCTGTTG GCTGTTTCTT CTCTTGAGAG TGGGTCACAC TGTGTCCTGC
29601 TTCTGTTGGC TGTTTCTTCT CTTGAGAGTG GGTCACACTG TGTCCTGCTT
29651 CTGTTGGCTG TTTCTTCTCT TGTGAGTGGG TCACCTGTGT CCTGCTTCTG
29701 TGGGCTGTTT CTTCTCTTGA GAGTGGGTCA CACTGTGTCC TGCTTCTGTG
29751 GGCTGTTTCT TCTCTTGAGA GTGGGTCACC TGTGTCCTGC TTCTCTGTTG
29801 GCTGTTTCTT CTCTTGAGAG TGGGTCACCT GTGTCCTGCT TCTGTTGTCT
29851 GTTTCTTCTC TTGAGAGTGG GTCACCTGTA TCCTGCTTCT GTTGGCTGTT
29901 TCTTCTCTTG AGAGTGGGTC ACACTGTGTC CTGCTTCTGT GGCTGTTTC
29951 TTCTCTTGAG AGTGGGTCAC ACTGTGTCCT GCTTCTGTGG GCTGTTTCTT
30001 CTCTTGAGAG TGGGTCACCT GTGTCCTGCT TCTGTTGGCT GTTTCTTCTC
30051 TTGAGAGTGG GTCACCTGTG TCCTGCTTCT GTTGGCTGTT TCTTCTCTTG
30101 AGAGTGGGTC ACACTGTGTC CTGCTTCTGT TGGCTGTTTC TTCTCTTTGG
30151 AGGGGGTCCC ATTTCCCCAC CTCTTTGCAT ACGCTGTAAT GTTTTGTTGG
30201 ATACTGCATG TTGTTTATTT AGAGCAGCAG TTCAGACTGA AGTAGGAGCT
30251 GTCATCCTGG AGGGGCTCCC TGCCTGTGTT GGGCATGTGG GGGGCTGCTC
30301 AGCCAGATCC AAACAGGACT TCAGCTGGAC TGGGACTGGG GGTCCCTCCA
30351 GCAAATTTCT GTTCAGCTCT AACACATATC CAAGGGACTG AACCCCTGGG
30401 TGGGGAAGTT TTTTCTTTTT TTTCTGTAGT GCCATAAGTG CCTGTCACTA
30451 ATAGAAGCTC AGTGAATACC TGATTGATTA ATTGATTGAT CGGTTGATTG
30501 ATTGAATGCA GCAAGTGTCT GGGAGCTCCC AGTTACAGGT GCGTGTCAGG
30551 CGTGAGTCTG GGCACCAGGG TGGGCCTTTG CTCAGCTGTG TTTGTGGGCT
30601 CTGCAGGTGC GTGTCAGGTG TGAGTCTGGG CACTGGTGGC GGGGGGGGCC
30651 TTTGCTCAGC TGTGTTTGTG GGCTCTGCAG GTGCGTGTCA GGTGTGAGTC
30701 TGGGCACTGG CGGGGTGGGG GTCCTTTGCT CAGCTGTGTT TGTGGGCTCT
30751 GCAGGTGCAT GTCAGGTGTG AGTCTGGGCA CCGGGGGGCC TTCGCTGAGC
30801 TGTGTTTGTG GGCCCTGGGA CGTGATTCCC TCTTGGGTGG TGTTTCCAGC
30851 CGCTGGCTGC CCGGGCAGCT CCAAATACTG AGCTGTCAGG TCGGTGGTCT
30901 CTCTATGTCT TTCTGTTATC TTGTTCTGCT TTGCTGGGAA TTTTCTCATT
30951 TTTTCAGTCC TTATTTAAAT AGTTTCTTAT TCTAGCAGTT ATTATTTTTC
31001 ATGTCTTAGA GCTTTTTTTT GTTTCTTAGT CGTTTTTTTA GACCTTGTTT
31051 ATAGATGCAG CCACTCACTA AATCCTAGCA CACTGGTGCA ATCAACAGAA
31101 TTTTTGAAAT TCTCATTTCT GGCCAGACAC AGTGGCTCAC GCCTGTAATC
31151 CCAGCACTTT GGGGGGCCAT GGCGGGGCCT CACTTGAGGT CTGTGGTTTG
31201 AGACCAGCCT GGCCAACATA GTGAAACCCC GTCTCTACTA AAAATACAAA
31251 AATTAGCTGT GTGTGGTGGT GGCATGCGCC TGTAATCCCA GCTGCTCAGG
31301 AGGCTGAGGT GGGAGAATCA CTTGAACCTG GGAGGCAGAG ATTGCAGTAA
31351 GCCGAGATGG CGCCCCTGCA CTCCAGCCTG GGCGACAGAG TCAGATTCCA
31401 TCTCGAAAAA AACAGAAACA AGAATGTTTG AAATCCTGAT TTCCTGAGGA
31451 CTGGTGCTCC CGATTCTGCT CCAGGCTCCG CGCCTCCTCC CACACCCGGG
31501 CACGTGGTCG TTCGTCTCCA AGGAAGCCTG GTTGAGTGCA GAGCCTCCTC
31551 TTTCTTGGAT AAGAGGGAAT GTTGTCTTGT GTGAGTCTCT GGAAGGCAGG
31601 GCCTCTGCCC GGAGGCTCGG TGTCCGTGCA TGCATGCAAG TGTGCGTGCG
31651 TGCATGTGTG CGTGTGTGCA TGTGTGATGG CCTAATGGGC AGGAAGTGGG
```

FIGURE 3-12

```
31701 GTGGCCTTGT TAGGATGAGA CAGATTTTGC CACAGGGCCG GCCCCCGCTC
31751 TGCTGGGTGT GACCCCAACT ACCCTTCTTG TTGGCCCAGA GAGGGGAGAG
31801 GCTGGCCAGG GCTGCCCCAA CCTGTGCACG CCCTTGGCAG ATGCTCCAGG
31851 GTGTCTGCAG CCCCACCTGA GGCCTGCCCT GCACTCTGGC TAACAGACAT
31901 TTTCAGTTTT CCAGGTCCCC TGGAGACAGG CAGGCCCAGG CCCACCCCCT
31951 GCCTTCTCTG CCTGCCTGCC TCTAGAAGGT TCTTGAATGT TTAGAGGTTC
32001 CCCCGTCACG GCCAGGCTCC CTTTTGTTTA ATTCAGGAAG GTTTGACAGG
32051 TGAGTGTGAG GTCTGCCAGC CTGGGCCTGG GCCCTCCAT GCAGGCCCTG
32101 CCTGGACCCC CTGTGACTCC CCCAAGTCCT ATCTCCACCC CCTTGGTCCC
32151 CAGCTCCAGC CTCTTCCTCC ACTGCCTAGA CTGTCCCCTC GGGATACACC
32201 TCCTCCCTGC AGCCTCCTCC CTGGCTGTCA CCCTCTTTGT GGCCTGCCTG
32251 GGGGACTCCT CTGGTTACTC CTGTCCTCAG CTCTAGGTGG GGCTGGCAGT
32301 CCTGGGGGCT CAGCCTCCAT GTGGCATCCA GCAGGTGCCC GGCAACTCCC
32351 TGTTTTTCCA CCTGACCTTA AGAGCCTGGC TTGAGCCTCT CATGGGGAGG
32401 GGCCTGTGCC CCCCAGGGCC CCCTCGGCCC TCTGGCTGGG TGCTGGCAAG
32451 TAGGTCTCAA CCCTGGAGCC TGACTGGGGC CTCCCACCGA CATCTTTCAT
32501 CTGGGTGCAG AGCAGAGAGG GGCTTTGGGA TGCTCAGAGT GATACCCTCA
32551 GATCTTTAGG ATTCAGATCT TTGGGCTGCC TGTGGGCTCC TGGCTTGGCT
32601 GACCCTGGGC CTCCTCCTGG TACAGTCCCA GGCTGTGCTT TGGGTCCCAG
32651 GCTGCGCTTC GGAGGGGAGG GACAGTGTGG GGGCTCTCAT TTAATCTTCA
32701 CCCCCCAGGA CGGGGTGTCA GGAGACCCCT GAGGCCAGGC ACGTCTGGGG
32751 TCACACCCAG GAGGGAGGCA GGCGTCTGCA GTCTGGCCCT GGCTCAGGCC
32801 CACCCTTGCC CATCTCCGGC TGCAGAGATG CCTGCCTCTG CTTGGAAGGG
32851 ACCTGGATCC TGGAACAGCC TAGGGCTGGG AAGCTGCTTC CTCCTCCACA
32901 ATCTGGTCCC CAGTGGGAGC TGCATCCCAC CTTTGTTTGG GTGCTGGGTT
32951 AGGAGGCGGG AGCCAGGCAG AGGCAGCGGA GCGGCTGCAG TGCGTGTGAA
33001 ATGCTTCAGG GTGGCACGAA TTTAACTAGA GAGGTTCTTT TCCAACGTGA
33051 GCAGTTGTCT CCCAAGAGAT GCGCCGCCCC TTCCCTCTGC ACCTGGCACT
33101 GGTGGGCGGT GGAGGCTGTG GGATCTATTG ATGTTCTGAG CGTGTGCTGA
33151 GGGCCTCGCT CCTTCCTGCC CCCTGCCCCA GCTCCTGTGT CGGGGCTGTT
33201 ACCGTGGGTG TGCAGGGTGG GGGTGCATAG AGCCTGGGTG CCCCCAGACT
33251 GAGGAGGCCG AAGGGTCGGG GAGCAAGGGC CTGGGTGCTA ATGAAGGAAC
33301 AAGGCTTCAA TGTCTGTGGC AACTTCAGAG GCCCCTCTCG GGGCAGGTGG
33351 GAGAACCCCC AGCCTGGGGA GCAAACCTGC CGGCCCAGCA CCGGGGTCTC
33401 TGCTGGAGAT GTGAGCACGG CGGCCTGACC AGGGCCCGGG AGAGAGGGGG
33451 CAGGTGGGGG TGGGGTCGGG GCAGGCTGGG GGTGTCACTG GCCTGCAGG
33501 GGGTCTAGCC TGAGGTTGGG GTGCCCCACG GGGGGAGGGT GGCACCTGTG
33551 CCTGGGCCGC ATCATCGGGT GTATTTGAGG CGGGGTCAGA GCCAACTGTG
33601 TGTCGGGTGA GAGCCCAGCC CAGCCCAGCC CCAGCTGTGG GCCCCCCATG
33651 AGCCCCTCAC GGGAGCATGC AGGTGGATGA TCAGGGGTGA GCCAAGTAGA
33701 TTGGGGGCGG GGGCTGGCCA GGCCTCATCG CAGCTCACAG CCCCCAGCCC
33751 CCTCCTGAGC TGTTTGGTAC CCTGTGTGTG CAGAGTCCCA GGTGGGGCCT
33801 GCCCTCCTCC AGCCGCTCCT CCACCCTGTC TGCCGTGTGC CACCCATGGG
33851 GTGCTCTGGG GAGGGGTGGG GGTCCCTGTA TTGCTGGGGA AGGTGTGCTG
33901 ACCACAAGGG GAGCAGCTTA TGGGGCCGAG GCTGGCTCAG GATGCCGGAG
33951 GCTCTGCGGT GGGCCCTGGC GAGTGAGGAG CTGTGGGGAC GGTGCAGAGG
34001 GGCCTGTGCG CCTCCTGAGT TTGCAGTTGC TACAGTGCCC ACACCCCGAG
34051 GATGCATGGC TGACAGTCCC CACTGGGTGG CCTTGACAAA GGTGTGGCCA
34101 GGGCAGGGCC TCTGAGGAGC TGAAGACCTG CTTCCAAGGA CACTCCTCCC
34151 TGACAGTCCT GTCCATGGTG CTGGAAGAGC TCTGGCGACC CCACAGGCAG
34201 GCAGGCCTGA CCGTCCAAGG CTCGGCTGCC TGTGGGGAAC TGGACACACT
34251 TCCTCCAGAG TCTCAGTTTT GCCAGCTGTT TGCCCAGCGC CATGTCCACT
34301 CCCCAAGCCA GGACCGAGGG GGTGACGGAG ATGAAGCTTG TGCTGGCCCC
```

FIGURE 3-13

```
34351 AGCTGGGGGC CGCTGCCCAC CCAGCAAGCC CCACAGCCAG TCCCAACCTG
34401 GTGATGTGGT GTCCGGAGGA TGGACCTCGA AGTCTCTCAG ACCTGGGTTT
34451 CTGAGCTCCT CAGGTGTCTG TGTCCCCTCC TGGGAAAGGG AACAGAGCTT
34501 TGCGAAGATC AAGGGGAGGG CAATGCAGCT TGGGAGCCTT AGCTCAGCCA
34551 GACAGCAGCC CGGAGGGTTA ATGTCCAGGT ACCTCCAGGG CCCATGCACC
34601 CAGGACCTCC CCAAGAGCTG TGCCTCCATG TACCTCAGGG CCTCCCCCAG
34651 AGCGGTGCCT CGTGGGGGAT GCGGTGCCTC GTGGGGGACA TGGTGCCTTG
34701 TGGGGTACGT GGTGGAGACG GTGGGGTCGT GGCCGTCCAG GCTTCAGAAA
34751 CGGCAGAACC AGGGACCCTC CCCACTGTCC TGTCCTTAGC GTCTTGAGGC
34801 TAGGGGTGAG TTCGAGACCT CGTAAATACT TCAGTGCAGA GCCTTCAGTT
34851 AGGAGCCGAG GCCTCTGGCC AGGTTCAGGC ACGTGGAGAG TGTGTGTGGG
34901 GAGAAGTTCT GAGACTGTGG GAGGGGTAGG GGTGTGCTGT GGCCACAGTG
34951 GTTCTGGAAT TTGAGGTGCC TTAGGAGGTT CATGATGAAG GATGCGGCCC
35001 ACAGTCGTGT GAGCAGAGGA CGGCACTCGC GAGCTCCCTG GGGCTCCTCA
35051 GACCCGGTCA CCGAACAGCA GAGACGTGCT CTTTCACATT CTGGAGGCGG
35101 GAAGTCCAAG GTCCAGGGTG GGCTGGCTCT TCCAAGGCCT CAAGGAAGCC
35151 CTGCCCCAAG CCTCCCCCGC TGGGCGTTCC GGGTGCCCCA GGCCTCCCCC
35201 GCTGGGCGTT CCGGGTGCCC CAGGCCTCCC CCGCTGGGCG TTCCGGGTGC
35251 CCCAGGCCTC CCCCGCTGGG CGTTCCGGGT GCCCCAGGCC TCCCCCGCTG
35301 GGCGTTCCGG GTGCCCCAGG CCTCCCCCGC TGAGTGTTCC CGGTGCCCCT
35351 GGGCCTGCAG AAGTGCTCCC CCACCCCCAT CTTGCTTTCA CCCTCACGTG
35401 GCGCCCCCAT CCCACCCCGT GTGTCCCCAG CCACACTTTC CTCGGCCTTT
35451 CTCTGATAGG AAGGCTGGTA GTTGGGTTTA GTGTCCACCC CAAATCTGGG
35501 GCTATGTTAT ATTGAGATCC ATAACTTAGA AACCTCTGCA GAGGCTGTTT
35551 TTCCAAGTCG GGTCACATTC ATGCGCCCCA GGCACTGGGA CACACATCTT
35601 TTGGGGGTCA CCATTCCACC CCCACATCCT CCAGCTGTGA TGTGGGGCCA
35651 TGGTGGACCC CTCGGCACCC CTGTGGCCTC CGGAACTGCT CCGTGAGCCC
35701 CGGGGAGCCC CACCATTCCC CTGGAGTGAC AGTGGGTCCT GCCGGCCAGG
35751 CGGAGGGAAG TCTCTGCTGG GTGTCCACCT GCGAGGCCCT CACCCCCTAC
35801 TGCCTCATGT GGGGGGTGCC CCAGCACTGG GTGGGTCTGA GTGTGGGGGC
35851 AAAAGGAAGA AGGACAGGGA GAGCCAGGTG GGGACAAGGT GTCCTGCCGG
35901 GGTGGCCCCC ACCTGCCCTC AGAATCCCTC CAGGCAGACA GTGGAGGCTG
35951 TGTGACCAGT GTGGGAGTTG GGGATAGGTG AGGGACCCCC TTCACTGGGG
36001 TGGGGCCAAG TGGCAGGAAC TCCCCCAACA TCTAAAGGAG AAGGGTCCAG
36051 GACCCTTCGC CAGGACCTGG GCTGCTTTGT GCCCCGGCAG GACGGGACAG
36101 CCACACACCT GCTGCCCTGC CCTCCATCTG CATCCAGCCA ACAGGCCATT
36151 CCTCCCGTGC TTCACCCTCC ATCCTGGCCT GGGAGGCCCA GGCTCAGGAC
36201 CCGTTGGGAC TGTTTGGACA GAGGGAGTCG GGGGGGCCAG GCAGGGCCCT
36251 GTGGAGCCTG CTGGGGGCTC TGGACCTGGG CCTCTGCCAG GTGGGCTCCC
36301 TGGGACCTAC TGGCGGGGGG GCAGGTTGCG GGGGTGGAGC AGGACCCCCT
36351 GGCCTGCATG CTTCCCCTTC CTGGGGCTCA CACACAGCAC CTCGTGGGCC
36401 CAGAGTGCTG GCGGGAGGGG TGTTCTCCCC GCCTCCATGG GCAAAGAATC
36451 TGGGGCCCTT GTCAGAGACC GCGGGGTCAG TGGGATTGGC GCCCAGGCCC
36501 TGCTGTGACG CCACGTGTTT CCCACTCAGC GAGGCTGTTC CTGCCAGGCG
36551 TGGGGACTCG GACCCTGGTC CTGAGTGCTG CCCCGAGGCC CGTGATGGGA
36601 AGCCTGACGT CTGCATCGTC CTGCGCTGCG TGGCCGGTCG GTCCCGGCGC
36651 TCTCAGCACT TGGAGTCTCA GCTCCCCGGG TCATCAGTCC AAGCCACTCA
36701 GCAGGTGGCT TCGGCTTAAG GCCTCTCAGG TGGCTCTGGT GAAGGCGTCA
36751 CCCAGGGCTG CCTGATCTGC AGGCTGGGCT GGAGGGGCTG CTTCCTGGGG
36801 GGTCCCGCAG GCTGTGTGGG GGCCTCGGGT CCTCAGCACG TGGACGCCCT
36851 GCAGGGCACT GCTGCCAGAC ATGCCCACTG AGCTCCCCAG AGTCCAGGAG
36901 GAAGCTGTGG TGTCCTTGTG GTCTGTGGAT GAGGCCCGCT TGGTCCCAGA
36951 GGTGCGGGTT GGTGACAGCG ACGGGGCAGG TTGTCACCTG TCCTGGTCTC
```

FIGURE 3-14

```
37001 TGGGAGCCGC CTCAGTGGGG TGGAGGCAGG GCAGGCCTGT CCAATGACCC
37051 CACCCCCTCA GGACGTTTCC TCCGTGCAGC CTGGGCCAGG GGCCACGGGA
37101 GGCTCTTCAC CTACAGGGGA CGCATTCAGC ACCGAGGTCA GCAGCCCATC
37151 CCGAGCCCCC CACACCCCCG CTCGTCTCCC ACTCTGTGTC CTCTCCACTG
37201 GCCTTGGGGT AGATGAGCTG CCCCCGTCCT TTCTTTGGGA ACCCACCCCC
37251 TTCTGGGCGA GGGTGGGTAG CAGGCACCCG ACAGGGTCCC CAGGTGGCAC
37301 TCCAGGCCGT GGCACTAGAT GTGCACTGTG GAGATGGGAA GAGGTGTGGG
37351 GCAGGGGAGG GCGTGGGGGG AACGCTGAGT TTCCTGGGTA CACCTGCCCC
37401 GGGCCAGTG CCTCAGGCCT CTGGAGAGCG GATTTGCGGC CTCATGGCTG
37451 GGGAGGGCTG AGGTTCTGCT GTCCGGTGTG GTGCCACGGT GAGCACACCT
37501 CACCTGTCCA GCCTTCCCCC TAAACCCAGT GCTCTGGACG GTGGGCTGGC
37551 CCCTGGCTCC TAGCCTGTGC GCGCCCATTC AGGAAAGCAA ACACCAGCAC
37601 ACACCGGTCC CTGTGGGGCC TTGGGTGCTC TGGGCACCCA GCTGCATGGG
37651 ACGGGCAGGG CCACGTGGCC ATCAGGGCCT GGATGGGGGC CTGGCACACA
37701 GCGGGCACTG GGGATGTGTG TGGGGCGTGC TCCGGGGATG TGTGTGGGGC
37751 GTGCTCCGGG GATGTGTGTG GGGCGTGCTC TGGGGATGTG TGTGGGGCGT
37801 GCTCTGGGGA TGTGTGTGGG GCGTGCTCTG CTGGCGACTG GGCTTGGATC
37851 TGTGGGGTGT AAATACCTGA GACGGCCCCT CCAGGGGAAA GAAGAGGCTT
37901 GAACTGTCAC TTTAATCCTT TCAGACTCCG CAGGAGACAG AGCACGCCGG
37951 GGAGGACACA TGTAGCCCTT GGGGGTGCCC AGTCCTGGCA AATCTCGGTC
38001 TCGAGCCTGG GTCTGTCCCC GCAAATGTAG AGTGTGCAGG GAAGGCCCTG
38051 GGTTGCTGGG AACTTGCAGA GGCCCTGGGT GAAGGTGCCG CGTGTCTTCT
38101 CTGTGTGACT CCTGCCTGGC CCTGGGTGAA GGTGCCCCGT GTCTTTTCTG
38151 TGTGACTCTC ACCTGTGAGG TGTCCTCCCT CCAGGAGGTG GTTGCTGGCA
38201 ACGGGGTGG GGGCAACAGA TGGGCCAGCA GCCACGTGGT GGGGAGCAGA
38251 GAGGACCTGG GGGTGCAGAC ACAGGATGTG GCGGGGCTGC TGGGGAGGAG
38301 CTCAGGATCC CTCAGCCAAG TGCATGTGGG GAGGGCCCTG TAGTGGCCAG
38351 CAGCAGGCAA GTCTATGAAA CGGGACCACT CCGCCTGGTG GGAAGCCCCC
38401 TGGGTCTGCA TGCGGGAGAT GGGGGGGCGG CACCCCAGGC TGTCCCCATA
38451 CCTGCTGCGC AACTTTAGTC TGGTGCGTGC CGGGGCGGTG AGGGGGCTGC
38501 GCGGGTCCT TCCCCAGTGC CAACACTGCC ACCTGCCCCA GGGCCCCCTA
38551 CCCAAACTAA AGAGCAGCCC GTCCAGCCCT AGGCTGGCTT GGCTCCTGGA
38601 CCTGCAGCCC CCCATCCCCT CTCTCCCCAC AGCCCCACTG GCTTCCTGGG
38651 GGCAGGGCGC TGCCGGCAGA GCTGCAGAAC TGAGCCCTCA CTGCCCCTCC
38701 AGAAAGTGCC AGCCCTCCTG GCACAACCCT GCCTGCCAGT CCTCCTGGGT
38751 AGCTGAGTGC AGGGGCAGGG GCTGTCCTGC TGCCTCGCCC GGCCCAGGCA
38801 GGAGAAGGCC CCTCACTTCT TGGCCAGCCT GGGACTTGAG TCAGGGCCTG
38851 CTCTCAGATA CCACGTGCAG GGTAGTCCTG GGGCTCCCTT TGACTCTCCT
38901 GGCCGGCTCA GGAGCACCTG GGGGCACCCG TGTTAACGTG CTAGTCTGCT
38951 CCCTGAGGCC CAGCATCCTC GTGGCATACC CGTGGCTTCC CTGGGATGCC
39001 CTGGGCTCC ACATGCCCAG GCCCTTCCCT GTGGGGGCG CAGGGAGACC
39051 CAGCACTCTT GGGCACCCGC CGGCACACGC TCCCACAGAA ATGGGGCCTG
39101 GCGTGAGCTG CTGTGCACCG CCTGCCCCCT CAGGGCCCTG GGCAGTGATC
39151 TGTGGCACTG CGTGCCTTCC CTCTCGACAG CCAAGCCTGT GTTTGTGTAA
39201 AGACAGCAAT TAGAGATGGA CTCTCAATTG GAAAATAAGC CACAGTGAGT
39251 TGCAGGGGA GATGATGAAG GGTGGCCCTG GGCTTCCCCG CTCCAGCTTC
39301 CAGTCCCCCA TCCTCCAGGC TACGGCCCAG TCAGGAGGGC CTCTCACAGC
39351 ACACTCCCCA CTCCCTGCCT CCAGAAAGTG GCAAAACTGC TCATAACCCA
39401 AACATTCTGC TCAGAGAAAC TCGGAGCTGA GGGATACCAG GACGCAGAGG
39451 CCTGCACTGC TGCCTAGGAC CCCAGGGAAG CTTTACCTAG GAGGGACGCC
39501 TCTATGCTGG GCTCTGAGGA GTGTGTAGGA GTCTTCAGAG TACAGTAATG
39551 GGGAAAGGAC TTTCTAGGCA TAGGGCAGC AAGTGAAAGA AGATGGAGGC
39601 AGGAGGAGTG ACCAGAGCTC CAGGATGCAG CTGGGACGG CTCTCCTACA
```

FIGURE 3-15

```
39651 TCCCAGCCTG CTGCGTCGTG GCTGCCTTTA CCTGAGCCAC TGCGAGGCTC
39701 CTGAGCATAG GCAGGAGGCT CTTGGTGGCT GTGGCTCCTC TGTGACTCTG
39751 TTGCTATTTG AGAGGCCACC TGCAGCCCCC AGACTCCAGC CTCAAGGACG
39801 TGGGCAGGAT CTATGGATGC GGCAGGCCCA CCCCCAGTGG CTCCATCCCC
39851 TCCGTAACCT CCTCTGGGAA GGTGGGTGCT TGCCAGGAAT GCCTTCTTCC
39901 ATGTGGTCCA CTGTCCTCAC AGCCCTTCTG AGCCACATGT GCTGGCAGGG
39951 GATGGAACCA CTGTTTCCTC ATCTGTGAAA TAGGGGTGAA GGGGCCCCAC
40001 TCAAAGCAGC GCCTGGAGCA AGGCCAGTGC TCCGAGACTT GGCTGTCCTG
40051 ATTTGTGCTG GGCCCAGCAG TGTCCTTTCA ATAAAGTTGG CCCAGGTGGT
40101 TGTCAGGCTC CCTCCCATTT TCAGTCCCCA CTTTCTTTCC TTTTCTGGAG
40151 GCAGGATTGT GCTCTCCACA CCTTTTGGCT CCTGTCATTC AAGGATGTGT
40201 GTGCACACTG GGAGTGTGCA TGTTTGTACG TATGTGTGCA TGATGGTATG
40251 TGCACGAGTG TGTGTGCACT GCGGGTGTGT GTGCATGTGC ACTGGGGTGT
40301 ATGTATGCAG TCGTGTGTAC ATGCATGGGT GTGTGTACAG GCGTGCGTAC
40351 TGTGTGTGCA TGGGTGTGTG CACACGGGTT ACTGGGGGTG TGCACTGGGT
40401 GCTTGTGTGC ACTGGAGGTG TGTACTGGGT GCGTGTGTGT GCACGGGTGT
40451 GTGCCCTTGG CGTGTGGGCG TGTGCACTGG GTGTGTCCTG GGTGTGTGTG
40501 CATGGGTGTG TGTACACGGG TGTGTCCTGG GTGCATGCAC ATGTGTACAC
40551 AGGTGTGTGT GCATGGGTGT GTGTCCTGGG TGCGTGCATG TGTGCACTCG
40601 GTGTGTGGGT GTGTGCACTG GGTGTGTGTG CACGTGTGCA TGGGTGTGTG
40651 TGCACGGGTG TGTGTCCTGG GTGCATGCGC GTGTGCATGG GTGTGTGTGC
40701 ACGCGGTGTG TGGCGTGTGC CCATGGGTGT GTCCTGGATG CATGTGCACA
40751 GGTGTGTGTG CACTCGTGTG GGTGTGTGCA CTGGGCGTGT GTCCTGGGTG
40801 TGTGTGCATG TGCGCACAGG TGTGTGTCCT GGGTGCATGT GCACTCGGTG
40851 TGTGGGTGTG TGCACATGGG TGTGTGTGCA CTGAGTGTAG GCACAGGGGT
40901 GTGCACGCAT GGAGGTATGC ACACACCTAG GGGTGTACAC AGGTGCATGT
40951 CTGTGTGCGT GGCCACACGT GCTGTCCCTG CCCAGGGCCC TGCTGCTCTG
41001 TCGACCAGCA TCCTGCTGTG CCCAGCAGTG AGCGTCTTCT GCGGTCTGGT
41051 CAGGTTTTGC CACTGTGCTC AGCAGTGAGC GTCTTCTGCG GTCTGGTCAG
41101 GTTTTGCCAC TGTGCTCAGC AGTGAGCGTC TTCTGCGGTC TGGTCAGGTT
41151 TTGCCACTGT GCTCAGCAGT GAGCGTCTTC TGCGGTCTGG TCAGGTTTTG
41201 CCACTGTGCT CAGCAGTGAG CGTCTTCTGC GGTCTGGTCA GGTTTTGCCA
41251 CTGTGCTCAG CAGTGAGCGT CTTCTGCGGT CTGGTCAGGT TTTGCCACTG
41301 TGCTCAGCAG TGAGCGTCTT CTGCGGTCTG GTCAGGTTTT GCCACTGTGC
41351 TCAGCAGTGA GCGTCTTCTG CGGTCTGGTC AGGTTTTGCC ACTGTGCTCA
41401 GCAGTGAGCG TCTTCTGCGG TCTGATCAGG TTTTGCCACT GTGCTCAGCA
41451 GTGAGCGTCT TCTGCGGTCT GGTCAGGTTT TGCCACTGTG CTCAGCAGTG
41501 AGCGTCTTCT GCGGTCTGGT CAGGTTTTGC CACTGTGCTC AGCAGTGAGC
41551 GTCTTCTGCG GTCTGGTCAG GTTTTGCCAC TGTGCTCAGC AGTGAGCGTC
41601 TTCTGCGGGG TCTGGTCAGG TTTTGCCACT GTGCTCAGCA GTGAGCGTCT
41651 TCTGCGGGGT CTGGTCAGGT TTTGCCACTG TGCTCAGCAG TGAGCGTCTT
41701 CTGCGGTCTG GTCAGGTTTT GCCACTGTGC CAGCAGTGA GCGTCTTCTG
41751 CGGTCTGGTC AGGTTTTGCC ACTGTGCCCA GCAGTGAGCG TCTTCTGCGG
41801 TCTGGTCAGG TTTTGCCACT GTGCTCAGCA GTGAGCGTCT TCTGCGGTCT
41851 GGTCAGGTTT TGCCACTGTG CTCAGCAGTG AGCGTCTTCT GCGGTCTGGT
41901 CAGGTTTTGC CACTGTGCTC AGCAGTGAGC GTCTTCTGCG GTCTGGTCAG
41951 GTTTTGCCAC TGTGCCCAGC AGTGAGCGTC TTCTGCGGTC TGGTCAGGTT
42001 TTGCCACTGT GCCCAGCAGT GAGCGTCTTC TGCGGTCTGG TCAGGTTTTG
42051 CCACTGTGCC AGCAGTGAG CGTCTTCTGC GGTCTGGTCA GGTTTTGCCA
42101 CTGTGCTCAG CAGTGAGCGT CTTCTGCGGT CTGGTCAGGT TTTGCCACTG
42151 TGCTCAGCAG TGAGCGTCTT CTGCGGTCTG GTCAGGTTTT GCCACTGTGC
42201 TCAGCAGTGA GCGTCTTCTG CGGTCTGGTC AGGTTTTGCC ACTGTGCTCA
42251 GCAGTGAGCG TCTTCTGCGG TCTGGTCAGG TTTTGCCACT GTGCTCAGCA
```

FIGURE 3-16

```
42301 GTGAGCGTCT TCTGCGGGGT CTGGTCAGGT TTTGCCACTG TGCCCAGCAG
42351 TGAGCGTCTT CTGCGGTCTG GTCAGGTTTT GCCACTGTGC CCAGCAGTGA
42401 GCGTCTTCTG CGGTCTGGTC AGGTTTTGCC ACTGTGCTCA GCAGTGAGCG
42451 TCTTCTGCGG TCTGGTCAGG TTTTGCCACT GTGCTCAGCA GTGAGCGTCT
42501 TCTGCGGTCT GGTCAGGTTT TGCCACTGTG CTCAGCAGTG AGCGTCTTCT
42551 GCGGTCTGGT CAGGTTTTGC CACTGTGCTC AGCAGTGAGC GTCTTCTGCG
42601 GTCTGGTCAG GTTTTGCCAC TGTGCTCAGC AGTGAGCGTC TTCTGCGGTC
42651 TGGTCAGGTT TTGCCACTGT GCTCAGCAGT GAGCGTCTTC TGCGGTCTGG
42701 TCAGGTTTTG CCACTGTGCC CAGCAGTGAG CGTCTTCTGC GGTCTGGTCA
42751 GGTTTTGCCA CTGTGCCCAG CAGTGAGCGT CTTCTGCGGT CTGGTCAGGT
42801 TTTGCCACTG TGCTCAGCAG TGAGCGTCTT CTGCGGTCTG GTCAGGTTTT
42851 GCCACTGTGC TCAGCAGTGA GCGTCTTCTG CGGTCTGGTC AGGTTTTGCC
42901 ACTGTGCTCA GCAGTGAGCG TCTTCTGCGG TCTGGTCAGG TTTTGCCACT
42951 GTGCTCAGCA GTGAGCGTCT TCTGCGGTCT GGTCAGGTTT TGCCACTGTG
43001 CTCAGCAGTG AGCGTCTTCT GCGGTCTGGT CAGGTTTTGC CACTGTCTAA
43051 CAGCTGCCCT GTGCCCTTGG TGGCTGTGCC CTAATGACTC CCCTCCTGTT
43101 TGGGGCCATC TTTTGTGAAA ATGCAGAGCC ACCAGGGCTT CGTCACCTAC
43151 CCTGGGAATG CTGTCCCGGT GCCCTTGGGG CTTTGACCA CAGCCTCCCT
43201 CCTGCTTCAC CCCTGCACCC TCATGATGCC CTGGGGCAGG GTGTGGGCCC
43251 TTCATCCTTT GGGGTCTCCT GAGGGTGCCT CATGCTGGGC ATTTCTGGGT
43301 CATTTCCTCC CTCCTTTGAG AGCCTCTGTC CTGGCCTCCG GCTGCATCCT
43351 CCCAGGAGTT TGTCCTGAGG GTTTTTAGGG GCTCCATGCC CTTCGGACCA
43401 GAGGCTTTTG TCACGGACCA CGCCTTAGCC TTGCAGCCAG GTTTGGGGGA
43451 CATTGAGCTC TTGCTCCTTT CCGTGTGTGG GGCTGAGTCC TTCCTGCAGG
43501 GACCCCTGCC CCGGGATGCA GGCCAGCCTC GTGCCTGGGG AGGGATGCGC
43551 TGTGGGCGCC TCCAGCCGCC CTGGATTATG GATGAAGGGC TCTAGGCCCT
43601 CCTGAGTGCT CCTCCGGCTG AGCGAATCAC AAGCCTTGTG CTGGATCAAA
43651 GGCCTTCAGG GAGAAGCAGC TCTTCCTCCA TGAGCACACC CTGCCGAGGC
43701 CACCCCCCAC CCCTGGCACT GGGCTCCCCT CTGTGCCCAG CCTGTGTCAC
43751 TGCCCGGCCT GCAGCTCCCC CTGCCTCTGG GGAAGCCCGC TTCTTCGGCA
43801 AGGTCCTGGG TCCCCCACCC GGCCTGGGCT CACCCAGATC CAGGCGTGAC
43851 GCCACACAGA TGAAACTGAC GGAAAGGGCA AAATAAAGCT AAAAGCCGAT
43901 GGGGCCGGGG GAATGGAGGT TTGACGCGTG AGACAAAGGA TTAATTTCCC
43951 AAAAAAATCA AAGGGCTCTT GCAAATTGGT AAGAAAATGC ACACATGTGC
44001 GTGCACCAGG ATAAAAACGA GAACAGGAAA GGAGCCCAGA GCACACCCAC
44051 ACGGTCAGTA AACACCGGTG ACGTCCCGCG GGTCAACAGG GCGAGGCCGA
44101 GTCTGGGTGA AATTTGAGCA CAGCGCGTGC ACGGAAGGAT GGCGGCCACT
44151 AAAGCCCAGT GGGAATGCCA GCCAGGATCT GGGTGTCTGG GCGCACCTAG
44201 GAGTGGGGTC CCCTGTGATA ACCTGGGCCG GCTCTGCGTG TCTGGGGGCA
44251 CCTAGGAGTG GGGTCCCCTG TGATAATATG GGCCGGCTCT GCGTGTCTGG
44301 GGGCACCTAG GAGTGGGGTC CCCTGTGATA ATATGGGCCA GGATCTGCGT
44351 GTCTGGGGGC ACCTAGGAGT GGGGTCCCCT GTGATAACCT GGGCCGGCTC
44401 TGGGTGTCGG CGCACCCAGG AGTGGGGTCC CCTGTGATAA CCTGGGCCGG
44451 CTCTGGGTGT CTGGGGGCAC CCAGGAGTGG GGTCCCCTGT GATAACCTGG
44501 GCCGGCTCTG GTGTCTGGG GGCACCCAGG AGTGGGGTCC TCTGTGATAA
44551 CCTGGGCCGG CTCTGGGTGT CTGGGGGCAC CTAGGAGTGG GGTCCCCGTG
44601 ATAACCTGGG CCGGCTCTGG GTGTCTGGGC GCACCTAGGA TTGGGGTCCC
44651 CTGTGATAAC CTGATCCCCC CATGGTTCCA ACATGCCCCA ACATGGAATG
44701 GCACATGAGT GCGCCTGAGG ACCTTTGATG GTAGGAAAGG GCCTGGGTTG
44751 TGGGCTCCTG GGGGCATCTC CAGTGTCAAG GCCACAGCTC AGGCCAGGTG
44801 GGGCTCAGGG GTGTGGCCGG GCTGTCCTGG GCAGGGGCAA GTATCTGGCT
44851 GTGAAAAGAG TGGGGAGAGG AGAAAGGGAG GGTGGGCCGA GGCGCGGAGG
44901 GGGACCGGGA CCGTGTGCCC AGCCAAGGCA CATTCCCAGA GCACCCTGCC
```

FIGURE 3-17

```
44951 TGCCTTTTAG GTGGGTCTGG GAAGGAAGGG GCTGCCGGGC CGTGGAGGTC
45001 TAGGGCAGTG CTGCCTGGGG AGCTACCTGG GGCCCGTCCT GGTGTCCTGG
45051 GGTGAACACA GGGCCGGGGC TCAGGTGCAG AGCATCTCAG CAGAGGAGGG
45101 GTGCCGGTGG GGGTCTCAGC GGAGGAGGGG TGCCGGTGGA TGTCTCAGCG
45151 GAGTAGGGGT GCCGGTGGGG GTCTCAGCGG AGGAGGGGTG CCGGTGGGGG
45201 TCTCGGCGGA GGAGGGGTGC CGGTGGGGGT CTCGGCGGAG GAGGGGTGCC
45251 GGTGGGGGTC TCGGCGGAGG AGGGGTGCCG GTGGGGTCT CGGCGGAGGA
45301 GGGGTGCCGG TGGGGGTCTC GGCGGAGGAG GGGTGCCGGT TGGGGTCTCG
45351 GCGGAGGAGG GGTTGCCGGT GGGGGTCTCG GCGGAAGAGA GGTGTCGGTA
45401 GTGGTCTCGG CGGAGGAGGG GTCGCTGTGG GTGTCTCGGC GGAGGAAGTA
45451 TGCCGGTGGG GGTCTCGGCG GAGGAGGGGT GTCGGTGGGG GTCTCCGCGG
45501 AAGGCTGCGT CTGAGGTATC TCTGCAGAAG GCTGCAAGTT GGGGGTCTCG
45551 GCAGGGTGTG CGAGGGACAG CCTTCTTGGG CCAGGCAGGC ACCTCGAGGG
45601 CACCCTGGCT CCCAGCTGAG GGTGGCTGAA GCTGAAGGGA GGGGATTTGG
45651 GTCCCTTGGA TGGGGAGAAG GCAAGCGGGC ACAGAGACTG AGAAGCCCAA
45701 CCGGGCGTGG AGGAAGACAC ACTTTCAGCC ACGTGACCCA CACTGACTGT
45751 CTGACACGAC CAGCGGCAGG GCTCCCTGGA AGCGGTGGAC CCTGCTTCAG
45801 ACGTGGAGGC TACAGCTGAG TCGTATATGT CAACTGTTCT GTGTAATGTA
45851 TCGCTCAATC AACACATACA CCGAAATAAG TTAAACTGGT CCTAATATAC
45901 TACTAATTAT CGTCCTCATC CGTTCGATGG AACTGCGNNN NNNNNNNNNN
45951 NNNNNNNTCT CGGCGGAGAG GGTGCCGGTG GGGGTCTCGG CGGTAGAGGG
46001 GTGCCGGTGG GGGTCTCGGC GGAGGAGGGG TGTCGGTGGG GGTCTCGGCG
46051 GAGGAGGGGT GCCGGTGGGG GTCTCGGCGG AGGAGGGGTG CCGGTGGGGG
46101 TCTCAGCGGA GGAGGGGTGT CGGTGGGGGT CTCGGCGGAG GGCTGCGGCT
46151 GAGGTATCTC TGCAGAAGGC TGCAGGTGGG GGTCTCGGCA GGGTGTGCGG
46201 GGGACAGCCT TCTTGGGCCA GGCAGGCACC TCGAGGGCAC CCTGGCTCCC
46251 AGCTGAGGGT GGCTGAAGGC TGAAGGGAGG GGATTTGGGT GCCTTGGGAT
46301 GGGGAGAGGG CGAGGGGGGC CACAGAGACC TGAGAAGCCC AAAGGGCCGG
46351 CGTGGAGGGA AGACACAGCT TTGCAGGGGC AGCGTGACGC CAGCACTGAG
46401 CTGTTCTGGA CAGCGACCCA GGCGGGCAGG GGCCTCCGGC CCTGGAGCGG
46451 GTGGGACCCC TGCTGTCCAG GACGTGGGAG GAGGCCCCCA ACCTGCACTG
46501 TCCGGCTGGG TGCTCGCTGC AGGCACCCTG GGTGGGTCTG AGCGCGGCTG
46551 CTTCTCTCCC GCAGGTCTGG TGAAGCTGGG GGTTCACTGC GTCACCTGCC
46601 AGAAGGTGGC CATCAAGATC GTCAACCGTG AGAAGCTCAG CGAGTCGGTG
46651 CTGATGAAGG TGGGTGGGGC CGGGGAGGGA GGCGGGGCCG GCGGTGGGGT
46701 GGGCGGGGA ATAGCACAGG GGTGGGAGCC AAGGTTGTGG GGACCTGCGG
46751 TGCTGGATGC GGGTGGGGGG GCGGGCCTGC AGGCTCCTGG GCCGCCACAC
46801 CCCTGCTGGT CCCCTGGTAG GGTGCCTTTG CTCTTGCTCC TCCCTCCAGC
46851 CCTGCCCACC TTTCTCCTGC CTCCAAGCAG AGTGGGCACC CCTGAGGGGA
46901 CAGGCTGCAG CTGGGCAGTT CAGTTGCTGC AGGACCTGCT GTGCTAGCAG
46951 GCGGGGCTTC AGTGTTCCCA GCTAGAATGG AGAGGAGTTC CCTGCCTCAG
47001 AGCACCCCTC TCCTACCAGG GCACAGCTTG GCAGAGGGGA GCTGCACCTT
47051 CCTCTTCCAC TGGGGCCTGG CCTCCGTCGG CTCCATCCGG TGGTGTCTGG
47101 TCACCATGGA GACCAGGCAG GCCCCCTGGG TGGAGGGTTT CTGGGCTGTG
47151 ACCCACCTCT CAGTGGGGAG GGGCGGCCC CGGCTGCTGG GAAGCCTGAC
47201 CCTGGGTGTA GAGGAAGAGG CTGGGCTCC CAGCTGCTCC GGGTCCCACC
47251 CACAGTGGGA CCTGGGCTGG CAGCGTGCGA CCCTCCCAGC ACTGGGGCCA
47301 GTCGAGCCCC CTCCTCTCCC TTCCTCTCCA TTCGCTCCTT GGCATGCAGG
47351 GCTGCGGGTG GGGCAGGACC CGGGGACGAG GCCAGTGGGA GTGGCCAAGA
47401 GAGGGAGGC TTGTGGAAGG TGCTAAGGGT TGGGGACTGT GACATGTTGG
47451 GCACCCCCA GCTGCTGGGG TGTGGAGGAA TTAACCAGAC TAAACTGGGG
47501 AGGCCTGGGG ACCCTATGGG GAGGTGGGGG TGGGGTTAAG GGCTGCTGAG
47551 GGCTGCCTGG ATGGGGCTGG CAGGGTCCCA CCCTGCCTTG GAGGAGAAAC
```

FIGURE 3-18

```
47601 AGAGGCCCTG GGAGTGATGG GGCCAGGACA GCGCCTGGCA GAGAGATCCA
47651 GTGTGGGGCG TAGCTGGGGA GAGTCCCATG CTGAATTTGG GAGGTGCCTG
47701 TGAGCCCCGA CTAAAGGAGG GCCTGGGGAT GCGGGAAAGG GGAGGTGTCC
47751 CTGTCACCTG CAGGCGCTGT GCACAGATGT CCGCCTGGGA GGGAAGGACT
47801 TGGGGACAGG CTGGCCAACT CGCCAGGGCT GGGACCCCAT CACAAGACTG
47851 GCCCTAGCTC CAAAGCCTGG TCCACGCTGG CTCCTGAGGG CTGGGACCCC
47901 AGGCCGTGGC CTCACTGGCC CCACCACTGA CACGGCCACT TCTTTGTGCT
47951 GGGCGGAGCA CCAGCTGCCC GTGGCCAGGC TTGCATGTCT GAGGGAGGGG
48001 GCCCTGCCTT ACCTCGGAGC AGGACTGGGT GTCCTGAGTC AGGTGCCCTC
48051 TGGGTCACTT CTGCCCCTCC CTGGGCCCTC CCCACTTGGG GGACAGTACC
48101 AGCTGGGAGC CTGTGGATGG GGGGCACGTG CCCTGCCCAC GGCCTGCACA
48151 CCTACTGTAT GTCCCACACA CAACAGGATG CCTGCCCCCA CCTCATGGGG
48201 CCCACAGAGG CCTGTCCCGG CCCCTCCTCC TGTGAGGCCT CCACCGTAAG
48251 GAAGGGCGGA GCCCAGGCAC AGCCTGCCTG GAAGGGCCCT GCATCCGACT
48301 GGCTGGGAGC CTGGGAGGCC TTATCTCCAA CAGCTCCAGG CCCCATTCCT
48351 GAGGCTGGGC TCACAGAGAG GCCCAGGCTG CCTGCCTTCC TGGGCAGTGT
48401 GGGGAGGGGC CCTCCTGCTC CAGGGGCCCC CAGTCCTCAG CCCTACAGGC
48451 TGGTGTCAGC CCGGCGGCCT GGGCTCCCTC CACTGAGGCC CCTGCCCTCT
48501 GCCCTCTCCA CCAGCCAGGG CCCCAGCTGA GCAGCCACG TCCCTGCATC
48551 CCCCACAGCT GGCACCAAAG GCCCCTGCGT CCCCCACAGC TGGCACCAAA
48601 GGCCCCTGCG TCCCCCACAG CTGGCACCAA AGGCCCCTGC GTCCCCCACA
48651 GCTGGCACCA AAGGCCCCTG CGTCCCCCAC AGCTGGCACC AAAGGCCCCT
48701 GCGACCCCCA CAGCTGGCAC CAAAGGCCCC TGCGACCCCC ACAGCTGGCA
48751 CCAAAGGCAG TGTCTGTGGG GAGCGATGCG TGCCCCAGCC CTGTGAGCGT
48801 GATGTTCTCT GGCCTCTCCC ATGCAGGTGG AGCGGGAGAT CGCGATCCTG
48851 AAGCTCATTG AGCACCCCCA CGTCCTAAAG CTGCACGACG TTTATGAAAA
48901 CAAAAAATAT TTGTAGGTAT TGCTGGGTCT GAAGAGCTGG GGTGGCGGAG
48951 GTGGCAGCTG TCGCTGCAGG GGTGGGTGTC TGGGGCTTGG GGAGCACAGG
49001 GGCTGGAGGC CAGGGGCGCC TGCTGCATCC CAGCAGCCCT GGCCCTGCTA
49051 GCATGAACAC CTGCCTGGGT AGGGTCTCAG CCCAGGCTGC TGTGGTCTCT
49101 GCTTCTGGAC CAAACCGGAG ACCTGGTCTG TGGAGGCTCG CAGAGCCACC
49151 AGCCTGAGGC TGGCAAGGGG GAACAGGACC TTCTGGAGGG GAGATAGGAG
49201 TTTCAGGGCA AGGGGCAGGA GCACCTGGCC CTCCCCACAT GGCCACGCTG
49251 AGCCTCCTGG CCTCTGCCCA GGACGTCCCC AGCCCTGGGC AGTGAGCCAT
49301 GTCTCTATCC CTGAGGCTCC CTCACACGAG GCACAGCCAC CAGGATCCCG
49351 CCCTGGCTGG ACCGTGGCTG AGTGTGGCTG AAAGTGTCAC CTCCGCAGCC
49401 GCTGAGGCCA GCAGAAATCC CTACCCTGTC CCAGGCATGC CTGGCTGTGA
49451 ACCCCATCCC CCCAGACCCA GCCTCAGGGA GCTCCTGGGA ATGGGCACAG
49501 TGGTCACTCA CGGCAGTCTC CTCTGTGTGC TCTGATGGGG CTTTCTGACA
49551 GATGAGGCGC TGCTGCCCAA GGGCTGTCTG GCCTTGAGCC TCATCTGACC
49601 CTCGCTGGTC CCAGGGCGGC GGCGTGACCT GCCAGGTGAT CCTAGCCGGG
49651 CATCTCTGAG GCATCAGGCT CTGAGGGAGC AGGGAACATA CAGGGCTGGG
49701 CTGGGGGCTG CCCTCAGGGT GAGCTGGCTG AGGGCCTGGC TGAACCCAGC
49751 AGCTCCCCTT CCCCCAGCAG CAACGTCCAC GCTTGCTCTG GCCTGGGTTT
49801 CTGCATTCTC GTGGGGAGCA TGTGCAGGTG GCCAGCTCGT GTGTAGCTGG
49851 GGAGAGGAAA CCCAGGGGTG GGGTGTGGGG AGCCCGCCTG CCCCACCATG
49901 AGCAGGGGCT CAGAAACTGT CACCAGAGGC CTGGGGGGGC GGGGGTGGTC
49951 CTGGCCCTGA TGCTGGCAAG GTGGACTGTG ACAAGGGGCA TGGCTTCCTC
50001 ATGGTGACAC GGTGCCGGTG CAGTGGGGTC CTGGGAGGC CTTCTCGGAG
50051 GGGAGGGCAG GGGAGTGCGG GGGGGATGGG CACAGCAGCC AAGGCCCAAG
50101 AACAGGAAAG AGCCCAGGAG GTGGGCATGG CCGGGCTCGC GGCTTCTCCC
50151 GAGGTCTGGC CCTGGGTGTT GTCCCACCCC CTCTGGACAC CATGTGGCCT
50201 ATGCTGAGCC TTGGGCCTGG CCGCCCCCT GCCCAGAATC CACCCTGGC
```

FIGURE 3-19

```
50251 CCCCACCACC TTCCCCTGCC CTGAGGGCTT CACACCTTCC TCTGCCCTGA
50301 GGGCTTCACA CCTTCCCCTG CCCTGGGGGC TTCACACCCT CCCCTGCCCT
50351 GAGGGCTTCA CACCTTCCCC TGCCCTGGGG GCTTCATATC TTCCCCTGCC
50401 CTGGGGGCTT CACACCTTCC CCTGCCCTGG GGGCTTCACC ACAACCTCTG
50451 CTCCCATCCC CACACTGGGC CCTTGACTCC TGCCAAAACC AGCTCCTGGG
50501 ACAGCCAGTC ATCCCAGTCC GCACGGCAGC TCTGAGCATG CACCAAGGTG
50551 CCACCCCCTT GGCTGTACAG CCCCCCTACA TCACCACAGC CACACCAGGG
50601 GCCACCACCC TCACAGGCCT CCCCCCCGAG CTGGTTCAGC CTGGGTGGAG
50651 CGGCCCCCAA GCAGCTGCAT GCAGCGTCCC ACGGGCCTCT CACCAGGAAC
50701 CAGCCCCTCA GGACCCTCCA TGTGGCTGAG ACCCCACGGG GGTGGTGCTG
50751 GGAGCCCACC AGGGCAGGAA GGGGAGGGCC AGGCCAACCT TTTCCTCACC
50801 CCCTTCCCCT GGCCCTCACA CCTCCTGTTC CCCCCACAGA GGCCCAGACA
50851 GTCCCTGGGC CCCTGGATGC GGCTGCGTGG TCTCCCTGCT CGGTGCCTGT
50901 GCCACTGAGG ACCACAGGGT GTGAGGGCCA GAGCAGGCAG GGCAGAGTCC
50951 CGAGGCTACC CCATGCACCG AGCCTTGGCC CCAGCACCCG CCACACTCAG
51001 CCTGTGGGTT CCAAACCCTC CCTGGCGGCT GTGCCCCAG AACCATCCCT
51051 TCACCTGTCC CTCCACCCTC ACCCCACCCC ACCCAACCC AGGCTCCTTG
51101 AAGACTCATT TGAGGTCCAC CCCCAGGAGC CCAGATGGTT TGAGATCCAC
51151 CATAGTCAGG GCTCCTCTCA GCTGCCCCCC CAGCCAGCAA GAGGATGGGG
51201 GCGGCCTGCA GAGAGGCTGG GCCAGGAGGC GGCTGTGGGA GGCCCTGGGA
51251 TGAGGAGGGG CGGCGGGCAG CCACAGCTGG GCGCACTGGT GGCCCCGTCT
51301 CCTGCAGGTA CCTGGTGCTA GAACACGTGT CAGGTGGTGA GCTCTTCGAC
51351 TACCTGGTGA AGAAGGGGAG GCTGACGCCT AAGGAGGCTC GGAAGTTCTT
51401 CCGGCAGATC ATCTCTGCGC TGGACTTCTG CCACAGCCAC TCCATATGGT
51451 GAGGCCCCAC CCCTGGTGCC CCCCACTCCC CAGGGACCCC CACACCCAGT
51501 GCGCTACCAC AGATGCCCCC TGTGCCCCAA GGACTACACC CCCTATGGTG
51551 CTATTCCGAG GTACANNNNN NNNNNNNNNN NNNNNNNNNN NNNNNNNNNN
51601 NNNNNNNNNN NNNNNNNNNN NNNNNNNNNN NNNNNNNNNN NNNNNNNNNN
51651 NNNNNNNNNN NNNNNNNNNN NNNNNNNNNN NNNNNNNNNN NNNNNNNNNN
51701 NNNNNNNNNN NNNNNNNNNN NNNNNNNNNN NNNNNNNNNN NNNNNNNNNN
51751 NNNNNNNNNN NNNNNNNNNN NNNNNNNNNN NNNNNNNNNN NNNNNNNNNN
51801 NNNNNNNNNN NNNNNNNNNN NNNNNNNNNN NNNNNNNNNN NNNNNNNNNN
51851 NNNNNNNNNN NNNNNNNNNN NNNNNNNNNN NNNNNNNNNN NNNNNNNNNN
51901 NNNNNNNNNN NNNNNNNNNN NNNNNNNNNN NNNNNNNNNN NNNNNNNNNN
51951 NNNNNNNNNN NNNNNNNNNN NNNNNNNNNN NNNNNNNNNN NNNNNNNNNN
52001 NNNNNNNNNN NNNNNNNNNN NNNNNNNNNN NNNNNNNNNN NNNNNNNNNN
52051 NNNNNNNNNN NNNNNNNNNN NNNNNNNNNN NNNNNNNNNN NNNNNNNNNN
52101 NNNNNNNNNN NNNNNNNNNN NNNNNNNNNN NNNNNNNCCC CCCCATTAGG
52151 CTACCCCTCA AGTGCACCGT CCACCCCATT AGCTACCCCT CAAGTGCACC
52201 GTCCCCCCAT TAGCTACCCC TCAAGTGCAC CATCCCCCTC ATTAGCTACC
52251 CCTCAGGTGC ATCATCCCCT CCTCATTAGC TGCCCCTCAA GTGCACCGTC
52301 CCCCCCATTA GCTACCCCTC AAGTGCACTG TCCCCCCCAC CCCATTAGCT
52351 ACCTCTCAAG TGCACCATGT GCACCAGGTG CTTCCCTTTT CCCCCTGAGG
52401 ACCCCCTGCA CCTCCCCTTT CCCGAGTGGG CAGTGTGTCG GGAAGTTTTC
52451 TGCCTGGCAC CCACCCAAGC ACTCTGGGAG CCCCTCGGCC TTTCCAGGGG
52501 CCATTGCTTG CATCCCTACG TGCCTGGGGG CCCTAGGTTG GTCTAGGCCA
52551 GAGCAGGTGT GCTAGGAGC AGGAGGGGGC AGGAAGGAGC CTGCCAGGGT
52601 GCAGGAGGGC ATGGCAGGAG AAACAGGGAT GCCTGACCAA AGGCCAGAGC
52651 CAAACGGACC AGGCAGGCGA CTTCTGATTG GCTGCCTATG ACATCACCAG
52701 GCTGGGCTGC TATTGGCCCT TATGTGTGAT TGGCGTTTGG AGAGGCAGTG
52751 GGCTCTGGGC AGGGGTCTC CAGGGCGGGG AGGCGCTCAA GGCAGAGACT
52801 GGCCCTGTTC AGCCTCACCA CCCTCCTCCC CAGCCACAGG GATCTGAAAC
52851 CTGAAAACCT CCTGCTGGAC GAGAAGAACA ACATCCGCAT CGCAGACTTT
```

FIGURE 3-20

```
52901 GGCATGGCGT CCCTGCAGGT TGGCGACAGC CTGTTGGAGA CCAGCTGTGG
52951 GTACGTGGCC CTCTGCCCTG GAGAGAGGCT GGGGGACAGG CTGGGCTGGG
53001 GGAAGAGGAG CCAGTGGACT GAGAGGCCCC CAGCCTGCCT GAGCCTCCCG
53051 GCACCCCACA GGCAGGCCCC CCACAATGTG CCTGAGCCTC CCAGTACCCC
53101 ACAGCCTGGT GGTGGTGGGG AGACAGGCCT CCCGGCACAG TAAGGGTAGG
53151 GGTACAGCCC TGGCCCTGGC CTGCCTGGGA GAGAGGCTGG GACCCACTTA
53201 CATGCCCCTC TCCTGGGGAC CCCCTGGCCC CTGCCCAGCC GAGTGGGCAG
53251 ACAGCTTTGG GCGCAGCAGA GACCCAGTGC CCCACCTTGA TCTCCTCCCA
53301 AAAGCCCGCC TGGGGATGCA GGGAATGTGG GGGCGTCTGG CACCACAGCC
53351 CTGGAGGCCT CCTTGAGGGC CCTGCGGTGC ACCATCACCC TGGGGGGAGG
53401 GCCTGGCAGC GCCCGGAGCC CCGCCGCTGA CCTCTGCCCT TGCCCGCAGG
53451 TCCCCCCACT ACGCCTGCCC CGAGGTGATC CGGGTGAGTC AGCGCCGCCG
53501 CGTGCAGCTC TGTGGGGCCC AGGGTGGCGG GGACCTGACC CTGGTGGGAC
53551 CCCAGCCTGC CGCACCCCCA GGTGCTGCTA GGCTGCCTGT CCCCGGGCCG
53601 ACTCCCTCTG AGCCCAGGCC CTCCAAGGCC CCCGCCCTGC CCTGCGCCCC
53651 CCAACAGCCC GGGCACTGCT GTCCACAGGG GGAGAAGTAT GACGGCCGGA
53701 AGGCGGACGT GTGGAGCTGC GGCGTCATCC TGTTCGCCTT GCTGGTGGTG
53751 AGACCCTGGC CCCCTCAACC CTGCCCTGGC CTCTCCCCAA ACCTGCCCCC
53801 CCACGCTGAC CCCCACACCC GGCCGCCCGC AGGGGGCTCT GCCCTTCGAC
53851 GATGACAACT TGCGACAGCT GCTGGAGAAG GTGAAGCGGG GCGTGTTCCA
53901 CATGCCGCAC TTTATCCCGC CCGACTGCCA GAGTCTGCTA CGGGGCATGA
53951 TCGAGGTGGA CGCCGCACGC CGCCTCACGG TGCGTGCCCT CGGAGCGGGG
54001 CGGCCCCAGA GCGTGGCGGG GGGCGCGGGG GCGGGCGTGT GCCTGTGTGT
54051 GCACAGGTGT GTGCCCAGAC GTGTGGGCAC CCAGGTGTGT GGGTCGGTGC
54101 CCAGGTGTGT GGACGTGTGC ACAGGTGTCG GCTTGTGTTC AGGTGTGGGT
54151 GACCAAATGT GGGCCCATGG CCGTGTGTGG GTGCCCAGGT GAGTGTTCAA
54201 GTGTGTGTGC GCACCCAGGT GTGGGAGTGC CCAGGCGTGT GTGGGCTCGT
54251 GTTCAGGTGT GTGGGTGCAC AAATGTAGGC ACATGCCCAG GTGTGTGTTC
54301 AAGGGTGTGG GGGTACCCAG GCACATGCCC AGGTTCATGT GATTGGGTGA
54351 GGGCGTAGGT GTGGGCATGT GCACGTGTGG GGAGGTGTGT CCAGGTGCTT
54401 ATGAGCACTT GTACCAGTGT GGGGTGTGCA CAGGTGTGGG GGGCTGTGTG
54451 CACATGTAGG TGAGACCTGG CTATAAGTTA CACAAAAGCA CTGGTGCTTC
54501 CCCATCACGG CCATCCTGCC TCCAGACGCT GCTGGGGCAA GCTCCAGGCA
54551 GCGTGAATAG TTCTGCTGAG TGCCCCCAGC AGCTGTGGGG GCTAGCAAGA
54601 GCCAAAGGTA GCCCCCAGCT GCTGGTCCTG ACCTCCTCCA GGGCTGCCTG
54651 GTGTGGGGAC CGCACGTGTC CACTTGACAG AAGCAGGTCA CACTCTGGGC
54701 TGACCCTTCC AGGGTAGCGT TGACCTGTTC CCAAGTGGCC ACTGCCTCAC
54751 ACCCCACGAG CTGTCCCTGA GTCAGGGTGG AGAGAAGGGG CCGTGTGGCT
54801 GGCCGGCCCT CCCAGCCTCC TGCCTGCACC TGCACCCAGC CCTGCCCCGC
54851 CGCACAGGTG GGCCGGGTTC TCCTGGCTTC AGCTCCCTCC TGGCTGCTCC
54901 CTGCTCTCCT GCCTTGGTTC CTTCCTAGAG CCACGGAGGG GCCCAGCCCA
54951 GGCAGCACAG GCACCTGGGG CTGCCCTGGC TCCAGCTTCC CTCCCTCCCC
55001 CTCTCCCTCC GCTCCCCAGG CCCCTGCCCC TACCTGGAGC ACCCCCTCCG
55051 ACTCCAGCTC CCCCGACTTC TCTCCTCCTT GAGGTGTGTG TTTTCTTCTC
55101 CACTTGGGAG AGGCAGGAGC AGGGGTGCTG GCCTTGAGCC TCTGGGAACG
55151 CAGCCCCCTC CCTATCTTCC TCCCCACCTT CCCCCCACTC ACTTGCCCTC
55201 ACCCTCTCCT GCTCTCTCCG TGCTCCCAGC GCCCCTGCCT TCCCCCTCAC
55251 CTCCTAATGT GGGCTCTTTC CGTCCCTCGT CCGTACTAAC TCCCTGTTTC
55301 TCTTTCCTTG TAGCTAGAGC ACATTCAGAA ACACATATGG TATATGTAAG
55351 TAGCTTTTCC ACCCACTAAT CGCCTGCTTT GCCTGTTGCT GTGGCCTGGA
55401 GGCCCTGCTA GGAAAGGCGG GGGGAGGGCG CCGGCCCAGC GCAGGTCCTG
55451 CCCTGCCTTG GCCCTCCGTG GCCTGCGCTG GGTGCGGGGT GCGGGCAGGA
55501 CGCAGGAGGC CTCCCCGGGC TGGGCACAGG GAGAGTGGCA GGATGAAGGG
```

FIGURE 3-21

```
55551 CCCCAGGTGA GGGCGGGCGT CCCACCCTCG CAGCCGCCCA GGCCCGGCCG
55601 GAGCTGATGA GCGGGTGGCC CGTCCTGTGT CCACAGAGGG GGCAAGAATG
55651 AGCCCGAACC AGAGCAGCCC ATTCCTCGCA AGGTGCAGAT CCGCTCGCTG
55701 CCCAGCCTGG AGGACATCGA CCCCGACGTG CTGGACAGCA TGCACTCACT
55751 GGGCTGCTTC CGAGACCGCA ACAAGCTGCT GCAGGACCTG CTGTCCGAGG
55801 AGTGCGTCTG GGGCTGCTCC CGGGTGGGGC ACGGGGCCTG AGGTGGGAGC
55851 GCTGCCCCGG AGGAGCCGGC GGCCCCGTGT GCCAGCGCGT CTCGCGCCTC
55901 TCGCCCGCTG TAGGGAGAAC CAGGAGAAGA TGATTTACTT CCTCCTCCTG
55951 GACCGGAAAG AAAGGTACCC GAGCCAGGAG GATGAGGACC TGCCCCCCCG
56001 GAACGAGATA GGTATGGGTC CAGGGGTGGC CTCCAGCCCG GCCTGCACTG
56051 CCCCACCGGG GTCCGGGGGC TGTCTGGCCT GACCTTCGTC TGTACTCAGA
56101 CCCTCCCCGG AAGCGTGTGG ACTCCCGAT GCTGAACCGG CACGGCAAGC
56151 GGCGGCCAGA ACGCAAATCC ATGGAGGTGC TCAGCGTGAC GGACGGCGGC
56201 TCCCCGGTGC CTGCGCGGCG GGCCATTGAG ATGGCCCAGC ACGGCCAGAG
56251 GTGTGTGTGC CCCGAGGCTG CTGGGCCTCC CTCCCTGGGC CCTGGCTGCG
56301 CGGCACTGCC GCCTGGCTCA TCGCTACCCA TTGGCCTGGG GTCTCGGCTG
56351 AGGCCATTGG GTGGGGCTGT ATGGGCTAAA CTGGGCTTAG CTGGGCTTGG
56401 CTGGGCTGGG CTGGGCTTAG CTGGGCTGGG CTGGGCTGGG AGCTGAGCTG
56451 GGCTGGGCTG TGCTGGACTG GACTGGGCTA GGCTGAGCTG GGCTGGCCTG
56501 GGCTGGGCTG GGCTGGTTTG GGCTGGGCTA GACTGCACTT GGTTGAGCCG
56551 AGCTGGGCTG TACTGGACTG CGCGGCTGAG CAGGGTTGAG TTGAATTAGG
56601 GTGGGCGGGG CTGGGCTGAG CTGGGCTGAG CTGGGCTAGG CTGCACTAGA
56651 ATGGGCTGAG ACGGATTTGA CTGGGCTGAG CTGGGCAGGG CTGGGCTGAG
56701 CTGGGCAGGG CTGGGCTGGG CTAAACTGGA TTTGGCTGAG CCGAGCCAGG
56751 CTGGGCAGGG CTGAGCTGGG CTGGGCTGGC TTGACCCAAG CTTGGCTGGG
56801 CTGAGCTGTG ATATGGTCAC ACCATGCTCA GAGCCATCAG CCCAGCAAGC
56851 CTGTCCCCCT GGTCCCAGCA ATGCTGGGCC CGTCTCTGGG TGGCAAGTGT
56901 GGTGTGTGTG GCCAGGGACA TCACAGAACT CAGCAGTGAT GAGCAGACCT
56951 GTGGCCGGAG GAAGGGCACC CAGCCCTCT GGAGCCTCTG CTGGGTGGGG
57001 GCAGGGCTGG GCTGCCCGCA CGAGGCCCTC AGCAAATCCT TGGAGCCGGT
57051 GCGGCCTCTT GGGGATGAGC TCAAACGTCC CTCACCAGGT GGCAGCTTCC
57101 AACACTTGGG GACAGCCCTT GCGCCAGAGA GCACACCAGG AGGTCCAGGA
57151 GCCCGGGCAG CAGTCTCTGG TCTGCCCTGT GATCTGGGCC TCAGCACCCC
57201 AGGGCCCCCT CCTTGTACTG GAGATGTGGG GGGTGGGACA GGCGTGGCCT
57251 GTTCCTCGGG AACTTGGGGG AAGCTGTGGG GAACTGCAAG GTAGCTTGGC
57301 AGCCATCAGG CTAAACCTGT TCCAGCCCCA GCCCTGGCCA GAGTACTGGT
57351 GGTCCCAGTT CTGGCAGCTC CCAGGCCATG GCCCCCTGGG AGTCCTAGGC
57401 CCTCCCCAGG GTTTCAGGCT GGCCCAGCTT CCAACGTGGG GTCCCAGCCC
57451 CCAGAACCTC CTTCCCAGGG CCCAGTCAGC GCAGCCCTGA CGCCAGTACT
57501 AGGGGGTAGC AAGGGGCCCT CCTATCTACA TTCTACTGTC CTGACCTTCA
57551 GTGGCCTGCA TGTCATGGGG GCACCACAAC CTGTAGCCCA GGTGCCTGCC
57601 TCCTGCCTGC GTGGCCACCT CCCCGGACTC CCGACCCTG CAGGGCAGGC
57651 CCCACCACCC CACTGCCTGG CCCCTCCGGT CAGCGGCGTG GGAGGCCGCC
57701 CTCTTGGCCT CTGCTGCAAC TCCAGGCCT GGCTGCCTGG GGCAGGTGTG
57751 GGATGGGCCA GGCCATGGAC CATTCCGGGG CCTCTGGAAG GCCACTAGTC
57801 CTGGCATGTC CCAGCCAGAT TCCACTCCTG GTGGGCCAC CTGTGCAGCC
57851 AGCAGAGACC CAGCTGCTTG GTGTTGGGCC ACACAGGGCT GCTGACTGGG
57901 GACGCAGGGG TCCTGGGGGC TGGGGTGGGG GCTACCAGGC CACCCTGCCC
57951 AGCAGTCACA CGGTGCGGGG TGTGCTGTCT GGCCCAGCCT CCTCTCTCGC
58001 CATCTTTGTG CAGCGGCCTC AGAGCCACGT GGAGTTCTTA CCCGGTGTGG
58051 CCCGGGCCCT GGGGCCGAC CTGTGCCCGC GTGTGGCCGT CAGTAACTGT
58101 GTTTTCTCGC TCTGTTCTGC TGTAGTAAAG CAATGTTCAG TAAAAGCCTG
58151 GATATCGCTG AGGCCCATCC CCAATTCAGC AAAGAAGACA GGTATACACC
```

FIGURE 3-22

```
58201 CCGACCACCC GTCCCCGCAC CTCCCAGCCC CAGACACGCT GTCCTGCCTC
58251 AGGCCGGGCA GGCACATGGG CGGGTCTGGT GGCGGGCTGG GCTGCAGGGC
58301 TCCTGCTGCG GTGAAGCCAG CCAGCAAGCC AGGCAAGGGC CCGCGGGCCA
58351 GGCAGAGGCC GAGGAGGGGT GGGGCTGCTG AGGCGTGGCC CACGCCTGCC
58401 TGTGAGGGAC CACGCACCAT GGCTTACAGG GCCTGGGGCT AGAGCCCGGC
58451 GTGGCTGCAG GCCGAGCCGC TCCTCCTGCC AGCCCTGTG CTGTGTCCGG
58501 TGGCCCTCGG TGGCCCTGCT GCCCCTGGGG CCGGCCAGAG TTGAAGCCGA
58551 GCAGCCGTCC TGTGCCCACC TGCAGGAGCT GAGGAGGGCA GGAGGCGCCG
58601 CCGTCAAGAG GGCCTCTAC CTGGGGCCAG TTTTGCGAGC CTGGGCGGGT
58651 GGCGCCGCCC CCAAGGCTGC AGTGTGCTGG CTGCCGGTCG GGGTCCTTCT
58701 CTTTGAGCCC TGGCCCCGTG CCTACCTGGG ACCCTCACCT GTGTGCCCTC
58751 ACTCTGCCTG CCCTGGCTGC CCTCAGGGCT GGCGCCGTCT CTCCTGCCCC
58801 TGCCCCAGCA ACTGTAGCTC AGTGTTCCCA GCAGCTGCCT GGCCGGATAG
58851 GACCAGGGCT CGGCCCCTCC ACCCCGGGGT TTCCAGCGCC TCTTCTGTCT
58901 TCCTCGTGCC CAGTCACGAG CTCTGGGCGG GCTCGACAGG AACCACAGGT
58951 CCAGGGCCTC ACTGGTGGCT GCTGCCCCA TGAGGGCTGT CCGCGCTCCC
59001 AGCTCAGCCC TGAAAGCTCT GGGTCCAGTT CCAGCCCTGG GTGTCATCCT
59051 GGCCCAGACA GGCTGGGTTG TGCATGGGGT CCCCGTCGCC TCCCTGCCCC
59101 TTGGCTGTGT CTGGTGAGGG AGTTGGAGGG TCGTCACCGT GGGGACCAGC
59151 CCCCGGGTGT CCGGGAGCCA GGTGTGTGGC CAGCGTGGCA CTCTCCACGG
59201 TCCGGGGCCT GGGCCGTGGT GTGGACTAGC GAGGCCCCTC GTGGCCGGCT
59251 GGCGGTGGGC AGGCCTGGTG GGCAGTGCAG GCCGGGCTTT TACTCTTCTC
59301 TGTCCTCTTC TCTTCGGCGG CTGCCTCGGC CCCTCCCTGC ATTTCCTTCC
59351 TCCAAGGATG GCAGCTGCCA CTGTCTGGGC ACGTGGGCGC CGGCTCGTCC
59401 GTGCAGTGTG GTGGAACGAC GCACAGCCGT CCTGGTCCCT GCACGGGGGT
59451 GGCGGCCACA CACCGGAGTC TCAGCCGGGC ACGCCGGGCC AGGGCCTCCC
59501 TCCTGCTGTG TGCAGGTCTC AGGCTGAGTA GGGCAGTGGT GGGACAAGGC
59551 CCCACCGTCC CTGCCAGCAG CTGCCCCAGC CTGGCCCTGC CCAGGCCCTC
59601 CTGGTTGTGG ACAAGGGAAG GGCCGGCCGC TGACCCAGGC ATCCCTCACG
59651 GGCATCTAGG GACATGGAGG ACCAGGCTGC AGGCCCTGTG AGAGCTCAGC
59701 CAGGGGGGGC TTGGCAGGTG GGAGGCTGGA GCCAGCACGA GGCCTGGAGC
59751 AGAAGGGGCT GCATACAGGA AGCTCCCGTC TGTCCCCTCG TCCTTCCGTC
59801 CACCCCCACG CTGGATGGTC CTTTGCCGCG GCTGTCTGAT GCCGTATCCT
59851 GTGCTGTGCC TGGGCTGCTG GCATGGGGTG GCCCCCACAC GTGGGCTCTG
59901 ATGGGGGCCC CAGTGGGGCT GGGCACAGCC AGGCGCCCTG GCCCTCCTG
59951 AATTGACAGG GTGTGCAGCA GGACCCAGGG CCTCGAGGCT CTTGGCCCGG
60001 GCTCCAGGCC TCCTGGAGGG TTTACCTGGG GGGAGCAGAG CCCAGCACCT
60051 GCTGCTCCAC TGCCCCCTGG CTGAGCAGTG GCCCTGTACC TTGTGACCTC
60101 CAGGTCTCGG TCCATCAGCG GTGCCTCCTC AGGCCTTTCC ACCAGCCCAC
60151 TCAGCAGCCC CCGGGTGAGT GACCCCCCGC CCCCACCCAG CTCGGATGCA
60201 CAGAGGCCCC AACCCTCCCA GTCAGCGTGT GCCAGGGTGG GGGCAGCCTC
60251 GTGGACCCTG GGAAGCAGCC CCAGGCGCCC CCCATGCCCA CGCTCCTGTG
60301 GCGGCTGCTG CTCTGTGGCG CAGGCTGCTC TGCTAACTGC ACGCTCTTTT
60351 GTTTTGTTTT GTTTGTTTTC TTGTGTGTCA CTTGTTTTCT TTTGTGGCTA
60401 ATCCTCCTGC CCATGCCTGC CTGCCTCCCC ACCCTCCCGC TCCCGCCTGT
60451 TTCTTTCTGG TCCTCCTGTG CCGTGTGCAT GCGGGGACT GGGGTGCATG
60501 TGCCGCGCGG CTGCCCCCAC CCCGCTCGCT CCCTGCGCCT CCCCGTAGCC
60551 TATTAGGAAG CTTGTCCTGC CCCCACCGCC CCCCGAGCCG CCCTTCGTGG
60601 CCCGCCCCCT GGCCACCTCC ACGGAGCCCG AAGCTTGTGG GAGCGCCTCG
60651 AGGCCTGGAC ACGTCCTCCC TCTGCAGGCC GCCCTGCGGC CCGACCCCAA
60701 GACCCAGACC TTGCCGTGCA AGGCCAAGCT GACCGACAAG CCTCTGCAGG
60751 GCACCAAGTC CAACCCCTTC CCGGCCAGCA CCCCAGCCCG GCCTCCCGCC
60801 ACTGGCCTTT GTCCCCAGCT GGCACCACCC CTGGGCCCGC CTGCCCTGCG
```

FIGURE 3-23

```
60851 GGTGCCCCCC CGGCCCCCAC CCGCCGGGAT TGAACCAAAC ACCAAATCTG
60901 TCCCCACCAT ACAGGTGACC CCTCACCCCT CACCAAGGGG CAGTCCCCTC
60951 CCCACCCCCA AGGGGACACC TGTCCACACG CCAAAGGAGA GCCCGGCTGG
61001 CACGCCCAAC CCCACGCCCC CGTCCAGCCC CAGCGTCGGA GGGGTGCCCT
61051 GGAGGGCGCG GCTCAACTCC ATCAAGAACA GCTTTCTGGG CTCACCCCGC
61101 TTCCACCGCC GGAAACTGCA AGGTGAGTGT CTGCCCGGAG GCGCCAGAGT
61151 GGGGCTGGGA GAGAGCAGAG GCTGCCTTGG GGAGGGCCCC GCCCGGCAGT
61201 GCCAGACCAG TCCGAGGGGC CTGTAGCTGC AGGGGTGGCC TGGGCCTGCC
61251 CACGTCTCAC TGTCCCGAAA GCGCCCAGCA GCAGCCTGTG TCCTACCTGT
61301 CGCACAGGCT GGTATCCCCT CCAGACATTC TGTGTTCCTG AGTCTACCCA
61351 CTCTGTGTCC TGGGGCCAGG CACACAGCAA GGAGAGCTGG CCACCGAGGG
61401 GGCACTGCCA GTCAGGAGGC CCCATGTGTG GGGCACCAAG GGCCAGCCAG
61451 TGCTGCTGGA GAAGGCACAG CCGACTTCAG CACCAGAGGC GGGGACAGCT
61501 CCCCTTAGCC TGGGGGGCGC CACTGCCAGT GGGCCTCTAA GGTGGCCGGG
61551 AGCTGGGGTG GACCAGTGCC CCTGGGGGGC TGTCCCAGTG TGTGTGGGTG
61601 GACTCCTGAT GACCCTGACC TCGGCGCAAG GTGGCCAGGG CAGGGGAAGG
61651 ATGGAGCGGT CACCACGCCT TTCCTCCTGT TCATCCTGTG TGCACAGTTC
61701 CGACGCCGGA GGAGATGTCC AACCTGACAC CAGAGTCGTC CCCAGAGTAA
61751 GTGGCCCCTG CTGGAGGCCT CCTGGTACCT GACACCAGGC TGGCCGGGAG
61801 AGGGGCATGG AACCCTTCCC CTATGGCCAA CGGGGTGCTC CTTCTCCACG
61851 TGGCCCCACC TCCCACTGCA GGCAGGCCCG TCTCGGCCAC TGAGTCTCTG
61901 AAGTTCGAAT TCCCGGCTGT GAGGGGAAGG CCAGCCAGGG GAGGAGCCCC
61951 CAGCCCTGTT GAGAAGCTTC AGGCCTTGGG AGAGCCTAGG GTTGGCTGGA
62001 GGCGAGCAGG GGGTACACTG GCAGAGTCT CCCCAGGGCC TGAGCTCGCC
62051 AAGGGCAGAG ACCGGGTCGC TCAGGTCTCA AGGAGAAAGC AGCCCGTGTT
62101 AAGAACAAAG GGGCAGCAGG CCTGGTGGGA ACACGTGTGC AGGGGCGGAG
62151 CGGAGCAGCC AAGCCGAGGT CTGGCCCCGC CGCCTTTCTG AGCCGTGAGA
62201 GGTGCCACTG CAGAGACTCT ACAGCGCCCA GGTGCTGAGA TGCCCTGGGG
62251 GCCGCTGTGA CTGGTGTCTG GACAAAGATG TCCCCAGAGA GACCCCTTCC
62301 CAGCGCCCAG GCCCTCTCCC TCCTCTCCAC GATGGCCTCA GTCACTGGGC
62351 AGTGTCTCGG AGACCAGGCG ACTGGCGGTG TACACATATG AGCCTGCAGC
62401 GTGACCCCAG GCCAGGCAGC GGCAGAGAGC GGCGGTCAGG CTGGAGTCAC
62451 TTCACAGGAG ACCCCGGGAA ATGAAGATGT GGCCAGCTGT GGACTGAGTA
62501 AGACGAGAAC CTTCGTCCTG CTGCTGGCTT TAAACCAGGG GCCCCTGTGG
62551 AAACTGCTCA GTGCTAAGCC CCAGGAGCAG CATCTGCAGC CTGTGCCAGG
62601 ATTCCACCCA GTGGCCTTTC TGCGCCGATC AGGTGGCCCT TCCAGCTGGG
62651 TGCCCAGGTC GGAGGTGTGT AGGTATTGTC GCAAGCCCAG ATGCACAGGG
62701 CTCAGCAGAC TTGGGAACCT TCCGCCTAGG CCCTGACATT GCCGTTTCTG
62751 CTGCTACCAA AAGCTTTCAT GAACAGACTC ATAATTATCT TCCTCAGAGA
62801 AGGTGGAAAA CATCAAAGCC GAGAAGGTGG CTTTGATGCC ACTGTGGCTG
62851 CCTGCGCTTC TCCCCTCCCC CATCTTGAGA TGGCCTGGAG GCCCTGACCC
62901 CTCTCAAGGG TCCGGCACGG ATGCCTCCCA CAGCCCCACC CAAGGGCCCG
62951 GCACAGACAC CCCTTCCCAA GGGTCCAGCA CAGATGCCTC CTACAGCTCC
63001 ACCCAAGGGC CCGGCACAGA TGCCTGCGAC AGCCGTTCCC GAGGGTCCAG
63051 CACAGACACC TCCCACAGCC CCACCCAAGG GCCCGGCACA GATGCCTGTG
63101 ACAGCCCTTA TTGAGGGTCC TGCACAGACG CCTTGGACGA GGGTCCAGCA
63151 CGGATGCCTC CCACAGTCCC TCTTTGGCGA CAACTCGCTT GCTGGGGACC
63201 TGAGATAACC CCCAGCCCCA GCTGCTGCCA GCCCCATGTC AACCAGGCAC
63251 CCCAGAGGAA CAGCACCAAG GGAGGCAGCT GGCTTCAGGA AGGGATGCAT
63301 GCGGTTGTCT GGGACACTCA GGGCTGATGT CCTTGAGTCT GAAGTGCTAG
63351 CTGGAAGCCC AGGCAGTTTC CAGGTTGCAG CCTCGAGGGG CGTTCTTTCC
63401 CCAGGAAGAC CGAACCTGGC GGATGCACCC ACCCTGTGAG GAAGGGTCCC
63451 CCGCCAGACT CAACAGGCGA CTGATTTAAG TTCGTCTCAT CTAAAAATAG
```

FIGURE 3-24

```
63501 CTTCATAGCA ACACCCAGAC TAGTGTCCGG CCAGGCTGTG CACTGCCCAC
63551 CACGTGGGTG CTGGAGTCAC AGTGCAGGCC CCTCACCCCT CGTCGGCCTG
63601 GCCTCCCTGG GCCGTCAGGC ATCTTTCACA CATGGGACTA TTTTTGCCAA
63651 ATGCTGCACC CCTGGGCCGC AAAGCAGAGA GTCACGTTTG TACCATCTGT
63701 CCTGTCTCTT CATCGGGCAG AACATCGACC ATGTAGAAAC TCACCTGTGC
63751 TTCCAGAACT GCCAGGCTGC TTTGTGCACT TCCTGGCTCC AGGCCCTGGC
63801 ATGGGCTGG GGTAAGGTCA GGGCCAGTGG TGGCCCTCGG AGTTTTGAAC
63851 CCAGAACAGA CAGCCGCCGA GACCGGCAGG ACACTGAGGA GGCGTCGAGG
63901 GGCTGAGTGA GGGTTGGACC TGGTCCCCGT GCTTGTCCGG CAGGACTCCC
63951 AGGCCGCACA GTGGCCGAGG AGGCAGCTCC AGGAATGGGC AAGGGAAAGG
64001 GGAGTTGTGA GGCCGCTGGG AGGGGCCTCA GAATCAGTCG GGAGAGGGCA
64051 CCACTGAGCC CCAGCCCTGC TGGCCCCTCC TCCCGGTCCC TGCCTCTGCC
64101 TCTCAGCACA CCTGGTTCCA CCTCCAGGCA GCAACGGCAG GGGACGCCAG
64151 CAGAGCGTGC CACCTCTGAA CAGCCACCCA GGCGCGCTCT GCCTGAGTCT
64201 CGGGCTGTGC TAGAGGCGCC TCTGGCCATG GTCCTCTCAC GGCTGGGCTT
64251 CCTGGCCCCC GCGCTGGTGG GTGGGGTTCG GGTGCTCTTG AGCTGGAGAG
64301 CAGAGGGCCT CTGCATGTTG GGGTGAGCCT GCCAGCAAGA CAGGAGTAGC
64351 CTTCTGTGGC CTCAGAAGCG CCTCCCCACT CTCCTGTTGG AAGCGAGTTG
64401 CAGGCCCCGC CTGCTCCTGG GGGTGGGGGG CACAGCTGAC TTCAGGAGCC
64451 CAGCTTGAGC CACCTCTCAC AGCGGCCTTG GTGAGGGGGG GCTCACCTGT
64501 GGGGGGCTCA CCTGTGGGGG GCTCACCTGT GGAGGGGCAT CCCCAGACTT
64551 GGGAGTGGGT GGCATATGGG CCAGGGTCAG GGCGTTAGGG CTTGGAGAAA
64601 GGTTAGGGTT GGGGTTGGGG TTAGAGCCAC GGTGATGGTC AGGGCATATG
64651 GGCTAGGGTT AGGGCGTTGG GGTCAGGGCC ATGGGTTCTG GCTAGCACTG
64701 TGGAGACAGC CGTTTCTATC ACGAAGCGAT GGAAGATTCC GCCGTTCCAA
64751 CCCCAGATTC GAGGGAGGCA GGGGTGTGGA CGGTGCCACA CCTCAATCCT
64801 CACAGCCTCT GTCTCCCACT GCCCAGGCTG GCGAAGAAGT CCTGGTTTGG
64851 GAACTTCATC AGCCTGGAGA AGGAGGAGCA GATCTTCGTG GTCATCAAAG
64901 ACAAACCTCT GAGCTCCATC AAGGCTGACA TCGTGCACGC CTTCCTGTCG
64951 GTGAGGCCAC AGGGCGCTGG GGGAGGCGGG CAGCCCTCCC AACCCCACAC
65001 GGCCCAGCCC CGAGAATCCA GCCTCCTCAC GTAGACAGGA CATGTCCACG
65051 CGCACAGCAC GGACGTCCGC TCACCCGTGG GCCTGCCTGG CCGCCTTCAC
65101 TGGACAGGCG CTCTCTCCTG CCCACCCTCG TGAGGGAGGG GTCACTGCCC
65151 ATCTGGGGTG CTTGGCCTGC GGAGGGAGTC AGGGCTTTGC TCACTGGTCC
65201 CCAGCAGCCC TAGGTGTGTG CCGGACAGGC CTGGGCAGCT GGCACGTGGG
65251 GCAGAAGGAA GGCTCCAGCT GGGTGGGTCT CAGAGGGGGA CATTTCCATC
65301 AGACTCGGGG AGAAGCCCTT GTGAGGCCAT GGCCCTAGGG ACCGGTGGGG
65351 CTCTGCTGGC CCTCAGTGGA CAGCCCCAGC CCTCAGGTGT CTCAGTTTCC
65401 CTGGTCTCAC CCTGCCCTCG GAGGCCGGGT GGCTCTCCAC AGAGTGGTCG
65451 CGCTCGGGGT CTTGGGTGGG CTTCATTTGT CTTTGCTGGG CATCTTTGGG
65501 TTAGGAGGAG CAGAAAGGCC CTAAAAGCCT CAAATGGAGA AAGTTTATTG
65551 CCAGGACTCC AGCACCCAGT CCCATCAGGA CGCCCCTTCC TTGCCGGCCC
65601 TGCCCCACCC TGTGCTGCAC CCAGCGCCCA GGCATCACAG GGGCTGCCCC
65651 CCACCCGCCT CCCCCACCGC CCCAGCCTG CCTCCCCAGG CTGCTGTCC
65701 TGCCCTGTGC TCACCACTGC CCGGGCGCCC TCCCTGGCCC CAGGGTCTTG
65751 GCAAGATCAG GCCGTGGTTC GCTTCGGCAG CCTCTCTAGC TAGGGACTGG
65801 CCCCCACCCC ACCATATGCT CTGCCCCCGG GCACTCAGGC CACTGCTGCC
65851 CTGGCTGCAG CTGAGCTTCC CTTACGCTGT GGGGACAGCT TGGAGCCCCT
65901 GCAGAAGGCT CCAGGGCCAG GAGAGCCCAG CGCTGGGCAG GGCAGGCCTC
65951 AGACTGCACT TGGACCCTGG CCTCAGGGGT CCTCAGCGTC CCCGTCCCCG
66001 TCCCCACAGG CTGCTCACTT CCTCGGCCTC CTCCCTCACC ACATCCCTTC
66051 ATGCTGCCCC TGGTTGCCAC GGCTAACCTC AGACTCAGCC CCTCCCCATG
66101 CCGGCCCCAG TGAGGCGGCT GTGTGCCAGC CTGGGCCCTG TGCGCTGGGT
```

FIGURE 3-25

```
66151 GGCCCTGAGT TCTGCTTCCT GCAGCTGCCC CCTCGGTACT GTGAAGCCCA
66201 CCCAGCCAGT GCCCAGCACC ATAGGTCCCG CAACCAGTGG GAGTCCCAGG
66251 AAGCCCCAGC AGGAGGGCAC AGCCCCAGCC CCGCCCTTGC ACCTCCCTCT
66301 CAGTGGCAGC TCCCAGACCC CCCACCTCCC ACTCAGCTCC ACCCTGGACC
66351 CCCACCTCAG GCTGCAGGGG TCACCTTCCA CCTCCATCTT TGCCCTTAAG
66401 GCTCCTCTGT AAGGTCCTGG TCATCCTGTG CTGTGGCTGC CTGAGAAAAG
66451 CCCGGCAGGG GCTTAGCTGT GCCCGCTAAG TGGACCAAAG CTTTGGAGGG
66501 TGGGGGCTGG AAACGCCCCT CCCCCTGCTC CAGCCGTCTC CAACCGCACT
66551 GTGCCCCTCA CGGAAGCAGA GGTGCCTGGG TGCTCACAAT GTGTGCACGG
66601 TGGGGCTGGC TCGCCCCAGG GCTGCCTCCC CAGAGGGCCA GGGTGGGACC
66651 TGCCAGGCCA GCCACGCTCA CGCTGCTCTC TCTCCACAGA TTCCCAGTCT
66701 CAGCCACAGC GTCATCTCCC AAACGAGCTT CCGGGCCGAG TACAAGGCCA
66751 CGGGGGGGCC AGCCGTGTTC CAGAAGCCGG TCAAGTTCCA GGTTGATATC
66801 ACCTACACGG AGGGTGGGGA GGCGCAGAAG GAGAACGGCA TCTACTCCGT
66851 CACCTTCACC CTGCTCTCAG GTGAGCTGGC GCCCCCAGGG CGGCTCCGGG
66901 CCCAGGCCCG TCCAGGGCAT AACCCCCTGT CTCCCCTAGG CCCCAGCCGT
66951 CGCTTCAAGA GGGTGGTGGA GACCATCCAG GCCCAGCTGC TGAGCACACA
67001 CGACCCGCCT GCGGCCCAGC ACTTGTCAGG TGAGGCGGGC TCAGCTCCGG
67051 CCAACCTGCG GCCTGCGAGT GGGGCGTGGC CAGCTGGTGC TGCGCGGACG
67101 GGAGGCGTGA GGACCCGGGC GCAGCCTCCT GGCCCCTCTT GACGGACGCC
67151 CCCACCTCCC TGCCCCGAGC TGTGGCTGCA CCCCTCAGGG AGCAGAGCCC
67201 CTCCCTGGCC TGGCGGGACC ACCCGCCTCG CCTCTGCACG CCAGGGACAT
67251 AGGGCGCAGC CGCACCACAC TGAAAGGCGC CTCTTGTCCA CCGTAGAACC
67301 CCCCCCACCA GCGCCAGGAC TAAGCTGGGG TGCTGGGCTT AAGGGCCAGA
67351 AGGTGGCCAC CAGCTACGAG AGTAGCCTCT GACGCTGGCA GGTAAGGCGC
67401 CCGGCCTGTG CTGGGCGGG GAGGGGCTGC GGGCAGGTCC TCGGCGGAGC
67451 CAGGCTGGCC CTGAGCAGGG CCCTCCATGC CCACCCACAG GTCTCGGCCC
67501 TGGACAGGCC AAGCATGCCC CGGGCGGCCC ATCTGCTAGG GCAGCCTGCA
67551 CAGGACCTGG GAGAGCAGTG ACAAGGCCCT GCCCTCGGGA CTCCCCGCCA
67601 TGGCACCCTA GGAGGGCCGC GGGCTGCCTG ACGGGCTGTG ACTTCTCATC
67651 TCTCCATACT TCCTGACAGC CCAGGGCCAT GCCTCCAGCA GGGCAGAGGG
67701 GCTTGAGCCC AGCCAGAGCG GGGGCTTCAC CACAGCCTGA TGGGCTCACA
67751 CAGGGGAGGG TTGCCCCAGC CTGGAACCAC CAGGGTCTAG GACCCGAGGG
67801 TCCGTGCCAC TCGGCATACG GCAGGGAGGG CTCCCCCCAC TCCCCTGGGC
67851 CCATGTGTGG TGGGGGCAGG GCGGAGCACT GGGCACATGC ATGGGCCTGG
67901 TCTGTCAGCA AGGGGGTGTG GGTGTGCCTC TGAACGCTGG TACGGCGTGG
67951 GGGCGCTGGG CGTCGTGGGG GAGCACCCGG CTGGACCCTG GGGGTCCCCT
68001 CTCCCAGCCT GCATCTCAGC AGCTCCGTGG CATGCTAGGG TCACCTCCTG
68051 TGTTTCCATG TGGGGTCCTG GAAGCCAAAG AGGGCCCCAC TGCCCCTCCC
68101 CATGACATCC TCATTCCATC ATCATGCCAT CACCTGTGGG AGCCCCCCCA
68151 GAGTGTGCTT CACCTTGCTG CGGGCTGGGG GCTGAGGTCC CCAACAGCCC
68201 TGGCCCTAAC CGAAGCCCCA GTGGGTGGAG GAGTAGCCCC CTTCTCCTGA
68251 TTTTGGGAGC CAGGCTGGCA CAGCGGGTAA GGAGGAGCAG GGTTCCAGGT
68301 GCTCGGCCCC GCAGGTACAC GTGGCGCTTC CCTACAGCGG AGGCCATGCC
68351 GTCGGCCGGC AGCAGCCTCT GGCTCTCTGA GCCTTGAAAG CCTTCATCTT
68401 AGGAAGGGAA ACCGAGGCCA GGGAACGACA GGGCAGCCAC CTAGGCCAGG
68451 GATGGACAGG GCTTGTCTGG TAGGGCAAGC AGAAACGGGC CCCGGGGTAC
68501 TGCCCAGGGT GTCCCCGCAC CTGAGCAGCC ATCTGGGTGC CTCAGTCGAG
68551 CGCTCCTGCG TGGGCTGTAG GCAAAGCTCC CCCAGCCTGG CCCCTTAAAG
68601 TGTGGTACCG CCTGTCAGCA CGCAGCACTC CCCTGGAGCC AACTCCAAGC
68651 CCCTCTCCAT TCCTGCCCCG GACCCTGACC TCAGTGGAGC CCACTGCAGA
68701 GGCTCTTGGG GGTCTATTCT GGGCCCCATC TATCTCCCTG TGGACTTGGG
68751 GAGCCCAGCC TATCCCCGTG ATCTCGCTAC GCCCAGCCCT TCCCAGCCCT
```

FIGURE 3-26

```
68801 GCCCCCCTCC CACACTGGAT GCTTTTGTCC AGTGAGCCCA GCTCCAAGGA
68851 TGTGTGGAAG GTGGCTAGCC AGCAGGGGGC CTCCTCAGAC ACTGCCCACC
68901 CCCCCAGAGA CTGCGGCCGA GGGAGGGGAG GCTGAGAGCC CCCAGTGAGC
68951 AGGCACAGGC AGACCAGGGC GTGTGTCCAC CCTGTGCAGG CGCCAGTGAG
69001 GGCCTTGAGG GAGTAGCCCC TCCCAGGGCC TTGCTCCCAC CCCAGTCCTG
69051 GACTGGCAGC ACCAACATCC CCAGGCCCAG CAGTAGGGAA GAGGGCCGAG
69101 GAAGAGGGTG CCTGCCTTGA GTTGAAGGGC AGCCAGAAGC CACAGGGCCC
69151 TGGAGCTGCT GAGTGGCACA GTGAGGATGC AGGCCACGGC CAGGGCAGAG
69201 TTGTCAGCCC AGGGGAGGGG CTAGGCCCAC CCAGGGCACC GGCCATATCC
69251 AGGCTCAGGC TCAGGCTGCT GGAGGTCCGG CTGCTGCCCA GGTGGCTCCG
69301 CCTTGTTCCC TGCCTCCGCA GCCCCGCCTC ACTCCAGGCC CTGCCCCTGC
69351 ACTGCCCCTT ATAAGCCCCG CCCCCTCTGG CTCTGGCCCC CCAGTATTC
69401 CCCACCCATG CCTCTGGGGC CCTACCCACT CCTGGCTCCA CCCCCTCCCC
69451 ATCGAGGCTG TGGGCGTCCA GCCAGAAGGC CCAGGACAGC CTTTCACTCA
69501 CTCCCTCCCT CCTCTCTCCA TTCTGTACTC CAGACACCAC TAACTGTATG
69551 GAAATGATGA CGGGGCGGCT TTCCAAATGT GGTAAGAATC CCCCACGCTC
69601 ACCTGGCACC TCCACCTGCC ACTTCACCGC TCACCCTCAG CCCGCTGTGG
69651 CCGCCACCTG CCGCCCGGGT TGTCCCGGCC TCCCTGTGTA GATGTAGGCA
69701 CCCAGCAGCC CAGATGTCCC CGGCCCCATC CTCTACCAGG AGCAGCCCCC
69751 GTCGCTCCCC TACCACAGCA AGCCCAGGCG GGGTTCCTGG CCAGACTCAC
69801 CTCTGCCAGG CCCTAGGATC AGGGCAGGCC CAAGAAGGGG CTCCCAAGGC
69851 CTGAAGCCAG TGAGGGTCCC GCTGGTCCCA CTGGTGCAGG CTGTGGCCTA
69901 GGGGAGGGGC CGGTGCCCAT CCCTCTGTCC ACTGGAGGCT GTGCCTGGCA
69951 GGGAGCGGAG GGGCCCACAG CTCAGGGCTC AGGTGGGGGT TAGGCTTAGG
70001 AAGTGGGATT GAGGGGCCTC CATCGACACA CCTGGGCAGT GAGCACAGGG
70051 CCCCAAGAAG GGTGGGCTCC CCATTTCCGC CCCTCTTCTC AGGACTGCCC
70101 CCATCCCAGG GACCCGGGAC ATGACTCTAG CTGCTTGCCC CCAGCCCCCC
70151 AGCCTGCCTC CCACATCCAC CCCTCCATGC TTGTCCACCC ATCTGTTCAT
70201 CTGTCTGTCT GCTGCTAAAC TGTGTCCAAG CTGGCCAGGG GTCGGGCTTC
70251 AGGCCTCTCT GGGGAGGTGT GGTGGGCACA CCCTCTCCCT GTCATCCACT
70301 GGCCCTCATG CAGTGGGGCC AGCAGCTGCC CCCAGGGTCC TGCGAGGCTT
70351 CAGAGCTCCC AGCAGGCCCT TGTCTTTACG CTG     (SEQ ID NO:3)
```

FEATURES:
Genewise results:
Start:  2258
Exon:   2258-2348
Exon:   46565-46659
Exon:   48827-48912
Exon:   51308-51448
Exon:   52834-52950
Exon:   53450-53483
Exon:   53679-53747
Exon:   53833-53983
Exon:   55318-55345
Exon:   55637-55801
Exon:   55914-56011
Exon:   56100-56250
Exon:   60104-60164
Exon:   60915-61122
Exon:   61698-61746
Exon:   64827-64950

FIGURE 3-27

Exon:  66690-66870
Exon:  66940-67029
Exon:  67297-67379
Stop:  67380

Sim4 results:
Exon:  2258-2348,   (Transcript Position: 1-91)
Exon:  46565-46659, (Transcript Position: 92-186)
Exon:  48827-48912, (Transcript Position: 187-272)
Exon:  51308-51448, (Transcript Position: 273-413)
Exon:  52834-52950, (Transcript Position: 414-530)
Exon:  53450-53483, (Transcript Position: 531-564)
Exon:  53679-53747, (Transcript Position: 565-633)
Exon:  53833-53979, (Transcript Position: 634-780)
Exon:  55314-55345, (Transcript Position: 781-812)
Exon:  55637-55801, (Transcript Position: 813-977)
Exon:  55914-56011, (Transcript Position: 978-1075)
Exon:  56100-56250, (Transcript Position: 1076-1226)
Exon:  60104-60164, (Transcript Position: 1227-1287)
Exon:  60915-61122, (Transcript Position: 1288-1495)
Exon:  61698-61746, (Transcript Position: 1496-1544)
Exon:  64827-64950, (Transcript Position: 1545-1668)
Exon:  66690-66870, (Transcript Position: 1669-1849)
Exon:  66940-67029, (Transcript Position: 1850-1939)
Exon:  67297-67382, (Transcript Position: 1940-2025)

CHROMOSOME MAP POSITION:
chromosome 11

ALLELIC VARIANTS (SNPs):

| DNA Position | Major | Minor | Domain | Protein Position | Major | Minor |
|---|---|---|---|---|---|---|
| 938 | G | C | Intron | | | |
| 3591 | A | G | Intron | | | |
| 3799 | T | C | Intron | | | |
| 3801 | C | T | Intron | | | |
| 3978 | T | G | Intron | | | |
| 4382 | C | T | Intron | | | |
| 4559 | A | G | Intron | | | |
| 5323 | A | G | Intron | | | |
| 8915 | G | A | Intron | | | |
| 9342 | A | C | Intron | | | |
| 9610 | A | G | Intron | | | |
| 10409 | T | C | Intron | | | |
| 16073 | G | A | Intron | | | |
| 16113 | G | A | Intron | | | |
| 19572 | C | G | Intron | | | |
| 25559 | A | G | Intron | | | |
| 25609 | T | C | Intron | | | |
| 25758 | C | G | Intron | | | |
| 26083 | G | A | Intron | | | |

FIGURE 3-28

| | | | | | | |
|---|---|---|---|---|---|---|
| 26655 | C | G | | Intron | | |
| 27511 | T | C | | Intron | | |
| 29276 | T | G | | Intron | | |
| 30637 | T | C | | Intron | | |
| 30647 | A | G | | Intron | | |
| 31815 | C | T | | Intron | | |
| 32010 | G | A | | Intron | | |
| 32258 | C | T | | Intron | | |
| 32488 | T | C | | Intron | | |
| 34431 | A | G | | Intron | | |
| 34590 | G | C | | Intron | | |
| 36326 | T | A | | Intron | | |
| 36470 | C | T | | Intron | | |
| 36566 | T | C | | Intron | | |
| 39133 | G | - | | Intron | | |
| 39635 | G | A | | Intron | | |
| 40009 | G | A | | Intron | | |
| 40257 | A | T | | Intron | | |
| 47527 | G | A | | Intron | | |
| 47654 | T | C | | Intron | | |
| 49643 | T | C | | Intron | | |
| 52314 | G | A | | Intron | | |
| 53161 | T | C A G | | Intron | | |
| 53245 | A | G | | Intron | | |
| 54358 | G | T | | Intron | | |
| 54374 | C | T | | Intron | | |
| 55833 | A | G | | Intron | | |
| 56950 | T | C | | Intron | | |
| 59273 | C | T | | Intron | | |
| 59422 | C | T | | Intron | | |
| 63028 | G | A | | Intron | | |
| 63084 | C | T | | Intron | | |
| 63178 | C | T | | Intron | | |
| 63307 | G | A | | Intron | | |
| 63483 | C | T | | Intron | | |
| 66192 | T | C | | Intron | | |
| 66193 | G | A | | Intron | | |
| 66229 | C | T | | Intron | | |
| 66754 | G | C | | Exon, coding | 578 | G | A |
| 67590 | A | G | | Intron | | |
| 67677 | C | T | | Intron | | |
| 67750 | A | G | | Intron | | |
| 67793 | - | G C | | Intron | | |
| 67954 | C | T | | Intron | | |
| 68164 | C | T | | Intron | | |
| 68235 | G | A | | Intron | | |
| 68278 | T | C | | Intron | | |
| 68499 | A | G | | Intron | | |
| 68713 | T | C | | Intron | | |
| 69097 | G | C | | Intron | | |
| 69135 | A | G | | Intron | | |
| 69749 | C | A | | Intron | | |
| 69750 | C | G | | Intron | | |

FIGURE 3-29

DNA
Position
938 TACACGGGCAAGATCTGGGACCCCCACTTCTGCAGCGTTCCGGGTCTCCCTCACCTCTCC
CCTCCCACCACCTTCTGCAGCACGGGCTTAAGGAAATACCAGTGTTTTTCTGCAAAGAAA
CAGAGGGTCCGTCCAGGTCTGGCTGCCTCTTCGGCTGCCTGTGTTTAGACCTCCAAAGGC
TGCTCCCGGCAACCCCTGCCCAGCTGCTCAACCTGAAAGAGGGGTCGGTAGCAAGGGCCG
GGAGGCGCCAGGGCGCTGCGGCCGGATCCCAGGTGAGTTCCTTGACTCCGCGCCGCGCAG
[G,C]
TCACTGTGGCATAACTGGGAAAACCGCCGCTTCTCCCTCGGGAGCGGAGGCGGAGGGCCA
CGTCCTCCCTGGGGGTGCACAATCTCTGCTTGGACAACGCCCGCGTGCAGTAGCCCCACA
GACTCCCATGCAGCCCCCCGCCACGTGTGCCGCATCCGCGCCCTGCATGCAACACCCGC
CCCCTCCAGCGCAGCATGCCCCTCGCTGGCGTGCAGCACCCCCCATGTGTGCAGCACCCC
TGCCCCGAATACAGCACCTCTCCCCAGTACAGCACTCCCGCCCCGCATGCAACACTCGCC 3591 CAATCCGAGAAGTTCCTTAGACCCGGGCGGGCAGGGGTGGAGGGAAGGAGGAGGAGAGCG
CTGGTGCAGGGTGGAGGCTCAGCCCCTCACGGCTGCACAGAGGAGGAGCTGGGAGGTGGC
GTTGGGGAAAGAAAGTGGGCCAGGCCCAGGCTCTTGGGGAGGGCCGTGGCTGTGATGTA
ACTACGGCAGAGCTGCAGGAAGGGGTTTAGACTGAGGGGTTCAGGGGAGCTGCCTCACCT
TGGGTGCACAGCCTTCCGCCACCCGCCACGGCACGGAAGGGCCCCTGGCCACAGGGCAGG
[A,G]
CCTGGGCAGGTGGGGTGGTGCAGCCTGGGTTGGAGAAGGAGGTGGCATTCAGCCCATGTC
ACCTGAGTTCAAAATTCTCGTCTTTCCCGGAAAGAAAAACTAGTGTGTGAAATCCGTGGT
GAAGGAGGGGCCCAGGGCAGCAGGATGCAGGAGTCAGTGAGATAATCCAATTACGGTCCC
AATAAAATGTTATTATAAGGAAACATCCGTGTGTAAATGAAGACACGATGAGTTATGTGC
TGTGCGCGGCCTCGGTGGGTAGGGGCTGGTCTCCACTCTTCATGGCATTCTGCTGGCGGC 3799 AGACTGAGGGGTTCAGGGGAGCTGCCTCACCTTGGGTGCACAGCCTTCCGCCACCCGCCA
CGGCACGGAAGGGCCCCTGGCCACAGGGCAGGGCCTGGGCAGGTGGGGTGGTGCAGCCTG
GGTTGGAGAAGGAGGTGGCATTCAGCCCATGTCACCTGAGTTCAAAATTCTCGTCTTTCC
CGGAAAGAAAAACTAGTGTGTGAAATCCGTGGTGAAGGAGGGGCCCAGGGCAGCAGGATG
CAGGAGTCAGTGAGATAATCCAATTACGGTCCCAATAAAATGTTATTATAAGGAAACATC
[T,C]
GTGTGTAAATGAAGACACGATGAGTTATGTGCTGTGCGCGGCCTCGGTGGGTAGGGGCTG
GTCTCCACTCTTCATGGCATTCTGCTGGCGGCAGTTAATTACGGGAGGTTTCCACTGTAA
TTAACAGTAATGAATACAAAAGGATGGGCTGTGTGTGTCTACAACGTGCTGAGAGAGATA
TTTAGAAAAACAGCTCGAGGGGGGGCACAAAGCGGCCCCTCTCTCCCGAGTTATGACGGGC
AGAGCGCAAGCGTGTCACCGGGAGGGCCCTGGAGAAGGCCACCATTTCTGTGCGTCTTCT 3801 ACTGAGGGGTTCAGGGGAGCTGCCTCACCTTGGGTGCACAGCCTTCCGCCACCCGCCACG
GCACGGAAGGGCCCCTGGCCACAGGGCAGGGCCTGGGCAGGTGGGGTGGTGCAGCCTGGG
TTGGAGAAGGAGGTGGCATTCAGCCCATGTCACCTGAGTTCAAAATTCTCGTCTTTCCCG
GAAAGAAAAACTAGTGTGTGAAATCCGTGGTGAAGGAGGGGCCCAGGGCAGCAGGATGCA
GGAGTCAGTGAGATAATCCAATTACGGTCCCAATAAAATGTTATTATAAGGAAACATCCG
[C,T]
GTGTAAATGAAGACACGATGAGTTATGTGCTGTGCGCGGCCTCGGTGGGTAGGGGCTGGT
CTCCACTCTTCATGGCATTCTGCTGGCGGCAGTTAATTACGGGAGGTTTCCACTGTAATT
AACAGTAATGAATACAAAAGGATGGGCTGTGTGTGTCTACAACGTGCTGAGAGAGATATT
TAGAAAAACAGCTCGAGGGGGGGCACAAAGCGGCCCCTCTCTCCCGAGTTATGACGGGCAG

FIGURE 3-30

```
         AGCGCAAGCGTGTCACCGGGAGGGCCCTGGAGAAGGCCACCATTTCTGTGCGTCTTCTGT

3978     CCGGAAAGAAAAACTAGTGTGTGAAATCCGTGGTGAAGGAGGGGCCCAGGGCAGCAGGAT
         GCAGGAGTCAGTGAGATAATCCAATTACGGTCCCAATAAAATGTTATTATAAGGAAACAT
         CCGTGTGTAAATGAAGACACGATGAGTTATGTGCTGTGCGCGGCCTCGGTGGGTAGGGGC
         TGGTCTCCACTCTTCATGGCATTCTGCTGGCGGCAGTTAATTACGGGAGGTTTCCACTGT
         AATTAACAGTAATGAATACAAAAGGATGGGCTGTGTGTGTCTACAACGTGCTGAGAGAGA
         [T,G]
         ATTTAGAAAACAGCTCGAGGGGGGGCACAAAGCGGCCCCTCTCTCCCGAGTTATGACGGG
         CAGAGCGCAAGCGTGTCACCGGGAGGGCCCTGGAGAAGGCCACCATTTCTGTGCGTCTTC
         TGTTGCTGCTGCTGAAGGGTCACCAGGAGTTGGGTGGACATGGGGCCTGGAGTGTGTGTG
         CTGGGCCACTTGGCACCAGATGCCAGGAGAGCTGCCAGGTCCCAAGCTCAAGAGGGAGAT
         AGGCTTCCTGCCAGGAGACCTCCGTGGGAGAACGGGAGGCTGGGCTTCTGGCCGCCACCA

4382     CATTTCTGTGCGTCTTCTGTTGCTGCTGCTGAAGGGTCACCAGGAGTTGGGTGGACATGG
         GGCCTGGAGTGTGTGTGCTGGGCCACTTGGCACCAGATGCCAGGAGAGCTGCCAGGTCCC
         AAGCTCAAGAGGGAGATAGGCTTCCTGCCAGGAGACCTCCGTGGGAGAACGGGAGGCTGG
         GCTTCTGGCCGCCACCACCCGAGGACGATCTGATCCTGCCGTTGAGAACGCTTCTCCTTC
         CAGGGACCTGGCCACAGGGGAGCTGTGGAGGCCTTGCTTGGGGGGCCATTGGTGTGGACG
         [C,T]
         GACTCCAGCCCCTTCCCCGTGTCTGTGGCTGGCAGCTTTGTTTGGCCCTCTCTGTTCATC
         TCTCTCAGCCTGAGACCTTGGAAGGAGGAGCTGCTCGACTTGAGGTGGCCACTGAGAGGG
         AGGTGGTCAGTGGCAGTGGCAGTGAGCCTTGTGGTGCCACGAGAGCCCTTCCACCCAGCT
         GACCCAAGCTGGGGCCTGCTGGACGGTGGGCCAAAGATGTGGTCCGAAACCTGCCCTTGG
         GGAGTCTGGCCGTGTGGGGAGGGGAGACCACGCAGCACCCCACCGGGGCCTGGAGGACG

4559     TGGGCTTCTGGCCGCCACCACCCGAGGACGATCTGATCCTGCCGTTGAGAACGCTTCTCC
         TTCCAGGGACCTGGCCACAGGGGAGCTGTGGAGGCCTTGCTTGGGGGGCCATTGGTGTGG
         ACGCGACTCCAGCCCCTTCCCCGTGTCTGTGGCTGGCAGCTTTGTTTGGCCCTCTCTGTT
         CATCTCTCTCAGCCTGAGACCTTGGAAGGAGGAGCTGCTCGACTTGAGGTGGCCACTGAG
         AGGGAGGTGGTCAGTGGCAGTGGCAGTGAGCCTTGTGGTGCCACGAGAGCCCTTCCACCC
         [A,G]
         GCTGACCCAAGCTGGGGCCTGCTGGACGGTGGGCCAAAGATGTGGTCCGAAACCTGCCCT
         TGGGGAGTCTGGCCGTGTGGGGAGGGGAGACCACGCAGCACCCCACCGGGGCCTGGAGG
         ACGCCCTTCTAGACGCCGCAGGGTCCGGTCGGCTGTCTTCTTCTGCCTTTCAGCGTGAGC
         GCTGCATGGTCTCACCTGTACGGCACCTGCCTGTCTTGTTGGGTCTGTGCGTCCTGCAGG
         GCCAGTGTGGCTGTAGGGTCGTCCTTCTGCATGGGGCGTCCTCTGCACAGCTCCCCTCGG

5323     AAAGGTGCTGCCTTAGCTTTTCTTGGGGCTGAGAAAGGCTTGTGTAGCCTCATCTGAGCT
         TGACCCCTGCAGAGATGCCGAGACACAGTCCCTGCCAGCAAGGGCAACCATGGAGGTTGG
         AGGGCGCAGACACTCCGAGTTGGAGCATGCAGGTCCAGGAGGGTGTGTGGCACGGGCTGG
         GTGGCTTTTGTCCCTGCGCGCCTTTGTCCCTGTGCCCCATCAGTACGTGGAGCAGGGCAC
         CTTCTTGCCCAAACCTCGGCTTAGCTCCTGAAATCTGGGAGGCCTGGGAGGGCCCTGTGG
         [A,G]
         AGGAGCTGGAGAACCTCGGGCCCTTGGAGCTGTTCTTGGGGGCAGGCGGGTGGCTGCAT
         GGGACGATGAGGGGCCTGCCTTCGGGAATCCTCTGTCTGGGGGGCGGGAGAAAGGAATAA
         TGGCCGCGATAGGGCTCCCTGCGAGGGAACGAAGGAGCTAGGATGAGGGGCTGCCCTGCA
         GCTCACCTGGCAGTGTTCACCTGCTGTGGCGTGGGGGAGGGACCTAGGCTGCCAGGGACC
         TGGGGCCGCCCCTCCATGTTCTCAATGGCCTTTAGGAAGGTTGAGCCCTGGTGGCTGCCA

8915     CCTCAGGGCCCCTGAGTGTAGAATGGGGTTTCCCTGAAGCTTGTGCGAGGTTCCAATGGC
         TGGAAACACCGTACCGCGCAGGAGGACGGCAGACCAGCATCTGTCAGGCCCCTTGGGGCT
         CACATGGCTGGTCCTCTGTGCTGCCCTGTGCTCTGCAGGAAGTTAACGGCACCCTGCCAC
```

FIGURE 3-31

```
          CTCCTCTGTGCAGGGCAGCCCCGCTTTCACCTGTAGGGCTGGTGCCTGTGTCAGGCCCAA
          GCCCCAGGTCCTAGCCTAGGCTGACCAAGCGGCCTGCAGATCTCCCTGAGGCCTCACCCC
          [G,A]
          GGGATGTCCGCCGGGCCAGGCTGCCCTGAGCCAGCTGCCTGGGGCTCTGGACAAGATGGA
          GGCTGGGCTGGGGCAGAGGCTGCAGGGACAAAGCACGGATTGTGCCAAGCCGGCTGCCTT
          TCAGGGCCCGGCCTGCCAGGTCCAGGCCTTGTTCTACCGCCTCTGAGGGGCCAGTGTTCT
          GGGCCCAGCAGCTGGGAGCCAGGCCCCACCCACAGAGCAGTGCTCCCGAAAGTCCTGCTG
          TTAAAGAGAAACTCCTCGTTTTCCTGGACGCCTCCAGCTTCCCAGGCTCGTTCTGCCTTC

9342      CCCGGCCTGCCAGGTCCAGGCCTTGTTCTACCGCCTCTGAGGGGCCAGTGTTCTGGGCCC
          AGCAGCTGGGAGCCAGGCCCCACCCACAGAGCAGTGCTCCCGAAAGTCCTGCTGTTAAAG
          AGAAACTCCTCGTTTTCCTGGACGCCTCCAGCTTCCCAGGCTCGTTCTGCCTTCAGTCCC
          GGGGCCCACGGAGGCCGTGGCTGCCCTACGCTGCTTTGCCCCAGGGGCCTGGGCTGCAGG
          CTGGGCCTGGCTTCCTCCCCGAAACCCTGGAGAGTGACAGCACCACCCCCAGTGGATGGCA
          [A,C]
          GGTCCCATCGGTTGGCATGTGTCTCTCTGGGCACCATGCTCCTCGTTGGGTGCCACGTCC
          TTGGGCTGAGCTTGGGTCCTGTCTGCCCTGGGGGTACCATCCTATGAGGACAGAGCTGCC
          TTTCCTGGGTGGCCATGGCAGCCTCATGGCACTGGCTGAGGGGAATGGACACTTCTGGGA
          TGGAGCTGGGCTGGGGTGGGGCTGGGTAGGGCCAGTGGGAGTTCTGGGCACCTTGGCCTG
          AGGGGGATGGGGGTGCCCAGGGCATTCACGCCATCACTGCCCACTTGGCTTAAGCTGGAG

9610      GAGAGTGACAGCACCACCCCCAGTGGATGGCAAGGTCCCATCGGTTGGCATGTGTCTCTC
          TGGGCACCATGCTCCTCGTTGGGTGCCACGTCCTTGGGCTGAGCTTGGGTCCTGTCTGCC
          CTGGGGGTACCATCCTATGAGGACAGAGCTGCCTTTCCTGGGTGGCCATGGCAGCCTCAT
          GGCACTGGCTGAGGGGAATGGACACTTCTGGGATGGAGCTGGGCTGGGGTGGGGCTGGGT
          AGGGCCAGTGGGAGTTCTGGGCACCTTGGCCTGAGGGGGATGGGGGTGCCCAGGGCATTC
          [A,G]
          CGCCATCACTGCCCACTTGGCTTAAGCTGGAGCCCAGGGCCCTGGAGGGCAGGCTGGCCT
          TCCCGGCCCCGGGCAGAGGTGGGAGGGCGCCTGGACGGCTGCCTGCATGATCCCCGTGAT
          ACAGCGGGGATGGCTGCACGTCGGGCTGAGTCCAGCTGTGGGTGGTTTGCGGGGGCACAG
          GGAGCCTGCCTGGCCAGGAATGTGGCCTCTGCGGGTGTCTTGGCCTGGGAGCCCCCGGGG
          AACCCTTTGTATGGGAGAAGGGGTCGGGATAGGGGCTGGGGGGCAGTGCCTGGTGGCCCT

10409     TGTGGTACCCGCCCCGGGAAGGGTGGTGGCCAGGGTGGCCATGTCAGGCGCCTTGGCCCT
          GCCCCCTGGGGATACAGGGGGTGGAGAGGCAGCCCCAAAGCTGGGTTCTCAGAGACCTGG
          GGTGGCCAGATGGGGGCTCATTCAGCTGCCCCTGTGCAGCCCCTTGGTGCCATTAACTT
          TCTGCAGAGCGCAGGGCAGCACAGAGGGCCAGCCAGGCCAGGGGGCCAGAGGTTCCCCTC
          CCACACAAGCTCCGAGGTGTCCAGACAGGAGGCGGTGGCCCCAGTCCGCATAGGCCTTTC
          [T,C]
          CCAGGGCAGCCCTTTCCCCAGGGTTAGGCTGCAGGCCCTGCCGGTGTGGCTTCAGGAGTC
          CTGGTCCCCGCACTCAAGCTTCCCTCCTGCTCATCTGTGATGGGGCCTGGGTGTACCCAG
          GTCCTTGGTAGGCGCCAGGAGATGTGTGGGGCCCCCTGGAGCCTGGAGCCCCCCAGCCC
          CTCCGCTTATCTTTGGTGTCTGGGGCGGAGACTGGCCCTTGGCACCCGCGGCCGTCCCTG
          GCTTTCGTCCTGCGCCGTCCTGGGTCTTTGGGTCCCTCTGCCAGCCCGTGGTGACTTCT

16073     TCTGGGTGAAAGCTTCCAGAGCCAGCACCCTCTCCACTGTCCCACAGAAGCTGGTGTGGG
          CACACAGCACCTCCAGCCTGGCCCTGGGAGGTTGGAGACTCAGCCCTGCGGCCACCCTTT
          GATTGCTGCCTGCCCCAGCTGCCCGCAATCTGGGTGCGCGGAGCTGTGTCCCTGCCCAGG
          GCCTCACTCCTCTGTGTTCCCCTCCTGTCTCTGGGCCCCGTGTCCTTGATGCTGCCCCTT
          TTCCTGACCCTGCTCTCCTATCACGTCCCCTCTTCAGGGGAGTGGCCACGGGAGGAGGCC
          [G,A]
          TCGTCCCAGCCAGCCCTCCGCCTGCCTCAGCCTCCCAGGGCAGACGTCCCTTTGGCCGAG
          AGTTGCACCTGCCTCTGATCCTTGCCCTTGCTCTGTCTTCCCCTCCGTCCCTGTCCCAGC
```

FIGURE 3-32

```
           ACCCAGAGGAGGTTGGGGTGGGGAAAGGTCCTCGGGGGAGACCATCTGCACGGCCCCTCC
           CTGGATGCCACAGAGCACCAGCCTTGGGAGGGCAGAGGGGGCGCCCCGGAGGTGGATGCC
           CTGCCCTGGTTCCTGATGTGGCCCCTGCCTCTAAGACCACAAGGCACTCAGGGACAGATG

16113      CCCACAGAAGCTGGTGTGGGCACACAGCACCTCCAGCCTGGCCCTGGGAGGTTGGAGACT
           CAGCCCTGCGGCCACCCTTTGATTGCTGCCTGCCCCAGCTGCCCGCAATCTGGGTGCGCG
           GAGCTGTGTCCCTGCCCAGGGCCTCACTCCTCTGTGTTCCCCTCCTGTCTCTGGGCCCCG
           TGTCCTTGATGCTGCCCCTTTTCCTGACCCTGCTCTCCTATCACGTCCCCTCTTCAGGGG
           AGTGGCCACGGGAGGAGGCCGTCGTCCCAGCCAGCCCTCCGCCTGCCTCAGCCTCCCAGG
           [G,A]
           CAGACGTCCCTTTGGCCGAGAGTTGCACCTGCCTCTGATCCTTGCCCTTGCTCTGTCTTC
           CCCTCCGTCCCTGTCCCAGCACCCAGAGGAGGTTGGGGTGGGGAAAGGTCCTCGGGGGAG
           ACCATCTGCACGGCCCCTCCCTGGATGCCACAGAGCACCAGCCTTGGGAGGGCAGAGGGG
           GCGCCCCGGAGGTGGATGCCCTGCCCTGGTTCCTGATGTGGCCCCTGCCTCTAAGACCAC
           AAGGCACTCAGGGACAGATGCTAATGTTTGGGAGGGTAGGAGCAACGGGCGTGGGCTTGC

19572      GGAGACCCCTTCCTTCATGGGGTGCCTCAGACCCCACCTCTGCAGGGGTTCTAGCAGCCT
           GGTTCTAGCAGCTCTGCAGGGGTTCTAGACCCTCTAGGGGCCTCGACGCAGCCCCTAAAC
           TAGGACACTAGCTTCAGAGACTGAATCACCAAATAGTTACAGGATTCAATCAAAATGTTT
           CATCGGGCTAATCTTTCAATATTGAATTGTGAAAACCAGTTAATAGAAGTCTAACGTGAT
           CAACTGGCTCCGCTGGGATTGGGTCCCGCCGCCTCCAGGCAGGTGCCACCTCCAGGAGGG
           [C,G]
           TTTCCCAGAGTGTGGGGCGGGCCCGGCAGGGAGGGGCTGTTTGCTGCTCCATTTGCCCAG
           TGTGCCCTCAGATCCACAGCCTCAGGGCACCTGTGCCCTCCAGGGAAGGCCGCCTGGGTC
           TCCTGCCCACCCTGGAGCTGAGCCCACCTGCCCTGCAGCTAGAGGGGGCAGGGGCTGCCT
           GGGCACCTCCTCCATCACCTCCTGGTGGAGGGGTTCCTGGTCCCAGGTCCTTCCACTCCA
           GAATCCACCTTTGAGCCCCATACTCTCTGCAGCCCATCCTCTGGCCTCCCTGGGGCAAAC

25559      GGGGCATCAGTGGCCCCAGAGCCAAGGAGCAGCCCCAGGGGCTGGAGCTCAGGTGAGGTC
           GGGTGGGTAAGGGGCTGCTGCTGCACAGTGGTGGGCAGCCACAGCGCCCAGCTCCGCCTT
           CCGCCCCGAGGAAAATGGGCTGCCTCCCACACTGGACACACAGCGCCAGCCACTTCCTCA
           CACGGTTTACTGTAGCCAGACTTGGAAATAGTCATGTGATCCCCAGGGATATATAACTGC
           GTTTTCTCCATCTGTGCTTAGTTTAAAAACAATTGTTCATTAATTTAAAAGGAAGAGTTT
           [A,G]
           CCTTCAAACATAAAGATATTCAAATTAAAGATACTCAAATTTTTCTGTATGAACTAGGAT
           TTGTGCTGGTCAAAAATACCACACCCCAAAGTTGCCATTGTCCCGTTGTTTAAAATTCTA
           TGTGCAAATAGAATCTCCAGAGGCCGGGCAGGAGGAGGACGGCCTGGGAGTGTCCAGGCT
           GCTTCTCCGCCTGGAAAGCTGTCTCCATGCCCCTGTGGCAGTTTGAGGCTGGGGATGCCA
           CTGCCCCACAGTGTGCTCCGGGGATCTCAGGGCGCTAGGAACTTCCCTCTGTAGAGAGTT

25609      AGGTGAGGTCGGGTGGGTAAGGGGCTGCTGCTGCACAGTGGTGGGCAGCCACAGCGCCCA
           GCTCCGCCTTCCGCCCCGAGGAAAATGGGCTGCCTCCCACACTGGACACACAGCGCCAGC
           CACTTCCTCACACGGTTTACTGTAGCCAGACTTGGAAATAGTCATGTGATCCCCAGGGAT
           ATATAACTGCGTTTTCTCCATCTGTGCTTAGTTTAAAAACAATTGTTCATTAATTTAAAA
           GGAAGAGTTTACCTTCAAACATAAAGATATTCAAATTAAAGATACTCAAATTTTTCTGTA
           [T,C]
           GAACTAGGATTTGTGCTGGTCAAAAATACCACACCCCAAAGTTGCCATTGTCCCGTTGTT
           TAAAATTCTATGTGCAAATAGAATCTCCAGAGGCCGGGCAGGAGGAGGACGGCCTGGGAG
           TGTCCAGGCTGCTTCTCCGCCTGGAAAGCTGTCTCCATGCCCCTGTGGCAGTTTGAGGCT
           GGGGATGCCACTGCCCCACAGTGTGCTCCGGGGATCTCAGGGCGCTAGGAACTTCCCTCT
           GTAGAGAGTTGGCATCACTGGGATCCCAGGATGAACTTATGTGTGGAATGCGGTGTTCAT

25758      ACTTGGAAATAGTCATGTGATCCCCAGGGATATATAACTGCGTTTTCTCCATCTGTGCTT
```

FIGURE 3-33

```
        AGTTTAAAAACAATTGTTCATTAATTTAAAAGGAAGAGTTTACCTTCAAACATAAAGATA
        TTCAAATTAAAGATACTCAAATTTTTCTGTATGAACTAGGATTTGTGCTGGTCAAAAATA
        CCACACCCCAAAGTTGCCATTGTCCCGTTGTTTAAAATTCTATGTGCAAATAGAATCTCC
        AGAGGCCGGGCAGGAGGAGGACGGCCTGGGAGTGTCCAGGCTGCTTCTCCGCCTGGAAAG
        [C,G]
        TGTCTCCATGCCCCTGTGGCAGTTTGAGGCTGGGGATGCCACTGCCCCACAGTGTGCTCC
        GGGGATCTCAGGGCGCTAGGAACTTCCCTCTGTAGAGAGTTGGCATCACTGGGATCCCAG
        GATGAACTTATGTGTGGAATGCGGTGTTCATTAGAAGCTAAGGAGCCTCAGAGTATGCTA
        AGGTGCAGCTTCAAAGGCAGCAATTGTTTGGAACTTAGGCCAAGGAAGATTTGTGTTTTG
        GAAATGGCATGTATTTTATCACTGACATTGTTTAGTGTAGGGTGATAAAAAGTAGACTGA

26083   TGAGGCTGGGGATGCCACTGCCCCACAGTGTGCTCCGGGGATCTCAGGGCGCTAGGAACT
        TCCCTCTGTAGAGAGTTGGCATCACTGGGATCCCAGGATGAACTTATGTGTGGAATGCGG
        TGTTCATTAGAAGCTAAGGAGCCTCAGAGTATGCTAAGGTGCAGCTTCAAAGGCAGCAAT
        TGTTTGGAACTTAGGCCAAGGAAGATTTGTGTTTTGGAAATGGCATGTATTTTATCACTG
        ACATTGTTTAGTGTAGGGTGATAAAAAGTAGACTGAATTTTTTTAATTAAAATGAAATTC
        [G,A]
        CATAATATAAAATTAACCATACAATTCAGGGACGGTTAGCGCATTCACGGTGCTACGCGG
        CCACCACTGTCTAGTTCCAGAATGTTCCACCCCAAGGGACCCTGCGCCACACGTTCTCTT
        GCCCCTCCTCCATCCGTGGGAGCGTGGCCTGCCTTCCGTTTCTGGACGTGTCACAGACAC
        TGGTCCCATGCTGTGCGTCCCTCTGCGTCTGGCTTCCTTCACACAGCAGAATGTACTCAG
        GGCCATCCCTGTTGTCATCCCTGTTGGGGTTTCCTTCCTTTTGAGGCTGAACACACTTAC

26655   TCCTTCCTTTTGAGGCTGAACACACTTACCTGTGTGGACAGACCACGTTGTTCGCCTATC
        ATCTGCCGTGGACATGTGGCTGCTTCCACCTTGTGGCTCTCAGGAGTGGCGCGCTGTGGA
        CGTGTGTGTGAGTACCCACGTGGGTCCCTGAGCTCAGTTCCTGGGAGCATAGACCTCAGA
        GTGGTAATTCTGTCTTTACCTTTTTTTTTTTTTTTTTTTGAGATGGAGTCTCGCTCTGT
        TGCCCAGGATGGAGTGCAGTGGCGTGATCTCGGCTCACTGCAAGCTCCGCCTCCAGGGTT
        [C,G]
        ACACCATTCTCTTGCCTCAGCCTCCTGAGTAGCTGGGACTACAGGCGCTCACCACCACGC
        CTGGCTAATTTTTTTGTATTTTTAGTAGAGAGGGGGTTTCACCATGTTAGCCAGGATGGTC
        TTGATCTCCTGACCTCATGATCCGCCCGTCTGGGCCTCCCAAAGTGCTGGGATTACAGGC
        ATGAGCCACTGCGCCTGGCCCTGTCTTTACCTTTTTAAAAAAATTAGTTCATTTATTTTT
        CTGAGACAGGGTCTCACTCTGTTGTCCAGCTGGAGTGCAGCGATTTGATTCTGGCTCACT

27511   TTACCTGCTCACTGCCCACACGGTGGTCCCAGCAGAGGACTTGGAGCGGCTGCCCCTTCT
        GTTGCACGGGCTCCACCACGGCCTCCTCGGCCACTGTCCCCTGGGAGGGCAGCTGTGGTA
        AAGGCCGGAGCTCCCAGCTTTGGGCAGGTGAGTGCCCCTGGCAGTTCTTTTCTGTGATGT
        AGGTTTTTCAGACTGGGAAAAGTTGAGAGTTTCAAAGTCCATTGCCAGTGGGAACTGGAA
        CCAGGCAAGCTGAACCAAGTTCATTAGTGCTCTTGGCAACCTCAGGGCTCACCTGGTGCA
        [T,C]
        GGGGACCTTTGCAATGGCCAGGGCCTGGGGCCACCCGAGCTAGGGCAAGGGGAGGGGGAG
        GGATGTGTTTATAAAATTTCTGTTTTAATTTCAAGTACAGTAATGTTGGTGGATAGAAAC
        ACACAAACCACAGCACTTTGATTTTGTCAGTAACTCTTAAGAGTACGGAGGGTCCTGAGG
        CTGGGGGGTCTCGTGGGCACAGAGTATGATGCCTGTGAGGACGTCCTTCCAGCCACACAG
        CCCGTGGACTGCAGCATTGAGTGTTCTATTTCCTGGGTGTCACGTCCGCAAAATCCGCTG

29276   GTCCTGCTTCTGTGGGCTGTTTCTTCTCTTGAGAGTGGGTCACACTGTGTCCTGCTTCTG
        TTGGCTGTTTCTTCTCTCTTGAGAGTGGGTCACCTGTGTCCTGCTTCTGTTGGCTGTTTCTT
        CTCTTGAGAGTGGGTCACACTGTGTCCTGCTTCTGTTGGCTGTTTCTTCTCTCTTGAGAGTG
        GGTCACACTGTGTCCTGCTTCTGTTGGCTGTTTCTTCTCTTGAGAGTGGGTCACACTGTG
        TCCTGCTTCTGTTGGCTGTTTCTTCTCTTGAGAGTGGGTCACACTGTGTCCTGCTTCTGT
        [T,G]
```

FIGURE 3-34

```
         GGCTGTTTCTTCTCTTGAGAGTGGGTCACCTGTGTCCTGCTTCTGTGGGCTGTTTCTTCT
         CTTGAGAGTGGGTCACCTGTGTCCTGCTTCTGTGGGCTGTTTCTTCTCTTGAGAGTGGGT
         CACACTGTGTCCTGCTTCTGTTGGCAGTTTCTTCTCTTGAGAGTGGTTCTCCTGTGTCCT
         GCTTCTGTTGGCTGTTTCTTCTCTTGAGAGTGGGTCACCTGTGTCCTGCTTCTGTTGGCA
         GTTTCTTCTCTTGAGAGTGGTTCTCCTGTGTCCTGCTTCTGTTGGCTGTTTCTTCTCTTG

30637    TGGGGGTCCCTCCAGCAAATTTCTGTTCAGCTCTAACACATATCCAAGGGACTGAACCCC
         TGGGTGGGGAAGTTTTTTCTTTTTTTTTCTGTAGTGCCATAAGTGCCTGTCACTAATAGAA
         GCTCAGTGAATACCTGATTGATTAATTGATTGATCGGTTGATTGATTGAATGCAGCAAGT
         GTCTGGGAGCTCCCAGTTACAGGTGCGTGTCAGGCGTGAGTCTGGGCACCAGGGTGGGCC
         TTTGCTCAGCTGTGTTTGTGGGCTCTGCAGGTGCGTGTCAGGTGTGAGTCTGGGCACTGG
         [T,C]
         GGCGGGGGGGGCCTTTGCTCAGCTGTGTTTGTGGGCTCTGCAGGTGCGTGTCAGGTGTGA
         GTCTGGGCACTGGCGGGGTGGGGGTCCTTTGCTCAGCTGTGTTTGTGGGCTCTGCAGGTG
         CATGTCAGGTGTGAGTCTGGGCACCGGGGGGCCTTCGCTGAGCTGTGTTTGTGGGCCCTG
         GGACGTGATTCCCTCTTGGGTGGTGTTTCCAGCCGCTGGCTGCCCGGGCAGCTCCAAATA
         CTGAGCTGTCAGGTCGGTGGTCTCTCTATGTCTTTCTGTTATCTTGTTCTGCTTTGCTGG

30647    TCCAGCAAATTTCTGTTCAGCTCTAACACATATCCAAGGGACTGAACCCCTGGGTGGGGA
         AGTTTTTTCTTTTTTTTTCTGTAGTGCCATAAGTGCCTGTCACTAATAGAAGCTCAGTGAA
         TACCTGATTGATTAATTGATTGATCGGTTGATTGATTGAATGCAGCAAGTGTCTGGGAGC
         TCCCAGTTACAGGTGCGTGTCAGGCGTGAGTCTGGGCACCAGGGTGGGCCTTTGCTCAGC
         TGTGTTTGTGGGCTCTGCAGGTGCGTGTCAGGTGTGAGTCTGGGCACTGGTGGCGGGGGG
         [A,G]
         GCCTTTGCTCAGCTGTGTTTGTGGGCTCTGCAGGTGCGTGTCAGGTGTGAGTCTGGGCAC
         TGGCGGGGTGGGGGTCCTTTGCTCAGCTGTGTTTGTGGGCTCTGCAGGTGCATGTCAGGT
         GTGAGTCTGGGCACCGGGGGGCCTTCGCTGAGCTGTGTTTGTGGGCCCTGGGACGTGATT
         CCCTCTTGGGTGGTGTTTCCAGCCGCTGGCTGCCCGGGCAGCTCCAAATACTGAGCTGTC
         AGGTCGGTGGTCTCTCTATGTCTTTCTGTTATCTTGTTCTGCTTTGCTGGGAATTTTCTC

31815    TCTCCAAGGAAGCCTGGTTGAGTGCAGAGCCTCCTCTTTCTTGGATAAGAGGGAATGTTG
         TCTTGTGTGAGTCTCTGGAAGGCAGGGCCTCTGCCCGGAGGCTCGGTGTCCGTGCATGCA
         TGCAAGTGTGCGTGCGTGCATGTGTGCGTGTGTGCATGTGTGATGGCCTAATGGGCAGGA
         AGTGGGGTGGCCTTGTTAGGATGAGACAGATTTTGCCACAGGGCCGGCCCCCGCTCTGCT
         GGGTGTGACCCCAACTACCCTTCTTGTTGGCCCAGAGAGGGGAGAGGCTGGCCAGGGCTG
         [C,T]
         CCCAACCTGTGCACGCCCTTGGCAGATGCTCCAGGGTGTCTGCAGCCCCACCTGAGGCCT
         GCCCTGCACTCTGGCTAACAGACATTTTCAGTTTTCCAGGTCCCCTGGAGACAGGCAGGC
         CCAGGCCCACCCCCTGCCTTCTCTGCCTGCCTGCCTCTAGAAGGTTCTTGAATGTTTAGA
         GGTTCCCCCGTCACGGCCAGGCTCCCTTTTGTTTAATTCAGGAAGGTTTGACAGGTGAGT
         GTGAGGTCTGCCAGCCTGGGCCTGGGCCCCTCCATGCAGGCCCTGCCTGGACCCCCTGTG

32010    TTAGGATGAGACAGATTTTGCCACAGGGCCGGCCCCCGCTCTGCTGGGTGTGACCCCAAC
         TACCCTTCTTGTTGGCCCAGAGAGGGGAGAGGCTGGCCAGGGCTGCCCCAACCTGTGCAC
         GCCCTTGGCAGATGCTCCAGGGTGTCTGCAGCCCCACCTGAGGCCTGCCCTGCACTCTGG
         CTAACAGACATTTTCAGTTTTCCAGGTCCCCTGGAGACAGGCAGGCCCAGGCCCACCCCC
         TGCCTTCTCTGCCTGCCTGCCTCTAGAAGGTTCTTGAATGTTTAGAGGTTCCCCCGTCAC
         [G,A]
         GCCAGGCTCCCTTTTGTTTAATTCAGGAAGGTTTGACAGGTGAGTGTGAGGTCTGCCAGC
         CTGGGCCTGGGCCCCTCCATGCAGGCCCTGCCTGGACCCCCTGTGACTCCCCAAGTCCT
         ATCTCCACCCCCTTGGTCCCCAGCTCCAGCCTCTTCCTCCACTGCCTAGACTGTCCCCTC
         GGGATACACCTCCTCCCTGCAGCCTCCTCCCTGGCTGTCACCCTCTTTGTGGCCTGCCTG
         GGGGACTCCTCTGGTTACTCCTGTCCTCAGCTCTAGGTGGGGCTGGCAGTCCTGGGGGCT
```

FIGURE 3-35

32258  CTGCCTGCCTGCCTCTAGAAGGTTCTTGAATGTTTAGAGGTTCCCCCGTCACGGCCAGGC
TCCCTTTTGTTTAATTCAGGAAGGTTTGACAGGTGAGTGTGAGGTCTGCCAGCCTGGGCC
TGGGCCCCTCCATGCAGGCCCTGCCTGGACCCCCTGTGACTCCCCCAAGTCCTATCTCCA
CCCCCTTGGTCCCCAGCTCCAGCCTCTTCCTCCACTGCCTAGACTGTCCCCTCGGGATAC
ACCTCCTCCCTGCAGCCTCCTCCCTGGCTGTCACCCTCTTTGTGGCCTGCCTGGGGACT
[C,T]
CTCTGGTTACTCCTGTCCTCAGCTCTAGGTGGGGCTGGCAGTCCTGGGGGCTCAGCCTCC
ATGTGGCATCCAGCAGGTGCCCGGCAACTCCCTGTTTTTTCCACCTGACCTTAAGAGCCTG
GCTTGAGCCTCTCATGGGGAGGGGCCTGTGCCCCCCAGGGCCCCCTCGGCCCTCTGGCTG
GGTGCTGGCAAGTAGGTCTCAACCCTGGAGCCTGACTGGGGCCTCCCACCGACATCTTTC
ATCTGGGTGCAGAGCAGAGAGGGGCTTTGGGATGCTCAGAGTGATACCCTCAGATCTTTA

32488  CTCGGGATACACCTCCTCCCTGCAGCCTCCTCCCTGGCTGTCACCCTCTTTGTGGCCTGC
CTGGGGGACTCCTCTGGTTACTCCTGTCCTCAGCTCTAGGTGGGGCTGGCAGTCCTGGGG
GCTCAGCCTCCATGTGGCATCCAGCAGGTGCCCGGCAACTCCCTGTTTTTCCACCTGACC
TTAAGAGCCTGGCTTGAGCCTCTCATGGGGAGGGGCCTGTGCCCCCCAGGGCCCCCTCGG
CCCTCTGGCTGGGTGCTGGCAAGTAGGTCTCAACCCTGGAGCCTGACTGGGGCCTCCCAC
[T,C]
GACATCTTTCATCTGGGTGCAGAGCAGAGAGGGGCTTTGGGATGCTCAGAGTGATACCCT
CAGATCTTTAGGATTCAGATCTTTGGGCTGCCTGTGGGCTCCTGGCTTGGCTGACCCTGG
GCCTCCTCCTGGTACAGTCCCAGGCTGTGCTTTGGGTCCCAGGCTGCGCTTCGGAGGGGA
GGGACAGTGTGGGGGCTCTCATTTAATCTTCACCCCCCAGGACGGGGTGTCAGGAGACCC
CTGAGGCCAGGCACGTCTGGGGTCACACCCAGGAGGGAGGCAGGCGTCTGCAGTCTGGCC

34431  CTTCCAAGGACACTCCTCCCTGACAGTCCTGTCCATGGTGCTGGAAGAGCTCTGGCGACC
CCACAGGCAGGCAGGCCTGACCGTCCAAGGCTCGGCTGCCTGTGGGGAACTGGACACACT
TCCTCCAGAGTCTCAGTTTTGCCAGCTGTTTGCCCAGCGCCATGTCCACTCCCCAAGCCA
GGACCGAGGGGGTGACGGAGATGAAGCTTGTGCTGGCCCCAGCTGGGGGCCGCTGCCCAC
CCAGCAAGCCCCACAGCCAGTCCCAACCTGGTGATGTGGTGTCCGGAGGATGGACCTCGA
[A,G]
GTCTCTCAGACCTGGGTTTCTGAGCTCCTCAGGTGTCTGTGTCCCCTCCTGGGAAAGGGA
ACAGAGCTTTGCGAAGATCAAGGGGAGGGCAATGCAGCTTGGGAGCCTTAGCTCAGCCAG
ACAGCAGCCCGGAGGGTTAATGTCCAGGTACCTCCAGGGCCCATGCACCCAGGACCTCCC
CAAGAGCTGTGCCTCCATGTACCTCAGGGCCTCCCCCAGAGCGGTGCCTCGTGGGGGATG
CGGTGCCTCGTGGGGGACATGGTGCCTTGTGGGGTACGTGGTGGAGACGGTGGGGTCGTG

34590  CCATGTCCACTCCCCAAGCCAGGACCGAGGGGGTGACGGAGATGAAGCTTGTGCTGGCCC
CAGCTGGGGGCCGCTGCCCACCCAGCAAGCCCCACAGCCAGTCCCAACCTGGTGATGTGG
TGTCCGGAGGATGGACCTCGAAGTCTCTCAGACCTGGGTTTCTGAGCTCCTCAGGTGTCT
GTGTCCCCTCCTGGGAAAGGGAACAGAGCTTTGCGAAGATCAAGGGGAGGGCAATGCAGC
TTGGGAGCCTTAGCTCAGCCAGACAGCAGCCCGGAGGGTTAATGTCCAGGTACCTCCAGG
[G,C]
CCCATGCACCCAGGACCTCCCCAAGAGCTGTGCCTCCATGTACCTCAGGGCCTCCCCCAG
AGCGGTGCCTCGTGGGGGATGCGGTGCCTCGTGGGGGACATGGTGCCTTGTGGGGTACGT
GGTGGAGACGGTGGGGTCGTGGCCGTCCAGGCTTCAGAAACGGCAGAACCAGGGACCCTC
CCCACTGTCCTGTCCTTAGCGTCTTGAGGCTAGGGGTGAGTTCGAGACCTCGTAAATACT
TCAGTGCAGAGCCTTCAGTTAGGAGCCGAGGCCTCTGGCCAGGTTCAGGCACGTGGAGAG

36326  CAACATCTAAAGGAGAAGGGTCCAGGACCCTTCGCCAGGACCTGGGCTGCTTTGTGCCCC
GGCAGGACGGGACAGCCACACACCTGCTGCCCTGCCCTCCATCTGCATCCAGCCAACAGG
CCATTCCTCCCGTGCTTCACCCTCCATCCTGGCCTGGGAGGCCCAGGCTCAGGACCCGTT
GGGACTGTTTGGACAGAGGGAGTCGGGGGGGCCAGGCAGGGCCCTGTGGAGCCTGCTGGG

FIGURE 3-36

```
        GGCTCTGGACCTGGGCCTCTGCCAGGTGGGCTCCCTGGGACCTACTGGCGGGGGGGCAGG
        [T,A]
        TGCGGGGGTGGAGCAGGACCCCCTGGCCTGCATGCTTCCCCTTCCTGGGGCTCACACACA
        GCACCTCGTGGGCCCAGAGTGCTGGCGGGAGGGGTGTTCTCCCCGCCTCCATGGGCAAAG
        AATCTGGGGCCCCTTGTCAGAGACCGCGGGGTCAGTGGGATTGGCGCCCAGGCCCTGCTGT
        GACGCCACGTGTTTCCCACTCAGCGAGGCTGTTCCTGCCAGGCGTGGGGACTCGGACCCT
        GGTCCTGAGTGCTGCCCCGAGGCCCGTGATGGGAAGCCTGACGTCTGCATCGTCCTGCGC

36470   CATCCTGGCCTGGGAGGCCCAGGCTCAGGACCCGTTGGGACTGTTTGGACAGAGGGAGTC
        GGGGGGGCCAGGCAGGGCCCTGTGGAGCCTGCTGGGGGCTCTGGACCTGGGCCTCTGCCA
        GGTGGGCTCCCTGGGACCTACTGGCGGGGGGGCAGGTTGCGGGGGTGGAGCAGGACCCCC
        TGGCCTGCATGCTTCCCCTTCCTGGGGCTCACACACAGCACCTCGTGGGCCCAGAGTGCT
        GGCGGGAGGGGTGTTCTCCCCGCCTCCATGGGCAAAGAATCTGGGGCCCTTGTCAGAGAC
        [C,T]
        GCGGGGTCAGTGGGATTGGCGCCCAGGCCCTGCTGTGACGCCACGTGTTTCCCACTCAGC
        GAGGCTGTTCCTGCCAGGCGTGGGGACTCGGACCCTGGTCCTGAGTGCTGCCCCGAGGCC
        CGTGATGGGAAGCCTGACGTCTGCATCGTCCTGCGCTGCGTGGCCGGTCGGTCCCGGCGC
        TCTCAGCACTTGGAGTCTCAGCTCCCCGGGTCATCAGTCCAAGCCACTCAGCAGGTGGCT
        TCGGCTTAAGGCCTCTCAGGTGGCTCTGGTGAAGGCGTCACCCAGGGCTGCCTGATCTGC

36566   GGCTCTGGACCTGGGCCTCTGCCAGGTGGGCTCCCTGGGACCTACTGGCGGGGGGGCAGG
        TTGCGGGGGTGGAGCAGGACCCCCTGGCCTGCATGCTTCCCCTTCCTGGGGCTCACACAC
        AGCACCTCGTGGGCCCAGAGTGCTGGCGGGAGGGGTGTTCTCCCCGCCTCCATGGGCAAA
        GAATCTGGGGCCCTTGTCAGAGACCGCGGGGTCAGTGGGATTGGCGCCCAGGCCCTGCTG
        TGACGCCACGTGTTTCCCACTCAGCGAGGCTGTTCCTGCCAGGCGTGGGGACTCGGACCC
        [T,C]
        GGTCCTGAGTGCTGCCCCGAGGCCCGTGATGGGAAGCCTGACGTCTGCATCGTCCTGCGC
        TGCGTGGCCGGTCGGTCCCGGCGCTCTCAGCACTTGGAGTCTCAGCTCCCCGGGTCATCA
        GTCCAAGCCACTCAGCAGGTGGCTTCGGCTTAAGGCCTCTCAGGTGGCTCTGGTGAAGGC
        GTCACCCAGGGCTGCCTGATCTGCAGGCTGGGCTGGAGGGGCTGCTTCCTGGGGGGTCCC
        GCAGGCTGTGTGGGGCCTCGGGTCCTCAGCACGTGGACGCCCTGCAGGGCACTGCTGCC

39133   GACTTGAGTCAGGGCCTGCTCTCAGATACCACGTGCAGGGTAGTCCTGGGGCTCCCTTTG
        ACTCTCCTGGCCGGCTCAGGAGCACCTGGGGGCACCCGTGTTAACGTGCTAGTCTGCTCC
        CTGAGGCCCAGCATCCTCGTGGCATACCCGTGGCTTCCCTGGGATGCCCTGGGGCTCCAC
        ATGCCCAGGCCCTTCCCTGTGGGGGGCGCAGGGAGACCCAGCACTCTTGGGCACCCGCCG
        GCACACGCTCCCACAGAAATGGGGCCTGGCGTGAGCTGCTGTGCACCGCCTGCCCCCTCA
        [G,-]
        GGCCCTGGGCAGTGATCTGTGGCACTGCGTGCCTTCCCTCTCGACAGCCAAGCCTGTGTT
        TGTGTAAAGACAGCAATTAGAGATGGACTCTCAATTGGAAAATAAGCCACAGTGAGTTGC
        AGGGGGAGATGATGAAGGGTGGCCCTGGGCTTCCCCGCTCCAGCTTCCAGTCCCCCATCC
        TCCAGGCTACGGCCCAGTCAGGAGGGCCTCTCACAGCACACTCCCCACTCCCTGCCTCCA
        GAAAGTGGCAAAACTGCTCATAACCCAAACATTCTGCTCAGAGAAACTCGGAGCTGAGGG

39635   GAGGGCCTCTCACAGCACACTCCCCACTCCCTGCCTCCAGAAAGTGGCAAAACTGCTCAT
        AACCCAAACATTCTGCTCAGAGAAACTCGGAGCTGAGGGATACCAGGACGCAGAGGCCTG
        CACTGCTGCCTAGGACCCCAGGGAAGCTTTACCTAGGAGGGACGCCTCTATGCTGGGCTC
        TGAGGAGTGTGTAGGAGTCTTCAGAGTACAGTAATGGGGAAAGGACTTTCTAGGCATAGG
        GGCAGCAAGTGAAAGAAGATGGAGGCAGGAGGAGTGACCAGAGCTCCAGGATGCAGCTGG
        [G,A]
        GACGGCTCTCCTACATCCCAGCCTGCTGCGTCGTGGCTGCCTTTACCTGAGCCACTGCGA
        GGCTCCTGAGCATAGGCAGGAGGCTCTTGGTGGCTGTGGCTCCTCTGTGACTCTGTTGCT
        ATTTGAGAGGCCACCTGCAGCCCCCAGACTCCAGCCTCAAGGACGTGGGCAGGATCTATG
```

FIGURE 3-37

```
        GATGCGGCAGGCCCACCCCCAGTGGCTCCATCCCCTCCGTAACCTCCTCTGGGAAGGTGG
        GTGCTTGCCAGGAATGCCTTCTTCCATGTGGTCCACTGTCCTCACAGCCCTTCTGAGCCA

40009   AGGCAGGAGGCTCTTGGTGGCTGTGGCTCCTCTGTGACTCTGTTGCTATTTGAGAGGCCA
        CCTGCAGCCCCCAGACTCCAGCCTCAAGGACGTGGGCAGGATCTATGGATGCGGCAGGCC
        CACCCCCAGTGGCTCCATCCCCTCCGTAACCTCCTCTGGGAAGGTGGGTGCTTGCCAGGA
        ATGCCTTCTTCCATGTGGTCCACTGTCCTCACAGCCCTTCTGAGCCACATGTGCTGGCAG
        GGGATGGAACCACTGTTTCCTCATCTGTGAAATAGGGGTGAAGGGGCCCCACTCAAAGCA
        [G,A]
        CGCCTGGAGCAAGGCCAGTGCTCCGAGACTTGGCTGTCCTGATTTGTGCTGGGCCCAGCA
        GTGTCCTTTCAATAAAGTTGGCCCAGGTGGTTGTCAGGCTCCCTCCCATTTTCAGTCCCC
        ACTTTCTTTCCTTTTCTGGAGGCAGGATTGTGCTCTCCACACCTTTTGGCTCCTGTCATT
        CAAGGATGTGTGTGCACACTGGGAGTGTGCATGTTTGTACGTATGTGTGCATGATGGTAT
        GTGCACGAGTGTGTGTGCACTGCGGGTGTGTGTGCATGTGCACTGGGGTGTATGTATGCA

40257   ACCACTGTTTCCTCATCTGTGAAATAGGGGTGAAGGGGCCCCACTCAAAGCAGCGCCTGG
        AGCAAGGCCAGTGCTCCGAGACTTGGCTGTCCTGATTTGTGCTGGGCCCAGCAGTGTCCT
        TTCAATAAAGTTGGCCCAGGTGGTTGTCAGGCTCCCTCCCATTTTCAGTCCCCACTTTCT
        TTCCTTTTCTGGAGGCAGGATTGTGCTCTCCACACCTTTTGGCTCCTGTCATTCAAGGAT
        GTGTGTGCACACTGGGAGTGTGCATGTTTGTACGTATGTGTGCATGATGGTATGTGCACG
        [A,T]
        GTGTGTGTGCACTGCGGGTGTGTGTGCATGTGCACTGGGGTGTATGTATGCAGTCGTGTG
        TACATGCATGGGTGTGTGTACAGGCGTGCGTACTGTGTGTGCATGGGTGTGTGCACACGG
        GTTACTGGGGGTGTGCACTGGGTGCTTGTGTGCACTGGAGGTGTGTACTGGGTGCGTGTG
        TGTGCACGGGTGTGTGCCCTTGGCGTGTGGGCGTGTGCACTGGGTGTGTCCTGGGTGTGT
        GTGCATGGGTGTGTGTACACGGGTGTGTCCTGGGTGCATGCACATGTGTACACAGGTGTG

47527   CTCCCAGCTGCTCCGGGTCCCACCCACAGTGGGACCTGGGCTGGCAGCGTGCGACCCTCC
        CAGCACTGGGGCCAGTCGAGCCCCCTCCTCTCCCTTCCTCTCCATTCGCTCCTTGGCATG
        CAGGGCTGCGGGTGGGGCAGGACCCGGGGACGAGGCCAGTGGGAGTGGCCAAGAGAGGGG
        AGGCTTGTGGAAGGTGCTAAGGGTTGGGGACTGTGACATGTTGGGCACCCCCCAGCTGCT
        GGGGTGTGGAGGAATTAACCAGACTAAACTGGGGAGGCCTGGGGACCCTATGGGGAGGTG
        [G,A]
        GGGTGGGGTTAAGGGCTGCTGAGGGCTGCCTGGATGGGGCTGGCAGGGTCCCACCCTGCC
        TTGGAGGAGAAACAGAGGCCCTGGGAGTGATGGGGCCAGGACAGCGCCTGGCAGAGAGAT
        CCAGTGTGGGCGTAGCTGGGGAGAGTCCCATGCTGAATTTGGGAGGTGCCTGTGAGCCC
        CGACTAAAGGAGGGCCTGGGGATGCGGGAAAGGGGAGGTGTCCCTGTCACCTGCAGGCGC
        TGTGCACAGATGTCCGCCTGGGAGGGAAGGACTTGGGGACAGGCTGGCCAACTCGCCAGG

47654   GCGGGTGGGGCAGGACCCGGGGACGAGGCCAGTGGGAGTGGCCAAGAGAGGGGAGGCTTG
        TGGAAGGTGCTAAGGGTTGGGGACTGTGACATGTTGGGCACCCCCCAGCTGCTGGGGTGT
        GGAGGAATTAACCAGACTAAACTGGGGAGGCCTGGGGACCCTATGGGGAGGTGGGGGTGG
        GGTTAAGGGCTGCTGAGGGCTGCCTGGATGGGGCTGGCAGGGTCCCACCCTGCCTTGGAG
        GAGAAACAGAGGCCCTGGGAGTGATGGGGCCAGGACAGCGCCTGGCAGAGAGATCCAGTG
        [T,C]
        GGGGCGTAGCTGGGGAGAGTCCCATGCTGAATTTGGGAGGTGCCTGTGAGCCCCGACTAA
        AGGAGGGCCTGGGGATGCGGGAAAGGGGAGGTGTCCCTGTCACCTGCAGGCGCTGTGCAC
        AGATGTCCGCCTGGGAGGGAAGGACTTGGGGACAGGCTGGCCAACTCGCCAGGGCTGGGA
        CCCCATCACAAGACTGGCCCTAGCTCCAAAGCCTGGTCCACGCTGGCTCCTGAGGGCTGG
        GACCCCAGGCCGTGGCCTCACTGGCCCCACCACTGACACGGCCACTTCTTTGTGCTGGGC

49643   GGATCCCGCCCTGGCTGGACCGTGGCTGAGTGTGGCTGAAAGTGTCACCTCCGCAGCCGC
        TGAGGCCAGCAGAAATCCCTACCCTGTCCCAGGCATGCCTGGCTGTGAACCCCATCCCCC
```

FIGURE 3-38

```
        CAGACCCAGCCTCAGGGAGCTCCTGGGAATGGGCACAGTGGTCACTCACGGCAGTCTCCT
        CTGTGTGCTCTGATGGGGCTTTCTGACAGATGAGGCGCTGCTGCCCAAGGGCTGTCTGGC
        CTTGAGCCTCATCTGACCCTCGCTGGTCCCAGGGCGGCGGCGTGACCTGCCAGGTGATCC
        [T,C]
        AGCCGGGCATCTCTGAGGCATCAGGCTCTGAGGGAGCAGGGAACATACAGGGCTGGGCTG
        GGGGCTGCCCTCAGGGTGAGCTGGCTGAGGGCCTGGCTGAACCCAGCAGCTCCCCTTCCC
        CCAGCAGCAACGTCCACGCTTGCTCTGGCCTGGGTTTCTGCATTCTCGTGGGGAGCATGT
        GCAGGTGGCCAGCTCGTGTGTAGCTGGGGAGAGGAAACCCAGGGGTGGGGTGTGGGGAGC
        CCGCCTGCCCCACCATGAGCAGGGGCTCAGAAACTGTCACCAGAGGCCTGGGGGGGCGGG
52314   CCCCCCCATTAGGCTACCCCTCAAGTGCACCGTCCACCCCATTAGCTACCCCTCAAGTGC
        ACCGTCCCCCCATTAGCTACCCCTCAAGTGCACCATCCCCCCTCATTAGCTACCCCTCAGG
        TGCATCATCCCCTCCTCATTAGCTGCCCCTCAAGTGCACCGTCCCCCCCATTAGCT
        [G,A]
        CCCCTCAAGTGCACTGTCCCCCCCACCCCATTAGCTACCTCTCAAGTGCACCATGTGCAC
        CAGGTGCTTCCCTTTTCCCCCTGAGGACCCCCTGCACCTCCCCTTTCCCGAGTGGGCAGT
        GTGTCGGGAAGTTTTCTGCCTGGCACCCACCCAAGCACTCTGGGAGCCCCTCGGCCTTTC
        CAGGGGCCATTGCTTGCATCCCTACGTGCCTGGGGGCCCTAGGTTGGTCTAGGCCAGAGC
        AGGTGTGCTAGGGAGCAGGAGGGGGCAGGAAGGAGCCTGCCAGGGTGCAGGAGGGCATGG
53161   CCTGCTGGACGAGAAGAACAACATCCGCATCGCAGACTTTGGCATGGCGTCCCTGCAGGT
        TGGCGACAGCCTGTTGGAGACCAGCTGTGGGTACGTGGCCCTCTGCCCTGGAGAGAGGCT
        GGGGGACAGGCTGGGCTGGGGGAAGAGGAGCCAGTGGACTGAGAGGCCCCCAGCCTGCCT
        GAGCCTCCCGGCACCCCACAGGCAGGCCCCCCACAATGTGCCTGAGCCTCCCAGTACCCC
        ACAGCCTGGTGGTGGTGGGGAGACAGGCCTCCCGGCACAGTAAGGGTAGGGGTACAGCCC
        [T,C,A,G]
        GGCCCTGGCCTGCCTGGGAGAGAGGCTGGGACCCACTTACATGCCCCTCTCCTGGGGACC
        CCCTGGCCCCTGCCCAGCCGAGTGGGCAGACAGCTTTGGGCGCAGCAGAGACCCAGTGCC
        CCACCTTGATCTCCTCCCAAAAGCCCGCCTGGGGATGCAGGGAATGTGGGGGCGTCTGGC
        ACCACAGCCCTGGAGGCCTCCTTGAGGGCCCTGCGGTGCACCATCACCCTGGGGGGAGGG
        CCTGGCAGCGCCCGGAGCCCCGCCGCTGACCTCTGCCCTTGCCCGCAGGTCCCCCCACTA
53245   CTGTGGGTACGTGGCCCTCTGCCCTGGAGAGAGGCTGGGGGACAGGCTGGGCTGGGGGAA
        GAGGAGCCAGTGGACTGAGAGGCCCCCAGCCTGCCTGAGCCTCCCGGCACCCCACAGGCA
        GGCCCCCCACAATGTGCCTGAGCCTCCCAGTACCCCACAGCCTGGTGGTGGTGGGGAGAC
        AGGCCTCCCGGCACAGTAAGGGTAGGGGTACAGCCCTGGCCCTGGCCTGCCTGGGAGAGA
        GGCTGGGACCCACTTACATGCCCCTCTCCTGGGGACCCCCTGGCCCCTGCCCAGCCGAGT
        [A,G]
        GGCAGACAGCTTTGGGCGCAGCAGAGACCCAGTGCCCCACCTTGATCTCCTCCCAAAAGC
        CCGCCTGGGGATGCAGGGAATGTGGGGGCGTCTGGCACCACAGCCCTGGAGGCCTCCTTG
        AGGGCCCTGCGGTGCACCATCACCCTGGGGGGAGGGCCTGGCAGCGCCCGGAGCCCCGCC
        GCTGACCTCTGCCCTTGCCCGCAGGTCCCCCCACTACGCCTGCCCCGAGGTGATCCGGGT
        GAGTCAGCGCCGCCGCGTGCAGCTCTGTGGGGCCCAGGGTGGCGGGGACCTGACCCTGGT
54358   TGTGTGCCCAGACGTGTGGGCACCCAGGTGTGTGGGTCGGTGCCCAGGTGTGTGGACGTG
        TGCACAGGTGTCGGCTTGTGTTCAGGTGTGGGTGACCAAATGTGGGCCCATGGCCGTGTG
        TGGGTGCCCAGGTGAGTGTTCAAGTGTGTGTGCGCACCCAGGTGTGGGAGTGCCCAGGCG
        TGTGTGGGCTCGTGTTCAGGTGTGTGGGTGCACAAATGTAGGCACATGCCCAGGTGTGTG
        TTCAAGGGTGTGGGGGTACCCAGGCACATGCCCAGGTTCATGTGATTGGGTGAGGGCGTA
        [G,T]
        GTGTGGGCATGTGCACGTGTGGGGAGGTGTGTCCAGGTGCTTATGAGCACTTGTACCAGT
        GTGGGGTGTGCACAGGTGTGGGGGGCTGTGTGCACATGTAGGTGAGACCTGGCTATAAGT
        TACACAAAAGCACTGGTGCTTCCCCATCACGGCCATCCTGCCTCCAGACGCTGCTGGGGC
```

FIGURE 3-39

```
           AAGCTCCAGGCAGCGTGAATAGTTCTGCTGAGTGCCCCCAGCAGCTGTGGGGGCTAGCAA
           GAGCCAAAGGTAGCCCCCAGCTGCTGGTCCTGACCTCCTCCAGGGCTGCCTGGTGTGGGG

54374      TGGGCACCCAGGTGTGTGGGTCGGTGCCCAGGTGTGTGGACGTGTGCACAGGTGTCGGCT
           TGTGTTCAGGTGTGGGTGACCAAATGTGGGCCCATGGCCGTGTGTGGGTGCCCAGGTGAG
           TGTTCAAGTGTGTGTGCGCACCCAGGTGTGGGAGTGCCCAGGCGTGTGTGGGCTCGTGTT
           CAGGTGTGTGGGTGCACAAATGTAGGCACATGCCCAGGTGTGTGTTCAAGGGTGTGGGGG
           TACCCAGGCACATGCCCAGGTTCATGTGATTGGGTGAGGGCGTAGGTGTGGGCATGTGCA
           [C,T]
           GTGTGGGGAGGTGTGTCCAGGTGCTTATGAGCACTTGTACCAGTGTGGGGTGTGCACAGG
           TGTGGGGGGCTGTGTGCACATGTAGGTGAGACCTGGCTATAAGTTACACAAAAGCACTGG
           TGCTTCCCCATCACGGCCATCCTGCCTCCAGACGCTGCTGGGGCAAGCTCCAGGCAGCGT
           GAATAGTTCTGCTGAGTGCCCCCAGCAGCTGTGGGGGCTAGCAAGAGCCAAAGGTAGCCC
           CCAGCTGCTGGTCCTGACCTCCTCCAGGGCTGCCTGGTGTGGGGACCGCACGTGTCCACT

55833      GAGTGGCAGGATGAAGGGCCCCAGGTGAGGGCGGGCGTCCCACCCTCGCAGCCGCCCAGG
           CCCGGCCGGAGCTGATGAGCGGGTGGCCCGTCCTGTGTCCACAGAGGGGGCAAGAATGAG
           CCCGAACCAGAGCAGCCCATTCCTCGCAAGGTGCAGATCCGCTCGCTGCCCAGCCTGGAG
           GACATCGACCCCGACGTGCTGGACAGCATGCACTCACTGGGCTGCTTCCGAGACCGCAAC
           AAGCTGCTGCAGGACCTGCTGTCCGAGGAGTGCGTCTGGGGCTGCTCCCGGGTGGGGCAC
           [A,G]
           GGGCCTGAGGTGGGAGCGCTGCCCCGGAGGAGCCGGCGGCCCCGTGTGCCAGCGCGTCTC
           GCGCCTCTCGCCCGCTGTAGGGAGAACCAGGAGAAGATGATTTACTTCCTCCTCCTGGAC
           CGGAAAGAAAGGTACCCGAGCCAGGAGGATGAGGACCTGCCCCCCCGGAACGAGATAGGT
           ATGGGTCCAGGGGTGGCCTCCAGCCCGGCCTGCACTGCCCCACCGGGGTCCGGGGCTGT
           CTGGCCTGACCTTCGTCTGTACTCAGACCCTCCCCGGAAGCGTGTGGACTCCCCGATGCT

56950      AATGGGCTGAGACGGATTTGACTGGGCTGAGCTGGGCAGGGCTGGGCTGAGCTGGGCAGG
           GCTGGGCTGGGCTAAACTGGATTTGGCTGAGCCGAGCCAGGCTGGGCAGGGCTGAGCTGG
           GCTGGGCTGGCTTGACCCAAGCTTGGCTGGGCTGAGCTGTGATATGGTCACACCATGCTC
           AGAGCCATCAGCCCAGCAAGCCTGTCCCCCTGGTCCCAGCAATGCTGGGCCCGTCTCTGG
           GTGGCAAGTGTGGTGTGTGTGGCCAGGGACATCACAGAACTCAGCAGTGATGAGCAGACC
           [T,C]
           GTGGCCGGAGGAAGGGCACCCAGCCCCTCTGGAGCCTCTGCTGGGTGGGGGCAGGGCTGG
           GCTGCCCGCACGAGGCCCTCAGCAAATCCTTGGAGCCGGTGCGGCCTCTTGGGGATGAGC
           TCAAACGTCCCTCACCAGGTGGCAGCTTCCAACACTTGGGGACAGCCCTTGCGCCAGAGA
           GCACACCAGGAGGTCCAGGAGCCCGGGCAGCAGTCTCTGGTCTGCCCTGTGATCTGGGCC
           TCAGCACCCCAGGGCCCCCTCCTTGTACTGGAGATGTGGGGGGTGGGACAGGCGTGGCCT

59273      TGCCCCCATGAGGGCTGTCCGCGCTCCCAGCTCAGCCCTGAAAGCTCTGGGTCCAGTTCC
           AGCCCTGGGTGTCATCCTGGCCCAGACAGGCTGGGTTGTGCATGGGGTCCCCGTCGCCTC
           CCTGCCCCTTGGCTGTGTCTGGTGAGGGAGTTGGAGGGTCGTCACCGTGGGGACCAGCCC
           CCGGGTGTCCGGGAGCCAGGTGTGTGGCCAGCGTGGCACTCTCCACGGTCCGGGGCCTGG
           GCCGTGGTGTGGACTAGCGAGGCCCCTCGTGGCCGGCTGGCGGTGGGCAGGCCTGGTGGG
           [C,T]
           AGTGCAGGCCGGGCTTTTACTCTTCTCTGTCCTCTTCTCTTCGGCGGCTGCCTCGGCCCC
           TCCCTGCATTTCCTTCCTCCAAGGATGGCAGCTGCCACTGTCTGGGCACGTGGGCGCCGG
           CTCGTCCGTGCAGTGTGGTGGAACGACGCACAGCCGTCCTGGTCCCTGCACGGGGTGGC
           GGCCACACACCGGAGTCTCAGCCGGGCACGCCGGGCCAGGGCCTCCCTCCTGCTGTGTGC
           AGGTCTCAGGCTGAGTAGGGCAGTGGTGGGACAAGGCCCCACCGTCCCTGCCAGCAGCTG

59422      GTTGGAGGGTCGTCACCGTGGGGACCAGCCCCGGGTGTCCGGGAGCCAGGTGTGTGGCC
           AGCGTGGCACTCTCCACGGTCCGGGGCCTGGGCCGTGGTGTGGACTAGCGAGGCCCCTCG
```

FIGURE 3-40

```
        TGGCCGGCTGGCGGTGGGCAGGCCTGGTGGGCAGTGCAGGCCGGGCTTTTACTCTTCTCT
        GTCCTCTTCTCTTCGGCGGCTGCCTCGGCCCCTCCCTGCATTTCCTTCCTCCAAGGATGG
        CAGCTGCCACTGTCTGGGCACGTGGGCGCCGGCTCGTCCGTGCAGTGTGGTGGAACGACG
        [C,T]
        ACAGCCGTCCTGGTCCCTGCACGGGGGTGGCGGCCACACACCGGAGTCTCAGCCGGGCAC
        GCCGGGCCAGGGCCTCCCTCCTGCTGTGTGCAGGTCTCAGGCTGAGTAGGGCAGTGGTGG
        GACAAGGCCCCACCGTCCCTGCCAGCAGCTGCCCCAGCCTGGCCCTGCCCAGGCCCTCCT
        GGTTGTGGACAAGGGAAGGCCGGCCGCTGACCCAGGCATCCCTCACGGGCATCTAGGGA
        CATGGAGGACCAGGCTGCAGGCCCTGTGAGAGCTCAGCCAGGGGGGGCTTGGCAGGTGGG

63028   AGGCCCTGACATTGCCGTTTCTGCTGCTACCAAAAGCTTTCATGAACAGACTCATAATTA
        TCTTCCTCAGAGAAGGTGGAAAACATCAAAGCCGAGAAGGTGGCTTTGATGCCACTGTGG
        CTGCCTGCGCTTCTCCCCTCCCCCATCTTGAGATGGCCTGGAGGCCCTGACCCCTCTCAA
        GGGTCCGGCACGGATGCCTCCCACAGCCCCACCCAAGGGCCCGGCACAGACACCCCTTCC
        CAAGGGTCCAGCACAGATGCCTCCTACAGCTCCACCCAAGGGCCCGGCACAGATGCCTGC
        [G,A]
        ACAGCCGTTCCCGAGGGTCCAGCACAGACACCTCCCACAGCCCCACCCAAGGGCCCGGCA
        CAGATGCCTGTGACAGCCCTTATTGAGGGTCCTGCACAGACGCCTTGGACGAGGGTCCAG
        CACGGATGCCTCCCACAGTCCCTCTTTGGCGACAACTCGCTTGCTGGGGACCTGAGATAA
        CCCCCAGCCCCAGCTGCTGCCAGCCCCATGTCAACCAGGCACCCCAGAGGAACAGCACCA
        AGGGAGGCAGCTGGCTTCAGGAAGGGATGCATGCGGTTGTCTGGGACACTCAGGGCTGAT

63084   ATTATCTTCCTCAGAGAAGGTGGAAAACATCAAAGCCGAGAAGGTGGCTTTGATGCCACT
        GTGGCTGCCTGCGCTTCTCCCCTCCCCCATCTTGAGATGGCCTGGAGGCCCTGACCCCTC
        TCAAGGGTCCGGCACGGATGCCTCCCACAGCCCCACCCAAGGGCCCGGCACAGACACCCC
        TTCCCAAGGGTCCAGCACAGATGCCTCCTACAGCTCCACCCAAGGGCCCGGCACAGATGC
        CTGCGACAGCCGTTCCCGAGGGTCCAGCACAGACACCTCCCACAGCCCCACCCAAGGGCC
        [C,T]
        GGCACAGATGCCTGTGACAGCCCTTATTGAGGGTCCTGCACAGACGCCTTGGACGAGGGT
        CCAGCACGGATGCCTCCCACAGTCCCTCTTTGGCGACAACTCGCTTGCTGGGGACCTGAG
        ATAACCCCCAGCCCCAGCTGCTGCCAGCCCCATGTCAACCAGGCACCCCAGAGGAACAGC
        ACCAAGGGAGGCAGCTGGCTTCAGGAAGGGATGCATGCGGTTGTCTGGGACACTCAGGGC
        TGATGTCCTTGAGTCTGAAGTGCTAGCTGGAAGCCCAGGCAGTTTCCAGGTTGCAGCCTC

63178   AGATGGCCTGGAGGCCCTGACCCCTCTCAAGGGTCCGGCACGGATGCCTCCCACAGCCCC
        ACCCAAGGGCCCGGCACAGACACCCCTTCCCAAGGGTCCAGCACAGATGCCTCCTACAGC
        TCCACCCAAGGGCCCGGCACAGATGCCTGCGACAGCCGTTCCCGAGGGTCCAGCACAGAC
        ACCTCCCACAGCCCCACCCAAGGGCCCGGCACAGATGCCTGTGACAGCCCTTATTGAGGG
        TCCTGCACAGACGCCTTGGACGAGGGTCCAGCACGGATGCCTCCCACAGTCCCTCTTTGG
        [C,T]
        GACAACTCGCTTGCTGGGGACCTGAGATAACCCCCAGCCCCAGCTGCTGCCAGCCCCATG
        TCAACCAGGCACCCCAGAGGAACAGCACCAAGGGAGGCAGCTGGCTTCAGGAAGGGATGC
        ATGCGGTTGTCTGGGACACTCAGGGCTGATGTCCTTGAGTCTGAAGTGCTAGCTGGAAGC
        CCAGGCAGTTTCCAGGTTGCAGCCTCGAGGGGCGTTCTTTTCCCCAGGAAGACCGAACCTG
        GCGGATGCACCCACCCTGTGAGGAAGGGTCCCCCGCCAGACTCAACAGGCGACTGATTTA

63307   GGGCCCGGCACAGATGCCTGCGACAGCCGTTCCCGAGGGTCCAGCACAGACACCTCCCAC
        AGCCCCACCCAAGGGCCCGGCACAGATGCCTGTGACAGCCCTTATTGAGGGTCCTGCACA
        GACGCCTTGGACGAGGGTCCAGCACGGATGCCTCCCACAGTCCCTCTTTGGCGACAACTC
        GCTTGCTGGGGACCTGAGATAACCCCCAGCCCCAGCTGCTGCCAGCCCCATGTCAACCAG
        GCACCCCAGAGGAACAGCACCAAGGGAGGCAGCTGGCTTCAGGAAGGGATGCATGCGGTT
        [G,A]
        TCTGGGACACTCAGGGCTGATGTCCTTGAGTCTGAAGTGCTAGCTGGAAGCCCAGGCAGT
```

FIGURE 3-41

```
        TTCCAGGTTGCAGCCTCGAGGGGCGTTCTTTCCCCAGGAAGACCGAACCTGGCGGATGCA
        CCCACCCTGTGAGGAAGGGTCCCCCGCCAGACTCAACAGGCGACTGATTTAAGTTCGTCT
        CATCTAAAAATAGCTTCATAGCAACACCCAGACTAGTGTCCGGCCAGGCTGTGCACTGCC
        CACCACGTGGGTGCTGGAGTCACAGTGCAGGCCCCTCACCCCTCGTCGGCCTGGCCTCCC

63483   ACTCGCTTGCTGGGGACCTGAGATAACCCCCAGCCCCAGCTGCTGCCAGCCCCATGTCAA
        CCAGGCACCCCAGAGGAACAGCACCAAGGGAGGCAGCTGGCTTCAGGAAGGGATGCATGC
        GGTTGTCTGGGACACTCAGGGCTGATGTCCTTGAGTCTGAAGTGCTAGCTGGAAGCCCAG
        GCAGTTTCCAGGTTGCAGCCTCGAGGGGCGTTCTTTCCCCAGGAAGACCGAACCTGGCGG
        ATGCACCCACCCTGTGAGGAAGGGTCCCCCGCCAGACTCAACAGGCGACTGATTTAAGTT
        [C,T]
        GTCTCATCTAAAAATAGCTTCATAGCAACACCCAGACTAGTGTCCGGCCAGGCTGTGCAC
        TGCCCACCACGTGGGTGCTGGAGTCACAGTGCAGGCCCCTCACCCCTCGTCGGCCTGGCC
        TCCCTGGGCCGTCAGGCATCTTTCACACATGGGACTATTTTTGCCAAATGCTGCACCCCT
        GGGCCGCAAAGCAGAGAGTCACGTTTGTACCATCTGTCCTGTCTCTTCATCGGGCAGAAC
        ATCGACCATGTAGAAACTCACCTGTGCTTCCAGAACTGCCAGGCTGCTTTGTGCACTTCC

66192   GGAGCCCCTGCAGAAGGCTCCAGGGCCAGGAGAGCCCAGCGCTGGGCAGGGCAGGCCTCA
        GACTGCACTTGGACCCTGGCCTCAGGGGTCCTCAGCGTCCCCGTCCCCGTCCCCACAGGC
        TGCTCACTTCCTCGGCCTCCTCCCTCACCACATCCCTTCATGCTGCCCCTGGTTGCCACG
        GCTAACCTCAGACTCAGCCCCTCCCCATGCCGGCCCCAGTGAGGCGGCTGTGTGCCAGCC
        TGGGCCCTGTGCGCTGGGTGGCCCTGAGTTCTGCTTCCTGCAGCTGCCCCCTCGGTACTG
        [T,C]
        GAAGCCCACCCAGCCAGTGCCCAGCACCATAGGTCCCGCAACCAGTGGGAGTCCCAGGAA
        GCCCCAGCAGGAGGGCACAGCCCCAGCCCCGCCCTTGCACCTCCCTCTCAGTGGCAGCTC
        CCAGACCCCCCACCTCCCACTCAGCTCCACCCTGGACCCCCACCTCAGGCTGCAGGGGTC
        ACCTTCCACCTCCATCTTTGCCCTTAAGGCTCCTCTGTAAGGTCCTGGTCATCCTGTGCT
        GTGGCTGCCTGAGAAAAGCCCGGCAGGGGCTTAGCTGTGCCCGCTAAGTGGACCAAAGCT

66193   GAGCCCCTGCAGAAGGCTCCAGGGCCAGGAGAGCCCAGCGCTGGGCAGGGCAGGCCTCAG
        ACTGCACTTGGACCCTGGCCTCAGGGGTCCTCAGCGTCCCCGTCCCCGTCCCCACAGGCT
        GCTCACTTCCTCGGCCTCCTCCCTCACCACATCCCTTCATGCTGCCCCTGGTTGCCACGG
        CTAACCTCAGACTCAGCCCCTCCCCATGCCGGCCCCAGTGAGGCGGCTGTGTGCCAGCCT
        GGGCCCTGTGCGCTGGGTGGCCCTGAGTTCTGCTTCCTGCAGCTGCCCCCTCGGTACTGT
        [G,A]
        AAGCCCACCCAGCCAGTGCCCAGCACCATAGGTCCCGCAACCAGTGGGAGTCCCAGGAAG
        CCCCAGCAGGAGGGCACAGCCCCAGCCCCGCCCTTGCACCTCCCTCTCAGTGGCAGCTCC
        CAGACCCCCCACCTCCCACTCAGCTCCACCCTGGACCCCCACCTCAGGCTGCAGGGGTCA
        CCTTCCACCTCCATCTTTGCCCTTAAGGCTCCTCTGTAAGGTCCTGGTCATCCTGTGCTG
        TGGCTGCCTGAGAAAAGCCCGGCAGGGGCTTAGCTGTGCCCGCTAAGTGGACCAAAGCTT

66229   AGCGCTGGGCAGGGCAGGCCTCAGACTGCACTTGGACCCTGGCCTCAGGGGTCCTCAGCG
        TCCCCGTCCCCGTCCCCACAGGCTGCTCACTTCCTCGGCCTCCTCCCTCACCACATCCCT
        TCATGCTGCCCCTGGTTGCCACGGCTAACCTCAGACTCAGCCCCTCCCCATGCCGGCCCC
        AGTGAGGCGGCTGTGTGCCAGCCTGGGCCCTGTGCGCTGGGTGGCCCTGAGTTCTGCTTC
        CTGCAGCTGCCCCCTCGGTACTGTGAAGCCCACCCAGCCAGTGCCCAGCACCATAGGTCC
        [C,T]
        GCAACCAGTGGGAGTCCCAGGAAGCCCCAGCAGGAGGGCACAGCCCCAGCCCCGCCCTTG
        CACCTCCCTCTCAGTGGCAGCTCCCAGACCCCCCACCTCCCACTCAGCTCCACCCTGGAC
        CCCCACCTCAGGCTGCAGGGGTCACCTTCCACCTCCATCTTTGCCCTTAAGGCTCCTCTG
        TAAGGTCCTGGTCATCCTGTGCTGTGGCTGCCTGAGAAAAGCCCGGCAGGGGCTTAGCTG
        TGCCCGCTAAGTGGACCAAAGCTTTGGAGGGTGGGGGCTGGAAACGCCCCTCCCCCTGCT
```

FIGURE 3-42

66754    GGCAGGGGCTTAGCTGTGCCCGCTAAGTGGACCAAAGCTTTGGAGGGTGGGGGCTGGAAA
         CGCCCCTCCCCCTGCTCCAGCCGTCTCCAACCGCACTGTGCCCCTCACGGAAGCAGAGGT
         GCCTGGGTGCTCACAATGTGTGCACGGTGGGGCTGGCTCGCCCCAGGGCTGCCTCCCCAG
         AGGGCCAGGGTGGGACCTGCCAGGCCAGCCACGCTCACGCTGCTCTCTCTCCACAGATTC
         CCAGTCTCAGCCACAGCGTCATCTCCCAAACGAGCTTCCGGGCCGAGTACAAGGCCACGG
         [G,C]
         GGGGCCAGCCGTGTTCCAGAAGCCGGTCAAGTTCCAGGTTGATATCACCTACACGGAGGG
         TGGGGAGGCGCAGAAGGAGAACGGCATCTACTCCGTCACCTTCACCCTGCTCTCAGGTGA
         GCTGGCGCCCCAGGGCGGCTCCGGGCCCAGGCCCGTCCAGGGCATAACCCCCTGTCTCC
         CCTAGGCCCCAGCCGTCGCTTCAAGAGGGTGGTGGAGACCATCCAGGCCCAGCTGCTGAG
         CACACACGACCCGCCTGCGGCCCAGCACTTGTCAGGTGAGGCGGGCTCAGCTCCGGCCAA

67590    ACCGTAGAACCCCCCCCACCAGCGCCAGGACTAAGCTGGGGTGCTGGGCTTAAGGGCCAG
         AAGGTGGCCACCAGCTACGAGAGTAGCCTCTGACGCTGGCAGGTAAGGCGCCCGGCCTGT
         GCTGGGGCGGGGAGGGGCTGCGGGCAGGTCCTCGGCGGAGCCAGGCTGGCCCTGAGCAGG
         GCCCTCCATGCCCACCCACAGGTCTCGGCCCTGGACAGGCCAAGCATGCCCCGGGCGGCC
         CATCTGCTAGGGCAGCCTGCACAGGACCTGGGAGAGCAGTGACAAGGCCCTGCCCTCGGG
         [A,G]
         CTCCCCGCCATGGCACCCTAGGAGGGCCGCGGGCTGCCTGACGGGCTGTGACTTCTCATC
         TCTCCATACTTCCTGACAGCCCAGGGCCATGCCTCCAGCAGGGCAGAGGGGCTTGAGCCC
         AGCCAGAGCGGGGGCTTCACCACAGCCTGATGGGCTCACACAGGGGAGGGTTGCCCCAGC
         CTGGAACCACCAGGGTCTAGGACCCGAGGGTCCGTGCCACTCGGCATACGGCAGGGAGGG
         CTCCCCCCACTCCCCTGGGCCCATGTGTGGTGGGGGCAGGGCGGAGCACTGGGCACATGC

67677    CTCTGACGCTGGCAGGTAAGGCGCCCGGCCTGTGCTGGGGCGGGGAGGGGCTGCGGGCAG
         GTCCTCGGCGGAGCCAGGCTGGCCCTGAGCAGGGCCCTCCATGCCCACCCACAGGTCTCG
         GCCCTGGACAGGCCAAGCATGCCCCGGGCGGCCCATCTGCTAGGGCAGCCTGCACAGGAC
         CTGGGAGAGCAGTGACAAGGCCCTGCCCTCGGGACTCCCCGCCATGGCACCCTAGGAGGG
         CCGCGGGCTGCCTGACGGGCTGTGACTTCTCATCTCTCCATACTTCCTGACAGCCCAGGG
         [C,T]
         CATGCCTCCAGCAGGGCAGAGGGGCTTGAGCCCAGCCAGAGCGGGGGCTTCACCACAGCC
         TGATGGGCTCACACAGGGGAGGGTTGCCCCAGCCTGGAACCACCAGGGTCTAGGACCCGA
         GGGTCCGTGCCACTCGGCATACGGCAGGGAGGGCTCCCCCCACTCCCCTGGGCCCATGTG
         TGGTGGGGGCAGGGCGGAGCACTGGGCACATGCATGGGCCTGGTCTGTCAGCAAGGGGGT
         GTGGGTGTGCCTCTGAACGCTGGTACGGCGTGGGGGCGCTGGGCGTCGTGGGGGAGCACC

67750    CCAGGCTGGCCCTGAGCAGGGCCCTCCATGCCCACCCACAGGTCTCGGCCCTGGACAGGC
         CAAGCATGCCCCGGGCGGCCCATCTGCTAGGGCAGCCTGCACAGGACCTGGGAGAGCAGT
         GACAAGGCCCTGCCCTCGGGACTCCCCGCCATGGCACCCTAGGAGGGCCGCGGGCTGCCT
         GACGGGCTGTGACTTCTCATCTCTCCATACTTCCTGACAGCCCAGGGCCATGCCTCCAGC
         AGGGCAGAGGGGCTTGAGCCCAGCCAGAGCGGGGGCTTCACCACAGCCTGATGGGCTCAC
         [A,G]
         CAGGGGAGGGTTGCCCCAGCCTGGAACCACCAGGGTCTAGGACCCGAGGGTCCGTGCCAC
         TCGGCATACGGCAGGGAGGGCTCCCCCCACTCCCCTGGGCCCATGTGTGGTGGGGGCAGG
         GCGGAGCACTGGGCACATGCATGGGCCTGGTCTGTCAGCAAGGGGGTGTGGGTGTGCCTC
         TGAACGCTGGTACGGCGTGGGGCGCTGGGCGTCGTGGGGAGCACCCGGCTGGACCCTG
         GGGGTCCCCTCTCCCAGCCTGCATCTCAGCAGCTCCGTGGCATGCTAGGGTCACCTCCTG

67793    CTCGGCCCTGGACAGGCCAAGCATGCCCCGGGCGGCCCATCTGCTAGGGCAGCCTGCACA
         GGACCTGGGAGAGCAGTGACAAGGCCCTGCCCTCGGGACTCCCCGCCATGGCACCCTAGG
         AGGGCCGCGGGCTGCCTGACGGGCTGTGACTTCTCATCTCTCCATACTTCCTGACAGCCC
         AGGGCCATGCCTCCAGCAGGGCAGAGGGGCTTGAGCCCAGCCAGAGCGGGGGCTTCACCA
         CAGCCTGATGGGCTCACACAGGGGAGGGTTGCCCCAGCCTGGAACCACCAGGGTCTAGGA

FIGURE 3-43

[-,G,C]
CCGAGGGTCCGTGCCACTCGGCATACGGCAGGGAGGGCTCCCCCCACTCCCCTGGGCCCA
TGTGTGGTGGGGGCAGGGCGGAGCACTGGGCACATGCATGGGCCTGGTCTGTCAGCAAGG
GGGTGTGGGTGTGCCTCTGAACGCTGGTACGGCGTGGGGGCGCTGGGCGTCGTGGGGGAG
CACCCGGCTGGACCCTGGGGGTCCCCTCTCCCAGCCTGCATCTCAGCAGCTCCGTGGCAT
GCTAGGGTCACCTCCTGTGTTTCCATGTGGGGTCCTGGAAGCCAAAGAGGGCCCCACTGC

67954  CCATACTTCCTGACAGCCCAGGGCCATGCCTCCAGCAGGGCAGAGGGGCTTGAGCCCAGC
CAGAGCGGGGGCTTCACCACAGCCTGATGGGCTCACACAGGGGAGGGTTGCCCCAGCCTG
GAACCACCAGGGTCTAGGACCCGAGGGTCCGTGCCACTCGGCATACGGCAGGGAGGGCTC
CCCCCACTCCCCTGGGCCCATGTGTGGTGGGGGCAGGGCGGAGCACTGGGCACATGCATG
GGCCTGGTCTGTCAGCAAGGGGGTGTGGGTGTGCCTCTGAACGCTGGTACGGCGTGGGGG
[C,T]
GCTGGGCGTCGTGGGGGAGCACCCGGCTGGACCCTGGGGGTCCCCTCTCCCAGCCTGCAT
CTCAGCAGCTCCGTGGCATGCTAGGGTCACCTCCTGTGTTTCCATGTGGGGTCCTGGAAG
CCAAAGAGGGCCCCACTGCCCCTCCCCATGACATCCTCATTCCATCATCATGCCATCACC
TGTGGGAGCCCCCCCAGAGTGTGCTTCACCTTGCTGCGGGCTGGGGGCTGAGGTCCCCAA
CAGCCCTGGCCCTAACCGAAGCCCCAGTGGGTGGAGGAGTAGCCCCCTTCTCCTGATTTT

68164  GGGCAGGGCGGAGCACTGGGCACATGCATGGGCCTGGTCTGTCAGCAAGGGGGTGTGGGT
GTGCCTCTGAACGCTGGTACGGCGTGGGGGCGCTGGGCGTCGTGGGGGAGCACCCGGCTG
GACCCTGGGGGTCCCCTCTCCCAGCCTGCATCTCAGCAGCTCCGTGGCATGCTAGGGTCA
CCTCCTGTGTTTCCATGTGGGGTCCTGGAAGCCAAAGAGGGCCCCACTGCCCCTCCCCAT
GACATCCTCATTCCATCATCATGCCATCACCTGTGGGAGCCCCCCCAGAGTGTGCTTCAC
[C,T]
TTGCTGCGGGCTGGGGGCTGAGGTCCCCAACAGCCCTGGCCCTAACCGAAGCCCCAGTGG
GTGGAGGAGTAGCCCCCTTCTCCTGATTTTTGGGAGCCAGGCTGGCACAGCGGGTAAGGAG
GAGCAGGGTTCCAGGTGCTCGGCCCCGCAGGTACACGTGGCGCTTCCCTACAGCGGAGGC
CATGCCGTCGGCCGGCAGCAGCCTCTGGCTCTCTGAGCCTTGAAAGCCTTCATCTTAGGA
AGGGAAACCGAGGCCAGGGAACGACAGGGCAGCCACCTAGGCCAGGGATGGACAGGGCTT

68235  CGCTGGTACGGCGTGGGGGCGCTGGGCGTCGTGGGGGAGCACCCGGCTGGACCCTGGGGG
TCCCCTCTCCCAGCCTGCATCTCAGCAGCTCCGTGGCATGCTAGGGTCACCTCCTGTGTT
TCCATGTGGGGTCCTGGAAGCCAAAGAGGGCCCCACTGCCCCTCCCCATGACATCCTCAT
TCCATCATCATGCCATCACCTGTGGGAGCCCCCCCAGAGTGTGCTTCACCTTGCTGCGGG
CTGGGGGCTGAGGTCCCCAACAGCCCTGGCCCTAACCGAAGCCCCAGTGGGTGGAGGAGT
[G,A]
GCCCCCTTCTCCTGATTTTTGGGAGCCAGGCTGGCACAGCGGGTAAGGAGGAGCAGGGTTC
CAGGTGCTCGGCCCCGCAGGTACACGTGGCGCTTCCCTACAGCGGAGGCCATGCCGTCGG
CCGGCAGCAGCCTCTGGCTCTCTGAGCCTTGAAAGCCTTCATCTTAGGAAGGGAAACCGA
GGCCAGGGAACGACAGGGCAGCCACCTAGGCCAGGGATGGACAGGGCTTGTCTGGTAGGG
CAAGCAGAAACGGGCCCCGGGGTACTGCCCAGGGTGTCCCCGCACCTGAGCAGCCATCTG

68278  CGGCTGGACCCTGGGGGTCCCCTCTCCCAGCCTGCATCTCAGCAGCTCCGTGGCATGCTA
GGGTCACCTCCTGTGTTTCCATGTGGGGTCCTGGAAGCCAAAGAGGGCCCCACTGCCCCT
CCCCATGACATCCTCATTCCATCATCATGCCATCACCTGTGGGAGCCCCCCCAGAGTGTG
CTTCACCTTGCTGCGGGCTGGGGGCTGAGGTCCCCAACAGCCCTGGCCCTAACCGAAGCC
CCAGTGGGTGGAGGAGTAGCCCCCTTCTCCTGATTTTTGGGAGCCAGGCTGGCACAGCGGG
[T,C]
AAGGAGGAGCAGGGTTCCAGGTGCTCGGCCCCGCAGGTACACGTGGCGCTTCCCTACAGC
GGAGGCCATGCCGTCGGCCGGCAGCAGCCTCTGGCTCTCTGAGCCTTGAAAGCCTTCATC
TTAGGAAGGGAAACCGAGGCCAGGGAACGACAGGGCAGCCACCTAGGCCAGGGATGGACA
GGGCTTGTCTGGTAGGGCAAGCAGAAACGGGCCCCGGGGTACTGCCCAGGGTGTCCCCGC

FIGURE 3-44

```
          ACCTGAGCAGCCATCTGGGTGCCTCAGTCGAGCGCTCCTGCGTGGGCTGTAGGCAAAGCT
68499     CCTGGCCCTAACCGAAGCCCCAGTGGGTGGAGGAGTAGCCCCCTTCTCCTGATTTTGGGA
          GCCAGGCTGGCACAGCGGGTAAGGAGGAGCAGGGTTCCAGGTGCTCGGCCCCGCAGGTAC
          ACGTGGCGCTTCCCTACAGCGGAGGCCATGCCGTCGGCCGGCAGCAGCCTCTGGCTCTCT
          GAGCCTTGAAAGCCTTCATCTTAGGAAGGGAAACCGAGGCCAGGGAACGACAGGGCAGCC
          ACCTAGGCCAGGGATGGACAGGGCTTGTCTGGTAGGGCAAGCAGAAACGGGCCCCGGGGT
          [A,G]
          CTGCCCAGGGTGTCCCCGCACCTGAGCAGCCATCTGGGTGCCTCAGTCGAGCGCTCCTGC
          GTGGGCTGTAGGCAAAGCTCCCCCAGCCTGGCCCCTTAAAGTGTGGTACCGCCTGTCAGC
          ACGCAGCACTCCCCTGGAGCCAACTCCAAGCCCCTCTCCATTCCTGCCCCGGACCCTGAC
          CTCAGTGGAGCCCACTGCAGAGGCTCTTGGGGGTCTATTCTGGGCCCCATCTATCTCCCT
          GTGGACTTGGGGAGCCCAGCCTATCCCCGTGATCTCGCTACGCCCAGCCCTTCCCAGCCC

68713     CGAGGCCAGGGAACGACAGGGCAGCCACCTAGGCCAGGGATGGACAGGGCTTGTCTGGTA
          GGGCAAGCAGAAACGGGCCCCGGGGTACTGCCCAGGGTGTCCCCGCACCTGAGCAGCCAT
          CTGGGTGCCTCAGTCGAGCGCTCCTGCGTGGGCTGTAGGCAAAGCTCCCCCAGCCTGGCC
          CCTTAAAGTGTGGTACCGCCTGTCAGCACGCAGCACTCCCCTGGAGCCAACTCCAAGCCC
          CTCTCCATTCCTGCCCCGGACCCTGACCTCAGTGGAGCCCACTGCAGAGGCTCTTGGGGG
          [T,C]
          CTATTCTGGGCCCCATCTATCTCCCTGTGGACTTGGGGAGCCCAGCCTATCCCCGTGATC
          TCGCTACGCCCAGCCCTTCCCAGCCCTGCCCCCCTCCCACACTGGATGCTTTTGTCCAGT
          GAGCCCAGCTCCAAGGATGTGTGGAAGGTGGCTAGCCAGCAGGGGGCCTCCTCAGACACT
          GCCCACCCCCCAGAGACTGCGGCCGAGGGAGGGGAGGCTGAGAGCCCCAGTGAGCAGG
          CACAGGCAGACCAGGGCGTGTGTCCACCCTGTGCAGGCGCCAGTGAGGGCCTTGAGGGAG

69097     CCCTGCCCCCCTCCCACACTGGATGCTTTTGTCCAGTGAGCCCAGCTCCAAGGATGTGTG
          GAAGGTGGCTAGCCAGCAGGGGGCCTCCTCAGACACTGCCCACCCCCCAGAGACTGCGG
          CCGAGGGAGGGGAGGCTGAGAGCCCCAGTGAGCAGGCACAGGCAGACCAGGGCGTGTGT
          CCACCCTGTGCAGGCGCCAGTGAGGGCCTTGAGGGAGTAGCCCCTCCCAGGGCCTTGCTC
          CCACCCCAGTCCTGGACTGGCAGCACCAACATCCCCAGGCCCAGCAGTAGGGAAGAGGGC
          [G,C]
          GAGGAAGAGGGTGCCTGCCTTGAGTTGAAGGGCAGCCAGAAGCCACAGGGCCCTGGAGCT
          GCTGAGTGGCACAGTGAGGATGCAGGCCACGGCCAGGGCAGAGTTGTCAGCCCAGGGGAG
          GGGCTAGGCCCACCCAGGGCACCGGCCATATCCAGGCTCAGGCTCAGGCTGCTGGAGGTC
          CGGCTGCTGCCCAGGTGGCTCCGCCTTGTTCCCTGCCTCCGCAGCCCCGCCTCACTCCAG
          GCCCTGCCCCTGCACTGCCCCTTATAAGCCCCGCCCCCTCTGGCTCTGGCCCCCCCAGTA

69135     AGCCCAGCTCCAAGGATGTGTGGAAGGTGGCTAGCCAGCAGGGGGCCTCCTCAGACACTG
          CCCACCCCCCAGAGACTGCGGCCGAGGGAGGGGAGGCTGAGAGCCCCAGTGAGCAGGC
          ACAGGCAGACCAGGGCGTGTGTCCACCCTGTGCAGGCGCCAGTGAGGGCCTTGAGGGAGT
          AGCCCCTCCCAGGGCCTTGCTCCCACCCCAGTCCTGGACTGGCAGCACCAACATCCCCAG
          GCCCAGCAGTAGGGAAGAGGGCCGAGGAAGAGGGTGCCTGCCTTGAGTTGAAGGGCAGCC
          [A,G]
          GAAGCCACAGGGCCCTGGAGCTGCTGAGTGGCACAGTGAGGATGCAGGCCACGGCCAGGG
          CAGAGTTGTCAGCCCAGGGGAGGGGCTAGGCCCACCCAGGGCACCGGCCATATCCAGGCT
          CAGGCTCAGGCTGCTGGAGGTCCGGCTGCTGCCCAGGTGGCTCCGCCTTGTTCCCTGCCT
          CCGCAGCCCCGCCTCACTCCAGGCCCTGCCCCTGCACTGCCCCTTATAAGCCCCGCCCCC
          TCTGGCTCTGGCCCCCCCAGTATTCCCCACCCATGCCTCTGGGGCCCTACCCACTCCTGG

69749     CCATCGAGGCTGTGGGCGTCCAGCCAGAAGGCCCAGGACAGCCTTTCACTCACTCCCTCC
          CTCCTCTCTCCATTCTGTACTCCAGACACCACTAACTGTATGGAAATGATGACGGGCGG
          CTTTCCAAATGTGGTAAGAATCCCCCACGCTCACCTGGCACCTCCACCTGCCACTTCACC
```

FIGURE 3-45

```
          GCTCACCCTCAGCCCGCTGTGGCCGCCACCTGCCGCCCGGGTTGTCCCGGCCTCCCTGTG
          TAGATGTAGGCACCCAGCAGCCCAGATGTCCCCGGCCCCATCCTCTACCAGGAGCAGCCC
          [C,A]
          CGTCGCTCCCCTACCACAGCAAGCCCAGGCGGGGTTCCTGGCCAGACTCACCTCTGCCAG
          GCCCTAGGATCAGGGCAGGCCCAAGAAGGGGCTCCCAAGGCCTGAAGCCAGTGAGGGTCC
          CGCTGGTCCCACTGGTGCAGGCTGTGGCCTAGGGGAGGGGCCGGTGCCCATCCCTCTGTC
          CACTGGAGGCTGTGCCTGGCAGGGAGCGGAGGGGCCCACAGCTCAGGGCTCAGGTGGGGG
          TTAGGCTTAGGAAGTGGGATTGAGGGGCCTCCATCGACACACCTGGGCAGTGAGCACAGG

69750   CATCGAGGCTGTGGGCGTCCAGCCAGAAGGCCCAGGACAGCCTTTCACTCACTCCCTCCC
          TCCTCTCTCCATTCTGTACTCCAGACACCACTAACTGTATGGAAATGATGACGGGGCGGC
          TTTCCAAATGTGGTAAGAATCCCCCACGCTCACCTGGCACCTCCACCTGCCACTTCACCG
          CTCACCCTCAGCCCGCTGTGGCCGCCACCTGCCGCCCGGGTTGTCCCGGCCTCCCTGTGT
          AGATGTAGGCACCCAGCAGCCCAGATGTCCCCGGCCCCATCCTCTACCAGGAGCAGCCCC
          [C,G]
          GTCGCTCCCCTACCACAGCAAGCCCAGGCGGGGTTCCTGGCCAGACTCACCTCTGCCAGG
          CCCTAGGATCAGGGCAGGCCCAAGAAGGGGCTCCCAAGGCCTGAAGCCAGTGAGGGTCCC
          GCTGGTCCCACTGGTGCAGGCTGTGGCCTAGGGGAGGGGCCGGTGCCCATCCCTCTGTCC
          ACTGGAGGCTGTGCCTGGCAGGGAGCGGAGGGGCCCACAGCTCAGGGCTCAGGTGGGGGT
          TAGGCTTAGGAAGTGGGATTGAGGGGCCTCCATCGACACACCTGGGCAGTGAGCACAGGG

69871   TTCCAAATGTGGTAAGAATCCCCCACGCTCACCTGGCACCTCCACCTGCCACTTCACCGC
          TCACCCTCAGCCCGCTGTGGCCGCCACCTGCCGCCCGGGTTGTCCCGGCCTCCCTGTGTA
          GATGTAGGCACCCAGCAGCCCAGATGTCCCCGGCCCCATCCTCTACCAGGAGCAGCCCCC
          GTCGCTCCCCTACCACAGCAAGCCCAGGCGGGGTTCCTGGCCAGACTCACCTCTGCCAGG
          CCCTAGGATCAGGGCAGGCCCAAGAAGGGGCTCCCAAGGCCTGAAGCCAGTGAGGGTCCC
          [G,A]
          CTGGTCCCACTGGTGCAGGCTGTGGCCTAGGGGAGGGGCCGGTGCCCATCCCTCTGTCCA
          CTGGAGGCTGTGCCTGGCAGGGAGCGGAGGGGCCCACAGCTCAGGGCTCAGGTGGGGGTT
          AGGCTTAGGAAGTGGGATTGAGGGGCCTCCATCGACACACCTGGGCAGTGAGCACAGGGC
          CCCAAGAAGGGTGGGCTCCCCATTTCCGCCCCTCTTCTCAGGACTGCCCCCATCCCAGGG
          ACCCGGGACATGACTCTAGCTGCTTGCCCCCAGCCCCCCAGCCTGCCTCCCACATCCACC

GENOMIC INFORMATION BASED ON SPLICE FORM 2:

1 TTCAGGGAGA AGCAGCTCTT CCTCCATGAG CACACCCTGC CGAGGCCACC
   51 CCCCACCCCT GGCACTGGGC TCCCCTCTGT GCCCAGCCTG TGTCACTGCC
  101 CGGCCTGCAG CTCCCCCTGC CTCTGGGGAA GCCCGCTTCT TCGGCAAGGT
  151 CCTGGGTCCC CCACCCGGCC TGGGCTCACC CAGATCCAGG CGTGACGCCA
  201 CACAGATGAA ACTGACGGAA AGGGCAAAAT AAAGCTAAAA GCCGATGGGG
  251 CCGGGGGAAT GGAGGTTTGA CGCGTGAGAC AAAGGATTAA TTTCCCAAAA
  301 AAATCAAAGG GCTCTTGCAA ATTGGTAAGA AAATGCACAC ATGTGCGTGC
  351 ACCAGGATAA AAACGAGAAC AGGAAAGGAG CCCAGAGCAC ACCCACACGG
  401 TCAGTAAACA CCGGTGACGT CCCGCGGGTC AACAGGGCGA GGCCGAGTCT
  451 GGGTGAAATT TGAGCACAGC GCGTGCACGG AAGGATGGCG GCCACTAAAG
  501 CCCAGTGGGA ATGCCAGCCA GGATCTGGGT GTCTGGGCGC ACCTAGGAGT
  551 GGGGTCCCCT GTGATAACCT GGGCCGGCTC TGCGTGTCTG GGGGCACCTA
  601 GGAGTGGGGT CCCCTGTGAT AATATGGGCC GGCTCTGCGT GTCTGGGGGC
  651 ACCTAGGAGT GGGGTCCCCT GTGATAATAT GGGCCAGGAT CTGCGTGTCT
  701 GGGGGCACCT AGGAGTGGGG TCCCTGTGTA TAACCTGGGC CGGCTCTGGG
  751 TGTCGGCGCA CCCAGGAGTG GGGTCCCCTG TGATAACCTG GGCCGGCTCT
  801 GGGTGTCTGG GGGCACCCAG GAGTGGGGTC CCCTGTGATA ACCTGGGCCG
```

FIGURE 3-46

```
 851 GCTCTGGGTG TCTGGGGGCA CCCAGGAGTG GGGTCCTCTG TGATAACCTG
 901 GGCCGGCTCT GGGTGTCTGG GGGCACCTAG GAGTGGGGTC CCCGTGATAA
 951 CCTGGGCCGG CTCTGGGTGT CTGGGCGCAC CTAGGATTGG GGTCCCCTGT
1001 GATAACCTGA TCCCCCCATG GTTCCAACAT GCCCCAACAT GGAATGGCAC
1051 ATGAGTGCGC CTGAGGACCT TTGATGGTAG GAAAGGGCCT GGGTTGTGGG
1101 CTCCTGGGGG CATCTCCAGT GTCAAGGCCA CAGCTCAGGC CAGGTGGGGC
1151 TCAGGGGTGT GGCCGGGCTG TCCTGGGCAG GGGCAAGTAT CTGGCTGTGA
1201 AAAGAGTGGG GAGAGGAGAA AGGGAGGGTG GGCCGAGGCG CGGAGGGGGA
1251 CCGGGACCGT GTGCCCAGCC AAGGCACATT CCCAGAGCAC CCTGCCTGCC
1301 TTTTAGGTGG GTCTGGGAAG GAAGGGGCTG CCGGGCCGTG GAGGTCTAGG
1351 GCAGTGCTGC CTGGGGAGCT ACCTGGGGCC CGTCCTGGTG TCCTGGGGTG
1401 AACACAGGGC CGGGGCTCAG GTGCAGAGCA TCTCAGCAGA GGAGGGGTGC
1451 CGGTGGGGGT CTCAGCGGAG GAGGGGTGCC GGTGGATGTC TCAGCGGAGT
1501 AGGGGTGCCG GTGGGGGTCT CAGCGGAGGA GGGGTGCCGG TGGGGGTCTC
1551 GGCGGAGGAG GGGTGCCGGT GGGGGTCTCG GCGGAGGAGG GGTGCCGGTG
1601 GGGGTCTCGG CGGAGGAGGG GTGCCGGTGG GGGTCTCGGC GGAGGAGGGG
1651 TGCCGGTGGG GGTCTCGGCG GAGGAGGGGT GCCGGTTGGG GTCTCGGCGG
1701 AGGAGGGGTT GCCGGTGGGG GTCTCGGCGG AAGAGAGGGT TCGGTAGTGG
1751 TCTCGGCGGA GGAGGGGTCG CTGTGGGTGT CTCGGCGGAG GAAGTATGCC
1801 GGTGGGGGTC TCGGCGGAGG AGGGGTGTCG GTGGGGGTCT CCGCGGAAGG
1851 CTGCGTCTGA GGTATCTCTG CAGAAGGCTG CAAGTTGGGG GTCTCGGCAG
1901 GGTGTGCGAG GGACAGCCTT CTTGGGCCAG GCAGGCACCT CGAGGGCACC
1951 CTGGCTCCCA GCTGAGGGTG GCTGAAGCTG AAGGGAGGGG ATTTGGGTCC
2001 CTTGGATGGG GAGAAGGCAA GCGGGCACAG AGACTGAGAA GCCCAACCGG
2051 GCGTGGAGGA AGACACACTT TCAGCCACGT GACCCACACT GACTGTCTGA
2101 CACGACCAGC GGCAGGGCTC CCTGGAAGCG GTGGACCCTG CTTCAGACGT
2151 GGAGGCTACA GCTGAGTCGT ATATGTCAAC TGTTCTGTGT AATGTATCGC
2201 TCAATCAACA CATACACCGA AATAAGTTAA ACTGGTCCTA ATATACTACT
2251 AATTATCGTC CTCATCCGTT CGATGGAACT GCGNNNNNNN NNNNNNNNNN
2301 NNNTCTCGGC GGAGAGGGTG CCGGTGGGGG TCTCGGCGGT AGAGGGGTGC
2351 CGGTGGGGGT CTCGGCGGAG GAGGGGTGTC GGTGGGGGTC TCGGCGGAGG
2401 AGGGGTGCCG GTGGGGGTCT CGGCGGAGGA GGGGTGCCGG TGGGGGTCTC
2451 AGCGGAGGAG GGGTGTCGGT GGGGGTCTCG GCGGAGGGCT GCGGCTGAGG
2501 TATCTCTGCA GAAGGCTGCA GGTGGGGGTC TCGGCAGGGT GTGCGGGGGA
2551 CAGCCTTCTT GGGCCAGGCA GGCACCTCGA GGGCACCCTG GCTCCCAGCT
2601 GAGGGTGGCT GAAGGCTGAA GGGAGGGGAT TTGGGTGCCT TGGGATGGGG
2651 AGAGGGCGAG GGGGGCCACA GAGACCTGAG AAGCCCAAAG GGCCGGCGTG
2701 GAGGGAAGAC ACAGCTTTGC AGGGGCAGCG TGACGCCAGC ACTGAGCTGT
2751 TCTGGACAGC GACCCAGGCG GGCAGGGCC TCCGGCCCTG GAGCGGGTGG
2801 GACCCCTGCT GTCCAGGACG TGGAGGAGG CCCCAACCT GCACTGTCCG
2851 GCTGGGTGCT CGCTGCAGGC ACCCTGGGTG GGTCTGAGCG CGGCTGCTTC
2901 TCTCCCGCAG GTCTGGTGAA GCTGGGGGTT CACTGCGTCA CCTGCCAGAA
2951 GGTGGCCATC AAGATCGTCA ACCGTGAGAA GCTCAGCGAG TCGGTGCTGA
3001 TGAAGGTGGG TGGGGCCGGG GAGGGAGGCG GGGCCGGCGG TGGGGTGGGG
3051 CGGGGAATAG CACAGGGGTG GGAGCCAAGG TTGTGGGGAC CTGCGGTGCT
3101 GGATGCGGGT GGGGGGGCGG GCCTGCAGGC TCCTGGGCCG CCACACCCCT
3151 GCTGGTCCCC TGGTAGGGTG CCTTTGCTCT TGCTCCTCCC TCCAGCCCTG
3201 CCCACCTTTC TCCTGCCTCC AAGCAGAGTG GGCACCCCTG AGGGACAGG
3251 CTGCAGCTGG GCAGTTCAGT TGCTGCAGGA CCTGCTGTGC TAGCAGGCGG
3301 GGCTTCAGTG TTCCCAGCTA GAATGGAGAG GAGTTCCCTG CCTCAGAGCA
3351 CCCCTCTCCT ACCAGGGCAC AGCTTGGCAG AGGGGAGCTG CACCTTCCTC
3401 TTCCACTGGG GCCTGGCCTC CGTCGGCTCC ATCCGGTGGT GTCTGGTCAC
3451 CATGGAGACC AGGCAGGCCC CCTGGGTGGA GGGTTTCTGG GCTGTGACCC
```

FIGURE 3-47

```
3501 ACCTCTCAGT GGGGAGGGGG CGGCCCCGGC TGCTGGGAAG CCTGACCCTG
3551 GGTGTAGAGG AAGAGGCTGG GGCTCCCAGC TGCTCCGGGT CCCACCCACA
3601 GTGGGACCTG GGCTGGCAGC GTGCGACCCT CCCAGCACTG GGGCCAGTCG
3651 AGCCCCCTCC TCTCCCTTCC TCTCCATTCG CTCCTTGGCA TGCAGGGCTG
3701 CGGGTGGGGC AGGACCCGGG GACGAGGCCA GTGGGAGTGG CCAAGAGAGG
3751 GGAGGCTTGT GGAAGGTGCT AAGGGTTGGG GACTGTGACA TGTTGGGCAC
3801 CCCCCAGCTG CTGGGGTGTG GAGGAATTAA CCAGACTAAA CTGGGGAGGC
3851 CTGGGACCC TATGGGGAGG TGGGGGTGGG GTTAAGGGCT GCTGAGGGCT
3901 GCCTGGATGG GGCTGGCAGG GTCCCACCCT GCCTTGGAGG AGAAACAGAG
3951 GCCCTGGGAG TGATGGGGCC AGGACAGCGC CTGGCAGAGA GATCCAGTGT
4001 GGGGCGTAGC TGGGGAGAGT CCCATGCTGA ATTTGGGAGG TGCCTGTGAG
4051 CCCCGACTAA AGGAGGGCCT GGGGATGCGG GAAAGGGGAG GTGTCCCTGT
4101 CACCTGCAGG CGCTGTGCAC AGATGTCCGC CTGGGAGGGA AGGACTTGGG
4151 GACAGGCTGG CCAACTCGCC AGGGCTGGGA CCCCATCACA AGACTGGCCC
4201 TAGCTCCAAA GCCTGGTCCA CGCTGGCTCC TGAGGGCTGG GACCCCAGGC
4251 CGTGGCCTCA CTGGCCCCAC CACTGACACG GCCACTTCTT TGTGCTGGGC
4301 GGAGCACCAG CTGCCCGTGG CCAGGCTTGC ATGTCTGAGG GAGGGGGCCC
4351 TGCCTTACCT CGGAGCAGGA CTGGGTGTCC TGAGTCAGGT GCCCTCTGGG
4401 TCACTTCTGC CCCTCCCTGG GCCCTCCCCA CTTGGGGGAC AGTACCAGCT
4451 GGGAGCCTGT GGATGGGGGG CACGTGCCCT GCCCACGGCC TGCACACCTA
4501 CTGTATGTCC CACACACAAC AGGATGCCTG CCCCCACCTC ATGGGGCCCA
4551 CAGAGGCCTG TCCCGGCCCC TCCTCCTGTG AGGCCTCCAC CGTAAGGAAG
4601 GGCGGAGCCC AGGCACAGCC TGCCTGGAAG GGCCCTGCAT CCGACTGGCT
4651 GGGAGCCTGG GAGGCCTTAT CTCCAACAGC TCCAGGCCCC ATTCCTGAGG
4701 CTGGGCTCAC AGAGAGGCCC AGGCTGCCTG CCTTCCTGGG CAGTGTGGGG
4751 AGGGGCCCTC CTGCTCCAGG GGCCCCAGT CCTCAGCCCT ACAGGCTGGT
4801 GTCAGCCCGG CGGCCTGGGC TCCCTCCACT GAGGCCCCTG CCCTCTGCCC
4851 TCTCCACCAG CCAGGGCCCC AGCTGAGCAG CCCACGTCCC TGCATCCCCC
4901 ACAGCTGGCA CCAAAGGCCC CTGCGTCCCC CACAGCTGGC ACCAAAGGCC
4951 CCTGCGTCCC CCACAGCTGG CACCAAAGGC CCTGCGTCC CCACAGCTG
5001 GCACCAAAGG CCCCTGCGTC CCCCACAGCT GGCACCAAAG GCCCCTGCGA
5051 CCCCCACAGC TGGCACCAAA GGCCCCTGCG ACCCCCACAG CTGGCACCAA
5101 AGGCAGTGTC TGTGGGGAGC GATGCGTGCC CCAGCCCTGT GAGCGTGATG
5151 TTCTCTGGCC TCTCCCATGC AGGTGGAGCG GGAGATCGCG ATCCTGAAGC
5201 TCATTGAGCA CCCCCACGTC CTAAAGCTGC ACGACGTTTA TGAAAACAAA
5251 AAATATTTGT AGGTATTGCT GGGTCTGAAG AGCTGGGGTG GCGGAGGTGG
5301 CAGCTGTCGC TGCAGGGGTG GGTGTCTGGG GCTTGGGGAG CACAGGGGCT
5351 GGAGGCCAGG GGCGCCTGCT GCATCCCAGC AGCCCTGGCC CTGCTAGCAT
5401 GAACACCTGC CTGGGTAGGG TCTCAGCCCA GGCTGCTGTG GTCTCTGCTT
5451 CTGGACCAAA CCGGAGACCT GGTCTGTGGA GGCTCGCAGA GCCACCAGCC
5501 TGAGGCTGGC AAGGGGGAAC AGGACCTTCT GGAGGGGAGA TAGGAGTTTC
5551 AGGGCAAGGG GCAGGAGCAC CTGGCCCTCC CCACATGGCC ACGCTGAGCC
5601 TCCTGGCCTC TGCCCAGGAC GTCCCCAGCC CTGGGCAGTG AGCCATGTCT
5651 CTATCCCTGA GGCTCCCTCA CACGAGGCAC AGCCACCAGG ATCCCGCCCT
5701 GGCTGGACCG TGGCTGAGTG TGGCTGAAAG TGTCACCTCC GCAGCCGCTG
5751 AGGCCAGCAG AAATCCCTAC CCTGTCCCAG GCATGCCTGG CTGTGAACCC
5801 CATCCCCCCA GACCCAGCCT CAGGGAGCTC CTGGGAATGG GCACAGTGGT
5851 CACTCACGGC AGTCTCCTCT GTGTGCTCTG ATGGGCTTTT CTGACAGATG
5901 AGGCGCTGCT GCCCAAGGGC TGTCTGGCCT TGAGCCTCAT CTGACCCTCG
5951 CTGGTCCCAG GCGGCGGCG TGACCTGCCA GGTGATCCTA GCCGGGCATC
6001 TCTGAGGCAT CAGGCTCTGA GGGAGCAGGG AACATACAGG GCTGGGCTGG
6051 GGGCTGCCCT CAGGGTGAGC TGGCTGAGGG CCTGGCTGAA CCCAGCAGCT
6101 CCCCTTCCCC CAGCAGCAAC GTCCACGCTT GCTCTGGCCT GGGTTTCTGC
```

FIGURE 3-48

```
6151 ATTCTCGTGG GGAGCATGTG CAGGTGGCCA GCTCGTGTGT AGCTGGGGAG
6201 AGGAAACCCA GGGGTGGGGT GTGGGGAGCC CGCCTGCCCC ACCATGAGCA
6251 GGGGCTCAGA AACTGTCACC AGAGGCCTGG GGGGGCGGGG GTGGTCCTGG
6301 CCCTGATGCT GGCAAGGTGG ACTGTGACAA GGGGCATGGC TTCCTCATGG
6351 TGACACGGTG CCGGTGCAGT GGGGTCCTGG GGAGGCCTTC TCGGAGGGGA
6401 GGGCAGGGGA GTGCGGGGGG GATGGGCACA GCAGCCAAGG CCCAAGAACA
6451 GGAAAGAGCC CAGGAGGTGG GCATGGCCGG GCTCGCGGCT TCTCCCGAGG
6501 TCTGGCCCTG GGTGTTGTCC CACCCCCTCT GGACACCATG TGGCCTATGC
6551 TGAGCCTTGG GCCTGGCCGC CCCCCTGCCC AGAATCCCAC CCTGGCCCCC
6601 ACCACCTTCC CCTGCCCTGA GGGCTTCACA CCTTCCTCTG CCCTGAGGGC
6651 TTCACACCTT CCCCTGCCCT GGGGGCTTCA CACCCTCCCC TGCCCTGAGG
6701 GCTTCACACC TTCCCCTGCC CTGGGGGCTT CATATCTTCC CCTGCCCTGG
6751 GGGCTTCACA CCTTCCCCTG CCCTGGGGGC TTCACCACAA CCTCTGCTCC
6801 CATCCCCACA CTGGGCCCTT GACTCCTGCC AAAACCAGCT CCTGGGACAG
6851 CCAGTCATCC CAGTCCGCAC GGCAGCTCTG AGCATGCACC AAGGTGCCAC
6901 CCCCTTGGCT GTACAGCCCC CCTACATCAC CACAGCCACA CCAGGGGCCA
6951 CCACCCTCAC AGGCCTCCCC CCCGAGCTGG TTCAGCCTGG GTGGAGCGGC
7001 CCCCAAGCAG CTGCATGCAG CGTCCCACGG GCCTCTCACC AGGAACCAGC
7051 CCCTCAGGAC CCTCCATGTG GCTGAGACCC CACGGGGGTG GTGCTGGGAG
7101 CCCACCAGGG CAGGAAGGGG AGGGCCAGGC CAACCTTTTC CTCACCCCCT
7151 TCCCCTGGCC CTCACACCTC CTGTTCCCCC CACAGAGGCC CAGACAGTCC
7201 CTGGGCCCCT GGATGCGGCT GCGTGGTCTC CCTGCTCGGT GCCTGTGCCA
7251 CTGAGGACCA CAGGGTGTGA GGGCCAGAGC AGGCAGGGCA GAGTCCCGAG
7301 GCTACCCCAT GCACCGAGCC TTGGCCCCAG CACCCGCCAC ACTCAGCCTG
7351 TGGGTTCCAA ACCCTCCCTG GCGGCTGTGC CCCCAGAACC ATCCCTTCAC
7401 CTGTCCCTCC ACCCTCACCC CACCCCACCC CAACCCAGGC TCCTTGAAGA
7451 CTCATTTGAG GTCCACCCCC AGGAGCCCAG ATGGTTTGAG ATCCACCATA
7501 GTCAGGGCTC CTCTCAGCTG CCCCCCCAGC CAGCAAGAGG ATGGGGCGG
7551 CCTGCAGAGA GGCTGGGCCA GGAGGCGGCT GTGGGAGGCC CTGGGATGAG
7601 GAGGGGCGGC GGGCAGCCAC AGCTGGGCGC ACTGGTGGCC CCGTCTCCTG
7651 CAGGTACCTG GTGCTAGAAC ACGTGTCAGG TGGTGAGCTC TTCGACTACC
7701 TGGTGAAGAA GGGGAGGCTG ACGCCTAAGG AGGCTCGGAA GTTCTTCCGG
7751 CAGATCATCT CTGCGCTGGA CTTCTGCCAC AGCCACTCCA TATGGTGAGG
7801 CCCCACCCCT GGTGCCCCCC ACTCCCCAGG GACCCCCACA CCCAGTGCGC
7851 TACCACAGAT GCCCCCTGTG CCCCAAGGAC TACACCCCCT ATGGTGCTAT
7901 TCCGAGGTAC ANNNNNNNNN NNNNNNNNNN NNNNNNNNNN NNNNNNNNNN
7951 NNNNNNNNNN NNNNNNNNNN NNNNNNNNNN NNNNNNNNNN NNNNNNNNNN
8001 NNNNNNNNNN NNNNNNNNNN NNNNNNNNNN NNNNNNNNNN NNNNNNNNNN
8051 NNNNNNNNNN NNNNNNNNNN NNNNNNNNNN NNNNNNNNNN NNNNNNNNNN
8101 NNNNNNNNNN NNNNNNNNNN NNNNNNNNNN NNNNNNNNNN NNNNNNNNNN
8151 NNNNNNNNNN NNNNNNNNNN NNNNNNNNNN NNNNNNNNNN NNNNNNNNNN
8201 NNNNNNNNNN NNNNNNNNNN NNNNNNNNNN NNNNNNNNNN NNNNNNNNNN
8251 NNNNNNNNNN NNNNNNNNNN NNNNNNNNNN NNNNNNNNNN NNNNNNNNNN
8301 NNNNNNNNNN NNNNNNNNNN NNNNNNNNNN NNNNNNNNNN NNNNNNNNNN
8351 NNNNNNNNNN NNNNNNNNNN NNNNNNNNNN NNNNNNNNNN NNNNNNNNNN
8401 NNNNNNNNNN NNNNNNNNNN NNNNNNNNNN NNNNNNNNNN NNNNNNNNNN
8451 NNNNNNNNNN NNNNNNNNNN NNNNNNNNNN NNNCCCCCCC ATTAGGCTAC
8501 CCCTCAAGTG CACCGTCCAC CCCATTAGCT ACCCCTCAAG TGCACCGTCC
8551 CCCCATTAGC TACCCCTCAA GTGCACCATC CCCCTCATTA GCTACCCCTC
8601 AGGTGCATCA TCCCCTCCTC ATTAGCTGCC CCTCAAGTGC ACCGTCCCCC
8651 CCATTAGCTA CCCCTCAAGT GCACTGTCCC CCCCACCCCA TTAGCTACCT
8701 CTCAAGTGCA CCATGTGCAC CAGGTGCTTC CCTTTTCCCC CTGAGGACCC
8751 CCTGCACCTC CCCTTTCCCG AGTGGGCAGT GTGTCGGGAA GTTTTCTGCC
```

FIGURE 3-49

```
8801  TGGCACCCAC CCAAGCACTC TGGGAGCCCC TCGGCCTTTC CAGGGGCCAT
8851  TGCTTGCATC CCTACGTGCC TGGGGGCCCT AGGTTGGTCT AGGCCAGAGC
8901  AGGTGTGCTA GGGAGCAGGA GGGGGCAGGA AGGAGCCTGC CAGGGTGCAG
8951  GAGGGCATGG CAGGAGAAAC AGGGATGCCT GACCAAAGGC CAGAGCCAAA
9001  CGGACCAGGC AGGCGACTTC TGATTGGCTG CCTATGACAT CACCAGGCTG
9051  GGCTGCTATT GGCCCTTATG TGTGATTGGC GTTTGGAGAG GCAGTGGGCT
9101  CTGGGCAGGG GGTCTCCAGG GCGGGGAGGC GCTCAAGGCA GAGACTGGCC
9151  CTGTTCAGCC TCACCACCCT CCTCCCCAGC CACAGGGATC TGAAACCTGA
9201  AAACCTCCTG CTGGACGAGA AGAACAACAT CCGCATCGCA GACTTTGGCA
9251  TGGCGTCCCT GCAGGTTGGC GACAGCCTGT TGGAGACCAG CTGTGGGTAC
9301  GTGGCCCTCT GCCCTGGAGA GAGGCTGGGG GACAGGCTGG GCTGGGGGAA
9351  GAGGAGCCAG TGGACTGAGA GGCCCCCAGC CTGCCTGAGC CTCCCGGCAC
9401  CCCACAGGCA GGCCCCCCAC AATGTGCCTG AGCCTCCCAG TACCCCACAG
9451  CCTGGTGGTG GTGGGGAGAC AGGCCTCCCG GCACAGTAAG GGTAGGGGTA
9501  CAGCCCTGGC CCTGGCCTGC CTGGGAGAGA GGCTGGGACC CACTTACATG
9551  CCCCTCTCCT GGGGACCCCC TGGCCCCTGC CCAGCCGAGT GGGCAGACAG
9601  CTTTGGGCGC AGCAGAGACC CAGTGCCCCA CCTTGATCTC CTCCCAAAAG
9651  CCCGCCTGGG GATGCAGGGA ATGTGGGGGC GTCTGGCACC ACAGCCCTGG
9701  AGGCCTCCTT GAGGGCCCTG CGGTGCACCA TCACCCTGGG GGGAGGGCCT
9751  GGCAGCGCCC GGAGCCCCGC CGCTGACCTC TGCCCTTGCC CGCAGGTCCC
9801  CCCACTACGC CTGCCCCGAG GTGATCCGGG TGAGTCAGCG CCGCCGCGTG
9851  CAGCTCTGTG GGGCCCAGGG TGGCGGGGAC CTGACCCTGG TGGGACCCCA
9901  GCCTGCCGCA CCCCCAGGTG CTGCTAGGCT GCCTGTCCCC GGGCCGACTC
9951  CCTCTGAGCC CAGGCCCTCC AAGGCCCCCG CCCTGCCCTG CGCCCCCCAA
10001 CAGCCCGGGC ACTGCTGTCC ACAGGGGGAG AAGTATGACG GCCGGAAGGC
10051 GGACGTGTGG AGCTGCGGCG TCATCCTGTT CGCCTTGCTG GTGGTGAGAC
10101 CCTGGCCCCC TCAACCCTGC CCTGGCCTCT CCCCAAACCT GCCCCCCCAC
10151 GCTGACCCCC ACACCCGGCC GCCCGCAGGG GGCTCTGCCC TTCGACGATG
10201 ACAACTTGCG ACAGCTGCTG GAGAAGGTGA AGCGGGGCGT GTTCCACATG
10251 CCGCACTTTA TCCCGCCCGA CTGCCAGAGT CTGCTACGGG GCATGATCGA
10301 GGTGGACGCC GCACGCCGCC TCACGGTGCG TGCCCTCGGA GCGGGGCGGC
10351 CCCAGAGCGT GGCGGGGGGC GCGGGGCGG GCGTGTGCCT GTGTGTGCAC
10401 AGGTGTGTGC CCAGACGTGT GGGCACCCAG GTGTGTGGGT CGGTGCCCAG
10451 GTGTGTGGAC GTGTGCACAG GTGTCGGCTT GTGTTCAGGT GTGGGTGACC
10501 AAATGTGGGC CCATGGCCGT GTGTGGGTGC CCAGGTGAGT GTTCAAGTGT
10551 GTGTGCGCAC CCAGGTGTGG GAGTGCCCAG GCGTGTGTGG GCTCGTGTTC
10601 AGGTGTGTGG GTGCACAAAT GTAGGCACAT GCCCAGGTGT GTGTTCAAGG
10651 GTGTGGGGGT ACCCAGGCAC ATGCCCAGGT TCATGTGATT GGGTGAGGGC
10701 GTAGGTGTGG GCATGTGCAC GTGTGGGGAG GTGTGTCCAG GTGCTTATGA
10751 GCACTTGTAC CAGTGTGGGG TGTGCACAGG TGTGGGGGC TGTGTGCACA
10801 TGTAGGTGAG ACCTGGCTAT AAGTTACACA AAAGCACTGG TGCTTCCCCA
10851 TCACGGCCAT CCTGCCTCCA GACGCTGCTG GGGCAAGCTC CAGGCAGCGT
10901 GAATAGTTCT GCTGAGTGCC CCAGCAGCT GTGGGGGCTA GCAAGAGCCA
10951 AAGGTAGCCC CCAGCTGCTG GTCCTGACCT CCTCCAGGGC TGCCTGGTGT
11001 GGGGACCGCA CGTGTCCACT TGACAGAAGC AGGTCACACT CTGGGCTGAC
11051 CCTTCCAGGG TAGCGTTGAC CTGTTCCCAA GTGGCCACTG CCTCACACCC
11101 CACGAGCTGT CCCTGAGTCA GGGTGGAGAG AAGGGGCCGT GTGGCTGGCC
11151 GGCCCTCCCA GCCTCCTGCC TGCACCTGCA CCCAGCCCTG CCCCGCCGCA
11201 CAGGTGGGCC GGGTTCTCCT GGCTTCAGCT CCCTCCTGGC TGCTCCCTGC
11251 TCTCCTGCCT TGGTTCCTTC CTAGAGCCAC GGAGGGGCCC AGCCCAGGCA
11301 GCACAGGCAC CTGGGGCTGC CCTGGCTCCA GCTTCCCTCC CTCCCCCTCT
11351 CCCTCCGCTC CCCAGGCCCC TGCCCCTACC TGGAGCACCC CCTCCGACTC
11401 CAGCTCCCCC GACTTCTCTC CTCCTTGAGG TGTGTGTTTT CTTCTCCACT
```

FIGURE 3-50

```
11451 TGGGAGAGGC AGGAGCAGGG GTGCTGGCCT TGAGCCTCTG GGAACGCAGC
11501 CCCCTCCCTA TCTTCCTCCC CACCTTCCCC CCACTCACTT GCCCTCACCC
11551 TCTCCTGCTC TCTCCGTGCT CCCAGCGCCC CTGCCTTCCC CCTCACCTCC
11601 TAATGTGGGC TCTTTCCGTC CCTCGTCCGT ACTAACTCCC TGTTTCTCTT
11651 TCCTTGTAGC TAGAGCACAT TCAGAAACAC ATATGGTATA TGTAAGTAGC
11701 TTTTCCACCC ACTAATCGCC TGCTTTGCCT GTTGCTGTGG CCTGGAGGCC
11751 CTGCTAGGAA AGGCGGGGGG AGGGCGCCGG CCCAGCGCAG GTCCTGCCCT
11801 GCCTTGGCCC TCCGTGGCCT GCGCTGGGTG CGGGGTGCGG GCAGGACGCA
11851 GGAGGCCTCC CCGGGCTGGG CACAGGGAGA GTGGCAGGAT GAAGGGCCCC
11901 AGGTGAGGGC GGGCGTCCCA CCCTCGCAGC CGCCCAGGCC CGGCCGGAGC
11951 TGATGAGCGG GTGGCCCGTC CTGTGTCCAC AGAGGGGGCA AGAATGAGCC
12001 CGAACCAGAG CAGCCCATTC CTCGCAAGGT GCAGATCCGC TCGCTGCCCA
12051 GCCTGGAGGA CATCGACCCC GACGTGCTGG ACAGCATGCA CTCACTGGGC
12101 TGCTTCCGAG ACCGCAACAA GCTGCTGCAG GACCTGCTGT CCGAGGAGTG
12151 CGTCTGGGGC TGCTCCCGGG TGGGCACGG GGCCTGAGGT GGGAGCGCTG
12201 CCCCGGAGGA GCCGGCGGCC CCGTGTGCCA GCGCGTCTCG CGCCTCTCGC
12251 CCGCTGTAGG GAGAACCAGG AGAAGATGAT TTACTTCCTC CTCCTGGACC
12301 GGAAAGAAAG GTACCCGAGC CAGGAGGATG AGGACCTGCC CCCCCGGAAC
12351 GAGATAGGTA TGGGTCCAGG GGTGGCCTCC AGCCCGGCCT GCACTGCCCC
12401 ACCGGGGTCC GGGGGCTGTC TGGCCTGACC TTCGTCTGTA CTCAGACCCT
12451 CCCCGGAAGC GTGTGGACTC CCCGATGCTG AACCGGCACG GCAAGCGGCG
12501 GCCAGAACGC AAATCCATGG AGGTGCTCAG CGTGACGGAC GGCGGCTCCC
12551 CGGTGCCTGC GCGGCGGGCC ATTGAGATGG CCCAGCACGG CCAGAGGTGT
12601 GTGTGCCCCG AGGCTGCTGG GCCTCCCTCC CTGGGCCCTG GCTGCGCGGC
12651 ACTGCCGCCT GGCTCATCGC TACCCATTGG CCTGGGGTCT CGGCTGAGGC
12701 CATTGGGTGG GGCTGTATGG GCTAAACTGG GCTTAGCTGG GCTTGGCTGG
12751 GCTGGGCTGG GCTTAGCTGG GCTGGGCTGG GCTGGGAGCT GAGCTGGGCT
12801 GGGCTGTGCT GGACTGGACT GGGCTAGGCT GAGCTGGGCT GGCCTGGGCT
12851 GGGCTGGGCT GGTTTGGGCT GGGCTAGACT GCACTTGGTT GAGCCGAGCT
12901 GGGCTGTACT GGACTGCGCG GCTGAGCAGG GTTGAGTTGA ATTAGGGTGG
12951 GCGGGGCTGG GCTGAGCTGG GCTGAGCTGG GCTAGGCTGC ACTAGAATGG
13001 GCTGAGACGG ATTTGACTGG GCTGAGCTGG GCAGGGCTGG GCTGAGCTGG
13051 GCAGGGCTGG GCTGGGCTAA ACTGGATTTG GCTGAGCCGA GCCAGGCTGG
13101 GCAGGGCTGA GCTGGGCTGG GCTGGCTTGA CCCAAGCTTG GCTGGGCTGA
13151 GCTGTGATAT GGTCACACCA TGCTCAGAGC CATCAGCCCA GCAAGCCTGT
13201 CCCCCTGGTC CCAGCAATGC TGGGCCCGTC TCTGGGTGGC AAGTGTGGTG
13251 TGTGTGGCCA GGGACATCAC AGAACTCAGC AGTGATGAGC AGACCTGTGG
13301 CCGGAGGAAG GGCACCCAGC CCCTCTGGAG CCTCTGCTGG GTGGGGGCAG
13351 GGCTGGGCTG CCCGCACGAG GCCCTCAGCA AATCCTTGGA GCCGGTGCGG
13401 CCTCTTGGGG ATGAGCTCAA ACGTCCCTCA CCAGGTGGCA GCTTCCAACA
13451 CTTGGGGACA GCCCTTGCGC CAGAGAGCAC ACCAGGAGGT CCAGGAGCCC
13501 GGGCAGCAGT CTCTGGTCTG CCCTGTGATC TGGGCCTCAG CACCCCAGGG
13551 CCCCCTCCTT GTACTGGAGA TGTGGGGGGT GGGACAGGCG TGGCCTGTTC
13601 CTCGGGAACT TGGGGAAGC TGTGGGGAAC TGCAAGGTAG CTTGGCAGCC
13651 ATCAGGCTAA ACCTGTTCCA GCCCCAGCCC TGGCCAGAGT ACTGGTGGTC
13701 CCAGTTCTGG CAGCTCCCAG GCCATGGCCC CCTGGGAGTC CTAGGCCCTC
13751 CCCAGGGTTT CAGGCTGGCC CAGCTTCCAA CGTGGGGTCC CAGCCCCCAG
13801 AACCTCCTTC CCAGGGCCCA GTCAGCGCAG CCCTGACGCC AGTACTAGGG
13851 GGTAGCAAGG GGCCCTCCTA TCTACATTCT ACTGTCCTGA CCTTCAGTGG
13901 CCTGCATGTC ATGGGGCAC CACAACCTGT AGCCCAGGTG CCTGCCTCCT
13951 GCCTGCGTGG CCACCTCCCC GGACTCCCCG ACCCTGCAGG GCAGGCCCCA
14001 CCACCCCACT GCCTGGCCCC TCCGGTCAGC GGCGTGGGAG GCCGCCCTCT
14051 TGGCCTCTGC TGCAACTCCC AGGCCTGGCT GCCTGGGGCA GGTGTGGGAT
```

FIGURE 3-51

```
14101 GGGCCAGGCC ATGGACCATT CCGGGGCCTC TGGAAGGCCA CTAGTCCTGG
14151 CATGTCCCAG CCAGATTCCA CTCCTGGTGG GGCCACCTGT GCAGCCAGCA
14201 GAGACCCAGC TGCTTGGTGT TGGGCCACAC AGGGCTGCTG ACTGGGGACG
14251 CAGGGGTCCT GGGGGCTGGG GTGGGGGCTA CCAGGCCACC CTGCCCAGCA
14301 GTCACACGGT GCGGGGTGTG CTGTCTGGCC CAGCCTCCTC TCTCGCCATC
14351 TTTGTGCAGC GGCCTCAGAG CCACGTGGAG TTCTTACCCG GTGTGGCCCG
14401 GGCCCTGGGG GCCGACCTGT GCCCGCGTGT GGCCGTCAGT AACTGTGTTT
14451 TCTCGCTCTG TTCTGCTGTA GTAAAGCAAT GTTCAGTAAA AGCCTGGATA
14501 TCGCTGAGGC CCATCCCCAA TTCAGCAAAG AAGACAGGTA TACACCCCGA
14551 CCACCCGTCC CCGCACCTCC CAGCCCCAGA CACGCTGTCC TGCCTCAGGC
14601 CGGGCAGGCA CATGGGCGGG TCTGGTGGCG GGCTGGGCTG CAGGGCTCCT
14651 GCTGCGGTGA AGCCAGCCAG CAAGCCAGGC AAGGGCCCGC GGGCCAGGCA
14701 GAGGCCGAGG AGGGGTGGGG CTGCTGAGGC GTGGCCCACG CCTGCCTGTG
14751 AGGGACCACG CACCATGGCT TACAGGGCCT GGGGCTAGAG CCCGGCGTGG
14801 CTGCAGGCCG AGCCGCTCCT CCTGCCAGCC CCTGTGCTGT GTCCGGTGGG
14851 CCTCGGTGGC CCTGCTGCCC CTGGGGCCGG CCAGAGTTGA AGCCGAGCAG
14901 CCGTCCTGTG CCCACCTGCA GGAGCTGAGG AGGGCAGGAG GCGCCGCCGT
14951 CAAGAGGGGC CTCTACCTGG GGCCAGTTTT GCGAGCCTGG GCGGGTGGCG
15001 CCGCCCCCAA GGCTGCAGTG TGCTGGCTGC CGGTCGGGGT CCTTCTCTTT
15051 GAGCCCTGGC CCCGTGCCTA CCTGGGACCC TCACCTGTGT GCCCTCACTC
15101 TGCCTGCCCT GGCTGCCCTC AGGGCTGGCG CCGTCTCTCC TGCCCCTGCC
15151 CCAGCAACTG TAGCTCAGTG TTCCCAGCAG CTGCCTGGCC GGATAGGACC
15201 AGGGCTCGGC CCCTCCACCC CGGGGTTTCC AGCGCCTCTT CTGTCTTCCT
15251 CGTGCCCAGT CACGAGCTCT GGGCGGGCTC GACAGGAACC ACAGGTCCAG
15301 GGCCTCACTG GTGGCTGCTG CCCCCATGAG GGCTGTCCGC GCTCCCAGCT
15351 CAGCCCTGAA AGCTCTGGGT CCAGTTCCAG CCCTGGGTGT CATCCTGGCC
15401 CAGACAGGCT GGGTTGTGCA TGGGGTCCCC GTCGCCTCCC TGCCCCTTGG
15451 CTGTGTCTGG TGAGGGAGTT GGAGGGTCGT CACCGTGGGG ACCAGCCCCC
15501 GGGTGTCCGG GAGCCAGGTG TGTGGCCAGC GTGGCACTCT CCACGGTCCG
15551 GGGCCTGGGC CGTGGTGTGG ACTAGCGAGG CCCCTCGTGG CCGGCTGGCG
15601 GTGGGCAGGC CTGGTGGGCA GTGCAGGCCG GGCTTTTACT CTTCTCTGTC
15651 CTCTTCTCTT CGGCGGCTGC CTCGGCCCCT CCCTGCATTT CCTTCCTCCA
15701 AGGATGGCAG CTGCCACTGT CTGGGCACGT GGGCGCCGGC TCGTCCGTGC
15751 AGTGTGGTGG AACGACGCAC AGCCGTCCTG GTCCCTGCAC GGGGGTGGCG
15801 GCCACACACC GGAGTCTCAG CCGGGCACGC CGGGCCAGGG CCTCCCTCCT
15851 GCTGTGTGCA GGTCTCAGGC TGAGTAGGGC AGTGGTGGGA CAAGGCCCCA
15901 CCGTCCCTGC CAGCAGCTGC CCCAGCCTGG CCCTGCCCAG GCCCTCCTGG
15951 TTGTGGACAA GGGAAGGGCC GGCCGCTGAC CCAGGCATCC CTCACGGGCA
16001 TCTAGGGACA TGGAGGACCA GGCTGCAGGC CCTGTGAGAG CTCAGCCAGG
16051 GGGGCTTGG CAGGTGGGAG CTGGAGCCA GCACGAGGCC TGGAGCAGAA
16101 GGGGCTGCAT ACAGGAAGCT CCCGTCTGTC CCTCGTCCT TCCGTCCACC
16151 CCCACGCTGG ATGGTCCTTT GCCGCGGCTG TCTGATGCCG TATCCTGTGC
16201 TGTGCCTGGG CTGCTGGCAT GGGGTGGCCC CCACACGTGG GCTCTGATGG
16251 GGGCCCCAGT GGGGCTGGGC ACAGCCAGGC GCCCTGGGCC CTCCTGAATT
16301 GACAGGGTGT GCAGCAGGAC CCAGGGCCTC GAGGCTCTTG GCCCGGGCTC
16351 CAGGCCTCCT GGAGGGTTTA CCTGGGGGGA GCAGAGCCCA GCACCTGCTG
16401 CTCCACTGCC CCCTGGCTGA GCAGTGGCCC TGTACCTTGT GACCTCCAGG
16451 TCTCGGTCCA TCAGCGGTGC CTCCTCAGGC CTTTCCACCA GCCCACTCAG
16501 CAGCCCCCGG GTGAGTGACC CCCCGCCCCC ACCCAGCTCG GATGCACAGA
16551 GGCCCCAACC CTCCCAGTCA GCGTGTGCCA GGGTGGGGC AGCCTCGTGG
16601 ACCCTGGGAA GCAGCCCCAG GCGCCCCCA TGCCCACGCT CCTGTGGCGG
16651 CTGCTGCTCT GTGGCGCAGG CTGCTCTGCT AACTGCACGC TCTTTTGTTT
16701 TGTTTTGTTT GTTTTCTTGT GTGTCACTTG TTTTCTTTTG TGGCTAATCC
```

```
16751 TCCTGCCCAT GCCTGCCTGC CTCCCCACCC TCCCGCTCCC GCCTGTTTCT
16801 TTCTGGTCCT CCTGTGCCGT GTGCATGCGG GGGACTGGGG TGCATGTGCC
16851 GCGCGGCTGC CCCCACCCCG CTCGCTCCCT GCGCCTCCCC GTAGCCTATT
16901 AGGAAGCTTG TCCTGCCCCC ACCGCCCCCC GAGCCGCCCT TCGTGGCCCG
16951 CCCCCTGGCC ACCTCCACGG AGCCCGAAGC TTGTGGGAGC GCCTCGAGGC
17001 CTGGACACGT CCTCCCTCTG CAGGCCGCCC TGCGGCCCGA CCCCAAGACC
17051 CAGACCTTGC CGTGCAAGGC CAAGCTGACC GACAAGCCTC TGCAGGGCAC
17101 CAAGTCCAAC CCCTTCCCGG CCAGCACCCC AGCCCGGCCT CCCGCCACTG
17151 GCCTTTGTCC CCAGCTGGCA CCACCCCTGG GCCCGCCTGC CCTGCGGGTG
17201 CCCCCCCGGC CCCCACCCGC CGGGATTGAA CCAAACACCA AATCTGTCCC
17251 CACCATACAG GTGACCCCTC ACCCCTCACC AAGGGGCAGT CCCCTCCCCA
17301 CCCCCAAGGG GACACCTGTC CACACGCCAA AGGAGAGCCC GGCTGGCACG
17351 CCCAACCCCA CGCCCCCGTC CAGCCCAGC GTCGGAGGGG TGCCCTGGAG
17401 GGCGCGGCTC AACTCCATCA AGAACAGCTT TCTGGGCTCA CCCCGCTTCC
17451 ACCGCCGGAA ACTGCAAGGT GAGTGTCTGC CCGGAGGCGC CAGAGTGGGG
17501 CTGGGAGAGA GCAGAGGCTG CCTTGGGGAG GGCCCCGCCC GGCAGTGCCA
17551 GACCAGTCCG AGGGGCCTGT AGCTGCAGGG GTGGCCTGGG CCTGCCCACG
17601 TCTCACTGTC CCGAAAGCGC CCAGCAGCAG CCTGTGTCCT ACCTGTCGCA
17651 CAGGCTGGTA TCCCCTCCAG ACATTCTGTG TTCCTGAGTC TACCCACTCT
17701 GTGTCCTGGG GCCAGGCACA CAGCAAGGAG AGCTGGCCAC CGAGGGGGCA
17751 CTGCCAGTCA GGAGGCCCCA TGTGTGGGGC ACCAAGGGCC AGCCAGTGCT
17801 GCTGGAGAAG GCACAGCCGA CTTCAGCACC AGAGGCGGGG ACAGCTCCCC
17851 TTAGCCTGGG GGCGCCACT GCCAGTGGGC CTCTAAGGTG GCCGGGAGCT
17901 GGGGTGGACC AGTGCCCCTG GGGGCTGTC CCAGTGTGTG TGGGTGGACT
17951 CCTGATGACC CTGACCTCGG CGCAAGGTGG CCAGGGCAGG GGAAGGATGG
18001 AGCGGTCACC ACGCCTTTCC TCCTGTTCAT CCTGTGTGCA CAGTTCCGAC
18051 GCCGGAGGAG ATGTCCAACC TGACACCAGA GTCGTCCCCA GAGTAAGTGG
18101 CCCCTGCTGG AGGCCTCCTG GTACCTGACA CCAGGCTGGC CGGGAGAGGG
18151 GCATGGAACC CTTCCCCTAT GGCCAACGGG GTGCTCCTTC TCCACGTGGC
18201 CCCACCTCCC ACTGCAGGCA GGCCCGTCTC GGCCACTGAG TCTCTGAAGT
18251 TCGAATTCCC GGCTGTGAGG GGAAGGCCAG CCAGGGGAGG AGCCCCCAGC
18301 CCTGTTGAGA AGCTTCAGGC CTTGGGAGAG CCTAGGGTTG GCTGGAGGCG
18351 AGCAGGGGGT ACACTGGGCA GAGTCTCCCC AGGGCCTGAG CTCGCCAAGG
18401 GCAGAGACCG GGTCGCTCAG GTCTCAAGGA GAAAGCAGCC CGTGTTAAGA
18451 ACAAAGGGGC AGCAGGCCTG GTGGGAACAC GTGTGCAGGG GCGGAGCGGA
18501 GCAGCCAAGC CGAGGTCTGG CCCCGCCGCC TTTCTGAGCC GTGAGAGGTG
18551 CCACTGCAGA GACTCTACAG CGCCCAGGTG CTGAGATGCC CTGGGGGCCG
18601 CTGTGACTGG TGTCTGGACA AAGATGTCCC CAGAGAGACC CCTTCCCAGC
18651 GCCCAGGCCC TCTCCCTCCT CTCCACGATG GCCTCAGTCA CTGGGCAGTG
18701 TCTCGGAGAC CAGGCGACTG GCGGTGTACA CATATGAGCC TGCAGCGTGA
18751 CCCCAGGCCA GGCAGCGGCA GAGAGCGGCG GTCAGGCTGG AGTCACTTCA
18801 CAGGAGACCC CGGGAAATGA AGATGTGGCC AGCTGTGGAC TGAGTAAGAC
18851 GAGAACCTTC GTCCTGCTGC TGGCTTTAAA CCAGGGGCCC CTGTGGAAAC
18901 TGCTCAGTGC TAAGCCCAG GAGCAGCATC TGCAGCCTGT GCCAGGATTC
18951 CACCCAGTGG CCTTTCTGCG CCGATCAGGT GGCCCTTCCA GCTGGGTGCC
19001 CAGGTCGGAG GTGTGTAGGT ATTGTCGCAA GCCCAGATGC ACAGGGCTCA
19051 GCAGACTTGG GAACCTTCCG CCTAGGCCCT GACATTGCCG TTTCTGCTGC
19101 TACCAAAAGC TTTCATGAAC AGACTCATAA TTATCTTCCT CAGAGAAGGT
19151 GGAAAACATC AAAGCCGAGA AGGTGGCTTT GATGCCACTG TGGCTGCCTG
19201 CGCTTCTCCC CTCCCCCATC TTGAGATGGC CTGGAGGCCC TGACCCCTCT
19251 CAAGGGTCCG GCACGGATGC CTCCCACAGC CCCACCCAAG GGCCCGGCAC
19301 AGACACCCCT TCCCAAGGGT CCAGCACAGA TGCCTCCTAC AGCTCCACCC
19351 AAGGGCCCGG CACAGATGCC TGCGACAGCC GTTCCCGAGG GTCCAGCACA
```

FIGURE 3-53

```
19401 GACACCTCCC ACAGCCCCAC CCAAGGGCCC GGCACAGATG CCTGTGACAG
19451 CCCTTATTGA GGGTCCTGCA CAGACGCCTT GGACGAGGGT CCAGCACGGA
19501 TGCCTCCCAC AGTCCCTCTT TGGCGACAAC TCGCTTGCTG GGGACCTGAG
19551 ATAACCCCCA GCCCCAGCTG CTGCCAGCCC CATGTCAACC AGGCACCCCA
19601 GAGGAACAGC ACCAAGGGAG GCAGCTGGCT TCAGGAAGGG ATGCATGCGG
19651 TTGTCTGGGA CACTCAGGGC TGATGTCCTT GAGTCTGAAG TGCTAGCTGG
19701 AAGCCCAGGC AGTTTCCAGG TTGCAGCCTC GAGGGGCGTT CTTTCCCCAG
19751 GAAGACCGAA CCTGGCGGAT GCACCCACCC TGTGAGGAAG GGTCCCCCGC
19801 CAGACTCAAC AGGCGACTGA TTTAAGTTCG TCTCATCTAA AAATAGCTTC
19851 ATAGCAACAC CCAGACTAGT GTCCGGCCAG GCTGTGCACT GCCCACCACG
19901 TGGGTGCTGG AGTCACAGTG CAGGCCCCTC ACCCCTCGTC GGCCTGGCCT
19951 CCCTGGGCCG TCAGGCATCT TTCACACATG GGACTATTTT TGCCAAATGC
20001 TGCACCCCTG GGCCGCAAAG CAGAGAGTCA CGTTTGTACC ATCTGTCCTG
20051 TCTCTTCATC GGGCAGAACA TCGACCATGT AGAAACTCAC CTGTGCTTCC
20101 AGAACTGCCA GGCTGCTTTG TGCACTTCCT GGCTCCAGGC CCTGGCATGG
20151 GGCTGGGGTA AGGTCAGGGC CAGTGGTGGC CCTCGGAGTT TTGAACCCAG
20201 AACAGACAGC CGCCGAGACC GGCAGGACAC TGAGGAGGCG TCGAGGGGCT
20251 GAGTGAGGGT TGGACCTGGT CCCCGTGCTT GTCCGGCAGG ACTCCCAGGC
20301 CGCACAGTGG CCGAGGAGGC AGCTCCAGGA ATGGGCAAGG GAAAGGGGAG
20351 TTGTGAGGCC GCTGGGAGGG GCCTCAGAAT CAGTCGGGAG AGGGCACCAC
20401 TGAGCCCCAG CCCTGCTGGC CCCTCCTCCC GGTCCCTGCC TCTGCCTCTC
20451 AGCACACCTG GTTCCACCTC CAGGCAGCAA CGGCAGGGA CGCCAGCAGA
20501 GCGTGCCACC TCTGAACAGC CACCCAGGCG CGCTCTGCCT GAGTCTCGGG
20551 CTGTGCTAGA GGCGCCTCTG GCCATGGTCC TCTCACGGCT GGGCTTCCTG
20601 GCCCCCGCGC TGGTGGGTGG GGTTCGGGTG CTCTTGAGCT GGAGAGCAGA
20651 GGGCCTCTGC ATGTTGGGGT GAGCCTGCCA GCAAGACAGG AGTAGCCTTC
20701 TGTGGCCTCA GAAGCGCCTC CCCACTCTCC TGTTGGAAGC GAGTTGCAGG
20751 CCCCGCCTGC TCCTGGGGGT GGGGGGCACA GCTGACTTCA GGAGCCCAGC
20801 TTGAGCCACC TCTCACAGCG GCCTTGGTGA GGGGGGGCTC ACCTGTGGGG
20851 GGCTCACCTG TGGGGGGCTC ACCTGTGGAG GGGCATCCCC AGACTTGGGA
20901 GTGGGTGGCA TATGGGCCAG GGTCAGGGCG TTAGGGCTTG GAGAAAGGTT
20951 AGGGTTGGGG TTGGGGTTAG AGCCACGGTG ATGGTCAGGG CATATGGGCT
21001 AGGGTTAGGG CGTTGGGGTC AGGGCCATGG GTTCTGGCTA GCACTGTGGA
21051 GACAGCCGTT TCTATCACGA AGCGATGGAA GATTCCGCCG TTCCAACCCC
21101 AGATTCGAGG GAGGCAGGGG TGTGGACGGT GCCACACCTC AATCCTCACA
21151 GCCTCTGTCT CCCACTGCCC AGGCTGGCGA AGAAGTCCTG GTTTGGGAAC
21201 TTCATCAGCC TGGAGAAGGA GGAGCAGATC TTCGTGGTCA TCAAAGACAA
21251 ACCTCTGAGC TCCATCAAGG CTGACATCGT GCACGCCTTC CTGTCGGTGA
21301 GGCCACAGGG CGCTGGGGGA GGCGGGCAGC CCTCCCAACC CCACACGGCC
21351 CAGCCCCGAG AATCCAGCCT CCTCACGTAG ACAGGACATG TCCACGCGCA
21401 CAGCACGGAC GTCCGCTCAC CCGTGGGCCT GCCTGGCCGC CTTCACTGGA
21451 CAGGCGCTCT CTCCTGCCCA CCCTCGTGAG GGAGGGGTCA CTGCCCATCT
21501 GGGGTGCTTG GCCTGCGGAG GGAGTCAGGG CTTTGCTCAC TGGTCCCCAG
21551 CAGCCCTAGG TGTGTGCCGG ACAGGCCTGG GCAGCTGGCA CGTGGGGCAG
21601 AAGGAAGGCT CCAGCTGGGT GGGTCTCAGA GGGGGACATT TCCATCAGAC
21651 TCGGGGAGAA GCCCTTGTGA GGCCATGGCC CTAGGGACCG GTGGGGCTCT
21701 GCTGGCCCTC AGTGGACAGC CCCAGCCCTC AGGTGTCTCA GTTTCCCTGG
21751 TCTCACCCTG CCCTCGGAGG CCGGGTGGCT CTCCACAGAG TGGTCGCGCT
21801 CGGGGTCTTG GGTGGGCTTC ATTTGTCTTT GCTGGGCATC TTTGGGTTAG
21851 GAGGAGCAGA AAGGCCCTAA AAGCCTCAAA TGGAGAAAGT TTATTGCCAG
21901 GACTCCAGCA CCCAGTCCCA TCAGGACGCC CCTTCCTTGC CGGCCCTGCC
21951 CCACCCTGTG CTGCACCCAG CGCCCAGGCA TCACAGGGGC TGCCCCCCAC
22001 CCGCCTCCCC CACCGCCCCC AGCCTGCCTC CCCAGGGCTG CTGTCCTGCC
```

FIGURE 3-54

```
22051 CTGTGCTCAC CACTGCCCGG GCGCCCTCCC TGGCCCCAGG GTCTTGGCAA
22101 GATCAGGCCG TGGTTCGCTT CGGCAGCCTC TCTAGCTAGG GACTGGCCCC
22151 CACCCCACCA TATGCTCTGC CCCCGGGCAC TCAGGCCACT GCTGCCCTGG
22201 CTGCAGCTGA GCTTCCCTTA CGCTGTGGGG ACAGCTTGGA GCCCCTGCAG
22251 AAGGCTCCAG GGCCAGGAGA GCCCAGCGCT GGGCAGGGCA GGCCTCAGAC
22301 TGCACTTGGA CCCTGGCCTC AGGGGTCCTC AGCGTCCCCG TCCCGTCCC
22351 CACAGGCTGC TCACTTCCTC GGCCTCCTCC CTCACCACAT CCCTTCATGC
22401 TGCCCCTGGT TGCCACGGCT AACCTCAGAC TCAGCCCCTC CCCATGCCGG
22451 CCCCAGTGAG GCGGCTGTGT GCCAGCCTGG GCCCTGTGCG CTGGGTGGCC
22501 CTGAGTTCTG CTTCCTGCAG CTGCCCCCTC GGTACTGTGA AGCCCACCCA
22551 GCCAGTGCCC AGCACCATAG GTCCCGCAAC CAGTGGGAGT CCCAGGAAGC
22601 CCCAGCAGGA GGGCACAGCC CCAGCCCCGC CCTTGCACCT CCCTCTCAGT
22651 GGCAGCTCCC AGACCCCCCA CCTCCCACTC AGCTCCACCC TGGACCCCCA
22701 CCTCAGGCTG CAGGGGTCAC CTTCCACCTC CATCTTTGCC CTTAAGGCTC
22751 CTCTGTAAGG TCCTGGTCAT CCTGTGCTGT GGCTGCCTGA GAAAAGCCCG
22801 GCAGGGGCTT AGCTGTGCCC GCTAAGTGGA CCAAAGCTTT GGAGGGTGGG
22851 GGCTGGAAAC GCCCCTCCCC CTGCTCCAGC CGTCTCCAAC CGCACTGTGC
22901 CCCTCACGGA AGCAGAGGTG CCTGGGTGCT CACAATGTGT GCACGGTGGG
22951 GCTGGCTCGC CCCAGGGCTG CCTCCCAGA GGGCCAGGGT GGGACCTGCC
23001 AGGCCAGCCA CGCTCACGCT GCTCTCTCTC CACAGATTCC CAGTCTCAGC
23051 CACAGCGTCA TCTCCCAAAC GAGCTTCCGG GCCGAGTACA AGGCCACGGG
23101 GGGGCCAGCC GTGTTCCAGA AGCCGGTCAA GTTCCAGGTT GATATCACCT
23151 ACACGGAGGG TGGGGAGGCG CAGAAGGAGA ACGGCATCTA CTCCGTCACC
23201 TTCACCCTGC TCTCAGGTGA GCTGGCGCCC CAGGGCGGC TCCGGGCCCA
23251 GGCCCGTCCA GGGCATAACC CCCTGTCTCC CCTAGGCCCC AGCCGTCGCT
23301 TCAAGAGGGT GGTGGAGACC ATCCAGGCCC AGCTGCTGAG CACACACGAC
23351 CCGCCTGCGG CCCAGCACTT GTCAGGTGAG GCGGGCTCAG CTCCGGCCAA
23401 CCTGCGGCCT GCGAGTGGGG CGTGGCCAGC TGGTGCTGCG CGGACGGGAG
23451 GCGTGAGGAC CCGGGCGCAG CCTCCTGGCC CCTCTTGACG GACGCCCCCA
23501 CCTCCCTGCC CCGAGCTGTG GCTGCACCCC TCAGGGAGCA GAGCCCCTCC
23551 CTGGCCTGGC GGGACCACCC GCCTCGCCTC TGCACGCCAG GGACATAGGG
23601 CGCAGCCGCA CCACACTGAA AGGCGCCTCT TGTCCACCGT AGAACCCCCC
23651 CCACCAGCGC CAGGACTAAG CTGGGGTGCT GGGCTTAAGG GCCAGAAGGT
23701 GGCCACCAGC TACGAGAGTA GCCTCTGACG CTGGCAGGTA AGGCGCCCGG
23751 CCTGTGCTGG GGCGGGGAGG GGCTGCGGGC AGGTCCTCGG CGGAGCCAGG
23801 CTGGCCCTGA GCAGGGCCCT CCATGCCCAC CCACAGGTCT CGGCCCTGGA
23851 CAGGCCAAGC ATGCCCCGGG CGGCCCATCT GCTAGGGCAG CCTGCACAGG
23901 ACCTGGGAGA GCAGTGACAA GGCCCTGCCC TCGGGACTCC CCGCCATGGC
23951 ACCCTAGGAG GGCCGCGGGC TGCCTGACGG GCTGTGACTT CTCATCTCTC
24001 CATACTTCCT GACAGCCCAG GGCCATGCCT CCAGCAGGGC AGAGGGGCTT
24051 GAGCCCAGCC AGAGCGGGGG CTTCACCACA GCCTGATGGG CTCACACAGG
24101 GGAGGGTTGC CCCAGCCTGG AACCACCAGG GTCTAGGACC CGAGGGTCCG
24151 TGCCACTCGG CATACGGCAG GGAGGGCTCC CCCCACTCCC CTGGGCCCAT
24201 GTGTGGTGGG GGCAGGCGG AGCACTGGGC ACATGCATGG GCCTGGTCTG
24251 TCAGCAAGGG GGTGTGGGTG TGCCTCTGAA CGCTGGTACG GCGTGGGGGC
24301 GCTGGGCGTC GTGGGGAGC ACCCGGCTGG ACCCTGGGGG TCCCCTCTCC
24351 CAGCCTGCAT CTCAGCAGCT CCGTGGCATG CTAGGGTCAC CTCCTGTGTT
24401 TCCATGTGGG GTCCTGGAAG CCAAAGAGGG CCCCACTGCC CCTCCCCATG
24451 ACATCCTCAT TCATCATCA TGCCATCACC TGTGGGAGCC CCCCCAGAGT
24501 GTGCTTCACC TTGCTGCGGG CTGGGGGCTG AGGTCCCCAA CAGCCCTGGC
24551 CCTAACCGAA GCCCAGTGG GTGGAGGAGT AGCCCCCTTC TCCTGATTTT
24601 GGGAGCCAGG CTGGCACAGC GGGTAAGGAG GAGCAGGGTT CCAGGTGCTC
24651 GGCCCCGCAG GTACACGTGG CGCTTCCCTA CAGCGGAGGC CATGCCGTCG
```

FIGURE 3-55

```
24701 GCCGGCAGCA GCCTCTGGCT CTCTGAGCCT TGAAAGCCTT CATCTTAGGA
24751 AGGGAAACCG AGGCCAGGGA ACGACAGGGC AGCCACCTAG GCCAGGGATG
24801 GACAGGGCTT GTCTGGTAGG GCAAGCAGAA ACGGGCCCCG GGGTACTGCC
24851 CAGGGTGTCC CCGCACCTGA GCAGCCATCT GGGTGCCTCA GTCGAGCGCT
24901 CCTGCGTGGG CTGTAGGCAA AGCTCCCCCA GCCTGGCCCC TTAAAGTGTG
24951 GTACCGCCTG TCAGCACGCA GCACTCCCCT GGAGCCAACT CCAAGCCCCT
25001 CTCCATTCCT GCCCCGGACC CTGACCTCAG TGGAGCCCAC TGCAGAGGCT
25051 CTTGGGGGTC TATTCTGGGC CCCATCTATC TCCCTGTGGA CTTGGGGAGC
25101 CCAGCCTATC CCCGTGATCT CGCTACGCCC AGCCCTTCCC AGCCCTGCCC
25151 CCCTCCCACA CTGGATGCTT TTGTCCAGTG AGCCCAGCTC CAAGGATGTG
25201 TGGAAGGTGG CTAGCCAGCA GGGGGCCTCC TCAGACACTG CCCACCCCCC
25251 CAGAGACTGC GGCCGAGGGA GGGGAGGCTG AGAGCCCCCA GTGAGCAGGC
25301 ACAGGCAGAC CAGGGCGTGT GTCCACCCTG TGCAGGCGCC AGTGAGGGCC
25351 TTGAGGGAGT AGCCCCTCCC AGGGCCTTGC TCCCACCCCA GTCCTGGACT
25401 GGCAGCACCA ACATCCCCAG GCCAGCAGT AGGGAAGAGG GCCGAGGAAG
25451 AGGGTGCCTG CCTTGAGTTG AAGGGCAGCC AGAAGCCACA GGGCCCTGGA
25501 GCTGCTGAGT GGCACAGTGA GGATGCAGGC CACGGCCAGG GCAGAGTTGT
25551 CAGCCCAGGG GAGGGGCTAG GCCCACCCAG GGCACCGGCC ATATCCAGGC
25601 TCAGGCTCAG GCTGCTGGAG GTCCGGCTGC TGCCCAGGTG GCTCCGCCTT
25651 GTTCCCTGCC TCCGCAGCCC CGCCTCACTC CAGGCCCTGC CCCTGCACTG
25701 CCCCTTATAA GCCCCGCCCC CTCTGGCTCT GGCCCCCCCA GTATTCCCCA
25751 CCCATGCCTC TGGGGCCCTA CCCACTCCTG GCTCCACCCC CTCCCCATCG
25801 AGGCTGTGGG CGTCCAGCCA GAAGGCCCAG GACAGCCTTT CACTCACTCC
25851 CTCCCTCCTC TCTCCATTCT GTACTCCAGA CACCACTAAC TGTATGGAAA
25901 TGATGACGGG GCGGCTTTCC AAATGTGGTA AGAATCCCCC ACGCTCACCT
25951 GGCACCTCCA CCTGCCACTT CACCGCTCAC CCTCAGCCCG CTGTGGCCGC
26001 CACCTGCCGC CCGGGTTGTC CCGGCCTCCC TGTGTAGATG TAGGCACCCA
26051 GCAGCCCAGA TGTCCCCGGC CCCATCCTCT ACCAGGAGCA GCCCCCGTCG
26101 CTCCCCTACC ACAGCAAGCC CAGGCGGGGT TCCTGGCCAG ACTCACCTCT
26151 GCCAGGCCCT AGGATCAGGG CAGGCCCAAG AAGGGGCTCC CAAGGCCTGA
26201 AGCCAGTGAG GGTCCGCTG GTCCCACTGG TGCAGGCTGT GGCCTAGGGG
26251 AGGGGCCGGT GCCCATCCCT CTGTCCACTG GAGGCTGTGC CTGGCAGGGA
26301 GCGGAGGGGC CCACAGCTCA GGGCTCAGGT GGGGGTTAGG CTTAGGAAGT
26351 GGGATTGAGG GGCCTCCATC GACACACCTG GGCAGTGAGC ACAGGGCCCC
26401 AAGAAGGGTG GGCTCCCCAT TTCCGCCCCT CTTCTCAGGA CTGCCCCCAT
26451 CCCAGGGACC CGGGACATGA CTCTAGCTGC TTGCCCCCAG CCCCCCAGCC
26501 TGCCTCCCAC ATCCACCCCT CCATGCTTGT CCACCCATCT GTTCATCTGT
26551 CTGTCTGCTG CTAAACTGTG TCCAAGCTGG CCAGGGGTCG GGCTTCAGGC
26601 CTCTCTGGGG AGGTGTGGTG GGCACACCCT CTCCCTGTCA TCCACTGGGC
26651 CTCATGCAGT GGGGCCAGCA GCTGCCCCA GGGTCCTGCG AGGCTTCAGA
26701 GCTCCCAGCA GGCCCTTGTC TTTACGCTG    (SEQ ID NO:6)
```

Genewise results:
Start:
Exon:   5167-5258
Exon:   7654-7794
Exon:   9180-9296
Exon:   9796-9829
Exon:   10025-10093
Exon:   10179-10329
Exon:   11664-11691
Exon:   11983-12147

FIGURE 3-56

```
Exon:    12260-12357
Exon:    12446-12596
Exon:    14472-14537
Exon:    16450-16510
Exon:    17261-17468
Exon:    18044-18092
Exon:    21173-21296
Exon:    23036-23216
Exon:    23286-23375
Exon:    23643-23725
Stop:    23726
```

Sim4 results:
```
Exon:    3000-3005,   (Transcript Position: 1-6)
Exon:    5173-5258,   (Transcript Position: 7-92)
Exon:    7654-7794,   (Transcript Position: 93-233)
Exon:    9180-9296,   (Transcript Position: 234-350)
Exon:    9796-9829,   (Transcript Position: 351-384)
Exon:    10025-10093, (Transcript Position: 385-453)
Exon:    10179-10325, (Transcript Position: 454-600)
Exon:    11660-11691, (Transcript Position: 601-632)
Exon:    11983-12147, (Transcript Position: 633-797)
Exon:    12260-12357, (Transcript Position: 798-895)
Exon:    12446-12596, (Transcript Position: 896-1046)
Exon:    14472-14537, (Transcript Position: 1047-1112)
Exon:    16450-16510, (Transcript Position: 1113-1173)
Exon:    17261-17468, (Transcript Position: 1174-1381)
Exon:    18044-18092, (Transcript Position: 1382-1430)
Exon:    21173-21296, (Transcript Position: 1431-1554)
Exon:    23036-23216, (Transcript Position: 1555-1735)
Exon:    23286-23375, (Transcript Position: 1736-1825)
Exon:    23643-23728, (Transcript Position: 1826-1911)
```

CHROMOSOME MAP POSITION:
chromosome 11

ALLELIC VARIANTS (SNPs):

| DNA Position | Major | Minor | Domain | Protein Position | Major | Minor |
|---|---|---|---|---|---|---|
| 3873 | G | A | Intron | | | |
| 4000 | T | C | Intron | | | |
| 5989 | T | C | Intron | | | |
| 8660 | G | A | Intron | | | |
| 9507 | T | C A G | Intron | | | |
| 9591 | A | G | Intron | | | |
| 10704 | G | T | Intron | | | |
| 10720 | C | T | Intron | | | |
| 12179 | A | G | Intron | | | |
| 13296 | T | C | Intron | | | |
| 15619 | C | T | Intron | | | |
| 15768 | C | T | Intron | | | |

FIGURE 3-57

| | | | | | | |
|---|---|---|---|---|---|---|
| 19374 | G | A | Intron | | | |
| 19430 | C | T | Intron | | | |
| 19524 | C | T | Intron | | | |
| 19653 | G | A | Intron | | | |
| 19829 | C | T | Intron | | | |
| 22538 | T | C | Intron | | | |
| 22539 | G | A | Intron | | | |
| 22575 | C | T | Intron | | | |
| 23100 | G | C | Exon, coding | 540 | G | A |
| 23936 | A | G | Intron | | | |
| 24023 | C | T | Intron | | | |
| 24096 | A | G | Intron | | | |
| 24139 | - | G C | Intron | | | |
| 24300 | C | T | Intron | | | |
| 24510 | C | T | Intron | | | |
| 24581 | G | A | Intron | | | |
| 24624 | T | C | Intron | | | |
| 24845 | A | G | Intron | | | |
| 25059 | T | C | Intron | | | |
| 25443 | G | C | Intron | | | |
| 25481 | A | G | Intron | | | |
| 26095 | C | A | Intron | | | |
| 26096 | C | G | Intron | | | |
| 26217 | G | A | Intron | | | |

Context:

DNA
Position
3873      CTCCCAGCTGCTCCGGGTCCCACCCACAGTGGGACCTGGGCTGGCAGCGTGCGACCCTCC
          CAGCACTGGGGCCAGTCGAGCCCCCTCCTCTCCCTTCCTCTCCATTCGCTCCTTGGCATG
          CAGGGCTGCGGGTGGGGCAGGACCCGGGGACGAGGCCAGTGGGAGTGGCCAAGAGAGGGG
          AGGCTTGTGGAAGGTGCTAAGGGTTGGGGACTGTGACATGTTGGGCACCCCCCAGCTGCT
          GGGGTGTGGAGGAATTAACCAGACTAAACTGGGGAGGCCTGGGGACCCTATGGGGAGGTG
          [G,A]
          GGGTGGGGTTAAGGGCTGCTGAGGGCTGCCTGGATGGGGCTGGCAGGGTCCCACCCTGCC
          TTGGAGGAGAAACAGAGGCCCTGGGAGTGATGGGGCCAGGACAGCGCCTGGCAGAGAGAT
          CCAGTGTGGGGCGTAGCTGGGGAGAGTCCCATGCTGAATTTGGGAGGTGCCTGTGAGCCC
          CGACTAAAGGAGGGCCTGGGGATGCGGGAAAGGGGAGGTGTCCCTGTCACCTGCAGGCGC
          TGTGCACAGATGTCCGCCTGGGAGGGAAGGACTTGGGGACAGGCTGGCCAACTCGCCAGG 4000      GCGGGTGGGGCAGGACCCGGGGACGAGGCCAGTGGGAGTGGCCAAGAGAGGGGAGGCTTG
          TGGAAGGTGCTAAGGGTTGGGGACTGTGACATGTTGGGCACCCCCCAGCTGCTGGGGTGT
          GGAGGAATTAACCAGACTAAACTGGGGAGGCCTGGGGACCCTATGGGGAGGTGGGGGTGG
          GGTTAAGGGCTGCTGAGGGCTGCCTGGATGGGGCTGGCAGGGTCCCACCCTGCCTTGGAG
          GAGAAACAGAGGCCCTGGGAGTGATGGGGCCAGGACAGCGCCTGGCAGAGAGATCCAGTG
          [T,C]
          GGGGCGTAGCTGGGGAGAGTCCCATGCTGAATTTGGGAGGTGCCTGTGAGCCCCGACTAA
          AGGAGGGCCTGGGGATGCGGGAAAGGGGAGGTGTCCCTGTCACCTGCAGGCGCTGTGCAC
          AGATGTCCGCCTGGGAGGGAAGGACTTGGGGACAGGCTGGCCAACTCGCCAGGGCTGGGA
          CCCCATCACAAGACTGGCCCTAGCTCCAAAGCCTGGTCCACGCTGGCTCCTGAGGGCTGG
          GACCCCAGGCCGTGGCCTCACTGGCCCCACCACTGACACGGCCACTTCTTTGTGCTGGGC

FIGURE 3-58

5989  GGATCCCGCCCTGGCTGGACCGTGGCTGAGTGTGGCTGAAAGTGTCACCTCCGCAGCCGC
TGAGGCCAGCAGAAATCCCTACCCTGTCCCAGGCATGCCTGGCTGTGAACCCCATCCCCC
CAGACCCAGCCTCAGGGAGCTCCTGGGAATGGGCACAGTGGTCACTCACGGCAGTCTCCT
CTGTGTGCTCTGATGGGGCTTTCTGACAGATGAGGCGCTGCTGCCCAAGGGCTGTCTGGC
CTTGAGCCTCATCTGACCCTCGCTGGTCCCAGGGCGGCGGCGTGACCTGCCAGGTGATCC
[T,C]
AGCCGGGCATCTCTGAGGCATCAGGCTCTGAGGGAGCAGGGAACATACAGGGCTGGGCTG
GGGGCTGCCCTCAGGGTGAGCTGGCTGAGGGCCTGGCTGAACCCAGCAGCTCCCCTTCCC
CCAGCAGCAACGTCCACGCTTGCTCTGGCCTGGGTTTCTGCATTCTCGTGGGGAGCATGT
GCAGGTGGCCAGCTCGTGTGTAGCTGGGGAGAGGAAACCCAGGGGTGGGGTGTGGGGAGC
CCGCCTGCCCCACCATGAGCAGGGGCTCAGAAACTGTCACCAGAGGCCTGGGGGGGCGGG

8660  CCCCCCCATTAGGCTACCCCTCAAGTGCACCGTCCACCCCATTAGCTACCCCTCAAGTGC
ACCGTCCCCCCATTAGCTACCCCTCAAGTGCACCATCCCCCTCATTAGCTACCCCTCAGG
TGCATCATCCCCTCCTCATTAGCTGCCCCTCAAGTGCACCGTCCCCCCCATTAGCT
[G,A]
CCCCTCAAGTGCACTGTCCCCCCCACCCCATTAGCTACCTCTCAAGTGCACCATGTGCAC
CAGGTGCTTCCCTTTTCCCCCTGAGGACCCCCTGCACCTCCCCTTTCCCGAGTGGGCAGT
GTGTCGGGAAGTTTTCTGCCTGGCACCCACCCAAGCACTCTGGGAGCCCCTCGGCCTTTC
CAGGGGCCATTGCTTGCATCCCTACGTGCCTGGGGGCCCTAGGTTGGTCTAGGCCAGAGC
AGGTGTGCTAGGGAGCAGGAGGGGGCAGGAAGGAGCCTGCCAGGGTGCAGGAGGGCATGG

9507  CCTGCTGGACGAGAAGAACAACATCCGCATCGCAGACTTTGGCATGGCGTCCCTGCAGGT
TGGCGACAGCCTGTTGGAGACCAGCTGTGGGTACGTGGCCCTCTGCCCTGGAGAGAGGCT
GGGGGACAGGCTGGGCTGGGGGAAGAGGAGCCAGTGGACTGAGAGGCCCCCAGCCTGCCT
GAGCCTCCCGGCACCCCACAGGCAGGCCCCCCACAATGTGCCTGAGCCTCCCAGTACCCC
ACAGCCTGGTGGTGGTGGGGAGACAGGCCTCCCGGCACAGTAAGGGTAGGGTACAGCCC
[T,C,A,G]
GGCCCTGGCCTGCCTGGGAGAGAGGCTGGGACCCACTTACATGCCCCTCTCCTGGGGACC
CCCTGGCCCCTGCCCAGCCGAGTGGGCAGACAGCTTTGGGCGCAGCAGAGACCCAGTGCC
CCACCTTGATCTCCTCCCAAAAGCCCGCCTGGGGATGCAGGGAATGTGGGGGCGTCTGGC
ACCACAGCCCTGGAGGCCTCCTTGAGGGCCCTGCGGTGCACCATCACCCTGGGGGGAGGG
CCTGGCAGCGCCCGGAGCCCCGCCGCTGACCTCTGCCCTTGCCCGCAGGTCCCCCCACTA

9591  CTGTGGGTACGTGGCCCTCTGCCCTGGAGAGAGGCTGGGGGACAGGCTGGGCTGGGGGAA
GAGGAGCCAGTGGACTGAGAGGCCCCCAGCCTGCCTGAGCCTCCCGGCACCCCACAGGCA
GGCCCCCCACAATGTGCCTGAGCCTCCCAGTACCCCACAGCCTGGTGGTGGTGGGGAGAC
AGGCCTCCCGGCACAGTAAGGGTAGGGTACAGCCCTGGCCCTGGCCTGCCTGGGAGAGA
GGCTGGGACCCACTTACATGCCCCTCTCCTGGGGACCCCCTGGCCCCTGCCCAGCCGAGT
[A,G]
GGCAGACAGCTTTGGGCGCAGCAGAGACCCAGTGCCCCACCTTGATCTCCTCCCAAAAGC
CCGCCTGGGGATGCAGGGAATGTGGGGGCGTCTGGCACCACAGCCCTGGAGGCCTCCTTG
AGGGCCCTGCGGTGCACCATCACCCTGGGGGGAGGGCCTGGCAGCGCCCGGAGCCCCGCC
GCTGACCTCTGCCCTTGCCCGCAGGTCCCCCCACTACGCCTGCCCCGAGGTGATCCGGGT
GAGTCAGCGCCGCCGCGTGCAGCTCTGTGGGCCCAGGGTGGCGGGACCTGACCCTGGT

10704  TGTGTGCCCAGACGTGTGGGCACCCAGGTGTGTGGGTCGGTGCCCAGGTGTGTGGACGTG
TGCACAGGTGTCGGCTTGTGTTCAGGTGTGGGTGACCAAATGTGGGCCCATGGCCGTGTG
TGGGTGCCCAGGTGAGTGTTCAAGTGTGTGTGCGCACCCAGGTGTGGGAGTGCCCAGGCG
TGTGTGGGCTCGTGTTCAGGTGTGTGGGTGCACAAATGTAGGCACATGCCCAGGTGTGTG
TTCAAGGGTGTGGGGGTACCCAGGCACATGCCCAGGTTCATGTGATTGGGTGAGGGCGTA
[G,T]

FIGURE 3-59

```
        GTGTGGGCATGTGCACGTGTGGGGAGGTGTGTCCAGGTGCTTATGAGCACTTGTACCAGT
        GTGGGGTGTGCACAGGTGTGGGGGGCTGTGTGCACATGTAGGTGAGACCTGGCTATAAGT
        TACACAAAAGCACTGGTGCTTCCCCATCACGGCCATCCTGCCTCCAGACGCTGCTGGGGC
        AAGCTCCAGGCAGCGTGAATAGTTCTGCTGAGTGCCCCCAGCAGCTGTGGGGGCTAGCAA
        GAGCCAAAGGTAGCCCCCAGCTGCTGGTCCTGACCTCCTCCAGGGCTGCCTGGTGTGGGG
10720   TGGGCACCCAGGTGTGTGGGTCGGTGCCCAGGTGTGTGGACGTGTGCACAGGTGTCGGCT
        TGTGTTCAGGTGTGGGTGACCAAATGTGGGCCCATGGCCGTGTGTGGGTGCCCAGGTGAG
        TGTTCAAGTGTGTGTGCGCACCCAGGTGTGGGAGTGCCCAGGCGTGTGTGGGCTCGTGTT
        CAGGTGTGTGGGTGCACAAATGTAGGCACATGCCCAGGTGTGTGTTCAAGGGTGTGGGGG
        TACCCAGGCACATGCCCAGGTTCATGTGATTGGGTGAGGGCGTAGGTGTGGGCATGTGCA
        [C,T]
        GTGTGGGGAGGTGTGTCCAGGTGCTTATGAGCACTTGTACCAGTGTGGGGTGTGCACAGG
        TGTGGGGGGCTGTGTGCACATGTAGGTGAGACCTGGCTATAAGTTACACAAAAGCACTGG
        TGCTTCCCCATCACGGCCATCCTGCCTCCAGACGCTGCTGGGGCAAGCTCCAGGCAGCGT
        GAATAGTTCTGCTGAGTGCCCCCAGCAGCTGTGGGGGCTAGCAAGAGCCAAAGGTAGCCC
        CCAGCTGCTGGTCCTGACCTCCTCCAGGGCTGCCTGGTGTGGGGACCGACGTGTCCACT
12179   GAGTGGCAGGATGAAGGGCCCCAGGTGAGGGCGGGCGTCCCACCCTCGCAGCCGCCCAGG
        CCCGGCCGGAGCTGATGAGCGGGTGGCCCGTCCTGTGTCCACAGAGGGGGCAAGAATGAG
        CCCGAACCAGAGCAGCCCATTCCTCGCAAGGTGCAGATCCGCTCGCTGCCCAGCCTGGAG
        GACATCGACCCCGACGTGCTGGACAGCATGCACTCACTGGGCTGCTTCCGAGACCGCAAC
        AAGCTGCTGCAGGACCTGCTGTCCGAGGAGTGCGTCTGGGGCTGCTCCCGGGTGGGGCAC
        [A,G]
        GGGCCTGAGGTGGGAGCGCTGCCCCGGAGGAGCCGGCGGCCCCGTGTGCCAGCGCGTCTC
        GCGCCTCTCGCCCGCTGTAGGGAGAACCAGGAGAAGATGATTTACTTCCTCCTCCTGGAC
        CGGAAAGAAAGGTACCCGAGCCAGGAGGATGAGGACCTGCCCCCCCCGGAACGAGATAGGT
        ATGGGTCCAGGGGTGGCCTCCAGCCCGGCCTGCACTGCCCCACCGGGGTCCGGGGGCTGT
        CTGGCCTGACCTTCGTCTGTACTCAGACCCTCCCCGGAAGCGTGTGGACTCCCCGATGCT
13296   AATGGGCTGAGACGGATTTGACTGGGCTGAGCTGGGCAGGGCTGGGCTGAGCTGGGCAGG
        GCTGGGCTGGGCTAAACTGGATTTGGCTGAGCCGAGCCAGGCTGGGCAGGGCTGAGCTGG
        GCTGGGCTGGCTTGACCCAAGCTTGGCTGGGCTGAGCTGTGATATGGTCACACCATGCTC
        AGAGCCATCAGCCCAGCAAGCCTGTCCCCCTGGTCCCAGCAATGCTGGGCCCGTCTCTGG
        GTGGCAAGTGTGGTGTGTGTGGCCAGGGACATCACAGAACTCAGCAGTGATGAGCAGACC
        [T,C]
        GTGGCCGGAGGAAGGGCACCCAGCCCCTCTGGAGCCTCTGCTGGGTGGGGGCAGGGCTGG
        GCTGCCCGCACGAGGCCCTCAGCAAATCCTTGGAGCCGGTGCGGCCTCTTGGGGATGAGC
        TCAAACGTCCCTCACCAGGTGGCAGCTTCCAACACTTGGGGACAGCCCTTGCGCCAGAGA
        GCACACCAGGAGGTCCAGGAGCCCGGGCAGCAGTCTCTGGTCTGCCCTGTGATCTGGGCC
        TCAGCACCCCAGGGCCCCCTCCTTGTACTGGAGATGTGGGGGGTGGGACAGGCGTGGCCT
15619   TGCCCCCATGAGGGCTGTCCGCGCTCCCAGCTCAGCCCTGAAAGCTCTGGGTCCAGTTCC
        AGCCCTGGGTGTCATCCTGGCCCAGACAGGCTGGGTTGTGCATGGGGTCCCCGTCGCCTC
        CCTGCCCCTTGGCTGTGTCTGGTGAGGGAGTTGGAGGGTCGTCACCGTGGGGACCAGCCC
        CCGGGTGTCCGGGAGCCAGGTGTGTGGCCAGCGTGGCACTCTCCACGGTCCGGGGCCTGG
        GCCGTGGTGTGGACTAGCGAGGCCCCTCGTGGCCGGCTGGCGGTGGGCAGGCCTGGTGGG
        [C,T]
        AGTGCAGGCCGGGCTTTTACTCTTCTCTGTCCTCTTCTCTTCGGCGGCTGCCTCGGCCCC
        TCCCTGCATTTCCTTCCTCCAAGGATGGCAGCTGCCACTGTCTGGGCACGTGGGCGCCGG
        CTCGTCCGTGCAGTGTGGTGGAACGACGCACAGCCGTCCTGGTCCCTGCACGGGGGTGGC
        GGCCACACACCGGAGTCTCAGCCGGGCACGCCGGGCCAGGGCCTCCCTCCTGCTGTGTGC
        AGGTCTCAGGCTGAGTAGGGCAGTGGTGGGACAAGGCCCCACCGTCCCTGCCAGCAGCTG
```

FIGURE 3-60

15768  GTTGGAGGGTCGTCACCGTGGGGACCAGCCCCCGGGTGTCCGGGAGCCAGGTGTGTGGCC
AGCGTGGCACTCTCCACGGTCCGGGGCCTGGGCCGTGGTGTGGACTAGCGAGGCCCCTCG
TGGCCGGCTGGCGGTGGGCAGGCCTGGTGGGCAGTGCAGGCCGGGCTTTTACTCTTCTCT
GTCCTCTTCTCTTCGGCGGCTGCCTCGGCCCCTCCCTGCATTTCCTTCCTCCAAGGATGG
CAGCTGCCACTGTCTGGGCACGTGGGCGCCGGCTCGTCCGTGCAGTGTGGTGGAACGACG
[C,T]
ACAGCCGTCCTGGTCCCTGCACGGGGGTGGCGGCCACACACCGGAGTCTCAGCCGGGCAC
GCCGGGCCAGGGCCTCCCTCCTGCTGTGTGCAGGTCTCAGGCTGAGTAGGGCAGTGGTGG
GACAAGGCCCCACCGTCCCTGCCAGCAGCTGCCCCAGCCTGGCCCTGCCCAGGCCCTCCT
GGTTGTGGACAAGGGAAGGGCCGGCCGCTGACCCAGGCATCCCTCACGGGCATCTAGGGA
CATGGAGGACCAGGCTGCAGGCCCTGTGAGAGCTCAGCCAGGGGGGCTTGGCAGGTGGG

19374  AGGCCCTGACATTGCCGTTTCTGCTGCTACCAAAAGCTTTCATGAACAGACTCATAATTA
TCTTCCTCAGAGAAGGTGGAAAACATCAAAGCCGAGAAGGTGGCTTTGATGCCACTGTGG
CTGCCTGCGCTTCTCCCCTCCCCCATCTTGAGATGGCCTGGAGGCCCTGACCCCTCTCAA
GGGTCCGGCACGGATGCCTCCCACAGCCCCACCCAAGGGCCCGGCACAGACACCCCTTCC
CAAGGGTCCAGCACAGATGCCTCCTACAGCTCCACCCAAGGGCCCCGGCACAGATGCCTGC
[G,A]
ACAGCCGTTCCCGAGGGTCCAGCACAGACACCTCCCACAGCCCCACCCAAGGGCCCGGCA
CAGATGCCTGTGACAGCCCTTATTGAGGGTCCTGCACAGACGCCTTGGACGAGGGTCCAG
CACGGATGCCTCCCACAGTCCCTCTTTGGCGACAACTCGCTTGCTGGGGACCTGAGATAA
CCCCCAGCCCCAGCTGCTGCCAGCCCCATGTCAACCAGGCACCCCAGAGGAACAGCACCA
AGGGAGGCAGCTGGCTTCAGGAAGGGATGCATGCGGTTGTCTGGGACACTCAGGGCTGAT

19430  ATTATCTTCCTCAGAGAAGGTGGAAAACATCAAAGCCGAGAAGGTGGCTTTGATGCCACT
GTGGCTGCCTGCGCTTCTCCCCTCCCCCATCTTGAGATGGCCTGGAGGCCCTGACCCCTC
TCAAGGGTCCGGCACGGATGCCTCCCACAGCCCCACCCAAGGGCCCGGCACAGACACCCC
TTCCCAAGGGTCCAGCACAGATGCCTCCTACAGCTCCACCCAAGGGCCCGGCACAGATGC
CTGCGACAGCCGTTCCCGAGGGTCCAGCACAGACACCTCCCACAGCCCCACCCAAGGGCC
[C,T]
GGCACAGATGCCTGTGACAGCCCTTATTGAGGGTCCTGCACAGACGCCTTGGACGAGGGT
CCAGCACGGATGCCTCCCACAGTCCCTCTTTGGCGACAACTCGCTTGCTGGGGACCTGAG
ATAACCCCCAGCCCCAGCTGCTGCCAGCCCCATGTCAACCAGGCACCCCAGAGGAACAGC
ACCAAGGGAGGCAGCTGGCTTCAGGAAGGGATGCATGCGGTTGTCTGGGACACTCAGGGC
TGATGTCCTTGAGTCTGAAGTGCTAGCTGGAAGCCCAGGCAGTTTCCAGGTTGCAGCCTC

19524  AGATGGCCTGGAGGCCCTGACCCCTCTCAAGGGTCCGGCACGGATGCCTCCCACAGCCCC
ACCCAAGGGCCCGGCACAGACACCCCTTCCCAAGGGTCCAGCACAGATGCCTCCTACAGC
TCCACCCAAGGGCCCCGGCACAGATGCCTGCGACAGCCGTTCCCGAGGGTCCAGCACAGAC
ACCTCCCACAGCCCCACCCAAGGGCCCGGCACAGATGCCTGTGACAGCCCTTATTGAGGG
TCCTGCACAGACGCCTTGGACGAGGGTCCAGCACGGATGCCTCCCACAGTCCCTCTTTGG
[C,T]
GACAACTCGCTTGCTGGGGACCTGAGATAACCCCCAGCCCCAGCTGCTGCCAGCCCCATG
TCAACCAGGCACCCCAGAGGAACAGCACCAAGGGAGGCAGCTGGCTTCAGGAAGGGATGC
ATGCGGTTGTCTGGGACACTCAGGGCTGATGTCCTTGAGTCTGAAGTGCTAGCTGGAAGC
CCAGGCAGTTTCCAGGTTGCAGCCTCGAGGGGCGTTCTTTCCCCAGGAAGACCGAACCTG
GCGGATGCACCCACCCTGTGAGGAAGGGTCCCCCGCCAGACTCAACAGGCGACTGATTTA

19653  GGGCCCGGCACAGATGCCTGCGACAGCCGTTCCCGAGGGTCCAGCACAGACACCTCCCAC
AGCCCCACCCAAGGGCCCGGCACAGATGCCTGTGACAGCCCTTATTGAGGGTCCTGCACA
GACGCCTTGGACGAGGGTCCAGCACGGATGCCTCCCACAGTCCCTCTTTGGCGACAACTC
GCTTGCTGGGGACCTGAGATAACCCCCAGCCCCAGCTGCTGCCAGCCCCATGTCAACCAG

FIGURE 3-61

```
         GCACCCCAGAGGAACAGCACCAAGGGAGGCAGCTGGCTTCAGGAAGGGATGCATGCGGTT
         [G,A]
         TCTGGGACACTCAGGGCTGATGTCCTTGAGTCTGAAGTGCTAGCTGGAAGCCCAGGCAGT
         TTCCAGGTTGCAGCCTCGAGGGGCGTTCTTTCCCCAGGAAGACCGAACCTGGCGGATGCA
         CCCACCCTGTGAGGAAGGGTCCCCCGCCAGACTCAACAGGCGACTGATTTAAGTTCGTCT
         CATCTAAAAATAGCTTCATAGCAACACCCAGACTAGTGTCCGGCCAGGCTGTGCACTGCC
         CACCACGTGGGTGCTGGAGTCACAGTGCAGGCCCCTCACCCCTCGTCGGCCTGGCCTCCC

19829    ACTCGCTTGCTGGGGACCTGAGATAACCCCCAGCCCCAGCTGCTGCCAGCCCCATGTCAA
         CCAGGCACCCCAGAGGAACAGCACCAAGGGAGGCAGCTGGCTTCAGGAAGGGATGCATGC
         GGTTGTCTGGGACACTCAGGGCTGATGTCCTTGAGTCTGAAGTGCTAGCTGGAAGCCCAG
         GCAGTTTCCAGGTTGCAGCCTCGAGGGGCGTTCTTTCCCCAGGAAGACCGAACCTGGCGG
         ATGCACCCACCCTGTGAGGAAGGGTCCCCCGCCAGACTCAACAGGCGACTGATTTAAGTT
         [C,T]
         GTCTCATCTAAAAATAGCTTCATAGCAACACCCAGACTAGTGTCCGGCCAGGCTGTGCAC
         TGCCCACCACGTGGGTGCTGGAGTCACAGTGCAGGCCCCTCACCCCTCGTCGGCCTGGCC
         TCCCTGGGCCGTCAGGCATCTTTTCACACATGGGACTATTTTTGCCAAATGCTGCACCCCT
         GGGCCGCAAAGCAGAGAGTCACGTTTGTACCATCTGTCCTGTCTCTTCATCGGGCAGAAC
         ATCGACCATGTAGAAACTCACCTGTGCTTCCAGAACTGCCAGGCTGCTTTGTGCACTTCC

22538    GGAGCCCCTGCAGAAGGCTCCAGGGCCAGGAGAGCCCAGCGCTGGGCAGGGCAGGCCTCA
         GACTGCACTTGGACCCTGGCCTCAGGGGTCCTCAGCGTCCCCGTCCCCGTCCCCACAGGC
         TGCTCACTTCCTCGGCCTCCTCCCTCACCACATCCCTTCATGCTGCCCCTGGTTGCCACG
         GCTAACCTCAGACTCAGCCCCTCCCCATGCCGGCCCCAGTGAGGCGGCTGTGTGCCAGCC
         TGGGCCCTGTGCGCTGGGTGGCCCTGAGTTCTGCTTCCTGCAGCTGCCCCCTCGGTACTG
         [T,C]
         GAAGCCCACCCAGCCAGTGCCCAGCACCATAGGTCCCGCAACCAGTGGGAGTCCCAGGAA
         GCCCCAGCAGGAGGGCACAGCCCCAGCCCCGCCCTTGCACCTCCCTCTCAGTGGCAGCTC
         CCAGACCCCCCACCTCCCACTCAGCTCCACCCTGGACCCCCACCTCAGGCTGCAGGGGTC
         ACCTTCCACCTCCATCTTTGCCCTTAAGGCTCCTCTGTAAGGTCCTGGTCATCCTGTGCT
         GTGGCTGCCTGAGAAAAGCCCGGCAGGGGCTTAGCTGTGCCCGCTAAGTGGACCAAAGCT

22539    GAGCCCCTGCAGAAGGCTCCAGGGCCAGGAGAGCCCAGCGCTGGGCAGGGCAGGCCTCAG
         ACTGCACTTGGACCCTGGCCTCAGGGGTCCTCAGCGTCCCCGTCCCCGTCCCCACAGGCT
         GCTCACTTCCTCGGCCTCCTCCCTCACCACATCCCTTCATGCTGCCCCTGGTTGCCACGG
         CTAACCTCAGACTCAGCCCCTCCCCATGCCGGCCCCAGTGAGGCGGCTGTGTGCCAGCCT
         GGGCCCTGTGCGCTGGGTGGCCCTGAGTTCTGCTTCCTGCAGCTGCCCCCTCGGTACTGT
         [G,A]
         AAGCCCACCCAGCCAGTGCCCAGCACCATAGGTCCCGCAACCAGTGGGAGTCCCAGGAAG
         CCCCAGCAGGAGGGCACAGCCCCAGCCCCGCCCTTGCACCTCCCTCTCAGTGGCAGCTCC
         CAGACCCCCCACCTCCCACTCAGCTCCACCCTGGACCCCCACCTCAGGCTGCAGGGGTCA
         CCTTCCACCTCCATCTTTGCCCTTAAGGCTCCTCTGTAAGGTCCTGGTCATCCTGTGCTG
         TGGCTGCCTGAGAAAAGCCCGGCAGGGGCTTAGCTGTGCCCGCTAAGTGGACCAAAGCTT

22575    AGCGCTGGGCAGGGCAGGCCTCAGACTGCACTTGGACCCTGGCCTCAGGGGTCCTCAGCG
         TCCCCGTCCCCGTCCCCACAGGCTGCTCACTTCCTCGGCCTCCTCCCTCACCACATCCCT
         TCATGCTGCCCCTGGTTGCCACGGCTAACCTCAGACTCAGCCCCTCCCCATGCCGGCCCC
         AGTGAGGCGGCTGTGTGCCAGCCTGGGCCCTGTGCGCTGGGTGGCCCTGAGTTCTGCTTC
         CTGCAGCTGCCCCCTCGGTACTGTGAAGCCCACCCAGCCAGTGCCCAGCACCATAGGTCC
         [C,T]
         GCAACCAGTGGGAGTCCCAGGAAGCCCCAGCAGGAGGGCACAGCCCCAGCCCCGCCCTTG
         CACCTCCCTCTCAGTGGCAGCTCCCAGACCCCCCACCTCCCACTCAGCTCCACCCTGGAC
         CCCCACCTCAGGCTGCAGGGGTCACCTTCCACCTCCATCTTTGCCCTTAAGGCTCCTCTG
```

FIGURE 3-62

```
           TAAGGTCCTGGTCATCCTGTGCTGTGGCTGCCTGAGAAAAGCCCGGCAGGGGCTTAGCTG
           TGCCCCGCTAAGTGGACCAAAGCTTTGGAGGGTGGGGGCTGGAAACGCCCCTCCCCCTGCT

23100      GGCAGGGGCTTAGCTGTGCCCGCTAAGTGGACCAAAGCTTTGGAGGGTGGGGCTGGAAA
           CGCCCCTCCCCCTGCTCCAGCCGTCTCCAACCGCACTGTGCCCCTCACGGAAGCAGAGGT
           GCCTGGGTGCTCACAATGTGTGCACGGTGGGGCTGGCTCGCCCCAGGGCTGCCTCCCCAG
           AGGGCCAGGGTGGGACCTGCCAGGCCAGCCACGCTCACGCTGCTCTCTCTCCACAGATTC
           CCAGTCTCAGCCACAGCGTCATCTCCCAAACGAGCTTCCGGGCCGAGTACAAGGCCACGG
           [G,C]
           GGGGCCAGCCGTGTTCCAGAAGCCGGTCAAGTTCCAGGTTGATATCACCTACACGGAGGG
           TGGGGAGGCGCAGAAGGAGAACGGCATCTACTCCGTCACCTTTCACCCTGCTCTCAGGTGA
           GCTGGCGCCCCAGGGCGGCTCCGGGCCCAGGCCCGTCCAGGGCATAACCCCCTGTCTCC
           CCTAGGCCCCAGCCGTCGCTTCAAGAGGGTGGTGGAGACCATCCAGGCCCAGCTGCTGAG
           CACACACGACCCGCCTGCGGCCCAGCACTTGTCAGGTGAGGCGGGCTCAGCTCCGGCCAA

23936      ACCGTAGAACCCCCCCCACCAGCGCCAGGACTAAGCTGGGGTGCTGGGCTTAAGGGCCAG
           AAGGTGGCCACCAGCTACGAGAGTAGCCTCTGACGCTGGCAGGTAAGGCGCCCGGCCTGT
           GCTGGGGCGGGGAGGGGCTGCGGGCAGGTCCTCGGCGGAGCCAGGCTGGCCCTGAGCAGG
           GCCCTCCATGCCCACCCACAGGTCTCGGCCCTGGACAGGCCAAGCATGCCCCGGGCGGCC
           CATCTGCTAGGGCAGCCTGCACAGGACCTGGGAGAGCAGTGACAAGGCCCTGCCCTCGGG
           [A,G]
           CTCCCCCGCCATGGCACCCTAGGAGGGCCGCGGGCTGCCTGACGGGCTGTGACTTCTCATC
           TCTCCATACTTCCTGACAGCCCAGGGCCATGCCTCCAGCAGGGCAGAGGGGCTTGAGCCC
           AGCCAGAGCGGGGGCTTCACCACAGCCTGATGGGCTCACACAGGGGAGGGTTGCCCCAGC
           CTGGAACCACCAGGGTCTAGGACCCGAGGGTCCGTGCCACTCGGCATACGGCAGGGAGGG
           CTCCCCCCACTCCCCTGGGCCCATGTGTGGTGGGGGCAGGGCGGAGCACTGGGCACATGC

24023      CTCTGACGCTGGCAGGTAAGGCGCCCGGCCTGTGCTGGGGCGGGGAGGGGCTGCGGGCAG
           GTCCTCGGCGGAGCCAGGCTGGCCCTGAGCAGGGCCCTCCATGCCCACCCACAGGTCTCG
           GCCCTGGACAGGCCAAGCATGCCCCGGGCGGCCCATCTGCTAGGGCAGCCTGCACAGGAC
           CTGGGAGAGCAGTGACAAGGCCCTGCCCTCGGGACTCCCCGCCATGGCACCCTAGGAGGG
           CCGCGGGCTGCCTGACGGGCTGTGACTTCTCATCTCTCCATACTTCCTGACAGCCCAGGG
           [C,T]
           CATGCCTCCAGCAGGGCAGAGGGGCTTGAGCCCAGCCAGAGCGGGGGCTTCACCACAGCC
           TGATGGGCTCACACAGGGGAGGGTTGCCCCAGCCTGGAACCACCAGGGTCTAGGACCCGA
           GGGTCCGTGCCACTCGGCATACGGCAGGGAGGGCTCCCCCCACTCCCCTGGGCCCATGTG
           TGGTGGGGGCAGGGCGGAGCACTGGGCACATGCATGGGCCTGGTCTGTCAGCAAGGGGGT
           GTGGGTGTGCCTCTGAACGCTGGTACGGCGTGGGGGCGCTGGGCGTCGTGGGGGAGCACC

24096      CCAGGCTGGCCCTGAGCAGGGCCCTCCATGCCCACCCACAGGTCTCGGCCCTGGACAGGC
           CAAGCATGCCCCGGGCGGCCCATCTGCTAGGGCAGCCTGCACAGGACCTGGGAGAGCAGT
           GACAAGGCCCTGCCCTCGGGACTCCCCGCCATGGCACCCTAGGAGGGCCGCGGGCTGCCT
           GACGGGCTGTGACTTCTCATCTCTCCATACTTCCTGACAGCCCAGGGCCATGCCTCCAGC
           AGGGCAGAGGGGCTTGAGCCCAGCCAGAGCGGGGGCTTCACCACAGCCTGATGGGCTCAC
           [A,G]
           CAGGGGAGGGTTGCCCCAGCCTGGAACCACCAGGGTCTAGGACCCGAGGGTCCGTGCCAC
           TCGGCATACGGCAGGGAGGGCTCCCCCCACTCCCCTGGGCCCATGTGTGGTGGGGGCAGG
           GCGGAGCACTGGGCACATGCATGGGCCTGGTCTGTCAGCAAGGGGGTGTGGGTGTGCCTC
           TGAACGCTGGTACGGCGTGGGGGCGCTGGGCGTCGTGGGGGAGCACCCGGCTGGACCCTG
           GGGGTCCCCTCTCCCAGCCTGCATCTCAGCAGCTCCGTGGCATGCTAGGGTCACCTCCTG

24139      CTCGGCCCTGGACAGGCCAAGCATGCCCCGGGCGGCCCATCTGCTAGGGCAGCCTGCACA
           GGACCTGGGAGAGCAGTGACAAGGCCCTGCCCTCGGGACTCCCCGCCATGGCACCCTAGG
```

FIGURE 3-63

```
              AGGGCCGCGGGCTGCCTGACGGGCTGTGACTTCTCATCTCTCCATACTTCCTGACAGCCC
              AGGGCCATGCCTCCAGCAGGGCAGAGGGGCTTGAGCCCAGCCAGAGCGGGGGCTTCACCA
              CAGCCTGATGGGCTCACACAGGGGAGGGTTGCCCCAGCCTGGAACCACCAGGGTCTAGGA
              [-,G,C]
              CCGAGGGTCCGTGCCACTCGGCATACGGCAGGGAGGGCTCCCCCCACTCCCCTGGGCCCA
              TGTGTGGTGGGGGCAGGGCGGAGCACTGGGCACATGCATGGGCCTGGTCTGTCAGCAAGG
              GGGTGTGGGTGTGCCTCTGAACGCTGGTACGGCGTGGGGGCGCTGGGCGTCGTGGGGGAG
              CACCCGGCTGGACCCTGGGGGTCCCCTCTCCCAGCCTGCATCTCAGCAGCTCCGTGGCAT
              GCTAGGGTCACCTCCTGTGTTTCCATGTGGGGTCCTGGAAGCCAAAGAGGGCCCCACTGC

24300      CCATACTTCCTGACAGCCCAGGGCCATGCCTCCAGCAGGGCAGAGGGGCTTGAGCCCAGC
              CAGAGCGGGGGCTTCACCACAGCCTGATGGGCTCACACAGGGGAGGGTTGCCCCAGCCTG
              GAACCACCAGGGTCTAGGACCCGAGGGTCCGTGCCACTCGGCATACGGCAGGGAGGGCTC
              CCCCCACTCCCCTGGGCCCATGTGTGGTGGGGGCAGGGCGGAGCACTGGGCACATGCATG
              GGCCTGGTCTGTCAGCAAGGGGGTGTGGGTGTGCCTCTGAACGCTGGTACGGCGTGGGGG
              [C,T]
              GCTGGGCGTCGTGGGGGAGCACCCGGCTGGACCCTGGGGGTCCCCTCTCCCAGCCTGCAT
              CTCAGCAGCTCCGTGGCATGCTAGGGTCACCTCCTGTGTTTCCATGTGGGGTCCTGGAAG
              CCAAAGAGGGCCCCACTGCCCCTCCCCATGACATCCTCATTCCATCATCATGCCATCACC
              TGTGGGAGCCCCCCCAGAGTGTGCTTCACCTTGCTGCGGGCTGGGGGCTGAGGTCCCCAA
              CAGCCCTGGCCCTAACCGAAGCCCCAGTGGGTGGAGGAGTAGCCCCCTTCTCCTGATTTT

24510      GGGCAGGGCGGAGCACTGGGCACATGCATGGGCCTGGTCTGTCAGCAAGGGGGTGTGGGT
              GTGCCTCTGAACGCTGGTACGGCGTGGGGGCGCTGGGCGTCGTGGGGGAGCACCCGGCTG
              GACCCTGGGGGTCCCCTCTCCCAGCCTGCATCTCAGCAGCTCCGTGGCATGCTAGGGTCA
              CCTCCTGTGTTTCCATGTGGGGTCCTGGAAGCCAAAGAGGGCCCCACTGCCCCTCCCCAT
              GACATCCTCATTCCATCATCATGCCATCACCTGTGGGAGCCCCCCCAGAGTGTGCTTCAC
              [C,T]
              TTGCTGCGGGCTGGGGGCTGAGGTCCCCAACAGCCCTGGCCCTAACCGAAGCCCCAGTGG
              GTGGAGGAGTAGCCCCCTTCTCCTGATTTTGGGAGCCAGGCTGGCACAGCGGGTAAGGAG
              GAGCAGGGTTCCAGGTGCTCGGCCCCGCAGGTACACGTGGCGCTTCCCTACAGCGGAGGC
              CATGCCGTCGGCCGGCAGCAGCCTCTGGCTCTCTGAGCCTTGAAAGCCTTCATCTTAGGA
              AGGGAAACCGAGGCCAGGGAACGACAGGGCAGCCACCTAGGCCAGGGATGGACAGGGCTT

24581      CGCTGGTACGGCGTGGGGGCGCTGGGCGTCGTGGGGGAGCACCCGGCTGGACCCTGGGGG
              TCCCCTCTCCCAGCCTGCATCTCAGCAGCTCCGTGGCATGCTAGGGTCACCTCCTGTGTT
              TCCATGTGGGGTCCTGGAAGCCAAAGAGGGCCCCACTGCCCCTCCCCATGACATCCTCAT
              TCCATCATCATGCCATCACCTGTGGGAGCCCCCCCAGAGTGTGCTTCACCTTGCTGCGGG
              CTGGGGGCTGAGGTCCCCAACAGCCCTGGCCCTAACCGAAGCCCCAGTGGGTGGAGGAGT
              [G,A]
              GCCCCCTTCTCCTGATTTTGGGAGCCAGGCTGGCACAGCGGGTAAGGAGGAGCAGGGTTC
              CAGGTGCTCGGCCCCGCAGGTACACGTGGCGCTTCCCTACAGCGGAGGCCATGCCGTCGG
              CCGGCAGCAGCCTCTGGCTCTCTGAGCCTTGAAAGCCTTCATCTTAGGAAGGGAAACCGA
              GGCCAGGGAACGACAGGGCAGCCACCTAGGCCAGGGATGGACAGGGCTTGTCTGGTAGGG
              CAAGCAGAAACGGGCCCCGGGGTACTGCCCAGGGTGTCCCCGCACCTGAGCAGCCATCTG

24624      CGGCTGGACCCTGGGGGTCCCCTCTCCCAGCCTGCATCTCAGCAGCTCCGTGGCATGCTA
              GGGTCACCTCCTGTGTTTCCATGTGGGGTCCTGGAAGCCAAAGAGGGCCCCACTGCCCCT
              CCCCATGACATCCTCATTCCATCATCATGCCATCACCTGTGGGAGCCCCCCCAGAGTGTG
              CTTCACCTTGCTGCGGGCTGGGGGCTGAGGTCCCCAACAGCCCTGGCCCTAACCGAAGCC
              CCAGTGGGTGGAGGAGTAGCCCCCTTCTCCTGATTTTGGGAGCCAGGCTGGCACAGCGGG
              [T,C]
              AAGGAGGAGCAGGGTTCCAGGTGCTCGGCCCCGCAGGTACACGTGGCGCTTCCCTACAGC
```

FIGURE 3-64

```
      GGAGGCCATGCCGTCGGCCGGCAGCAGCCTCTGGCTCTCTGAGCCTTGAAAGCCTTCATC
      TTAGGAAGGGAAACCGAGGCCAGGGAACGACAGGGCAGCCACCTAGGCCAGGGATGGACA
      GGGCTTGTCTGGTAGGGCAAGCAGAAACGGGCCCCGGGGTACTGCCCAGGGTGTCCCCGC
      ACCTGAGCAGCCATCTGGGTGCCTCAGTCGAGCGCTCCTGCGTGGGCTGTAGGCAAAGCT

24845 CCTGGCCCTAACCGAAGCCCCAGTGGGTGGAGGAGTAGCCCCCTTCTCCTGATTTTGGGA
      GCCAGGCTGGCACAGCGGGTAAGGAGGAGCAGGGTTCCAGGTGCTCGGCCCCGCAGGTAC
      ACGTGGCGCTTCCCTACAGCGGAGGCCATGCCGTCGGCCGGCAGCAGCCTCTGGCTCTCT
      GAGCCTTGAAAGCCTTCATCTTAGGAAGGGAAACCGAGGCCAGGGAACGACAGGGCAGCC
      ACCTAGGCCAGGGATGGACAGGGCTTGTCTGGTAGGGCAAGCAGAAACGGGCCCCGGGGT
      [A,G]
      CTGCCCAGGGTGTCCCCGCACCTGAGCAGCCATCTGGGTGCCTCAGTCGAGCGCTCCTGC
      GTGGGCTGTAGGCAAAGCTCCCCCAGCCTGGCCCCTTAAAGTGTGGTACCGCCTGTCAGC
      ACGCAGCACTCCCCTGGAGCCAACTCCAAGCCCCTCTCCATTCCTGCCCCGGACCCTGAC
      CTCAGTGGAGCCCACTGCAGAGGCTCTTGGGGGTCTATTCTGGGCCCCATCTATCTCCCT
      GTGGACTTGGGGAGCCCAGCCTATCCCCGTGATCTCGCTACGCCCAGCCCTTCCCAGCCC

25059 CGAGGCCAGGGAACGACAGGGCAGCCACCTAGGCCAGGGATGGACAGGGCTTGTCTGGTA
      GGGCAAGCAGAAACGGGCCCCGGGGTACTGCCCAGGGTGTCCCCGCACCTGAGCAGCCAT
      CTGGGTGCCTCAGTCGAGCGCTCCTGCGTGGGCTGTAGGCAAAGCTCCCCCAGCCTGGCC
      CCTTAAAGTGTGGTACCGCCTGTCAGCACGCAGCACTCCCCTGGAGCCAACTCCAAGCCC
      CTCTCCATTCCTGCCCCGGACCCTGACCTCAGTGGAGCCCACTGCAGAGGCTCTTGGGGG
      [T,C]
      CTATTCTGGGCCCCATCTATCTCCCTGTGGACTTGGGGAGCCCAGCCTATCCCCGTGATC
      TCGCTACGCCCAGCCCTTCCCAGCCCTGCCCCCCTCCCACACTGGATGCTTTTGTCCAGT
      GAGCCCAGCTCCAAGGATGTGTGGAAGGTGGCTAGCCAGCAGGGGGCCTCCTCAGACACT
      GCCCACCCCCCAGAGACTGCGGCCGAGGGAGGGGAGGCTGAGAGCCCCCAGTGAGCAGG
      CACAGGCAGACCAGGGCGTGTGTCCACCCTGTGCAGGCGCCAGTGAGGGCCTTGAGGGAG

25443 CCCTGCCCCCCTCCCACACTGGATGCTTTTGTCCAGTGAGCCCAGCTCCAAGGATGTGTG
      GAAGGTGGCTAGCCAGCAGGGGGCCTCCTCAGACACTGCCCACCCCCCAGAGACTGCGG
      CCGAGGGAGGGGAGGCTGAGAGCCCCCAGTGAGCAGGCACAGGCAGACCAGGGCGTGTGT
      CCACCCTGTGCAGGCGCCAGTGAGGGCCTTGAGGGAGTAGCCCCTCCCAGGGCCTTGCTC
      CCACCCCAGTCCTGGACTGGCAGCACCAACATCCCCAGGCCCAGCAGTAGGGAAGAGGGC
      [G,C]
      GAGGAAGAGGGTGCCTGCCTTGAGTTGAAGGGCAGCCAGAAGCCACAGGGCCCTGGAGCT
      GCTGAGTGGCACAGTGAGGATGCAGGCCACGGCCAGGGCAGAGTTGTCAGCCCAGGGGAG
      GGGCTAGGCCCACCCAGGGCACCGGCCATATCCAGGCTCAGGCTCAGGCTGCTGGAGGTC
      CGGCTGCTGCCCAGGTGGCTCCGCCTTGTTCCCTGCCTCCGCAGCCCCGCCTCACTCCAG
      GCCCTGCCCCTGCACTGCCCCTTATAAGCCCCGCCCCCTCTGGCTCTGGCCCCCCCAGTA

25481 AGCCCAGCTCCAAGGATGTGTGGAAGGTGGCTAGCCAGCAGGGGGCCTCCTCAGACACTG
      CCCACCCCCCAGAGACTGCGGCCGAGGGAGGGGAGGCTGAGAGCCCCCAGTGAGCAGGC
      ACAGGCAGACCAGGGCGTGTGTCCACCCTGTGCAGGCGCCAGTGAGGGCCTTGAGGGAGT
      AGCCCCTCCCAGGGCCTTGCTCCCACCCCAGTCCTGGACTGGCAGCACCAACATCCCCAG
      GCCCAGCAGTAGGGAAGAGGGCCGAGGAAGAGGGTGCCTGCCTTGAGTTGAAGGGCAGCC
      [A,G]
      GAAGCCACAGGGCCCTGGAGCTGCTGAGTGGCACAGTGAGGATGCAGGCCACGGCCAGGG
      CAGAGTTGTCAGCCCAGGGGAGGGGCTAGGCCCACCCAGGGCACCGGCCATATCCAGGCT
      CAGGCTCAGGCTGCTGGAGGTCCGGCTGCTGCCCAGGTGGCTCCGCCTTGTTCCCTGCCT
      CCGCAGCCCCGCCTCACTCCAGGCCCTGCCCCTGCACTGCCCCTTATAAGCCCCGCCCCC
      TCTGGCTCTGGCCCCCCCAGTATTCCCCACCCATGCCTCTGGGGCCCTACCCACTCCTGG
```

FIGURE 3-65

| | |
|---|---|
| 26095 | CCATCGAGGCTGTGGGCGTCCAGCCAGAAGGCCCAGGACAGCCTTTCACTCACTCCCTCC |
| | CTCCTCTCTCCATTCTGTACTCCAGACACCACTAACTGTATGGAAATGATGACGGGGCGG |
| | CTTTCCAAATGTGGTAAGAATCCCCCACGCTCACCTGGCACCTCCACCTGCCACTTCACC |
| | GCTCACCCTCAGCCCGCTGTGGCCGCCACCTGCCGCCCGGGTTGTCCCGGCCTCCCTGTG |
| | TAGATGTAGGCACCCAGCAGCCCAGATGTCCCCGGCCCCATCCTCTACCAGGAGCAGCCC |
| | [C,A] |
| | CGTCGCTCCCCTACCACAGCAAGCCCAGGCGGGGTTCCTGGCCAGACTCACCTCTGCCAG |
| | GCCCTAGGATCAGGGCAGGCCCAAGAAGGGGCTCCCAAGGCCTGAAGCCAGTGAGGGTCC |
| | CGCTGGTCCCACTGGTGCAGGCTGTGGCCTAGGGGAGGGGCCGGTGCCCATCCCTCTGTC |
| | CACTGGAGGCTGTGCCTGGCAGGGAGCGGAGGGGCCCACAGCTCAGGGCTCAGGTGGGGG |
| | TTAGGCTTAGGAAGTGGGATTGAGGGGCCTCCATCGACACACCTGGGCAGTGAGCACAGG |
| 26096 | CATCGAGGCTGTGGGCGTCCAGCCAGAAGGCCCAGGACAGCCTTTCACTCACTCCCTCCC |
| | TCCTCTCTCCATTCTGTACTCCAGACACCACTAACTGTATGGAAATGATGACGGGGCGGC |
| | TTTCCAAATGTGGTAAGAATCCCCCACGCTCACCTGGCACCTCCACCTGCCACTTCACCG |
| | CTCACCCTCAGCCCGCTGTGGCCGCCACCTGCCGCCCGGGTTGTCCCGGCCTCCCTGTGT |
| | AGATGTAGGCACCCAGCAGCCCAGATGTCCCCGGCCCCATCCTCTACCAGGAGCAGCCCC |
| | [C,G] |
| | GTCGCTCCCCTACCACAGCAAGCCCAGGCGGGGTTCCTGGCCAGACTCACCTCTGCCAGG |
| | CCCTAGGATCAGGGCAGGCCCAAGAAGGGGCTCCCAAGGCCTGAAGCCAGTGAGGGTCCC |
| | GCTGGTCCCACTGGTGCAGGCTGTGGCCTAGGGGAGGGGCCGGTGCCCATCCCTCTGTCC |
| | ACTGGAGGCTGTGCCTGGCAGGGAGCGGAGGGGCCCACAGCTCAGGGCTCAGGTGGGGGT |
| | TAGGCTTAGGAAGTGGGATTGAGGGGCCTCCATCGACACACCTGGGCAGTGAGCACAGGG |
| 26217 | TTCCAAATGTGGTAAGAATCCCCCACGCTCACCTGGCACCTCCACCTGCCACTTCACCGC |
| | TCACCCTCAGCCCGCTGTGGCCGCCACCTGCCGCCCGGGTTGTCCCGGCCTCCCTGTGTA |
| | GATGTAGGCACCCAGCAGCCCAGATGTCCCCGGCCCCATCCTCTACCAGGAGCAGCCCCC |
| | GTCGCTCCCCTACCACAGCAAGCCCAGGCGGGGTTCCTGGCCAGACTCACCTCTGCCAGG |
| | CCCTAGGATCAGGGCAGGCCCAAGAAGGGGCTCCCAAGGCCTGAAGCCAGTGAGGGTCCC |
| | [G,A] |
| | CTGGTCCCACTGGTGCAGGCTGTGGCCTAGGGGAGGGGCCGGTGCCCATCCCTCTGTCCA |
| | CTGGAGGCTGTGCCTGGCAGGGAGCGGAGGGGCCCACAGCTCAGGGCTCAGGTGGGGGTT |
| | AGGCTTAGGAAGTGGGATTGAGGGGCCTCCATCGACACACCTGGGCAGTGAGCACAGGGC |
| | CCCAAGAAGGGTGGGCTCCCCATTTCCGCCCCTCTTCTCAGGACTGCCCCCATCCCAGGG |
| | ACCCGGGACATGACTCTAGCTGCTTGCCCCCAGCCCCCCAGCCTGCCTCCCACATCCACC |

FIGURE 3-66

SEQUENCE LISTING

<160> NUMBER OF SEQ ID NOS: 10

<210> SEQ ID NO 1
<211> LENGTH: 2025
<212> TYPE: DNA
<213> ORGANISM: Homo sapiens

<400> SEQUENCE: 1

```
atgacatcga cggggaagga cggcggcgcg cagcacgcgc agtatgttgg gccctaccgg      60
ctggagaaga cgctgggcaa ggggcagaca ggtctggtga agctgggggt tcactgcgtc     120
acctgccaga aggtggccat caagatcgtc aaccgtgaga agctcagcga gtcggtgctg     180
atgaaggtgg agcgggagat cgcgatcctg aagctcattg agcaccccca cgtcctaaag     240
ctgcacgacg tttatgaaaa caaaaaatat ttgtacctgg tgctagaaca cgtgtcaggt     300
ggtgagctct tcgactacct ggtgaagaag gggaggctga cgcctaagga ggctcggaag     360
ttcttccggc agatcatctc tgcgctggac ttctgccaca gccactccat atgccacagg     420
gatctgaaac ctgaaaacct cctgctggac gagaagaaca catccgcat cgcagacttt     480
ggcatggcgt ccctgcaggt tggcgacagc ctgttagaga ccagctgtgg gtcccccac      540
tacgcctgcc ccgaggtgat ccgggggag aagtatgacg gccggaaggc ggacgtgtgg     600
agctgcggcg tcatcctgtt cgccttgctg gtggggctc tgcccttcga cgatgacaac     660
ttgcgacagc tgctggagaa ggtgaagcgg ggcgtgttcc acatgccgca ctttatcccg     720
cccgactgcc agagtctgct acggggcatg atcgaggtgg acgccgcacg ccgcctcacg     780
ctagagcaca ttcagaaaca catatggtat ataggggca agaatgagcc cgaaccagag     840
cagcccattc ctcgcaaggt gcagatccgc tcgctgccca gctggagga catcgacccc     900
gacgtgctgg acagcatgca ctcactgggc tgcttccgag accgcaacaa gctgctgcag     960
gacctgctgt ccgaggagga gaaccaggag aagatgattt acttcctcct cctggaccgg    1020
aaagaaaggt acccgagcca ggaggatgag gacctgcccc ccggaacga gatagaccct    1080
ccccggaagc gtgtggactc cccgatgctg aaccggcacg gcaagcggcg gccagaacgc    1140
aaatccatgg aggtgctcag cgtgacggac ggcggctccc cggtgcctgc gcggcgggcc    1200
attgagatgg cccagcacgg ccagaggtct cggtccatca gcgtgcctc ctcaggcctt    1260
tccaccagcc cactcagcag cccccgggtg accctcacc cctcaccaag gggcagtccc    1320
ctccccaccc ccaagggggac acctgtccac acgccaaagg agagcccggc tggcacgccc    1380
aaccccacgc ccccgtccag ccccagcgtc ggagggggtgc cctggagggc gcggctcaac    1440
tccatcaaga cagctttct gggctcaccc cgcttccacc gccggaaact gcaagttccg    1500
acgccggagg agatgtccaa cctgacacca gagtcgtccc cagagctggc gaagaagtcc    1560
tggtttggga acttcatcag cctggagaag gaggagcaga tcttcgtggt catcaaagac    1620
aaacctctga gctccatcaa ggctgacatc gtgcacgcct tcctgtcgat tcccagtctc    1680
agccacagcg tcatctccca aacgagcttc cgggccgagt acaaggccac gggggggcca    1740
gccgtgttcc agaagccggt caagttccag gttgatatca cctacacgga gggtgggggag    1800
gcgcagaagg agaacggcat ctactccgtc accttcaccc tgctctcagg ccccagccgt    1860
cgcttcaaga gggtggtgga gaccatccag gcccagctgc tgagcacaca cgacccgcct    1920
gcggcccagc acttgtcaga accccccca ccagcgccag gactaagctg gggtgctggg    1980
cttaagggcc agaaggtggc caccagctac gagagtagcc tctga                    2025
```

<210> SEQ ID NO 2
<211> LENGTH: 674
<212> TYPE: PRT
<213> ORGANISM: Homo sapiens

<400> SEQUENCE: 2

Met Thr Ser Thr Gly Lys Asp Gly Gly Ala Gln His Ala Gln Tyr Val

-continued

```
  1               5              10              15
Gly Pro Tyr Arg Leu Glu Lys Thr Leu Gly Lys Gly Gln Thr Gly Leu
             20              25              30

Val Lys Leu Gly Val His Cys Val Thr Cys Gln Lys Val Ala Ile Lys
             35              40              45

Ile Val Asn Arg Glu Lys Leu Ser Glu Ser Val Leu Met Lys Val Glu
             50              55              60

Arg Glu Ile Ala Ile Leu Lys Leu Ile Glu His Pro His Val Leu Lys
65              70              75              80

Leu His Asp Val Tyr Glu Asn Lys Lys Tyr Leu Tyr Leu Val Leu Glu
             85              90              95

His Val Ser Gly Gly Glu Leu Phe Asp Tyr Leu Val Lys Lys Gly Arg
            100             105             110

Leu Thr Pro Lys Glu Ala Arg Lys Phe Phe Arg Gln Ile Ile Ser Ala
            115             120             125

Leu Asp Phe Cys His Ser His Ser Ile Cys His Arg Asp Leu Lys Pro
            130             135             140

Glu Asn Leu Leu Leu Asp Glu Lys Asn Asn Ile Arg Ile Ala Asp Phe
145             150             155             160

Gly Met Ala Ser Leu Gln Val Gly Asp Ser Leu Leu Glu Thr Ser Cys
            165             170             175

Gly Ser Pro His Tyr Ala Cys Pro Glu Val Ile Arg Gly Glu Lys Tyr
            180             185             190

Asp Gly Arg Lys Ala Asp Val Trp Ser Cys Gly Val Ile Leu Phe Ala
            195             200             205

Leu Leu Val Gly Ala Leu Pro Phe Asp Asp Asp Asn Leu Arg Gln Leu
            210             215             220

Leu Glu Lys Val Lys Arg Gly Val Phe His Met Pro His Phe Ile Pro
225             230             235             240

Pro Asp Cys Gln Ser Leu Leu Arg Gly Met Ile Glu Val Asp Ala Ala
            245             250             255

Arg Arg Leu Thr Leu Glu His Ile Gln Lys His Ile Trp Tyr Ile Gly
            260             265             270

Gly Lys Asn Glu Pro Glu Pro Glu Gln Pro Ile Pro Arg Lys Val Gln
            275             280             285

Ile Arg Ser Leu Pro Ser Leu Glu Asp Ile Asp Pro Asp Val Leu Asp
            290             295             300

Ser Met His Ser Leu Gly Cys Phe Arg Asp Arg Asn Lys Leu Leu Gln
305             310             315             320

Asp Leu Leu Ser Glu Glu Glu Asn Gln Glu Lys Met Ile Tyr Phe Leu
            325             330             335

Leu Leu Asp Arg Lys Glu Arg Tyr Pro Ser Gln Glu Asp Glu Asp Leu
            340             345             350

Pro Pro Arg Asn Glu Ile Asp Pro Pro Arg Lys Arg Val Asp Ser Pro
            355             360             365

Met Leu Asn Arg His Gly Lys Arg Arg Pro Glu Arg Lys Ser Met Glu
            370             375             380

Val Leu Ser Val Thr Asp Gly Gly Ser Pro Val Pro Ala Arg Arg Ala
385             390             395             400

Ile Glu Met Ala Gln His Gly Gln Arg Ser Arg Ser Ile Ser Gly Ala
            405             410             415

Ser Ser Gly Leu Ser Thr Ser Pro Leu Ser Ser Pro Arg Val Thr Pro
            420             425             430
```

-continued

```
His Pro Ser Pro Arg Gly Ser Pro Leu Pro Thr Pro Lys Gly Thr Pro
        435                 440                 445
Val His Thr Pro Lys Glu Ser Pro Ala Gly Thr Pro Asn Pro Thr Pro
    450                 455                 460
Pro Ser Ser Pro Ser Val Gly Gly Val Pro Trp Arg Ala Arg Leu Asn
465                 470                 475                 480
Ser Ile Lys Asn Ser Phe Leu Gly Ser Pro Arg Phe His Arg Arg Lys
                485                 490                 495
Leu Gln Val Pro Thr Pro Glu Glu Met Ser Asn Leu Thr Pro Glu Ser
            500                 505                 510
Ser Pro Glu Leu Ala Lys Lys Ser Trp Phe Gly Asn Phe Ile Ser Leu
        515                 520                 525
Glu Lys Glu Glu Gln Ile Phe Val Val Ile Lys Asp Lys Pro Leu Ser
    530                 535                 540
Ser Ile Lys Ala Asp Ile Val His Ala Phe Leu Ser Ile Pro Ser Leu
545                 550                 555                 560
Ser His Ser Val Ile Ser Gln Thr Ser Phe Arg Ala Glu Tyr Lys Ala
                565                 570                 575
Thr Gly Gly Pro Ala Val Phe Gln Lys Pro Val Lys Phe Gln Val Asp
            580                 585                 590
Ile Thr Tyr Thr Glu Gly Gly Glu Ala Gln Lys Glu Asn Gly Ile Tyr
        595                 600                 605
Ser Val Thr Phe Thr Leu Leu Ser Gly Pro Ser Arg Arg Phe Lys Arg
    610                 615                 620
Val Val Glu Thr Ile Gln Ala Gln Leu Leu Ser Thr His Asp Pro Pro
625                 630                 635                 640
Ala Ala Gln His Leu Ser Glu Pro Pro Pro Ala Pro Gly Leu Ser
                645                 650                 655
Trp Gly Ala Gly Leu Lys Gly Gln Lys Val Ala Thr Ser Tyr Glu Ser
            660                 665                 670
Ser Leu
```

<210> SEQ ID NO 3
<211> LENGTH: 70383
<212> TYPE: DNA
<213> ORGANISM: Homo sapiens
<220> FEATURE:
<221> NAME/KEY: misc_feature
<222> LOCATION: (1)...(70383)
<223> OTHER INFORMATION: n = A,T,C or G

<400> SEQUENCE: 3

```
ggatgtcaca aaggtgcgtc tgactctgct gcagcctggg aggccaggtg accatggcag    60
cagagagagg gcatctcagg tcaagtgccc ctgccctctg gctgtggcct gacgccctct   120
cctggtctcc tgcacaccct cggcctctgt tggcacctgg accagaccac tcccagtcag   180
cctccagcca gacctcactg cttgacagtt tctccagctg gaggtcccag tctacattca   240
gctaaaaatg tctgctgtcc ccactcacag cagcagcagc gggggaaagg ggagtgccct   300
ctgcctctgt cccatgctct cagcccccct ccctgcccc cactggtggg gccctgattg   360
ctcatgctca gaggccccag aattgggtag ggaggaccct tagtccacag catttgaagg   420
gaagcagggc gggcgggtgc aggccgagag tggacaggtg ctttgggcc cactcccctt   480
ccccagctgg aaatacagac agcccaaaga gcagagggc gcactgggaa gaccccgcag   540
tttcctgagc tcatacgggc ttaccagcgt ggggagcgga ccacggtcag cagcagtgtg   600
```

-continued

```
tggcagagcc cgcaggggaa acgttgcccg cagaccatac acgggcaaga tctgggaccc      660
ccacttctgc agcgttccgg gtctccctca cctctcccct cccaccacct tctgcagcac      720
gggcttaagg aaataccagt gttttttctgc aaagaaacag agggtccgtc caggtctggc     780
tgcctcttcg gctgcctgtg tttagacctc caaaggctgc tcccggcaac ccctgcccag      840
ctgctcaacc tgaaagaggg gtcggtagca agggccggga ggcgccaggg cgctgcggcc      900
ggatcccagg tgagttcctt gactccgcgc cgcgcagctc actgtggcat aactgggaaa     960
accgccgctt ctccctcggg agcggaggcg gagggccacg tcctccctgg gggtgcacaa     1020
tctctgcttg gacaacgccc gcgtgcagta gccccacaga ctcccatgca gccccccgc      1080
cacgtgtgcc gcatccgcgc cctgcatgca acacccgccc cctccagcgc agcatgcccc    1140
tcgctggcgt gcagcacccc ccatgtgtgc agcacccctg ccccgaatac agcacctctc    1200
cccagtacag cactcccgcc ccgcatgcaa cactcgcccc cctccagggc agcatcccca    1260
tcccccgcgc gtgcagcacc cctcgagggg gcgggaaact ctttgggaca cccggggtca    1320
cgccctgcag ggtaaaaccc ccgtccaggg cagccatctg cacccccctcg ccatgggccc    1380
actgcctgct ccgtcccggg atgcgcctta atggcgggtc gggcggcagc gggagctctg    1440
ctgcctggtg ggaccggacg tggcagccgg cgggctggag gctcccaggt cccggcctcg    1500
ccctggcctc gcctcgcccc ctagagtctc cccgagcgct cgtagcggcg gggcggggtg    1560
gggaggcgct gattggccgg cgcgggcacc gcttgccgcc gccacggcat cccgctgcgt    1620
tcgtacaggc tcgtgtcgac tcggctccgt tgcgcggccc ggctcggctc ccctcagctg    1680
cgctcgactc cgctgttcgg ctcggctgtt cggcttggct acagggctcg gctgttcggc    1740
ttggctacat ggctcggctg cgcggctcgg ctctgttcgg ctcggctcgg ctgctgggct    1800
cggctgttcg gctcagctgc gcggctcggc tcgtctcggc tctgttcggc tcggctcggc    1860
tgctgggctc ggctgttcgg ctcagctgca cggctcggct cggctcggct cggctcggct    1920
gcgcggccgc tgacgggcgt gcgctggggg cgcgggcgc ggggcgcggg cctcggcggc    1980
ggcggcggcg gcggcggcgg aagccaggtg ccccgcccg ccctgtcctc tcgacgaggc    2040
ggaggcgtcg ccgcgggcca ggcctcggac tgccgcgtcg gagtggacgc ggggggcggc    2100
ggcgcggggcg gacgcgggcg gcgcgaagca gcggggcccg cggggcgcc ccggccgggt    2160
cggcgcggac ggcactcggc ggacgcgggc ggacgctggg cggcccctcc ctgcccgcgc    2220
gcccgggcgc ccctggccgg cgctgggccc cagagcgatg acatcgacgg ggaaggacgg    2280
cggcgcgcag cacgcgcagt atgttgggcc ctaccggctg agaagacgc tgggcaaggg    2340
gcagacaggt gcgtgcggcc ggggcgggga ccggggccgg ggaggccgcg ctggcagcgc    2400
gctgggtggg gggcgcccga gggaggcccc ggccgcgaag ccgcaggccc ggcccgggcc    2460
ccggccgcga acaatgggcg gccgtgcgc ccccgtccgc tcgtgcgccc cggttccgcc    2520
gcggatcccg caggccgctt ggctgcggtc ggccgggcgc ggcccaagga cacgcggcgc    2580
ggcgcggggc gcgcaggcgg acaggggcgc acgggacggc gcccctcggg ccccgctgca    2640
ggtgcgcggc ccgggccgca ttgtgcgccc cagcgaccgg gcccattgtg ccgcgggagg    2700
agggggccgc gcgggcgccc atctgccgtc tgccgcggcc gcgctaatag gcgtgctgcc    2760
cgagcagctg cgccccggg gggactccca cctccgcgcg ccggccaccg gggcctccgg    2820
gcaggcccga tctccctccg cggtgggggc gggagagtgc ggggacctgc agagggctgg    2880
acagcgcctt gcgctgctcc ggctcgggct cgggcggggcg gagcgtctgt gacctgcatt   2940
```

-continued

```
cccacggggc agggagaggc cattggtgct gggaccagaa gtgcgtggga cctgacccgt    3000
ggagcagccc cgcggcctgc cggtggaggg ggcttcccgg tggggcctgg ctgtcattct    3060
agggaacagg ccgggtccct gcggggccga acccaggcca gaggcaaccc agctaccctc    3120
gcatgtggcc aactctcccc ggcccgctgg gtttggctag cccttcatct ggtcaggcac    3180
attcacagag tcgcctttgt ggaggctggg gctcagccat tttctttctt ctctcaggac    3240
cggcctgtct cttggtgtcc ccgaggtccc acggcactgc ctctcccttc caatccgaga    3300
agttccttag acccgggcgg gcaggggtgg agggaaggag gaggagagcg ctggtgcagg    3360
gtggaggctc agcccctcac ggctgcacag aggaggagct gggaggtggc gttggggaaa    3420
gaaagtgggc caggcccagg ctcttggggg agggccgtgg ctgtgatgta actacggcag    3480
agctgcagga aggggtttag actgagaggt tcaggggagc tgcctcacct tgggtgcaca    3540
gccttccgcc acccgccacg gcacggaagg gcccctggcc acagggcagg gcctgggcag    3600
gtggggtggt gcagcctggg ttggagaagg agtggcatt cagcccatgt cacctgagtt     3660
caaaattctc gtctttcccg gaaagaaaaa ctagtgtgtg aaatccgtgg tgaaggaggg    3720
gcccagggca gcaggatgca ggagtcagtg agataatcca attacggtcc caataaaatg    3780
ttattataag gaaacatccg tgtgtaaatg aagacacgat gagttatgtg ctgtgcgcgg    3840
cctcggtggg taggggctgg tctccactct tcatggcatt ctgctggcgg cagttaatta    3900
cgggaggttt ccactgtaat taacagtaat gaatacaaaa ggatgggctg tgtgtgtcta    3960
caacgtgctg agagagatat ttagaaaaca gctcgagggg gggcacaaag cggcccctct    4020
ctcccgagtt atgacgggca gagcgcaagc gtgtcaccgg gagggccctg agaaggcca     4080 ccatttctgt gcgtcttctg ttgctgctgc tgaagggtca ccaggagttg ggtggacatg    4140
gggcctggag tgtgtgtgct gggccacttg gcaccagatg ccaggagagc tgccaggtcc    4200
caagctcaag agggagatag gcttcctgcc aggagacctc cgtgggagaa cgggaggctg    4260
ggcttctggc cgccaccacc cgaggacgat ctgatcctgc cgttgagaac gcttctcctt    4320
ccagggacct ggccacaggg gagctgtgga ggccttgctt gggggggccat tggtgtggac    4380 gcgactccag cccccttcccc gtgtctgtgg ctggcagctt tgtttggccc tctctgttca    4440
tctctctcag cctgagacct tggaaggagg agctgctcga cttgaggtgg ccactgagag    4500
ggaggtggtc agtggcagtg gcagtgagcc ttgtggtgcc acgagagccc ttccacccag    4560
ctgacccaag ctggggcctg ctggacggtg ggccaaagat gtggtccgaa acctgcccttt   4620 gggggagtctg gccgtgtggg gagggagac cacgcagcac ccccaccggg gcctggagga    4680
cgcccttcta gacgccgcag ggtccggtcg gctgtcttct tctgcctttc agcgtgagcg    4740
ctgcatggtc tcacctgtac ggcacctgcc tgtcttgttg ggtctgtgcg tcctgcaggg    4800
ccagtgtggc tgtagggtcg tccttctgca tggggcgtcc tctgcacagc tcccctcggt    4860
ggctgtgggg gttgccttca gtggtctcac tgccggtgcc aggcaccagg tgaagccgtc    4920
agagcactga gcatctgtgg aagcctcctc gccggctgct tggtggtttc tggccaagac    4980 ttaggggat gtaggctggg gttggggtgg gaacccacct gcaaaggtgc tgccttagct     5040
tttcttgggg ctgagaaagg cttgtgtagc ctcatctgag cttgaccct gcagagatgc     5100 cgagacacag tccctgccag caagggcaac catggaggtt ggagggcgca gacactccga    5160
gttggagcat gcaggtccag gagggtgtgt ggcacgggct gggtggcttt tgtccctgcg    5220
cgcctttgtc cctgtgcccc atcagtacgt ggagcagggc accttcttgc ccaaacctcg    5280
gcttagctcc tgaaatctgg gaggcctggg agggccctgt gggaggagct ggagaacctc    5340
```

```
gggcccttgg agctgttctt gggggcaggc gggtgggctg catgggacga tgagggcct      5400
gccttcggga atcctctgtc tgggggcgg gagaaaggaa taatggccgc gatagggctc      5460
cctgcgaggg aacgaaggag ctaggatgag ggctgccct gcagctcacc tggcagtgtt      5520
cacctgctgt ggcgtggggg agggacctag gctgccaggg acctggggcc gccctccat      5580
gttctcaatg cctttagga aggttgagcc ctggtggctg ccaggtgga gagggtcct       5640
gggatgggag gagtcattga agatggaaca ggtgagggga gggagagcct gtgcctggga     5700
gaccctgggg gtgaccccag gcccagaagc tggaggcaga tgtggagggg aaggaagctg     5760
gtctgagatg gggtctgttt agaaagttga gcaggacggg cagcgatggg ctgtggtgtg     5820
caggtccctg gagatgggcc atggagatgg gtcctggaga tgggtcctgg agatgggccc     5880
ctggagatgg gccatggaga tgggtcctgg agatgggccc tggagatgg gccatggagg     5940
tgggtcctgg agatgggtcc tggagatggg ccatggagat gggtccctgg agatgggccc     6000
ctggagatgg gccatggaga tgggtcctgg agatgggtcc tggagatggg ccatggagat     6060
gggccatgga gatgggccat ggagatgggt ccctggagat gggcccctgg agatgggcca     6120
tggagatggg ccatggagat ggctccctga gatgggccat gcagatgcgt cctggagatg     6180
ggccatggag atgggtcctg gagatgggtc ctggagatgg gccctggaga tgggcatgga     6240
gatgggtcct ggagatgggt cctggagatg ggccatggag atgggtcctg gagatgggcc     6300
atggagatgg gtcctggaga tgggtcctgg agatgggcca tggagatggg tcctggagat     6360
gggtccctgg agatgggtcc tggagatggg tcctggagat gggtccctgg agatgggcca     6420
tggagatggg tcctggagat gggtcctgga gatgggcccc tggagatggg ccatggagat     6480
gggtcctgga gatgggtcct ggagatgggc catggagatg gtcctggag atgggtcctg      6540
gagatgggcc cctggagatg ggccatggag atgggtcctg gaggtgggtc ctggagatgg     6600
gccatggaga tgggtcctgg agatgggtcc tggagatggg tcctggagat gggcccctgg     6660
agatgggcca tggagatggg tcctggagat gggcccctgg agatgggctg tgcagggctg     6720
agcccggaga gcgcatgggt agacaggacc cggcagcctc cccagccatg aaggtgaagg     6780
tggactcagc gtgggtgtc tgctgcgaga ccccaggaat tctgtggcct tccccacatc      6840
aggcctggc catctgaccc cagctgtttt gtcaggcag cagcagcctg ggctggact       6900
gaacccctca tctgccctgc acggggtttc tacaagctga ggtctcagga cgctgttctc     6960
aggggcgccg tgcacagagc ccggggagcc agcatggtgg gtagccctcc catctgaagt     7020
ctccctggcc ccctgaagtc cctggaaagg cccattttggt gtcgctgggc gccatgtcag    7080
tgactgcgcc agggtggagg cctcaagatg ctgcccctgg cgtcttcctg ccctgcatgc     7140
cctccacagg gagccccctt tccagctgag agctggcctt gagtgtccct gtcagggccc     7200
ttggcacaga ggttccgggt ggtgaggacg gcagttcccc taggcggggg cgggagggtc     7260
gttggaggcg ggagccctag gcccttgtcc tgtccccacc cactgtggcc ctgggcacct     7320
cagtgtgtg tgtccctgtt gacgtgggtc tccctgcctt gtcactggca atggctggaa      7380
aagacacgct gggcagaggg caccgcccgg ccctgatcgt gctggccgtg ctggccctgc     7440
tctgctgagg tgcgtgcacg ccgtggattt cctggatgtg gaagcctcaa ggccaggctg     7500
tgccccctcc cccagctgtg ccaggagggg ctttccagag tcaccgtggc tggctgctgc     7560
cccgcctgct ccaccatctg cccgagcagg gagttgtgtc cagaaccact ggggaatgca     7620
gggcctgggc tgtgatgtga ggttggcctc taggcttcaa ggggatctgt ttctggcaaa     7680
```

```
tctcacgcag gcccagctgg agctactatc aagggccgtg gctcctgccc acgacccaag    7740
ctccagggcc tctgggtccc caccatcgtt ggctgccgag gtggccaggt cccttccttg    7800
ctctgagggt ggctgggagt gtcttaaggt tgtcgctgtg ccaggtgtgt gtggacccct    7860
gcgtcccccg ctcctcgtct ctcttccctt ccacccacgt ccccactcc tggtccctct    7920 tcccttccac ccacgtcccc cactcctggt ccctcttccc ttccacccac gtccccact    7980 cctggtccct cttcccttac agccgcctcg aggactgcat ggggccagca aggcctgtac    8040
cccaggacac cagagttgct cggaccggct cccggacctg gcctaagcg agctctcctg    8100 gttctcactc ccgagtctgc ggagtgaccc cgggccctct catcatggcc tcaccctgct    8160
ccggcgctct gggtgctttg aagcagacag gagacccct ccaggctggc ccgagggcag    8220 gtcagaccccc agtccctggg aacagcctga gtgggctgtg cctccccgtc ggccactggc    8280
gctcaggagg agccgtcggg aaggccccctt tgccatcacc tggtggcgct tgcttgaggg    8340
cttctgtgcc ttccagtcct cactgggcac agactagctt cttttgggcac ctggggaggg    8400 tcaggctgtc tctgaagtca gcagccctgc tgggcagccg gcaccaggag aggaggcggg    8460
ctggtccccg tgactgccgg ccgccggcat ccacctatgt ggggctgtgc ctagatggtg    8520
gcactgtggg gcatcactgt gcagttctgg gccctgccct cagctctgga cagcccacct    8580
ggaccctggc ccctcggaag tggaaggact gggacctcag ggcccctgag tgtagaatgg    8640
ggtttccctg aagcttgtgc gaggttccaa tggctggaaa caccgtaccg cgcaggagga    8700
cggcagacca gcatctgtca ggccccttgg ggctcacatg gctggtcctc tgtgctgccc    8760
tgtgctctgc aggaagttaa cggcaccctg ccacctcctc tgtgcagggc agccccgctt    8820
tcacctgtag ggctggtgcc tgtgtcaggc ccaagcccca ggtcctagcc taggctgacc    8880
aagcggcctg cagatctccc tgaggcctca ccccgggggat gtccgccggg ccaggctgcc    8940
ctgagccagc tgcctggggc tctggacaag atggaggctg ggctggggca gaggctgcag    9000
ggacaaagca cggattgtgc caagccggct gcctttcagg gcccggcctg ccaggtccag    9060
gccttgttct accgcctctg aggggccagt gttctgggcc cagcagctgg gagccaggcc    9120
ccacccacag agcagtgctc ccgaaagtcc tgctgttaaa gagaaactcc tcgtttttcct    9180 ggacgcctcc agcttcccag gctcgttctg ccttcagtcc cggggcccac ggaggccgtg    9240
gctgccctac gctgctttgc cccaggggcc tgggctgcag gctgggcctg gcttcctccc    9300
cgaaccctgg agagtgacag caccaccccc agtggatggc aagtccccat cggttggcat    9360
gtgtctctct gggcaccatg ctcctcgttg ggtgccacgt ccttgggctg agcttgggtc    9420
ctgtctgccc tgggggtacc atcctatgag gacagagctg cctttcctgg gtggccatgg    9480
cagcctcatg gcactggctg aggggaatgg acacttctgg gatggagctg ggctggggtg    9540
gggctgggta gggccagtgg gagttctggg caccttggcc tgagggggat ggggggtgccc    9600 agggcattca cgccatcact gcccacttgg cttaagctgg agcccagggc cctggagggc    9660
aggctggcct tccggccccc gggcagaggt gggagggcgc ctggacggct gcctgcatga    9720
tccccgtgat acagcgggga tggctgcacg tcgggctgag tccagctgtg ggtggtttgc    9780
gggggcacag ggagcctgcc tggccaggaa tgtggcctct gcgggtgtct tggcctggga    9840
gcccccgggg aaccctttgt atgggagaag ggtcgggat aggggctggg gggcagtgcc    9900
tggtggccct ccatgctgag ggaaagcccc tcttcacagc tagcatcggg cctcgtgtcc    9960
tcagcaccct gaatcagctg cagggctagc tgctgcctga gctgcctggt tggggctggc   10020 ctgggccccct gattggctgc ttccctgggc ggggggtgacg ttgctgccct gggtccgaga   10080
```

```
gttatcttgt gcggacagag gtaataggtg tggtacccgc cccgggaagg gtggtggcca   10140
gggtggccat gtcaggcgcc ttggccctgc ccctgggga tacagggggt ggagaggcag   10200
ccccaaagct gggttctcag agacctgggg tggccagatg ggggctcatt cagctgcccc   10260
ctgtgcagcc ccttggtgcc attaactttc tgcagagcgc agggcagcac agagggccag   10320
ccaggccagg gggccagagg ttcccctccc acacaagctc cgaggtgtcc agacaggagg   10380
cggtggcccc agtccgcata ggcctttctc cagggcagcc ctttcccag  ggttaggctg    10440 caggccctgc cggtgtggct tcaggagtcc tggtccccgc actcaagctt ccctcctgct   10500
catctgtgat ggggcctggg tgtacccagg tccttggtag gcgccaggag atgtgtgggg   10560 cccctggag  cctggagccc cccagcccc  tccgcttatc tttggtgtct ggggcggaga    10620
ctggcccttg gcacccgcgg ccgtccctgg ctttcgtcct gcgccgtcct ggtctttgg    10680 gtccctctgc cagcccgtg  gtgacttctt gcacacaggg tttgcagggg gctgcggaa    10740 tgactccgtc ccttccacag cacacgggca cctccagcca ggaaggagct gggcaggcag   10800
ccccgcccca ggccagagcc acagagccgt tgtgactggg ggtctctggc caggacgttc   10860
ctgtgctgtc tgttgtgggc aggccccca  ggcagggcc  acctccaggg tacttggttc    10920
cagacgctgg ctgagtggtc acttgtgtcc acaccgcagt ttccctatct gtgaagtggc   10980
ttggatagga tggtggggtg gtgccagggg gttgctcttg ccgggactga gcccagggcc   11040
tggccctgcc actggggcca gcgtcagcct caggacagcc gaggagggga gatggcttgt   11100
gggccaggat gcccgagggt ggggagaagc agctcagatg gcgtcactgt gttgccttcc   11160
cccagccgat gggatttttg tggagctctc tctgctgggg acaatgagag gggagccgtg   11220
agccgtgata gggattgtgg caaggccggg ctggtcagct ggggatgcca gggccgcaca   11280
gtccctcggg gctcaaactg gcagctgtcc cccagggct  ctgggctggt gaggagcttg    11340
tcctgcccgt ccctctgctg ccacagtaac cccggacaca tcccatgtca tctgctgtgg   11400
ccctgccttc tgccgggtgg acatggggga tttggggtac agggaagcag tgagttctgg   11460
gccgaccaaa ttccccggtg ccgtcgggcc cagcctcctt cttccttggc accctggggt   11520
gtgtcgtggc tgagccccag ctctgtggtt cccgaggctt ttctgggatg gaggcctcgc   11580
tccgggtcct ggtgttttca catgggagca gaggagagtg ccccaagcct ggcgagcacc   11640
gcctgtagcc gccagcaaca cccccacct  ccgttacgca ggaatagtcc cagccaccat    11700
ttattgtaaa catttggtct gcacatataa cagagaaact cttgaaaacc aaagggccgt   11760
tatcaccctg agaaattagc actgatttct agaaactggc aggaagccag tcggatgctg   11820
ggattttaac tttaaaagaa catttcccag gcctgggcct ccgccgccag cccagtctcc   11880
ctgcaggagg gagtgggcag gcgctgggct ctgcgtgggg ccgtggactc agtctcccgc   11940
cccctccatg gctgggggct gttcccaggg gccctaagcc tcagctttcc ccggaggccc   12000
gggcatgggg tgggcctggg ctctgcatct ctcagaagtt tccaggtgat gctgacgctg   12060
gttgggggac cccacttgga gagctggggt ggcggtggcc tcctcttcca taacccctga   12120
ccctgggcgg tggcctcctc ttccataacc cctgaccctg ggcagtgacc gcctcttcca   12180 taaccctga  ccctgtatag cggccgtggg tactgtcttc cacccgtcca catccttcct    12240 ggcaccgaa  cactgccagc accaagccag gcacggggcc agcaaaatgc cctgcccgcc    12300
tggggacaca catgctggaa cgttcactgt gtgtcacaca cgtgcaggtg gtctcggggg   12360
gcagatgcca catgggagga atgggcccct gtcagctgtg ttctccattg tggtcggggg   12420
```

```
tggggcagg tagtggagga cctgccggct ctgcctgggc cctgcggcca cccacccgg       12480 acactgtggc actgggaggg gtgcagatga ggagccggtc cagggctagg gcccttcctg      12540
tctagccatg gccctcccca ggctcctcgt ggtgctggga ccctgtggcg tctgctcctc      12600
tggcccagtg gctgtcggcg gcggggccgt gtgaccctcc ttccttccat ccctgctggt      12660
gcatgcccag ctcccagcct ggcctcaatg cggggcatga gggctcattt cattcaggcc      12720
acatgagtgt caggacagcc accgttgggc atcaggaggg accagcagac agaatagtgg      12780
tggagccggt cacagagctg cacggggcag ggtggagccg gtcacagagc tgcatggggc      12840
aggggacgcc ctgcccactc cgcaggcctc taggctcccg tcttcacaga gttctcctgc      12900
tgaggcacct ggcctgtgtc ctcagcacat gcccccggca tcacacctca cccgtgagca      12960
actgatgcac ggctaccctc gcgggtctgt attttgggat ttcctgccag tgtctgtgag      13020
tcggggctca cgcccggggt gcgggtgccc tcctggaagt gtctgtgtct catagtgagt      13080
ctgtctgcct gggattgtca caacctggaa gaataggtcg ctcttccagt cccccacctt      13140
cctgcacggt ccagggtcgc tcaggagccc ctgggaccag gccagcata ccctggagta      13200 tgttcctgga gccagggaac atcactcctg ggccagcagc cccacctcct gcaggctgca      13260
ccgagcccct tcgggcccat gccaaccgcc ggtgcagcct ctgcccgtcc tctctggtct      13320
ccagggaagg cggcagcagc cgtggtggt atggaagccc ctgctctgct gcgtcgtgcc      13380
agagcggact gtggggacac agcagggagt ttgccgactt tgaggaggag gaaaggacct      13440
tatgccctgt tcgggaggcg gagaggccct caggagctg tccagcacca gccgtgctga      13500
agtctgcagc ttcctcctcc cgcgagggcg cctgccttgg cgctgggtcc tcacagccca      13560
gctgcagctg gaaagaagct atgtgagggc cggtgatttt tggcaagatc ccaaacctgt      13620
cgtcagctgt gggtctctgg ttctgtgctg aggagggca ggaggaaacc agatgtgttc      13680
ggtgcctcct gctggccagt cccccagccc tgggccctga gcagaccac aggacccacc      13740 cctcgtgccc cgccagggcc tctctgtctt taacttacag gggagaggga gggccagggc      13800
cccgcagagc tgagggtgcc cctgcgtgtg ggtgccggag agcaggcatg gagcagcctg      13860
gggaaggctg ggggccctga ccttgcgctc tccagaggcg gtgggtgtcg gggctccccg      13920
gggcggggca ggcacagcag gctgtggtgg ggtctgatcc atgtcccctg gagcgcactc      13980
ctgggagccc tttgtgacag actcctccaa gtcaccttgt ttcagggctc atgtggccta      14040
agggtaggtt agttgcagga gtttgagaag gtggccttgg gggtggatgg tcatgggcag      14100
aggagctact gccgcaaact cagctccaag ctgcctccac ctgaaccttg tccgtgcctg      14160
agccccgcct ccggggagga gcatcgcaaa ggatgggtgg tgctgcgtgt aaccctctgg      14220
ctgccccacc cttctccggg gacttgcccc tcaggccagc ccagccagcc ctcctgactc      14280
ctcctggggg gtgagggca gcgtctccct ggagctcccc acacacagga gagggttctc      14340
tagggcctca tctgatcctg cctgggcact ggcagagggc caggactcag gaggccagga      14400
cagaaaaggc cactgaggcc cacagcccct cactcaggga cacagggtct cctgccaaag      14460
gcagagggag tggagtgggg gcagctgaca cacggggagg gaacaggccc ccagcagagg      14520
aggcgggagc ggcgctgagc tcggcagagt gaggggctgt gactgcctct gaggagatgg      14580
agggctcgga tctgcttgga ggtttgttga ccctaaaccc caaatcccg gggatttgtg      14640 actcatcgta aagtgcacag atgagcgccc tctccagcaa aagccagagc cgccgagggc      14700
gtttgcagat ggcgtggtg ggaggacggg cggggccccc cagggccacc acggggtagg      14760
tgcctggctg cagacctctg cccggcctct cacccatggg gtgttgagtc ccccattcca      14820
```

```
cagctcaact gtggggtcag ctggcttggg gccttatcct cggggggcct gtgtcacgct    14880 accccttcccc tggggcagtg cccttgtcac tgcctgctgt gaccggactg ccagccttg    14940 tctgctggag ggaacgtggc agttgtcccc cagcccagga tggaggctgc tgtgcgtggc    15000
agagcacgtg aggcagccac ccctcaccgc aggccacagc gtcactggct caccggtcac    15060 tgtgggtcc tccccaccag ggctaccctg ctggtgcccc tgctggtgct ggggttggag    15120
ctgaaggctg ctcttgggcc tgggggccct gcgctcctgg tctcagcccc ctctctgctc    15180
cttccactca ggaggccacg aaacccgcag gctcatggga tgggcagggg ctgcggagga    15240
ggggcccagg cggttggagc tggctgtttg gtgtgaaagg gggataactg ataccccacc    15300
tctgacggtg tgtcctgagc tcccatcacc ccagttcagt ggtgtctgac agcccccctta    15360 ggtccctcac ctgctggtga cagtcctgtt gtggcacctg gtgcactgat ggtcgcctgt    15420
ggacccccat gctggtgaga cagaagtggg ctctgttctg ggctctgtgg ctcctggtgg    15480
cgttggataa accaagcccc cacagggcct gtgcagagag tgacctggaa gtgtcctggc    15540
ttctctgggg gaaacacgtt gagcgcttcc ccacgtgggg aggcggccgg gctccaggcc    15600
ccactgccca acttgggacg gtggcatcac gggagttggg atgggaggcg ggcggtgggc    15660
ctggtcagat ggggcgaatg gggtgagcct ggcctggagt tgtacccaag cccctgcccc    15720
tctcctgggc ttcgctcttt gaccagtgaa gtgtgagcag agttcacatc tgtctgggtg    15780
aaagcttcca gagccagcac cctctccact gtcccacaga agctggtgtg ggcacacagc    15840
acctccagcc tggccctggg aggttggaga ctcagccctg cggccaccct ttgattgctg    15900
cctgccccag ctgcccgcaa tctgggtgcg cggagctgtg tccctgccca gggcctcact    15960
cctctgtgtt cccctcctgt ctctgggccc cgtgtccttg atgctgcccc ttttcctgac    16020
cctgctctcc tatcacgtcc cctcttcagg ggagtggcca cgggaggagg ccgtcgtccc    16080 agccagcccct ccgcctgcct cagcctccca gggcagacgt cccttttggcc gagagttgca    16140 cctgcctctg atccttgccc ttgctctgtc ttcccctccg tccctgtccc agcacccaga    16200
ggaggttggg gtggggaaag gtcctcgggg gagaccatct gcacggcccc tccctggatg    16260
ccacagagca ccagccttgg gagggcagag ggggcgcccc ggaggtggat gccctgccct    16320
ggttcctgat gtgccccctg cctctaagac cacaaggcac tcaggacag atgctaatgt    16380 ttgggagggt aggagcaacg ggcgtgggct tgcagcccct gcctctcccc tctctgccct    16440
tcccgcaagc cgcccgctac ccactgccca ctaagcagct ctattcttac cgcgccctgg    16500
agattactgc tgcgacggct cctctgggac aggcaggctc gccgggctgg gggcagggct    16560
cagcactccc gctctgtggg agggtggccg cagggccctg cgtggagtcc ctccccagcc    16620
ctcgctgccc ctgtgtcctg acacaaggcc cccaaggtgt ggcaggcagg cgggcgtgca    16680
ggcctctgtc tctggtggtc taggggtgg ggtggctct ctgaggggtg tgggcctcca    16740
tctctggtgg tctaggggggt tgtagggggg ctctctgagg ggtgtgggcc tccatctctg    16800
gtggtctagg ggggttgtagg ggggctctct gaggggcctg agcagcctcc agcccctccc    16860
cagggaggtc agtcaccctg ggaggggggtt gggagcggcc cgggccaggc tgcctcatcc    16920
acagccctgg gccagtcagt ggggcaggga atgtggacac tgccctccta gccctctgcc    16980
tgggatcctc tacgtctccc cacttgggac aggagctgac gttgctcctg gagccctgcg    17040
tgccagctgg ggtgggaggt gtgtgcgtct gtgtatgtgt gtgtggtgtg tctgcatatg    17100
caggtgtgtg tgtgcgtgcc cacctgtgtg tgcaggtgcc agccttgccc agccttcccc    17160
```

-continued

```
ctgtggctcg tgaagctcag gatggctggg ggagctggtg gcagccccac tgcatgatag   17220
ttgagaagtt gggatcctag ggcttgcctg cagccagcac cccacagtta caggcagcga   17280
gctgccagcc ccagcccctt cctctaggaa aacatgccct gtcctgccca ggggtctggg   17340
atgggggacc gaccagcggc gccagctacc cccaagggca caggcttggc cgttgacctt   17400
tgctccccag ctttgaggac ccaggggttga gccaggaaga tggggtgcgg agctcttggg   17460
ctcagggcag cctaaagatt gtgctctgtg ccgaggtggg gaggtccgtc ctttcctgag   17520
tgtggcccca gccagcagcc cgcatctcca gcgctcggtc cttcctgcct acctgcgtgg   17580
cagtgacccc atccagcccc tgctccttgg ccccgcaggc cccacacccc ttgccgagtg   17640
attggcccag ccccaggcgc cccttctgtc cacgtcagac gctggtctgc acctgtgcca   17700
ttccatcccc agccttccca gacccccaca agccccaca ggctcctaaa cccacccaag   17760
atacggagac aggaacctcc caactctgtc ccagctcctc acactgtttg ttgcccgctc   17820
ccctgccgag gtcagggtgt ccctcggcca gcggctcctc ctgcccagcc ttcccctcct   17880
cctgcctggc cttcctctcc ctgcccagcc gccagaggtc ccttcttagg agataaactg   17940
ggccgggcgc agtggctcac gcctgtaatc ccagcacttt gggaggccaa ggctgccaag   18000
gtcaggagat ggagaccatc ctggctaaca cggtgaaacc ccatctctac taaaaataca   18060
aaacaaaaca aaaattagcc gggcatggtg gtgggtgcct gtagttccag ctactgggga   18120
ggctgaggcg ggagaatggc atgaacccgg gaggcggagc ttgcagtgag ctgagatcac   18180
gccactgcac tccagcctgg gtgatagagc aagactctgt ctcaataaaa agataaactg   18240
agccacacct gggctgtccc tgccactcag gaccccagag agctcagcaa attgcatggg   18300
gggcgagcgg agctggtatt tggcaacaca ggagggcggg ggcccaaacc cctgcagagg   18360
atgccagcaa gccccaggct ctcaggatgg gccacacgga gctggcatga ggaggcctgc   18420
agaggccagg acagctgtgt gtccagcact cggccgcctg ctggctgtgc tgctggaggg   18480
tgcgggggtg ggcctgtcgc tgggccacat cccagggcct gtggtggggc tggcagggtg   18540
tcagcctgca gcttggaaaa gaggagccca ggcatctgct ccctccacga ggtacacgca   18600
tgtgtgtgca tgtccatgtg caggtttgtg tgcgcctgca tatctgtgtg tctgtgtgcg   18660
tgtgtgtgtg tggtgcgtct gcatgtgcag gtgtgtgcgt gcgtgcctgc ctgtgcgtgc   18720
aaacgtgtgt gcgcatgtgt gtggtctgtg catccttgtc tgcctgcacc taggatgaca   18780
ggcggaggct cctagggttt cccagggaag gggtcccaa cgtcaccaca gcgacttggt   18840
agccattccc tgggctgccg agggtggggc ctggcaggtc cagagcggag ggagctgcag   18900
gccctgagg aggctgctgt ggtggctgtg gtgtctgcgt gggtccccca catctgatgt   18960
ctccttccca cccctgccct ctctgagctt ggtgtgggtc accggctctg actggctccc   19020
gctggccacc tctgctgtgt ccacgacagc cccactgcct gcagagggcc ctgctgcccc   19080
ctatgccctc tggcaacacc gtggtgtccc cacaggaagt aggttcctgg ccccacagag   19140
tccacttggg gggcttctca catcggaccc ttggccacag tgccacccgt cttcctgcac   19200
gggcctcccc tccgaggccc ttgttcctgc cgcctgccct gcatgacctt caaggaaatt   19260
gctgaccccc aggagacccc ttccttcatg gggtgcctca gaccccacct ctgcagggt   19320
tctagcagcc tggttctagc agctctgcag gggttctaga ccctctaggg gcctcgacgc   19380
agccctaaa ctaggacact agcttcagag actgaatcac caaatagtta caggattcaa   19440
tcaaaatgtt tcatcgggct aatctttcaa tattgaattg tgaaaaccag ttaatagaag   19500
tctaacgtga tcaactggct ccgctgggat tgggtcccgc cgcctccagg caggtgccac   19560
```

```
ctccaggagg gctttcccag agtgtggggc gggcccggca gggaggggct gtttgctgct    19620
ccatttgccc agtgtgccct cagatccaca gcctcagggc acctgtgccc tccagggaag    19680
gccgcctggg tctcctgccc accctggagc tgagcccacc tgccctgcag ctagagggga    19740
caggggctgc ctgggcacct cctccatcac ctcctggtgg aggggttcct ggtcccaggt    19800
ccttccactc cagaatccac ctttgagccc catactctct gcagcccatc ctctggcctc    19860
cctggggcaa actgtgaggc ttatggcgtg gggagcacag gcgggcctgg cctcgggccc    19920
cagcctccct ccgcctgttc ctagagccca cagttccact gctggagctt tctcttggcc    19980
acctgaccag ttcccctccc tgtgtccagc agtcctctgc agtcccacac tcatgcccca    20040
ggaatccatc cagctcctgc tgatcctctc atagcccctg gctttgggga gggtggagtc    20100
cagggtccca ggtcaccatc caccttagaa gtccagcgtc cagccccagg gcagcagcca    20160
cgggagaact ggggagaagg ctgtatgggg tgggggtctt cacacagcgg ccaccaggct    20220
ggggggtatcc tgaggtcaaa gcctgtgcca cgtcccccca tcttcccagg agacacctga    20280
gtgctatggc cactccttgt caggtccagg gcctggaccc tcaaggacac ccctgtggct    20340
gccatcctga caggcggaat tcatcgcaga ccctcaacct gatggcacag gtcagggttc    20400
acgtcggaac cctccccgct ggtccttact agatctgaga gtgagtcagg tggggtgtgt    20460
gtgtgtgcac atctgcctgt gcaggggtat gtgtgtgcac gtctgcctgt gcaggggtgt    20520
gtgtgtgttt gtgcaagggt gtgtgtttgc ctgtgctggt gtgtgtgtgt gtgtgtgtgt    20580
gtggctgtgc tggggtgtgt gtgcatatct gcctgtacag gggtgtgtat gtctgcctta    20640
tggaggttta tgtgtgtctg cctgtgcaag ggtgtgtgtg tgtatgtatc tgtatacagg    20700
tgtttgcctg tgcaggtgtg tgtgtgtgtg tgtgtatgtc tgtgcagggg tgtgcatatg    20760
tgtctgccta tgcagggatg tatgtgtgtc tgcctgtaca ggggtgtgtg tgtatgtgtg    20820
tgcctgtgta agggtgtgtg tacacacatc tgtgtgtgcc gtctgaccct ggaggcatgg    20880
gcctggcttt cctcagggcc tgcatttccc tctctgtttc tctgccccgc cccagccatc    20940
cccttcaccc cttgcagcct ggagctgggg gagtcaggga gaggctgggg ctgcagacgg    21000
ggcagctggc atcctcatgc tcccgtgccc gcctcttctc cctgtgctca gtcgtgctgc    21060
ttgggccgtg ggagtggagc tccttcgcac aggtgttagt catctgtgtt tccttagcga    21120
tttacctgtc cttggctcat ttaaaacagt tggagtgttg gtggttttgt aacgaactgg    21180
tcagagcacc ttccgtgaga agggcctttt cccccagttc accggggctc ccctgctcag    21240
ggtgtgccgg gggctttgag tcacttctgt gtctccttgg aggctgtgtg gcgtccgtgg    21300
aagttggcgt ctgtgcggtg tggttctgtt tatgggtgtt gtagagaagg cgccgtccag    21360
agacagagcc actgctgagg tgggtggggg gtgtatgaag ggcacaagga cgctttgggg    21420
gtgtcaggta tgacgccct caggtcatgg tttcacacgc gtgtgcttta aatgcgtgct    21480
ggctgtcacg tgtcagtcgt gcctccacag agcttcagga accaccgaga tggggagcct    21540
gccggagaca caggttttct gagcgcacca gcggctccaa aagcagaggg aagagccctg    21600
cgtgcaggtg gggcgctcat ggcgtcggcc tcgcagagcg gtgacggaca cagagtccgt    21660
gtttgggggg gtttgggacg tcggcctcgc agagcggtga cggtcgcaga gtctgtgttt    21720
tgggggggttt gtgacgagtc cgtgtttggg ggggtttgtg acgtcggcct cgcagagcgg    21780
tgacggtcgc agagtctgtg ttttggggggg tttgtgacga gtctgtgttt gggggggttt    21840
gtgacgtcgg cctcgcagag cggtgacggt cgcagagtct gtgttttggg gggtttgtga    21900
```

-continued

```
cgagttcgtg tttgggggggg tttgtgacgt cggcctcgca gagtggtgac ggacacagag   21960
tccgtgtttg gggggtttg tgacgtcggc ctcgcagagc ggtgacagtt gcagagtccg   22020
tgtttggggg ggtttgtgac gtcggcctcg cagagcggtg acagttgcag agtccgtgtt   22080
tggggggtt tgtgacgtcg gcctcgcaga gcggtgacgg tcgcagagtc cgtgtttggg   22140
ggggtttgtg acgtcggcct cgcagagcgg tgacagttgc agagtccgtg tttggggcg   22200
ccgtgaaagc acccagcgta gtcatgctgc tgtgtgcgat gggtgctggg cccgcagact   22260
tcggtgcttc aaaggcctca ctgctgagca cgagacgccg cttttgatgt cgtcaggctc   22320
tctggtcccc gggagtggac tcgggggctc cgagtgcagg gctcacactg tgtctttgag   22380
ggctggtcac ccacccaggc acacctgtgg ccctgagtca gcactgcctg acgcccaccc   22440
tcaggagccc ccgcctgcct agggtgggac catgggggag gctggtcctc cattctcagg   22500
ggctggggga cacccttct ggttgagaag gccacaggtg gcccccccgc cacccggcag   22560
gcacagcagg gcaccaccga gaccactgtg gcctgaggag gagcttcagc agccacttgg   22620
taggagggcc ttcgacggcc cttttgtgca gaaggtgggt gttccccagt ctcagaggcc   22680
agggccctg ctggctgggg tgggggctcc agcccagggc cccgctgagg ggggcaggag   22740
caggggcgga gagaacagcc gtgcgtctgc cttttctgct cccatcacca tggcaacaga   22800
tggagatttg gcaggaagga ggaggggcg ggctttggag gaggcagccc aggtttggag   22860
accagctggg gatcctcagg ggcctagggt gggggctcca gtctcaggct ggctagttcc   22920
tccttcctgg tcactgagcc agccttgctg aggggagagc gggttctgga cgtgctctga   22980
gcttccttcc tcacagccctt gctcctgggc cagatcagca ggaaagcagc cagtgccccg   23040
ccatggcctg cccgggtggg gtcctgaagc tggggccgga gcaggggca cagttctgcc   23100
ccatctggcc ctagtttggg gagggagcct ggtagggcac cagcctcacc ccatgagccc   23160
tgagggccac cccagccgat gggcacgtcc ccgccggccc tgcatctgtc cttcctccct   23220
ctgctcccca agagagccca ggtctggccc agcggtgggc aggggagggg ccgcacatca   23280
cagagtgcca gctggccaca ctcccggccc acagctgctc cagccgcacc tccaccttcc   23340
tcaaggccag acctggctct gcctgcagcc cagcccagca ggtgcgtgcc acgctccctg   23400
gctggccagg gcccctcgag ggaggagtgt gttcatgtgt gagggatgca gcccccacgg   23460
cagggacggg ggacctcgcc agcactggtg ggctgcacct gctgggaggg ccagctgtgc   23520
gggttcctac gctggcgctg cctgccccta tgtggagagg cgcctgcccc tatgtggaga   23580
ggctcctgcc cactggcccg gcctggcatc cgggccctca tcttgccctc ccaaaaagag   23640
ctctgccccc tgtgctgccc catcctgtgg ggaacgtggc cttggtcacc agccttaaca   23700
gcagtcctgc ggtgggtgga gtctcagctg cgccgcccg tcctgcggtg ggtggagtct   23760
cagctgcgcc gccccgtcct gcggtgggtg gagtctcagc tgcgccgccc cgtcctgcgg   23820
tgggtggagt ctcagctgcg ccgccccgtc ctgcggtggg tggagtccca gctgcgccgc   23880
cccgtcctgc ggtgggtgga gtctcagctg cgccgcccg tcctgcggtg gtggagtct   23940
cagctgtgct gccccgtcct gtgattggtg aactctgagc tgtgctgctc tgtcctctct   24000
ggtctgtgaa gtctgagctg tttggtaggc ggggccgagg gagcaggcgc cctcagaaaa   24060
tgcgagacag gtcgggttg cggggagggc gtccagtggt gggaggggcc cagcagagct   24120
gaggtttctg tgggaaaacc tttactgagc cagggacagt ggctgggggg tcagataagg   24180
cagccccagc ccagagggga tcctcctgcc tgctgggagt gggcaacggt gccctggctg   24240
cacagatcaa cccaggcccg ttggatcact agccctggcc gcacacagca accccgcgtc   24300
```

```
ccaggcaacc ctgcgtccca ggcccgtcgg gtctctggcc cagggcacag tagtggcagt    24360
cactcacatg ggacgggacc gcccatggcc tcccaccgtg cacgccctt  ctgactgctg    24420 taggcctgag gggtggatgg gcggggctca ctgcaggcgc tgcccccggc accccaggcc    24480
ctggcctcct tcttcccatg ttaggagcct gcgttcagaa cccgcattcc tggggaggat    24540
ggggctgggc agggactggg gtgggtctct cccatctca  tggcaccagc tcagacctaa    24600
gccaggatct ctgactggag ccagccagat gtccagctgc catgagctcc cctgggggct    24660
tctgcctccc agacgcccc  tggggacggc ccctcgggac accccctcag gtgtggtgtg    24720
ccctgacccc actgtccact ggggtcagcc caggagaccc tccctctggc ccaccctcc    24780 caccctgca  gccccttgca ggggccacgg ggagactcac agaggcagtg ccccaggacc    24840
atggtaggag actcatcctt cttggaggcc agaggcttct gcagggcctg agctgtctct    24900
gtccagcccc gagggccctg gcagtggtat ctctgcaggt ggaggggccc tgtgcccagg    24960
ctgtgccctg accttctgcc ctgggagccc tacagcccac atgggccctg gcatccagct    25020
ccccagtaga acttccccaa gccaggaagg aagtggtcat gggcgtctgg ggtctgtgtg    25080
cctggagctg ggccatgtgg cctgggctcc ctgcactgcc caccacccac tgaccctgac    25140
aacacaggtc catggcgggg cctgggcaga acggggaac  caaaaggagg ggcctgagct    25200
gagcctgggg tggtggggcc tggcacccc  actccatcag cccctcctgc catctctggg    25260
ggcatcagtg gccccagagc caaggagcag ccccaggggc tggagctcag gtgaggtcgg    25320
gtgggtaagg ggctgctgct gcacagtggt gggcagccac agcgcccagc tccgccttcc    25380
gccccgagga aaatgggctg cctcccacac tggacacaca gcgccagcca cttcctcaca    25440
cggtttactg tagccagact tggaaatagt catgtgatcc ccaggatat  ataactgcgt    25500 tttctccatc tgtgcttagt ttaaaaacaa ttgttcatta atttaaaagg aagagtttac    25560
cttcaaacat aaagatattc aaattaaaga tactcaaatt tttctgtatg aactaggatt    25620
tgtgctggtc aaaaatacca caccccaaag ttgccattgt cccgttgttt aaaattctat    25680
gtgcaaatag aatctccaga ggccgggcag gaggaggacg gcctgggagt gtccaggctg    25740
cttctccgcc tggaaagctg tctccatgcc cctgtggcag tttgaggctg gggatgccac    25800
tgccccacag tgtgctccgg ggatctcagg gcgctaggaa cttccctctg tagagagttg    25860
gcatcactgg gatcccagga tgaacttatg tgtggaatgc ggtgttcatt agaagctaag    25920
gagcctcaga gtatgctaag gtgcagcttc aaaggcagca attgtttgga acttaggcca    25980
aggaagattt gtgttttgga aatggcatgt attttatcac tgacattgtt tagtgtaggg    26040
tgataaaaag tagactgaat ttttttaatt aaaatgaaat tcgcataata taaaattaac    26100
catacaattc agggacggtt agcgcattca cggtgctacg cggccaccac tgtctagttc    26160
cagaatgttc cacccaagg  gaccctgcgc cacacgttct cttgccctc  ctccatccgt    26220 gggagcgtgg cctgccttcc gtttctggac gtgtcacaga cactggtccc atgctgtgcg    26280
tccctctgcg tctggcttcc ttcacacagc agaatgtact cagggccatc cctgttgtca    26340
tccctgttgg ggtttccttc cttttgaggc tgaacacact tacctgtgtg gacagaccac    26400
gttgttcgcc tatcatctgc cgtggacatg tggctgcttc caccttgtgg ctctcaggag    26460
tggcgcgctg tggacgtgtg tgtgagtacc cacgtgggtc cctgagctca gttcctggga    26520
gcatagacct cagagtggta attctgtctt tacctttttt ttttttttt  tttgagatg     26580 gagtctcgct ctgttgccca ggatggagtg cagtggcgtg atctcggctc actgcaagct    26640
```

```
ccgcctccag ggttcacacc attctcttgc ctcagcctcc tgagtagctg ggactacagg    26700
cgctcaccac cacgcctggc taattttttg tatttttagt agagagggggg tttcaccatg    26760
ttagccagga tggtcttgat ctcctgacct catgatccgc ccgtctgggc ctcccaaagt    26820
gctgggatta caggcatgag ccactgcgcc tggccctgtc tttaccttt taaaaaaatt     26880
agttcattta tttttctgag acagggtctc actctgttgt ccagctggag tgcagcgatt    26940
tgattctggc tcactgcagc cttggcctcc caacatgcta agattacagg cttgagccac    27000
tgcacctggc ttgtgtttaa ctttgaggag ctgccagact ttctcattgg acccagtttt    27060
agtcagcctc atttgggttt tttaaggccc cacagaaaag gcagccctgg tccctgctgg    27120
atagctggca cccctgcctg cccggggcct gctctgcccc cttgggtccc tcactttcct    27180
tcatagaatt cactggcttg gaggaaccca ttacctgctc actgcccaca cggtggtccc    27240
agcagaggac ttggagcggc tgccccttct gttgcacggg ctccaccacg gcctcctcgg    27300
ccactgtccc ctgggagggc agctgtggta aggccggag ctcccagctt tgggcaggtg     27360
agtgcccctg gcagttcttt tctgtgatgt aggttttttca gactgggaaa agttgagagt    27420
ttcaaagtcc attgccagtg ggaactggaa ccaggcaagc tgaaccaagt tcattagtgc    27480
tcttggcaac ctcagggctc acctggtgca cggggacctt tgcaatggcc agggcctggg    27540
gccacccgag ctagggcaag gggaggggga gggatgtgtt tataaaattt ctgttttaat    27600
ttcaagtaca gtaatgttgg tggatagaaa cacacaaacc acagcacttt gattttgtca    27660
gtaactctta agagtacgga gggtcctgag gctgggggt ctcgtgggca cagagtatga     27720
tgcctgtgag gacgtccttc cagccacaca gcccgtggac tgcagcattg agtgttctat    27780
ttcctggggtg tcacgtccgc aaaatccgct gttttgcagg gtcagtcttc gagaaatgct    27840
cttgtaagaa caggttttta ggctcatgtg ccccttccc agtgcccgtc acctctccct     27900
gaggctgtgg cctgggctca cctccctcgg accgaagggc ttcccacacg tctgtgtcca    27960
acacgttccc ccggctttca tttaactacc ggcggctgta tttagcctca gttttggagg    28020
atacttttgc tgaatgtaga attctggggtt tcctttgagt gcttagcagg tgctacacca    28080
tggtcctctg ctggtgagag gcagccacca ctgaggccct gggtatgatg tgtgtctctg    28140
gctgcttttg aggtttttctt tttatccttc ggttttgtgt gtttcgcagt gacccacctt    28200
ggtgtgttcc tccaggtgtc tgtcctgctt gaggttcagt gagccccgtg gatccacggg    28260
ctgatgtatt tagtacattt ggggaaattc ttcattgttc tctcttaaaa tgtggcctct    28320
tcagccaggc gcggtggctc atgcctgtaa tcccaacact ttgggaggtc aaggagggcg    28380
gatcacgagg tcaggcgttc gagaccagcc tggccaacat ggtgaaaccc catctctact    28440
aaaaatacaa aaattagcca ggtgtagtgg caggcacctg taatcccagc cactcgggag    28500
gctgaggcag gagaattgct tgagcctggg aggtggagtt tgcggtgagc tgagattgca    28560
ccactgcact ccacactggg ggataaagcg agactccatc tcagaaaaaa ataaaaataa    28620
aatgcgccct tttccctatt tgctctttcc tgtattgagg gactctggga acaagtgcct    28680
tagactatga gggggctcca taggcacctg acatgctgtg aggtctccac ctccctttt     28740
tgctttggtg cttgtcagga tagtttctgc tggctggtca ttgaggtcac tgttcttcta    28800
ttgtacccac gctgctgttc agccaatcca ctgaattaat ttcgttcatc ttttctcca     28860
atgaaatata tatatgtgtg atattatctt atcctttct gaaaattcta gcatttagat     28920
cacctgtgtc ctgcttctgt tggctgtttc ttctcttgag agtgggtcac actgtgtcct    28980
gcttctgtgg gctgtttctt ctcttgagag tgggtcacac tgtgtcctgc ttctgttggc    29040
```

-continued

```
tgtttcttct cttgagagtg ggtcacctgt gtcctgcttc tgttggctgt ttcttctctt    29100
gagagtgggt cacactgtgt cctgcttctg ttggctgttt cttctcttga gagtgggtca    29160
cactgtgtcc tgcttctgtt ggctgtttct tctcttgaga gtgggtcaca ctgtgtcctg    29220
cttctgttgg ctgtttcttc tcttgagagt gggtcacact gtgtcctgct tctgttggct    29280
gtttcttctc ttgagagtgg gtcacctgtg tcctgcttct gtgggctgtt tcttctcttg    29340
agagtgggtc acctgtgtcc tgcttctgtg gctgttttct tctcttgaga gtgggtcaca    29400
ctgtgtcctg cttctgttgg cagtttcttc tcttgagagt ggttctcctg tgtcctgctt    29460
ctgttggctg tttcttctct tgagagtggg tcacctgtgt cctgcttctg ttggcagttt    29520
cttctcttga gagtggttct cctgtgtcct gcttctgttg ctgtttcttc tcttgagag     29580
tgggtcacac tgtgtcctgc ttctgttggc tgtttcttct tgagagtg ggtcacactg      29640
tgtcctgctt ctgttggctg tttcttctct tgtgagtggg tcacctgtgt cctgcttctg    29700
tgggctgttt cttctcttga gagtgggtca cactgtgtcc tgcttctgtg gctgttttct    29760
tctcttgaga gtgggtcacc tgtgtcctgc ttctctgttg ctgtttcttc tcttgagag     29820
tgggtcacct gtgtcctgct tctgttgtct gtttcttctc ttgagagtgg gtcacctgta    29880
tcctgcttct gttggctgtt tcttctcttg agagtgggtc acactgtgtc ctgcttctgt    29940
tggctgtttc ttctcttgag agtgggtcac actgtgtcct gcttctgtgg gctgtttctt    30000
ctcttgagag tgggtcacct gtgtcctgct tctgttggct gtttcttctc ttgagagtgg    30060
gtcacctgtg tcctgcttct gttggctgtt tcttctcttg agagtgggtc acactgtgtc    30120
ctgcttctgt tggctgtttc ttctctttgg aggggtccc atttccccac ctctttgcat     30180
acgctgtaat gttttgttgg atactgcatg ttgtttattt agagcagcag ttcagactga    30240
agtaggagct gtcatcctgg aggggctccc tgcctgtgtt gggcatgtgg ggggctgctc    30300
agccagatcc aaacaggact tcagctggac tgggactggg ggtccctcca gcaaatttct    30360
gttcagctct aacacatatc caagggactg aaccccgtggg tggggaagtt tttcttttt    30420
tttctgtagt gccataagtg cctgtcacta atagaagctc agtgaatacc tgattgatta    30480
attgattgat cggttgattg attgaatgca gcaagtgtct gggagctccc agttacaggt    30540
gcgtgtcagg cgtgagtctg ggcaccaggg tgggcctttg ctcagctgtg tttgtgggct    30600
ctgcaggtgc gtgtcaggtg tgagtctggg cactggtggc gggggggggcc tttgctcagc    30660
tgtgtttgtg ggctctgcag gtgcgtgtca ggtgtgagtc tgggcactgg cggggtgggg    30720
gtccttttgct cagctgtgtt tgtgggctct gcaggtgcat gtcaggtgtg agtctgggca    30780
ccgggggggcc ttcgctgagc tgtgtttgtg ggccctggga cgtgattccc tcttgggtgg    30840
tgtttccagc cgctggctgc ccgggcagct ccaaatactg agctgtcagg tcggtggtct    30900
ctctatgtct ttctgttatc ttgttctgct ttgctgggaa ttttctcatt ttttcagtcc    30960
ttatttaaat agtttcttat tctagcagtt attattttc atgtcttaga gctttttttt    31020
gtttcttagt cgttttttta gaccttgttt atagatgcag ccactcacta atcctagca     31080
cactggtgca atcaacagaa tttttgaaat tctcatttct ggccagacac agtggctcac    31140
gcctgtaatc ccagcacttt ggggggccat ggcgggggcct cacttgaggt ctgtggtttg    31200
agaccagcct ggccaacata gtgaaacccc gtctctacta aaaatacaaa aattagctgt    31260
gtgtggtggt ggcatgcgcc tgtaatccca gctgctcagg aggctgaggt gggagaatca    31320
cttgaacctg ggaggcagag attgcagtaa gccgagatgg cgcccctgca ctccagcctg    31380
```

-continued

```
ggcgacagag tcagattcca tctcgaaaaa aacagaaaca agaatgtttg aaatcctgat    31440
ttcctgagga ctggtgctcc cgattctgct ccaggctccg cgcctcctcc cacacccggg    31500
cacgtggtcg ttcgtctcca aggaagcctg gttgagtgca gagcctcctc tttcttggat    31560
aagagggaat gttgtcttgt gtgagtctct ggaaggcagg gcctctgccc ggaggctcgg    31620
tgtccgtgca tgcatgcaag tgtgcgtgcg tgcatgtgtg cgtgtgtgca tgtgtgatgg    31680
cctaatgggc aggaagtggg gtggccttgt taggatgaga cagattttgc cacagggccg    31740
gcccccgctc tgctgggtgt gaccccaact accccttcttg ttggcccaga gaggggagag    31800
gctggccagg gctgccccaa cctgtgcacg cccttggcag atgctccagg gtgtctgcag    31860
ccccacctga ggcctgccct gcactctggc taacagacat tttcagtttt ccaggtcccc    31920
tggagacagg caggcccagg cccacccct gccttctctg cctgcctgcc tctagaaggt    31980
tcttgaatgt ttagaggttc ccccgtcacg gccaggctcc cttttgttta attcaggaag    32040
gtttgacagg tgagtgtgag gtctgccagc ctgggcctgg gcccctccat gcaggccctg    32100
cctggacccc ctgtgactcc cccaagtcct atctccaccc ccttggtccc cagctccagc    32160
ctcttcctcc actgcctaga ctgtcccctc gggatacacc tcctccctgc agcctcctcc    32220
ctggctgtca ccctctttgt ggcctgcctg ggggactcct ctggttactc ctgtcctcag    32280
ctctaggtgg ggctggcagt cctgggggct cagcctccat gtggcatcca gcaggtgccc    32340
ggcaactccc tgttttttcca cctgaccta agagcctggc ttgagcctct catggggagg    32400
ggcctgtgcc ccccagggcc ccctcggccc tctggctggg tgctggcaag taggtctcaa    32460
ccctggagcc tgactggggc ctcccaccga catctttcat ctgggtgcag agcagagagg    32520
ggctttggga tgctcagagt gataccctca gatctttagg attcagatct ttgggctgcc    32580
tgtgggctcc tggcttggct gaccctgggc ctcctcctgg tacagtccca ggctgtgctt    32640
tgggtcccag gctgcgcttc ggaggggagg gacagtgtgg gggctctcat ttaatcttca    32700 cccccccagga cggggtgtca ggagacccct gaggccaggc acgtctgggg tcacacccag    32760
gagggaggca ggcgtctgca gtctggccct ggctcaggcc cacccttgcc catctccggc    32820
tgcagagatg cctgcctctg cttggaaggg acctggatcc tggaacagcc tagggctggg    32880
aagctgcttc ctcctccaca atctggtccc cagtgggagc tgcatcccac ctttgtttgg    32940
gtgctgggtt aggaggcggg agccaggcag aggcagcgga gcggctgcag tgcgtgtgaa    33000
atgcttcagg gtggcacgaa tttaactaga gaggttcttt tccaacgtga gcagttgtct    33060
cccaagagat gcgccgcccc ttccctctgc acctggcact ggtgggcggt ggaggctgtg    33120
ggatctattg atgttctgag cgtgtgctga gggcctcgct ccttcctgcc ccctgcccca    33180
gctcctgtgt cggggctgtt accgtggtg tgcagggtgg gggtgcatag agcctgggtg    33240
cccccagact gaggaggccg aagggtcggg gagcaagggc ctgggtgcta atgaaggaac    33300
aaggcttcaa tgtctgtggc aacttcagag gcccctctcg gggcaggtgg gagaacccc    33360 agcctgggga gcaaacctgc cggcccagca ccggggtctc tgctggagat gtgagcacgg    33420
cggcctgacc agggcccggg agagagggg caggtggggg tggggtcggg gcaggctggg    33480
ggtgtcactg ggcctgcagg gggtctagcc tgaggttggg gtgccccacg gggggaggggt    33540 ggcacctgtg cctgggccgc atcatcgggt gtatttgagg cggggtcaga gccaactgtg    33600
tgtcgggtga gagcccagcc cagcccagcc ccagctgtgg gccccccatg agcccctcac    33660
gggagcatgc agtggatga tcaggggtga gccaagtaga ttgggggcgg gggctggcca    33720
ggcctcatcg cagctcacag cccccagccc cctcctgagc tgtttggtac cctgtgtgtg    33780
```

-continued

```
cagagtccca ggtggggcct gccctcctcc agccgctcct ccaccctgtc tgccgtgtgc    33840
cacccatggg gtgctctggg gagggtggg ggtccctgta ttgctgggga aggtgtgctg    33900
accacaaggg gagcagctta tggggccgag gctggctcag gatgccggag gctctgcggt    33960
gggccctggc gagtgaggag ctgtggggac ggtgcagagg ggcctgtgcg cctcctgagt    34020
ttgcagttgc tacagtgccc acaccccgag gatgcatggc tgacagtccc cactgggtgg    34080
ccttgacaaa ggtgtggcca gggcagggcc tctgaggagc tgaagacctg cttccaagga    34140
cactcctccc tgacagtcct gtccatggtg ctggaagagc tctggcgacc ccacaggcag    34200
gcaggcctga ccgtccaagg ctcggctgcc tgtggggaac tggacacact tcctccagag    34260
tctcagtttt gccagctgtt tgcccagcgc catgtccact ccccaagcca ggaccgaggg    34320
ggtgacggag atgaagcttg tgctggcccc agctggggc cgctgcccac ccagcaagcc    34380
ccacagccag tcccaacctg gtgatgtggt gtccggagga tggacctcga agtctctcag    34440
acctgggttt ctgagctcct caggtgtctg tgtcccctcc tgggaaaggg aacagagctt    34500
tgcgaagatc aaggggaggg caatgcagct tgggagcctt agctcagcca gacagcagcc    34560
cggagggtta atgtccaggt acctccaggg cccatgcacc caggacctcc ccaagagctg    34620
tgcctccatg tacctcaggg cctccccag agcggtgcct cgtgggggat gcggtgcctc    34680
gtgggggaca tggtgccttg tggggtacgt ggtgagacg gtggggtcgt ggccgtccag    34740
gcttcagaaa cggcagaacc agggaccctc cccactgtcc tgtccttagc gtcttgaggc    34800 tagggtgag ttcgagacct cgtaaatact tcagtgcaga gccttcagtt aggagccgag    34860
gcctctggcc aggttcaggc acgtggagag tgtgtgtggg gagaagttct gagactgtgg    34920
gaggggtagg ggtgtgctgt ggccacagtg gttctggaat ttgaggtgcc ttaggaggtt    34980
catgatgaag gatgcggccc acagtcgtgt gagcagagga cggcactcgc gagctccctg    35040
gggctcctca gacccggtca ccgaacagca gagacgtgct ctttcacatt ctggaggcgg    35100
gaagtccaag gtccagggtg ggctggctct tccaaggcct caaggaagcc ctgccccaag    35160
cctcccccgc tgggcgttcc gggtgcccca ggcctccccc gctgggcgtt ccgggtgccc    35220
caggcctccc ccgctgggcg ttccgggtgc ccaggcctc cccgctgggc gttccgggt    35280 gccccaggcc tccccgctg gcgttccgg gtgcccagg cctcccccgc tgagtgttcc    35340
cggtgcccct gggcctgcag aagtgctccc ccaccccat cttgctttca ccctcacgtg    35400
gcgcccccat cccaccccgt gtgtcccag ccacactttc ctcggccttt ctctgatagg    35460
aaggctggta gttgggttta gtgtccaccc caaatctggg gctatgttat attgagatcc    35520
ataacttaga aacctctgca gaggctgttt ttccaagtcg ggtcacattc atgcgcccca    35580
ggcactggga cacacatctt tgggggtca ccattccacc cccacatcct ccagctgtga    35640
tgtggggcca tggtggaccc ctcggcaccc ctgtggcctc cggaactgct ccgtgagccc    35700
cggggagccc caccattccc ctggagtgac agtgggtcct gccggccagg cggagggaag    35760
tctctgctgg gtgtccacct gcgaggccct caccccctac tgcctcatgt gggggtgcc    35820 ccagcactgg gtgggtctga gtgtgggggc aaaaggaaga aggacaggga gagccaggtg    35880
gggacaaggt gtcctgccgg ggtggccccc acctgccctc agaatccctc caggcagaca    35940
gtggaggctg tgtgaccagt gtgggagttg gggataggtg agggacccc ttcactgggg    36000 tggggccaag tggcaggaac tcccccaaca tctaaaggag aagggtccag gacccttcgc    36060
caggacctgg gctgctttgt gccccggcag gacgggacag ccacacacct gctgccctgc    36120
```

-continued

```
cctccatctg catccagcca acaggccatt cctcccgtgc ttcaccctcc atcctggcct    36180 ggggaggccca ggctcaggac ccgttgggac tgtttggaca gagggagtcg gggggggccag   36240 gcagggccct gtggagcctg ctgggggctc tggacctggg cctctgccag gtgggctccc    36300
tgggacctac tggcgggggg gcaggttgcg ggggtggagc aggacccccct ggcctgcatg   36360 cttcccctcc ctgggctca cacacagcac ctcgtgggcc cagagtgctg gcgggagggg    36420
tgttctcccc gcctccatgg gcaaagaatc tggggcccctt gtcagagacc gcggggtcag   36480
tgggattggc gcccaggccc tgctgtgacg ccacgtgttt cccactcagc gaggctgttc    36540
ctgccaggcg tggggactcg gaccctggtc ctgagtgctg ccccgaggcc cgtgatggga    36600
agcctgacgt ctgcatcgtc ctgcgctgcg tggccggtcg gtcccggcgc tctcagcact    36660
tggagtctca gctcccccggg tcatcagtcc aagccactca gcaggtggct tcggcttaag   36720
gcctctcagg tggctctggt gaaggcgtca cccagggctg cctgatctgc aggctgggct    36780
ggaggggctc cttcctgggg ggtcccgcag gctgtgtggg ggcctcgggt cctcagcacg    36840
tggacgccct gcagggcact gctgccagac atgcccactg agctccccag agtccaggag    36900
gaagctgtgg tgtccttgtg gtctgtggat gaggcccgct tggtcccaga ggtgcgggtt    36960
ggtgacagcg acggggcagg ttgtcacctg tcctggtctc tgggagccgc ctcagtgggg    37020
tggaggcagg gcaggcctgt ccaatgaccc caccccctca ggacgtttcc tccgtgcagc    37080
ctgggccagg ggccacggga ggctcttcac ctacagggga cgcattcagc accgaggtca    37140
gcagcccatc ccgagccccc cacacccccg ctcgtctccc actctgtgtc ctctccactg    37200
gccttggggt agatgagctg cccccgtcct ttctttggga acccaccccc ttctgggcga    37260
gggtgggtag caggcacccg acagggtccc caggtggcac tccaggccgt ggcactagat    37320
gtgcactgtg gagatgggaa gaggtgtggg gcaggggagg gcgtgggggg aacgctgagt    37380
ttcctgggta cacctgcccc ggggccagtg cctcaggcct ctggagagcg gatttgcggc    37440
ctcatggctg gggagggctg aggttctgct gtccggtgtg gtgccacggt gagcacacct    37500
cacctgtcca gccttccccc taaacccagt gctctggacg gtgggctggc ccctggctcc    37560
tagcctgtgc gcgcccattc aggaaagcaa acaccagcac acaccggtcc ctgtggggcc    37620
ttgggtgctc tggcaccca gctgcatggg acgggcaggg ccacgtgcc atcagggcct    37680 ggatggggc ctggcacaca gcgggcactg gggatgtgtg tggggcgtgc tccggggatg   37740
tgtgtggggc gtgctccggg gatgtgtgtg gggcgtgctc tggggatgtg tgtggggcgt    37800
gctctgggga tgtgtgtggg gcgtgctctg ctggcgactg gcttggatc tgtggggtgt    37860 aaatacctga gacggcccct ccaggggaaa gaagaggctt gaactgtcac tttaatccctt   37920 tcagactccg caggagacag agcacgccgg ggaggacaca tgtagcccctt gggggtgccc    37980 agtcctggca aatctcggtc tcgagcctgg gtctgtcccc gcaaatgtag agtgtgcagg    38040
gaaggccctg ggttgctggg aacttgcaga ggccctgggt gaaggtgccg cgtgtcttct    38100
ctgtgtgact cctgcctggc cctgggtgaa ggtgcccccgt gtcttttctg tgtgactctc    38160
acctgtgagg tgtcctcccct ccaggaggtg gttgctggca acggggtgg gggcaacaga    38220 tgggccagca gccacgtggt ggggagcaga gaggacctgg gggtgcagac acaggatgtg    38280
gcggggctgc tggggaggag ctcaggatcc ctcagccaag tgcatgtggg gagggccctg    38340
tagtggccag cagcaggcaa gtctatgaaa cgggaccact ccgcctggtg ggaagccccc    38400
tgggtctgca tgcggagat ggggggggcgg cacccccaggc tgtcccccata cctgctgcgc    38460 aactttagtc tggtgcgtgc cggggcggtg aggggggctgc gcggggtcct tccccagtgc    38520
```

```
caacactgcc acctgcccca gggcccccta cccaaactaa agagcagccc gtccagccct    38580
aggctggctt ggctcctgga cctgcagccc cccatcccct ctctccccac agccccactg    38640
gcttcctggg ggcagggcgc tgccggcaga gctgcagaac tgagccctca ctgcccctcc    38700
agaaagtgcc agccctcctg cacaaccct gcctgccagt cctcctgggt agctgagtgc     38760
aggggcaggg gctgtcctgc tgcctcgccc ggcccaggca ggagaaggcc cctcacttct    38820
tggccagcct gggacttgag tcagggcctg ctctcagata ccacgtgcag ggtagtcctg    38880
gggctcccc tgactctcct ggccggctca ggagcacctg ggggcacccg tgttaacgtg     38940
ctagtctgct ccctgaggcc cagcatcctc gtggcatacc cgtggcttcc ctgggatgcc    39000
ctggggctcc acatgcccag gcccttccct gtgggggcg cagggagacc cagcactctt     39060
gggcacccgc cggcacacgc tcccacagaa atggggcctg gcgtgagctg ctgtgcaccg    39120
cctgccccct cagggccctg ggcagtgatc tgtggcactg cgtgccttcc ctctcgacag    39180
ccaagcctgt gtttgtgtaa agacagcaat tagagatgga ctctcaattg gaaaataagc    39240
cacagtgagt tgcaggggga gatgatgaag ggtggccctg gcttccccg ctccagcttc     39300
cagtccccca tcctccaggc tacggcccag tcaggagggc ctctcacagc acactcccca    39360
ctccctgcct ccagaaagtg gcaaaactgc tcataaaccca acattctgc tcagagaaac    39420
tcggagctga gggataccag gacgcagagg cctgcactgc tgcctaggac cccagggaag    39480
ctttacctag gagggacgcc tctatgctgg gctctgagga gtgtgtagga gtcttcagag    39540
tacagtaatg gggaaaggac tttctaggca taggggcagc aagtgaaaga agatggaggc    39600
aggaggagtg accagagctc caggatgcag ctggggacgg ctctcctaca tcccagcctg    39660
ctgcgtcgtg gctgccttta cctgagccac tgcgaggctc ctgagcatag gcaggaggct    39720
cttggtggct gtggctcctc tgtgactctg ttgctatttg agaggccacc tgcagccccc    39780
agactccagc ctcaaggacg tgggcaggat ctatggatgc ggcaggccca cccccagtgg    39840
ctccatcccc tccgtaacct cctctgggaa ggtgggtgct tgccaggaat gccttcttcc    39900
atgtggtcca ctgtcctcac agcccttctg agccacatgt gctggcaggg gatggaacca    39960
ctgtttcctc atctgtgaaa tagggtgaa ggggccccac tcaaagcagc gcctggagca    40020
aggccagtgc tccgagactt ggctgtcctg atttgtgctg ggcccagcag tgtcctttca    40080
ataaagttgg cccaggtggt tgtcaggctc cctcccattt tcagtcccca cttttctttcc   40140
ttttctggag gcaggattgt gctctccaca ccttttggct cctgtcattc aaggatgtgt    40200
gtgcacactg ggagtgtgca tgtttgtacg tatgtgtgca tgatggtatg tgcacgagtg    40260
tgtgtgcact gcgggtgtgt gtgcatgtgc actgggtgt atgtatgcag tcgtgtgtac    40320
atgcatgggt gtgtgtacag gcgtgcgtac tgtgtgtgca tgggtgtgtg cacacgggtt    40380
actggggtg tgcactgggt gcttgtgtgc actggaggtg tgtactgggt gcgtgtgtgt    40440
gcacgggtgt gtgcccttgg cgtgtgggcg tgtgcactgg gtgtgtcctg ggtgtgtgtg    40500
catgggtgtg tgtacacggg tgtgtcctgg gtgcatgcac atgtgtacac aggtgtgtgt    40560
gcatgggtgt gtgtcctggg tgcgtgcatg tgtgcactcg gtgtgtgggt gtgtgcactg    40620
ggtgtgtgtg cacgtgtgca tgggtgtgtg tgcacgggtg tgtgtcctgg gtgcatgcgc    40680
gtgtgcatgg gtgtgtgtgc acgcggtgtg tggcgtgtgc ccatgggtgt gtcctggatg    40740
catgtgcaca ggtgtgtgtg cactcgtgtg gtgtgtgca ctgggcgtgt gtcctgggtg     40800
tgtgtgcatg tgcgcacagg tgtgtgtcct gggtgcatgt gcactcggtg tgtgggtgtg    40860
```

-continued

```
tgcacatggg tgtgtgtgca ctgagtgtag gcacaggggt gtgcacgcat ggaggtatgc    40920
acacacctag gggtgtacac aggtgcatgt ctgtgtgcgt ggccacacgt gctgtccctg    40980
cccagggccc tgctgctctg tcgaccagca tcctgctgtg cccagcagtg agcgtcttct    41040
gcggtctggt caggttttgc cactgtgctc agcagtgagc gtcttctgcg gtctggtcag    41100
gttttgccac tgtgctcagc agtgagcgtc ttctgcggtc tggtcaggtt ttgccactgt    41160
gctcagcagt gagcgtcttc tgcggtctgg tcaggttttg ccactgtgct cagcagtgag    41220
cgtcttctgc ggtctggtca ggttttgcca ctgtgctcag cagtgagcgt cttctgcggt    41280
ctggtcaggt tttgccactg tgctcagcag tgagcgtctt ctgcggtctg gtcaggtttt    41340
gccactgtgc tcagcagtga gcgtcttctg cggtctggtc aggttttgcc actgtgctca    41400
gcagtgagcg tcttctgcgg tctgatcagg ttttgccact gtgctcagca gtgagcgtct    41460
tctgcggtct ggtcaggttt tgccactgtg ctcagcagtg agcgtcttct gcggtctggt    41520
caggttttgc cactgtgctc agcagtgagc gtcttctgcg gtctggtcag ttttgccac    41580
tgtgctcagc agtgagcgtc ttctgcgggg tctggtcagg ttttgccact gtgctcagca    41640
gtgagcgtct tctgcggggt ctggtcaggt tttgccactg tgctcagcag tgagcgtctt    41700
ctgcggtctg gtcaggtttt gccactgtgc ccagcagtga gcgtcttctg cggtctggtc    41760
aggttttgcc actgtgccca gcagtgagcg tcttctgcgg tctggtcagg ttttgccact    41820
gtgctcagca gtgagcgtct tctgcggtct ggtcaggttt tgccactgtg ctcagcagtg    41880
agcgtcttct gcggtctggt caggttttgc cactgtgctc agcagtgagc gtcttctgcg    41940
gtctggtcag gttttgccac tgtgcccagc agtgagcgtc ttctgcggtc tggtcaggtt    42000
ttgccactgt gcccagcagt gagcgtcttc tgcggtctgg tcaggttttg ccactgtgcc    42060
cagcagtgag cgtcttctgc ggtctggtca ggttttgcca ctgtgctcag cagtgagcgt    42120
cttctgcggt ctggtcaggt tttgccactg tgctcagcag tgagcgtctt ctgcggtctg    42180
gtcaggtttt gccactgtgc tcagcagtga gcgtcttctg cggtctggtc aggttttgcc    42240
actgtgctca gcagtgagcg tcttctgcgg tctggtcagg ttttgccact gtgctcagca    42300
gtgagcgtct tctgcggggt ctggtcaggt tttgccactg tgcccagcag tgagcgtctt    42360
ctgcggtctg gtcaggtttt gccactgtgc ccagcagtga gcgtcttctg cggtctggtc    42420
aggttttgcc actgtgctca gcagtgagcg tcttctgcgg tctggtcagg ttttgccact    42480
gtgctcagca gtgagcgtct tctgcggtct ggtcaggttt tgccactgtg ctcagcagtg    42540
agcgtcttct gcggtctggt caggttttgc cactgtgctc agcagtgagc gtcttctgcg    42600
gtctggtcag gttttgccac tgtgctcagc agtgagcgtc ttctgcggtc tggtcaggtt    42660
ttgccactgt gctcagcagt gagcgtcttc tgcggtctgg tcaggttttg ccactgtgcc    42720
cagcagtgag cgtcttctgc ggtctggtca ggttttgcca ctgtgcccag cagtgagcgt    42780
cttctgcggt ctggtcaggt tttgccactg tgctcagcag tgagcgtctt ctgcggtctg    42840
gtcaggtttt gccactgtgc tcagcagtga gcgtcttctg cggtctggtc aggttttgcc    42900
actgtgctca gcagtgagcg tcttctgcgg tctggtcagg ttttgccact gtgctcagca    42960
gtgagcgtct tctgcggtct ggtcaggttt tgccactgtg ctcagcagtg agcgtcttct    43020
gcggtctggt caggttttgc cactgtctaa cagctgccct gtgccttgg tggctgtgcc    43080
ctaatgactc ccctcctgtt tggggccatc ttttgtgaaa atgcagagcc accagggctt    43140
cgtcacctac cctgggaatg ctgtcccggt gcccttgggg gctttgacca cagcctccct    43200
cctgcttcac ccctgcaccc tcatgatgcc ctggggcagg gtgtgggccc ttcatccttt    43260
```

```
ggggtctcct gagggtgcct catgctgggc atttctgggt catttcctcc ctccttgag    43320 agcctctgtc ctggcctccg gctgcatcct cccaggagtt tgtcctgagg gttttagggg   43380
gctccatgcc cttcggacca gaggcttttg tcacggacca cgccttagcc ttgcagccag   43440
gtttggggga cattgagctc ttgctccttt ccgtgtgtgg ggctgagtcc ttcctgcagg   43500 gaccctgcc ccgggatgca ggccagcctc gtgcctgggg agggatgcgc tgtgggcgcc    43560
tccagccgcc ctggattatg gatgaagggc tctaggccct cctgagtgct cctccggctg   43620
agcgaatcac aagccttgtg ctggatcaaa ggccttcagg gagaagcagc tcttcctcca   43680
tgagcacacc ctgccgaggc cacccccac ccctggcact gggctcccct ctgtgcccag    43740
cctgtgtcac tgcccggcct gcagctcccc ctgcctctgg ggaagcccgc ttcttcggca   43800
aggtcctggg tccccacccc ggcctgggct cacccagatc caggcgtgac gccacacaga   43860
tgaaactgac ggaaagggca aaataaagct aaaagccgat ggggccgggg gaatggaggt   43920
ttgacgcgtg agacaaagga ttaatttccc aaaaaaatca aagggctctt gcaaattggt   43980
aagaaaatgc acacatgtgc gtgcaccagg ataaaaacga aacaggaaa ggagcccaga    44040 gcacacccac acggtcagta aacaccggtg acgtcccgcg ggtcaacagg gcgaggccga   44100
gtctgggtga aatttgagca cagcgcgtgc acggaaggat ggcggccact aaagcccagt   44160
gggaatgcca gccaggatct gggtgtctgg gcgcacctag gagtgggtc ccctgtgata    44220 acctgggccg gctctgcgtg tctggggca cctaggagtg gggtccctg tgataatatg     44280 ggccggctct gcgtgtctgg gggcacctag gagtgggtc ccctgtgata atatgggcca    44340
ggatctgcgt gtctgggggc acctaggagt gggtcccct gtgataacct gggccggctc    44400
tgggtgtcgg cgcacccagg agtggggtcc cctgtgataa cctgggccgg ctctgggtgt   44460 ctggggcac ccaggagtgg ggtcccctgt gataacctgg gccggctctg ggtgtctggg    44520
ggcacccagg agtggggtcc tctgtgataa cctgggccgg ctctggtgt ctgggggcac    44580 ctaggagtgg ggtccccgtg ataacctggg ccggctctgg gtgtctgggc gcacctagga   44640
ttggggtccc ctgtgataac ctgatccccc catggttcca acatgcccca acatggaatg   44700
gcacatgagt gcgcctgagg acctttgatg gtaggaaagg gcctgggttg tgggctcctg   44760
ggggcatctc cagtgtcaag gccacagctc aggccaggtg gggctcaggg gtgtggccgg   44820
gctgtcctgg gcaggggcaa gtatctggct gtgaaaagag tggggagagg agaaagggag   44880
ggtgggccga ggcgcggagg gggaccggga ccgtgtgccc agccaaggca cattcccaga   44940
gcaccctgcc tgccttttag gtgggtctgg gaaggaaggg gctgccgggc cgtggaggtc   45000
tagggcagtg ctgcctgggg agctacctgg ggcccgtcct ggtgtcctgg ggtgaacaca   45060
gggccggggc tcaggtgcag agcatctcag cagaggaggg gtgccggtgg gggtctcagc   45120
ggaggagggg tgccggtgga tgtctcagcg gagtaggggt gccggtgggg gtctcagcgg   45180
aggaggggtg ccggtggggg tctcggcgga ggaggggtgc cggtgggggt ctcggcggag   45240
gaggggtgcc ggtgggggtc tcggcggagg agggtgccg tgggggtct cggcggagga    45300 ggggtgccgg tggggtctc ggcggaggag ggtgccggt tgggtctcg gcggaggagg     45360 ggttgccggt gggggtctcg gcggaagaga ggtgtcggta gtggtctcgg cggaggaggg   45420
gtcgctgtgg gtgtctcggc ggaggaagta tgccggtggg ggtctcggcg gagagggggt   45480
gtcggtgggg gtctccgcgg aaggctgcgt ctgaggtatc tctgcagaag gctgcaagtt   45540
gggggtctcg gcagggtgtg cgagggacag ccttcttggg ccaggcaggc acctcgaggg   45600
```

```
cacccctggct cccagctgag ggtggctgaa gctgaaggga ggggatttgg gtcccttgga   45660
tggggagaag gcaagcgggc acagagactg agaagcccaa ccgggcgtgg aggaagacac   45720
actttcagcc acgtgaccca cactgactgt ctgacacgac cagcggcagg gctccctgga   45780
agcggtggac cctgcttcag acgtggaggc tacagctgag tcgtatatgt caactgttct   45840
gtgtaatgta tcgctcaatc aacacataca ccgaaataag ttaaactggt cctaatatac   45900
tactaattat cgtcctcatc cgttcgatgg aactgcgnnn nnnnnnnnnn nnnnnnntct   45960
cggcggagag ggtgccggtg ggggtctcgg cggtagaggg gtgccggtgg gggtctcggc   46020
ggaggagggg tgtcggtggg ggtctcggcg gaggaggggt gccggtgggg gtctcggcgg   46080
aggaggggtg ccggtggggg tctcagcgga ggagggtgt cggtggggt ctcggcggag   46140
ggctgcggct gaggtatctc tgcagaaggc tgcaggtggg ggtctcggca gggtgtgcgg   46200
gggacagcct tcttgggcca ggcaggcacc tcgagggcac cctggctccc agctgagggt   46260
ggctgaaggc tgaagggagg ggatttgggt gccttgggat gggagaggg cgaggggggc   46320
cacagagacc tgagaagccc aaagggccgg cgtggaggga agacacagct tgcaggggc   46380
agcgtgacgc cagcactgag ctgttctgga cagcgaccca ggcgggcagg ggcctccggc   46440
cctggagcgg gtgggacccc tgctgtccag gacgtgggag gaggccccca acctgcactg   46500
tccggctggg tgctcgctgc aggcaccctg ggtgggtctg agcgcggctg cttctctccc   46560
gcaggtctgg tgaagctggg ggttcactgc gtcacctgcc agaaggtggc catcaagatc   46620
gtcaaccgtg agaagctcag cgagtcggtc ctgatgaagg tgggtggggc cggggaggga   46680
ggcgggggccg gcggtggggt ggggcgggga atagcacagg ggtgggagcc aaggttgtgg   46740
ggacctgcgg tgctggatgc gggtgggggg gcgggcctgc aggctcctgg gccgccacac   46800
ccctgctggt cccctggtag ggtgcctttg ctcttgctcc tccctccagc cctgcccacc   46860
tttctcctgc ctccaagcag agtgggcacc cctgagggga caggctgcag ctgggcagtt   46920
cagttgctgc aggacctgct gtgctagcag gcggggcttc agtgttccca gctagaatgg   46980
agaggagttc cctgcctcag agcacccctc tcctaccagg gcacagcttg gcagagggga   47040
gctgcacctt cctcttccac tggggcctgg cctccgtcgg ctccatccgg tggtgtctgg   47100
tcaccatgga gaccaggcag gcccctggg tggagggttt ctgggctgtg acccacctct   47160
cagtggggag ggggcggccc cggctgctgg gaagcctgac cctgggtgta gaggaagagg   47220
ctggggctcc cagctgctcc gggtcccacc cacagtggga cctgggctgg cagcgtgcga   47280
ccctcccagc actgggccaa gtcgagcccc ctcctctccc ttcctctcca ttcgctcctt   47340
ggcatgcagg gctgcgggtg gggcaggacc cggggacgag gccagtggga gtggccaaga   47400
gaggggaggc ttgtggaagg tgctaagggt tggggactgt gacatgttgg gcaccccca   47460
gctgctgggg tgtggaggaa ttaaccagac taaactgggg aggcctgggg accctatggg   47520
gaggtggggg tggggttaag ggctgctgag ggctgcctgg atgggctgg cagggtccca   47580
ccctgccttg gaggagaaac agaggccctg ggagtgatgg ggccaggaca gcgcctggca   47640
gagagatcca gtgtggggcg tagctgggga gagtcccatg ctgaatttgg gaggtgcctg   47700
tgagccccga ctaaaggagg gcctgggat gcgggaaagg ggaggtgtcc ctgtcacctg   47760
caggcgctgt gcacagatgt ccgcctggga gggaaggact tggggacagg ctggccaact   47820
cgccagggct gggaccccat cacaagactg gccctagctc caaagcctgg tccacgctgg   47880
ctcctgaggt ctgggacccc aggccgtggc ctcactggcc ccaccactga cacggccact   47940
tctttgtgct gggcggagca ccagctgccc gtggccaggc ttgcatgtct gagggagggg   48000
```

```
gccctgcctt acctcggagc aggactgggt gtcctgagtc aggtgccctc tgggtcactt    48060
ctgcccctcc ctgggccctc cccacttggg ggacagtacc agctgggagc ctgtggatgg    48120
ggggcacgtg ccctgcccac ggcctgcaca cctactgtat gtcccacaca caacaggatg    48180
cctgccccca cctcatgggg cccacagagg cctgtcccgg cccctcctcc tgtgaggcct    48240
ccaccgtaag gaagggcgga gcccaggcac agcctgcctg gaagggccct gcatccgact    48300
ggctgggagc ctgggaggcc ttatctccaa cagctccagg ccccattcct gaggctgggc    48360
tcacagagag gcccaggctg cctgccttcc tgggcagtgt ggggaggggc cctcctgctc    48420
cagggggcccc cagtcctcag ccctacaggc tggtgtcagc ccggcggcct gggctccctc    48480
cactgaggcc cctgccctct gccctctcca ccagccaggg cccagctga gcagcccacg    48540
tccctgcatc ccccacagct ggcaccaaag gccctgcgt ccccacagc tggcaccaaa    48600
ggcccctgcg tccccacag ctggcaccaa aggccctgc gtccccaca gctggcacca    48660
aaggcccctg cgtccccac agctggcacc aaaggcccct gcgaccccca cagctggcac    48720
caaaggcccc tgcgaccccc acagctggca ccaaaggcag tgtctgtggg gagcgatgcg    48780
tgccccagcc ctgtgagcgt gatgttctct ggcctctccc atgcaggtgg agcggagat    48840
cgcgatcctg aagctcattg agcaccccca cgtcctaaag ctgcacgacg tttatgaaaa    48900
caaaaaatat ttgtaggtat tgctgggtct gaagagctgg ggtggcggag gtggcagctg    48960
tcgctgcagg ggtgggtgtc tgggcttgg ggagcacagg ggctggaggc caggggcgcc    49020
tgctgcatcc cagcagccct ggccctgcta gcatgaacac ctgcctgggt agggtctcag    49080
cccaggctgc tgtggtctct gcttctggac caaaccggag acctggtctg tggaggctcg    49140
cagagccacc agcctgaggc tggcaagggg gaacaggacc ttctggaggg gagataggag    49200
tttcagggca aggggcagga gcacctggcc ctccccacat ggccacgctg agcctcctgg    49260
cctctgccca ggacgtcccc agccctgggc agtgagccat gtctctatcc ctgaggctcc    49320
ctcacacgag gcacagccac caggatcccg ccctggctgg accgtggctg agtgtggctg    49380
aaagtgtcac ctccgcagcc gctgaggcca gcagaaatcc ctaccctgtc ccaggcatgc    49440
ctggctgtga accccatccc cccagaccca gcctcaggga gctcctggga atgggcacag    49500
tggtcactca cggcagtctc ctctgtgtgc tctgatgggg cttctgaca gatgaggcgc    49560
tgctgcccaa gggctgtctg gccttgagcc tcatctgacc ctcgctggtc ccagggcggc    49620
ggcgtgacct gccaggtgat cctagccggg catctctgag gcatcaggct ctgagggagc    49680
agggaacata cagggctggg ctggggggctg ccctcagggt gagctggctg agggcctggc    49740
tgaacccagc agctccccctt cccccagcag caacgtccac gcttgctctg gcctgggttt    49800
ctgcattctc gtggggagca tgtgcaggtg gccagctcgt gtgtagctgg ggagaggaaa    49860
cccagggggtg gggtgtgggg agcccgcctg ccccaccatg agcagggggct cagaaactgt    49920
caccagaggc ctggggggggc gggggtggtc ctggccctga tgctggcaag gtggactgtg    49980
acaaggggca tggcttcctc atggtgacac ggtgccggtg cagtgggtc ctggggaggc    50040
cttctcggag gggagggcag gggagtgcgg gggggatggg cacagcagcc aaggcccaag    50100
aacaggaaag agcccaggag gtgggcatgg ccgggctcgc ggcttctccc gaggtctggc    50160
cctgggtgtt gtcccacccc ctctggacac catgtggcct atgctgagcc ttgggcctgg    50220
ccgcccccct gccagaatc ccaccctggc ccccaccacc ttccctgcc ctgagggctt    50280
cacaccttcc tctgccctga gggcttcaca ccttcccctg ccctgggggc ttcacaccct    50340
```

```
ccctgccct gagggcttca caccttcccc tgccctgggg gcttcatatc ttccctgcc   50400
ctggggcttt cacaccttcc cctgccctgg gggcttcacc acaacctctg ctcccatccc  50460
cacactgggc ccttgactcc tgccaaaacc agctcctggg acagccagtc atcccagtcc  50520
gcacggcagc tctgagcatg caccaaggtg ccacccctt ggctgtacag cccccctaca   50580
tcaccacagc cacaccaggg gccaccaccc tcacaggcct ccccccgag ctggttcagc   50640
ctgggtggag cggcccccaa gcagctgcat gcagcgtccc acgggcctct caccaggaac  50700
cagcccctca ggaccctcca tgtggctgag accccacggg ggtggtgctg ggagcccacc  50760
agggcaggaa ggggagggcc aggccaacct tttcctcacc cccttcccct ggccctcaca  50820
cctcctgttc cccccacaga ggcccagaca gtccctgggc ccctggatgc ggctgcgtgg  50880
tctccctgct cggtgcctgt gccactgagg accacagggt gtgagggcca gagcaggcag  50940
ggcagagtcc cgaggctacc ccatgcaccg agccttggcc ccagcacccg ccacactcag  51000
cctgtgggtt ccaaaccctc cctggcggct gtgcccccag aaccatccct tcacctgtcc  51060
ctccacccctc accccacccc acccaaccc aggctccttg aagactcatt tgaggtccac  51120
ccccaggagc ccagatggtt tgagatccac catagtcagg gctcctctca gctgcccccc  51180
cagccagcaa gaggatgggg gcggcctgca gagaggctgg gccaggaggc ggctgtggga  51240
ggccctggga tgaggagggg cggcgggcag ccacagctgg gcgcactggt ggccccgtct  51300
cctgcaggta cctggtgcta aacacgtgt caggtggtga gctcttcgac tacctggtga   51360
agaaggggag gctgacgcct aaggaggctc ggaagttctt ccggcagatc atctctgcgc  51420
tggacttctg ccacagccac tccatatggt gaggccccac ccctggtgcc ccccactccc  51480
cagggacccc cacacccagt gcgctaccac agatgccccc tgtgcccaa ggactacacc   51540
ccctatggtg ctattccgag gtacannnnn nnnnnnnnn nnnnnnnnnn nnnnnnnnnn   51600
nnnnnnnnn nnnnnnnnnn nnnnnnnnnn nnnnnnnnnn nnnnnnnnnn nnnnnnnnnn  51660
nnnnnnnnn nnnnnnnnnn nnnnnnnnnn nnnnnnnnnn nnnnnnnnnn nnnnnnnnnn  51720
nnnnnnnnn nnnnnnnnnn nnnnnnnnnn nnnnnnnnnn nnnnnnnnnn nnnnnnnnnn  51780
nnnnnnnnn nnnnnnnnnn nnnnnnnnnn nnnnnnnnnn nnnnnnnnnn nnnnnnnnnn  51840
nnnnnnnnn nnnnnnnnnn nnnnnnnnnn nnnnnnnnnn nnnnnnnnnn nnnnnnnnnn  51900
nnnnnnnnn nnnnnnnnnn nnnnnnnnnn nnnnnnnnnn nnnnnnnnnn nnnnnnnnnn  51960
nnnnnnnnn nnnnnnnnnn nnnnnnnnnn nnnnnnnnnn nnnnnnnnnn nnnnnnnnnn  52020
nnnnnnnnn nnnnnnnnnn nnnnnnnnnn nnnnnnnnnn nnnnnnnnnn nnnnnnnnnn  52080
nnnnnnnnn nnnnnnnnnn nnnnnnnnnn nnnnnnnnnn nnnnnnnnnn nnnnnncccc  52140
ccccattagg ctaccctca agtgcaccgt ccacccatt agctacccct caagtgcacc   52200
gtccccccat tagctacccc tcaagtgcac catcccctc attagctacc cctcaggtgc   52260
atcatcccct cctcattagc tgcccctcaa gtgcaccgtc ccccccatta gctacccctc   52320
aagtgcactg tccccccac cccattagct acctctcaag tgcaccatgt gcaccaggtg   52380
cttccctttt cccctgagg accccctgca cctccccttt cccagtgggg cagtgtgtcg  52440
ggaagttttc tgcctggcac ccacccaagc actctgggag cccctcggcc tttccagggg  52500
ccattgcttg catccctacg tgcctggggg ccctaggttg gtctaggcca gagcaggtgt  52560
gctagggagc aggaggggc aggaaggagc ctgccagggt gcaggagggc atggcaggag   52620
aaacagggat gcctgaccaa aggccagagc caaacggacc aggcaggcga cttctgattg  52680
gctgcctatg acatcaccag gctgggctgc tattggccct tatgtgtgat tggcgtttgg  52740
```

-continued

```
agaggcagtg ggctctgggc aggggtctc cagggcgggg aggcgctcaa ggcagagact    52800
ggccctgttc agcctcacca ccctcctccc cagccacagg gatctgaaac ctgaaaacct    52860
cctgctggac gagaagaaca acatccgcat cgcagacttt ggcatggcgt ccctgcaggt    52920
tggcgacagc ctgttggaga ccagctgtgg gtacgtggcc ctctgccctg agagaggct    52980
gggggacagg ctgggctggg ggaagaggag ccagtggact gagaggcccc cagcctgcct    53040
gagcctcccg gcaccccaca ggcaggcccc ccacaatgtg cctgagcctc ccagtacccc    53100
acagcctggt ggtggtgggg agacaggcct cccggcacag taagggtagg ggtacagccc    53160
tggccctggc ctgcctggga gagaggctgg gacccactta catgcccctc tcctggggac    53220
cccctggccc ctgcccagcc gagtgggcag acagctttgg gcgcagcaga gacccagtgc    53280
cccaccttga tctcctccca aaagcccgcc tggggatgca gggaatgtgg gggcgtctgg    53340
caccacagcc ctggaggcct ccttgagggc cctgcggtgc accatcaccc tggggggagg    53400
gcctggcagc gcccggagcc ccgccgctga cctctgccct tgcccgcagg tcccccact     53460
acgcctgccc cgaggtgatc cgggtgagtc agcgccgccg cgtgcagctc tgtgggcccc    53520
agggtggcgg ggacctgacc ctggtgggac cccagcctgc cgcaccccca ggtgctgcta    53580
ggctgcctgt ccccgggccg actccctctg agcccaggcc ctccaaggcc ccgcccctgc    53640
cctgcgcccc caacagccc gggcactgct gtccacaggg ggagaagtat gacggccgga    53700
aggcggacgt gtggagctgc ggcgtcatcc tgttcgcctt gctggtggtg agacctggc    53760
cccctcaacc ctgccctggc ctctcccaa acctgcccc ccacgctgac ccccacaccc    53820
ggccgcccgc aggggctct gcccttcgac gatgacaact tgcgacagct gctggagaag    53880
gtgaagcggg gcgtgttcca catgccgcac tttatcccgc ccgactgcca gagtctgcta    53940
cggggcatga tcgaggtgga cgccgcacgc cgcctcacgg tgcgtgccct cggagcgggg    54000
cggccccaga gcgtggcggg gggcgcgggg gcgggcgtgt gcctgtgtgt gcacaggtgt    54060
gtgcccagac gtgtgggcac ccaggtgtgt gggtcggtgc ccaggtgtgt ggacgtgtgc    54120
acaggtgtcg gcttgtgttc aggtgtgggt gaccaaatgt gggcccatgg ccgtgtgtgg    54180
gtgcccaggt gagtgttcaa gtgtgtgtgc gcacccaggt gtgggagtgc ccaggcgtgt    54240
gtgggctcgt gttcaggtgt gtgggtgcac aaatgtaggc acatgcccag gtgtgtgttc    54300
aagggtgtgg gggtacccag gcacatgccc aggttcatgt gattgggtga gggcgtaggt    54360
gtgggcatgt gcacgtgtgg ggaggtgtgt ccaggtgctt atgagcactt gtaccagtgt    54420
ggggtgtgca caggtgtggg gggctgtgtg cacatgtagg tgagacctgg ctataagtta    54480
cacaaaagca ctggtgcttc cccatcacgg ccatcctgcc tccagacgct gctggggcaa    54540
gctccaggca gcgtgaatag ttctgctgag tgccccagc agctgtgggg gctagcaaga    54600
gccaaaggta gccccagct gctggtcctg acctcctcca gggctgcctg gtgtggggac    54660
cgcacgtgtc cacttgacag aagcaggtca cactctgggc tgaccccttcc agggtagcgt    54720
tgacctgttc ccaagtggcc actgcctcac acccacgag ctgtccctga gtcagggtgg    54780
agagaagggg ccgtgtggct ggccggccct ccagcctcc tgcctgcacc tgcacccagc    54840
cctgccccgc cgcacaggtg ggccgggttc tcctggcttc agctccctcc tggctgctcc    54900
ctgctctcct gccttggttc cttcctagag ccacggaggg gcccagccca ggcagcacag    54960
gcacctgggg ctgccctggc tccagcttcc ctccctcccc ctctccctcc gctccccagg    55020
cccctgcccc tacctggagc accccctccg actccagctc ccccgacttc tctcctcctt    55080
```

-continued

```
gaggtgtgtg ttttcttctc cacttgggag aggcaggagc aggggtgctg gccttgagcc    55140
tctgggaacg cagcccctc cctatcttcc tccccaccctt ccccccactc acttgccctc    55200
accctctcct gctctctccg tgctcccagc gccctgcct tccccctcac ctcctaatgt    55260
gggctctttc cgtccctcgt ccgtactaac tccctgtttc tctttccttg tagctagagc    55320
acattcagaa acacatatgg tatatgtaag tagcttttcc acccactaat cgcctgcttt    55380
gcctgttgct gtggcctgga ggccctgcta ggaaaggcgg ggggagggcg ccggcccagc    55440
gcaggtcctg ccctgccttg gccctccgtg gcctgcgctg ggtgcggggt gcgggcagga    55500
cgcaggaggc ctccccgggc tgggcacagg gagagtggca ggatgaaggg ccccaggtga    55560
gggcgggcgt cccaccctcg cagccgccca ggcccggccg gagctgatga gcgggtggcc    55620
cgtcctgtgt ccacagaggg ggcaagaatg agcccgaacc agagcagccc attcctcgca    55680
aggtgcagat ccgctcgctg cccagcctgg aggacatcga ccccgacgtg ctggacagca    55740
tgcactcact gggctgcttc cgagaccgca acaagctgct gcaggacctg ctgtccgagg    55800
agtgcgtctg gggctgctcc cgggtggggc acggggcctg aggtgggagc gctgccccgg    55860
aggagccggc ggccccgtgt gccagcgcgt ctcgcgcctc tcgcccgctg tagggagaac    55920
caggagaaga tgatttactt cctcctcctg gaccggaaag aaaggtaccc gagccaggag    55980
gatgaggacc tgcccccccg gaacgagata ggtatgggtc caggggtggc ctccagcccg    56040
gcctgcactg ccccaccggg gtccggggc tgtctggcct gaccttcgtc tgtactcaga    56100
ccctccccgg aagcgtgtgg actccccgat gctgaaccgg cacggcaagc ggcggccaga    56160
acgcaaatcc atggaggtgc tcagcgtgac ggacggcggc tccccggtgc ctgcgcggcg    56220
ggccattgag atgcccagc acggccgag gtgtgtgtgc cccgaggctg ctgggcctcc    56280
ctccctgggc cctggctgcg cggcactgcc gcctggctca tcgctaccca ttggcctggg    56340
gtctcggctg aggccattgg gtggggctgt atgggctaaa ctgggcttag ctgggcttgg    56400
ctgggctggg ctgggcttag ctgggctggg ctgggctggg agctgagctg ggctgggctg    56460
tgctggactg gactgggcta ggctgagctg ggctggcctg ggctgggctg ggctggtttg    56520
ggctgggcta gactgcactt ggttgagccg agctgggctg tactggactg cgcggctgag    56580
cagggttgag ttgaattagg gtgggcgggg ctgggctgag ctgggctgag ctgggctagg    56640
ctgcactaga atgggctgag acggatttga ctgggctgag ctgggcaggg ctgggctgag    56700
ctgggcaggg ctgggctggg ctaaactgga tttggctgag ccgagccagg ctgggcaggg    56760
ctgagctggg ctggctggc ttgacccaag cttggctggg ctgagctgtg atatggtcac    56820
accatgctca gagccatcag cccagcaagc ctgtcccct ggtccagca atgctgggcc    56880 cgtctctggg tggcaagtgt ggtgtgtgtg gccaggaca tcacagaact cagcagtgat    56940
gagcagacct gtggccggag gaagggcacc cagcccctct ggagcctctg ctgggtgggg    57000
gcagggctgg gctgcccgca cgaggccctc agcaaatcct tggagccggt gcggcctctt    57060
ggggatgagc tcaaacgtcc ctcaccaggt ggcagcttcc aacacttggg gacagcccctt    57120 gcgccagaga gcacaccagg aggtccagga gcccgggcag cagtctctgg tctgccctgt    57180
gatctgggcc tcagcacccc agggccccct ccttgtactg gagatgtggg gggtgggaca    57240
ggcgtggcct gttcctcggg aacttggggg aagctgtggg gaactgcaag gtagcttggc    57300
agccatcagg ctaaacctgt tccagcccca gccctggcca gagtactggt ggtcccagtt    57360
ctggcagctc ccaggccatg gcccctggg agtcctaggc cctccccagg gtttcaggct    57420
ggcccagctt ccaacgtggg gtcccagccc ccagaacctc cttcccaggg cccagtcagc    57480
```

-continued

```
gcagccctga cgccagtact aggggggtagc aagggggccct cctatctaca ttctactgtc    57540
ctgaccttca gtggcctgca tgtcatgggg gcaccacaac ctgtagccca ggtgcctgcc    57600
tcctgcctgc gtggccacct ccccggactc cccgaccctg cagggcaggc cccaccaccc    57660
cactgcctgg cccctccggt cagcggcgtg ggaggccgcc ctcttggcct ctgctgcaac    57720
tcccaggcct ggctgcctgg ggcaggtgtg ggatgggcca ggccatggac cattccgggg    57780
cctctggaag gccactagtc ctggcatgtc ccagccagat tccactcctg gtggggccac    57840
ctgtgcagcc agcagagacc cagctgcttg gtgttgggcc acacagggct gctgactggg    57900
gacgcagggg tcctgggggc tggggtgggg gctaccaggc caccctgccc agcagtcaca    57960
cggtgcgggg tgtgctgtct ggcccagcct cctctctcgc catctttgtg cagcggcctc    58020
agagccacgt ggagttctta cccggtgtgg cccgggccct gggggccgac ctgtgcccgc    58080
gtgtggccgt cagtaactgt gttttctcgc tctgttctgc tgtagtaaag caatgttcag    58140
taaaagcctg gatatcgctg aggcccatcc ccaattcagc aaagaagaca ggtatacacc    58200
ccgaccaccc gtccccgcac ctcccagccc cagacacgct gtcctgcctc aggccgggca    58260
ggcacatggg cgggtctggt ggcgggctgg gctgcagggc tcctgctgcg gtgaagccag    58320
ccagcaagcc aggcaagggc ccgcgggcca ggcagaggcc gaggaggggt ggggctgctg    58380
aggcgtggcc cacgcctgcc tgtgagggac cacgcaccat ggcttacagg gcctgggggct   58440
agagcccggc gtggctgcag gccgagccgc tcctcctgcc agccctgtg ctgtgtccgg    58500
tgggcctcgg tggccctgct gccctgggg ccggccagag ttgaagccga gcagccgtcc    58560
tgtgcccacc tgcaggagct gaggagggca ggaggcgccg ccgtcaagag gggcctctac    58620
ctggggccag ttttgcgagc ctgggcgggt ggcgccgccc ccaaggctgc agtgtgctgg    58680
ctgccggtcg gggtccttct ctttgagccc tggccccgtg cctacctggg accctcacct    58740
gtgtgccctc actctgcctg ccctggctgc cctcagggct ggcgccgtct ctcctgcccc    58800
tgccccagca actgtagctc agtgttccca gcagctgcct ggccggatag gaccagggct    58860
cggcccctcc accccgggt tccagcgcc tcttctgtct tcctcgtgcc cagtcacgag     58920
ctctgggcgg gctcgacagg aaccacaggt ccagggcctc actggtggct gctgccccca    58980
tgagggctgt ccgcgctccc agctcagccc tgaaagctct gggtccagtt ccagccctgg    59040
gtgtcatcct ggcccagaca ggctgggttg tgcatggggt cccgtcgcc tccctgcccc     59100
ttggctgtgt ctggtgaggg agttggaggg tcgtcaccgt ggggaccagc ccccgggtgt    59160
ccgggagcca ggtgtgtggc cagcgtggca ctctccacgg tccggggcct gggccgtggt    59220
gtggactagc gaggcccctc gtggccggct ggcggtgggc aggcctggtg ggcagtgcag    59280
gccgggcttt tactcttctc tgtcctcttc tcttcggcgg ctgcctcggc cctccctgc    59340
atttccttcc tccaaggatg gcagctgcca ctgtctgggc acgtgggcgc cggctcgtcc    59400
gtgcagtgtg gtggaacgac gcacagccgt cctggtccct gcacgggggt ggcggccaca    59460
caccggagtc tcagccgggc acgccgggcc agggcctccc tcctgctgtg tgcaggtctc    59520
aggctgagta gggcagtggt gggacaaggc cccaccgtcc ctgccagcag ctgccccagc    59580
ctggcccctgc ccaggccctc ctggttgtgg acaagggaag ggccggccgc tgacccaggc    59640
atccctcacg ggcatctagg gacatggagg accaggctgc aggccctgtg agagctcagc    59700
cagggggggc ttggcaggtg ggaggctgga gccagcacga ggcctggagc agaaggggct    59760
gcatacagga agctcccgtc tgtcccctcg tccttccgtc caccccacg ctggatggtc     59820
```

```
ctttgccgcg gctgtctgat gccgtatcct gtgctgtgcc tgggctgctg gcatggggtg   59880
gcccccacac gtgggctctg atgggggccc cagtggggct gggcacagcc aggcgccctg   59940
ggccctcctg aattgacagg gtgtgcagca ggacccaggg cctcgaggct cttggcccgg   60000
gctccaggcc tcctggaggg tttacctggg gggagcagag cccagcacct gctgctccac   60060
tgcccctgg ctgagcagtg gccctgtacc ttgtgacctc caggtctcgg tccatcagcg    60120
gtgcctcctc aggcctttcc accagcccac tcagcagccc ccgggtgagt gaccccccgc   60180
ccccacccag ctcggatgca cagaggcccc aaccctccca gtcagcgtgt gccagggtgg   60240
gggcagcctc gtggaccctg ggaagcagcc caggcgcccc ccatgccca cgctcctgtg     60300
gcggctgctg ctctgtggcg caggctgctc tgctaactgc acgctctttt gttttgtttt   60360
gtttgttttc ttgtgtgtca cttgtttct tttgtggcta atcctcctgc ccatgcctgc    60420
ctgcctcccc accctcccgc tcccgcctgt ttctttctgg tcctcctgtg ccgtgtgcat   60480
gcggggact ggggtgcatg tgccgcgcgg ctgcccccac cccgctcgct ccctgcgcct    60540
ccccgtagcc tattaggaag cttgtcctgc ccccaccgcc cccgagccg cccttcgtgg     60600
cccgcccct ggccacctcc acggagcccg aagcttgtgg gagcgcctcg aggcctggac    60660
acgtcctccc tctgcaggcc gccctgcggc ccgaccccaa gacccagacc ttgccgtgca   60720
aggccaagct gaccgacaag cctctgcagg gcaccaagtc caacccctc ccggccagca    60780
ccccagcccg gcctcccgcc actggccttt gtccccagct ggcaccaccc ctgggcccgc   60840
ctgcctgcg ggtgccccc cggccccac ccgccgggat tgaaccaaac accaaatctg      60900
tccccaccat acaggtgacc cctcacccct caccaagggg cagtcccctc cccaccccca   60960
aggggacacc tgtccacacg ccaaaggaga gcccggctgg cacgcccaac cccacgcccc   61020
cgtccagccc cagcgtcgga ggggtgccct ggagggcgcg gctcaactcc atcaagaaca   61080
gctttctggg ctcaccccgc ttccaccgcc ggaaactgca aggtgagtgt ctgcccggag   61140
gcgccagagt ggggctggga gagagcagag gctgccttgg ggagggcccc gcccggcagt   61200
gccagaccag tccgaggggc ctgtagctgc aggggtggcc tgggcctgcc cacgtctcac   61260
tgtcccgaaa gcgcccagca gcagcctgtg tcctacctgt cgcacaggct ggtatcccct   61320
ccagacattc tgtgttcctg agtctaccca ctctgtgtcc tggggccagg cacacagcaa   61380
ggagagctgg ccaccgaggg ggcactgcca gtcaggaggc cccatgtgtg gggcaccaag   61440
ggccagccag tgctgctgga gaaggcacag ccgacttcag caccagaggc ggggacagct   61500
cccttagcc tggggggcgc cactgccagt gggcctctaa ggtggccggg agctggggtg    61560
gaccagtgcc cctgggggc tgtcccagtg tgtgtgggtg gactcctgat gaccctgacc    61620
tcggcgcaag gtgccaggg caggggaagg atggagcggt caccacgcct ttcctcctgt    61680
tcatcctgtg tgcacagttc cgacgccgga ggagatgtcc aacctgacac cagagtcgtc   61740
cccagagtaa gtgccccctg ctggaggcct cctggtacct gacaccaggc tggccggag    61800
agggcatgg aaccccttccc ctatggccaa cggggtgctc cttctccacg tggccccacc   61860
tcccactgca ggcaggcccg tctcggccac tgagtctctg aagttcgaat tcccggctgt   61920
gagggaagg ccagccaggg gaggagcccc cagccctgtt gagaagcttc aggccttggg    61980
agagcctagg gttggctgga ggcgagcagg ggtacactg gcagagtct ccccaggcc      62040
tgagctcgcc aagggcagag accgggtcgc tcaggtctca aggagaaagc agcccgtgtt   62100
aagaacaaag gggcagcagg cctggtggga acacgtgtgc aggggcggag cggagcagcc   62160
aagccgaggt ctgcccccgc cgcctttctg agccgtgaga ggtgccactg cagagactct   62220
```

-continued

```
acagcgccca ggtgctgaga tgccctgggg gccgctgtga ctggtgtctg gacaaagatg    62280
tccccagaga gacccttcc cagcgcccag gccctctccc tcctctccac gatggcctca    62340
gtcactgggc agtgtctcgg agaccaggcg actggcggtg tacacatatg agcctgcagc    62400 gtgacccag gccaggcagc ggcagagagc ggcggtcagg ctggagtcac ttcacaggag    62460
accccgggaa atgaagatgt ggccagctgt ggactgagta agacgagaac cttcgtcctg    62520
ctgctggctt taaaccaggg gcccctgtgg aaactgctca gtgctaagcc ccaggagcag    62580
catctgcagc ctgtgccagg attccaccca gtggcctttc tgcgccgatc aggtggccct    62640
tccagctggg tgcccaggtc ggaggtgtgt aggtattgtc gcaagcccag atgcacaggg    62700
ctcagcagac ttgggaacct tccgcctagg ccctgacatt gccgtttctg ctgctaccaa    62760
aagctttcat gaacagactc ataattatct tcctcagaga aggtggaaaa catcaaagcc    62820
gagaaggtgg ctttgatgcc actgtggctg cctgcgcttc tcccctcccc catcttgaga    62880
tggcctggag gccctgaccc ctctcaaggg tccggcacgg atgcctccca cagccccacc    62940
caagggcccg gcacagacac ccttcccaa gggtccagca cagatgcctc ctacagctcc    63000
acccaagggc ccggcacaga tgcctgcgac agccgttccc gagggtccag cacagacacc    63060
tcccacagcc ccacccaagg gcccggcaca gatgcctgtg acagcccta ttgagggtcc    63120 tgcacagacg ccttggacga gggtccagca cggatgcctc ccacagtccc tctttggcga    63180
caactcgctt gctggggacc tgagataacc cccagcccca gctgctgcca gccccatgtc    63240
aaccaggcac cccagaggaa cagcaccaag ggaggcagct ggcttcagga agggatgcat    63300
gcggttgtct gggacactca gggctgatgt ccttgagtct gaagtgctag ctggaagccc    63360
aggcagtttc caggttgcag cctcgagggg cgttctttcc ccaggaagac cgaacctggc    63420
ggatgcaccc accctgtgag gaagggtccc ccgccagact caacaggcga ctgatttaag    63480
ttcgtctcat ctaaaaatag cttcatagca acacccagac tagtgtccgg ccaggctgtg    63540
cactgcccac cacgtgggtg ctggagtcac agtgcaggcc cctcacccct cgtcggcctg    63600
gcctccctgg gccgtcaggc atctttcaca catgggacta tttttgccaa atgctgcacc    63660
cctgggccgc aaagcagaga gtcacgtttg taccatctgt cctgtctctt catcgggcag    63720
aacatcgacc atgtagaaac tcacctgtgc ttccagaact gccaggctgc tttgtgcact    63780
tcctggctcc aggccctggc atggggctgg ggtaaggtca gggccagtgg tggccctcgg    63840
agttttgaac ccagaacaga cagccgccga gaccggcagg acactgagga ggcgtcgagg    63900
ggctgagtga gggttggacc tggtccccgt gcttgtccgg caggactccc aggccgcaca    63960
gtggccgagg aggcagctcc aggaatgggc aagggaaagg ggagttgtga ggccgctggg    64020 agggcctca gaatcagtcg ggagagggca ccactgagcc ccagccctgc tggcccctcc    64080
tcccggtccc tgcctctgcc tctcagcaca cctggttcca cctccaggca gcaacggcag    64140
gggacgccag cagagcgtgc cacctctgaa cagccaccca ggcgcgctct gcctgagtct    64200
cgggctgtgc tagaggcgcc tctggccatg gtcctctcac ggctgggctt cctggccccc    64260
gcgctggtgg gtggggttcg ggtgctcttg agctggagag cagagggcct ctgcatgttg    64320
gggtgagcct gccagcaaga caggagtagc cttctgtggc ctcagaagcg cctccccact    64380
ctcctgttgg aagcgagttg caggcccgc ctgctcctgg gggtggggg cacagctgac    64440 ttcaggagcc cagcttgagc cacctctcac agcggccttg gtgagggggg gctcacctgt    64500
ggggggctca cctgtggggg gctcacctgt ggaggggcat ccccagactt gggagtgggt    64560
```

```
ggcatatggg ccagggtcag ggcgttaggg cttggagaaa ggttagggtt ggggttgggg   64620
ttagagccac ggtgatggtc agggcatatg ggctagggtt agggcgttgg ggtcagggcc   64680
atgggttctg gctagcactg tggagacagc cgtttctatc acgaagcgat ggaagattcc   64740
gccgttccaa ccccagattc gagggaggca ggggtgtgga cggtgccaca cctcaatcct   64800
cacagcctct gtctcccact gcccaggctg gcgaagaagt cctggtttgg gaacttcatc   64860
agcctggaga aggaggagca gatcttcgtg gtcatcaaag acaaacctct gagctccatc   64920
aaggctgaca tcgtgcacgc cttcctgtcg gtgaggccac agggcgctgg gggaggcggg   64980
cagccctccc aaccccacac ggcccagccc cgagaatcca gcctcctcac gtagacagga   65040
catgtccacg cgcacagcac ggacgtccgc tcacccgtgg gcctgcctgg ccgccttcac   65100
tggacaggcg ctctctcctg cccaccctcg tgagggaggg gtcactgccc atctgggtg    65160 cttggcctgc ggagggagtc agggctttgc tcactggtcc ccagcagccc taggtgtgtg   65220
ccggacaggc ctgggcagct ggcacgtggg gcagaaggaa ggctccagct gggtgggtct   65280
cagaggggga catttccatc agactcgggg agaagccctt gtgaggccat ggccctaggg   65340
accggtgggg ctctgctggc cctcagtgga cagccccagc cctcaggtgt ctcagtttcc   65400
ctggtctcac cctgccctcg gaggccgggt ggctctccac agagtggtcg cgctcgggt   65460 cttgggtggg cttcatttgt cttgctggg catctttggg ttaggaggag cagaaaggcc   65520
ctaaaagcct caaatggaga aagtttattg ccaggactcc agcacccagt cccatcagga   65580
cgccccttcc ttgccggccc tgccccaccc tgtgctgcac ccagcgccca ggcatcacag   65640
gggctgcccc ccacccgcct cccccaccgc cccagcctg cctccccagg gctgctgtcc    65700
tgccctgtgc tcaccactgc ccgggcgccc tccctggccc cagggtcttg gcaagatcag   65760
gccgtggttc gcttcggcag cctctctagc tagggactgg ccccacccc accatatgct    65820 ctgcccccgg gcactcaggc cactgctgcc ctggctgcag ctgagcttcc cttacgctgt   65880
ggggacagct tggagcccct gcagaaggct ccagggccag gagagcccag cgctgggcag   65940
ggcaggcctc agactgcact tggaccctgg cctcagggt cctcagcgtc cccgtccccg     66000
tccccacagg ctgctcactt cctcggcctc ctccctcacc acatcccttc atgctgcccc   66060
tggttgccac ggctaacctc agactcagcc cctccccatg ccggcccag tgaggcggct    66120 gtgtgccagc ctgggccctg tgcgctgggt ggccctgagt tctgcttcct gcagctgccc   66180
cctcggtact gtgaagccca cccagccagt gcccagcacc ataggtcccg caaccagtgg   66240
gagtcccagg aagcccagc aggagggcac agccccagcc ccgcccttgc acctccctct    66300
cagtggcagc tcccagaccc cccacctccc actcagctcc accctggacc cccacctcag   66360
gctgcagggg tcaccttcca cctccatctt tgcccttaag gctcctctgt aaggtcctgg   66420
tcatcctgtg ctgtggctgc ctgagaaaag cccggcaggg gcttagctgt gcccgctaag   66480
tggaccaaag ctttggaggg tgggggctgg aaacgcccct cccctgctc cagccgtctc    66540 caaccgcact gtgcccctca cggaagcaga ggtgcctggg tgctcacaat gtgtgcacgg   66600
tggggctggc tcgcccagg gctgcctccc cagagggcca gggtgggacc tgccaggcca    66660
gccacgctca cgctgctctc tctccacaga ttcccagtct cagccacagc gtcatctccc   66720
aaacgagctt ccgggccgag tacaaggcca cgggggggcc agccgtgttc cagaagccgg   66780
tcaagttcca ggttgatatc acctacacgg agggtgggga ggcgcagaag gagaacggca   66840
tctactccgt caccttcacc ctgctctcag gtgagctggc gccccagggg cggctccggg   66900
cccaggcccg tccagggcat aaccccctgt ctccctagg ccccagccgt cgcttcaaga    66960
```

-continued

```
gggtggtgga gaccatccag gcccagctgc tgagcacaca cgacccgcct gcggcccagc    67020
acttgtcagg tgaggcgggc tcagctccgg ccaacctgcg gcctgcgagt ggggcgtggc    67080
cagctggtgc tgcgcggacg ggaggcgtga ggacccgggc gcagcctcct ggcccctctt    67140
gacggacgcc cccacctccc tgccccgagc tgtggctgca cccctcaggg agcagagccc    67200
ctccctggcc tggcgggacc acccgcctcg cctctgcacg ccagggacat agggcgcagc    67260
cgcaccacac tgaaaggcgc ctcttgtcca ccgtagaacc ccccccacca gcgccaggac    67320
taagctgggg tgctgggctt aagggccaga aggtggccac cagctacgag agtagcctct    67380
gacgctggca ggtaaggcgc ccggcctgtg ctggggcggg gaggggctgc gggcaggtcc    67440
tcggcggagc caggctggcc ctgagcaggg ccctccatgc ccacccacag gtctcggccc    67500
tggacaggcc aagcatgccc cgggcggccc atctgctagg gcagcctgca caggacctgg    67560
gagagcagtg acaaggccct gccctcggga ctccccgcca tggcaccta ggagggccgc    67620 gggctgcctg acgggctgtg acttctcatc tctccatact tcctgacagc ccagggccat    67680
gcctccagca gggcagaggg gcttgagccc agccagagcg ggggcttcac cacagcctga    67740
tgggctcaca caggggaggg ttgccccagc ctggaaccac cagggtctag gacccgaggg    67800
tccgtgccac tcggcatacg gcagggaggg ctccccccac tcccctgggc ccatgtgtgg    67860 tggggggcagg gcggagcact gggcacatgc atgggcctgg tctgtcagca aggggggtgtg   67920 ggtgtgcctc tgaacgctgg tacggcgtgg gggcgctggg cgtcgtgggg gagcacccgg    67980
ctggaccctg ggggtcccct ctcccagcct gcatctcagc agctccgtgg catgctaggg    68040
tcacctcctg tgtttccatg tggggtcctg gaagccaaag agggcccac tgcccctccc    68100 catgacatcc tcattccatc atcatgccat cacctgtggg agccccccca gagtgtgctt    68160
caccttgctg cgggctgggg gctgaggtcc ccaacagccc tggccctaac cgaagcccca    68220
gtgggtggag gagtagcccc cttctcctga ttttgggagc caggctggca cagcgggtaa    68280
ggaggagcag ggttccaggt gctcggcccc gcaggtacac gtggcgcttc cctacagcgg    68340
aggccatgcc gtcggccggc agcagcctct ggctctctga gccttgaaag ccttcatctt    68400
aggaagggaa accgaggcca gggaacgaca gggcagccac ctaggccagg gatggacagg    68460
gcttgtctgg tagggcaagc agaaacgggc cccggggtac tgcccagggt gtccccgcac    68520
ctgagcagcc atctgggtgc ctcagtcgag cgctcctgcg tgggctgtag gcaaagctcc    68580
cccagcctgg cccctttaaag tgtggtaccg cctgtcagca cgcagcactc ccctggagcc    68640
aactccaagc ccctctccat tcctgccccg gaccctgacc tcagtggagc ccactgcaga    68700
ggctcttggg ggtctattct gggccccatc tatctccctg tggacttggg gagcccagcc    68760
tatccccgtg atctcgctac gcccagccct tcccagccct gcccccctcc cacactggat    68820
gcttttgtcc agtgagccca gctccaagga tgtgtgaag gtggctagcc agcaggggc    68880 ctcctcagac actgcccacc cccccagaga ctgcggccga gggaggggag gctgagagcc    68940
cccagtgagc aggcacaggc agaccagggc gtgtgtccac cctgtgcagg cgccagtgag    69000
ggccttgagg gagtagcccc tcccagggcc ttgctcccac cccagtcctg gactggcagc    69060
accaacatcc ccaggcccag cagtagggaa gagggccgag gaagagggtg cctgccttga    69120
gttgaagggc agccagaagc cacagggccc tggagctgct gagtggcaca gtgaggatgc    69180
aggccacggc cagggcagag ttgtcagccc aggggagggg ctaggcccac ccagggcacc    69240
ggccatatcc aggctcaggc tcaggctgct ggaggtccgg ctgctgccca ggtggctccg    69300
```

-continued

| | |
|---|---|
| ccttgttccc tgcctccgca gccccgcctc actccaggcc ctgcccctgc actgccccct | 69360 |
| ataagccccg cccctctgg ctctggcccc ccagtattc cccacccatg cctctggggc | 69420 |
| cctacccact cctggctcca cccctcccc atcgaggctg tgggcgtcca gccagaaggc | 69480 |
| ccaggacagc ctttcactca ctccctccct cctctctcca ttctgtactc cagacaccac | 69540 |
| taactgtatg gaaatgatga cggggcggct ttccaaatgt ggtaagaatc ccccacgctc | 69600 |
| acctggcacc tccacctgcc acttcaccgc tcaccctcag cccgctgtgg ccgccacctg | 69660 |
| ccgcccgggt tgtcccggcc tccctgtgta gatgtaggca cccagcagcc cagatgtccc | 69720 |
| cggcccatc tctaccagg agcagcccc gtcgctcccc taccacagca agcccaggcg | 69780 |
| gggttcctgg ccagactcac ctctgccagg ccctaggatc agggcaggcc caagaagggg | 69840 |
| ctcccaaggc ctgaagccag tgaggtccc gctggtccca ctggtgcagg ctgtggccta | 69900 |
| ggggagggc cggtgcccat ccctctgtcc actggaggct gtgcctggca gggagcggag | 69960 |
| gggcccacag ctcagggctc aggtgggggt taggcttagg aagtgggatt gaggggcctc | 70020 |
| catcgacaca cctgggcagt gagcacaggg cccaagaag gtgggctcc ccatttccgc | 70080 |
| ccctcttctc aggactgccc ccatcccagg gacccgggac atgactctag ctgcttgccc | 70140 |
| ccagccccc agcctgcctc ccacatccac ccctccatgc ttgtccaccc atctgttcat | 70200 |
| ctgtctgtct gctgctaaac tgtgtccaag ctggccaggg gtcgggcttc aggcctctct | 70260 |
| ggggaggtgt ggtgggcaca ccctctccct gtcatccact gggcctcatg cagtggggcc | 70320 |
| agcagctgcc cccagggtcc tgcgaggctt cagagctccc agcaggccct tgtctttacg | 70380 |
| ctg | 70383 |

```
<210> SEQ ID NO 4
<211> LENGTH: 1911
<212> TYPE: DNA
<213> ORGANISM: Homo sapiens

<400> SEQUENCE: 4
```

| | |
|---|---|
| atgaaggtgg agcgggagat cgcgatcctg aagctcattg agcaccccca cgtcctaaag | 60 |
| ctgcacgacg tttatgaaaa caaaaaatat ttgtacctgg tgctagaaca cgtgtcaggt | 120 |
| ggtgagctct tcgactacct ggtgaagaag gggaggctga cgcctaagga ggctcggaag | 180 |
| ttcttccggc agatcatctc tgcgctggac ttctgccaca gccactccat atgccacagg | 240 |
| gatctgaaac tgaaaacct cctgctggac gagaagaaca catccgcat cgcagacttt | 300 |
| ggcatggcgt ccctgcaggt tggcgacagc ctgttggaga ccagctgtgg gtcccccac | 360 |
| tacgcctgcc ccgaggtgat ccgggggag aagtatgacg gccggaaggc ggacgtgtgg | 420 |
| agctgcggcg tcatcctgtt cgccttgctg gtggggctc tgcccttcga cgatgacaac | 480 |
| ttgcgacagc tgctggagaa ggtgaagcgg ggcgtgttcc acatgccgca ctttatcccg | 540 |
| cccgactgcc agagtctgct acggggcatg atcgaggtgg acgccgcacg ccgcctcacg | 600 |
| ctagagcaca ttcagaaaca catatggtat ataggggca agaatgagcc cgaaccagag | 660 |
| cagcccattc ctcgcaaggt gcagatccgc tcgctgccca gctggagga catcgacccc | 720 |
| gacgtgctgg acagcatgca ctcactgggc tgcttccgag accgcaacaa gctgctgcag | 780 |
| gacctgctgt ccgaggagga gaaccaggag aagatgattt acttcctcct cctgaccgg | 840 |
| aaagaaaggt acccgagcca ggaggatgag gacctgcccc ccggaacga gatagaccct | 900 |
| cccccggaagc gtgtggactc cccgatgctg aaccggcacg gcaagcggcg gccagaacgc | 960 |
| aaatccatgg aggtgctcag cgtgacggac ggcggctccc cggtgcctgc gcggcgggcc | 1020 |

-continued

```
attgagatgg cccagcacgg ccagagtaaa gcaatgttca gtaaaagcct ggatatcgct   1080
gaggcccatc cccaattcag caaagaagac aggtctcggt ccatcagcgg tgcctcctca   1140
ggcctttcca ccagcccact cagcagcccc cgggtgaccc ctcacccctc accaaggggc   1200
agtcccctcc ccaccccaa ggggacacct gtccacacgc caaggagag cccggctggc    1260 acgcccaacc ccacgcccc gtccagcccc agcgtcggag gggtgccctg gagggcgcgg   1320
ctcaactcca tcaagaacag ctttctgggc tcaccccgct ccaccgccg gaaactgcaa    1380 gttccgacgc cggaggagat gtccaacctg acaccagagt cgtccccaga gctggcgaag   1440
aagtcctggt ttgggaactt catcagcctg gagaaggagg agcagatctt cgtggtcatc   1500
aaagacaaac tctctgagctc catcaaggct gacatcgtgc acgccttcct gtcgattccc   1560
agtctcagcc acagcgtcat ctcccaaacg agcttccggg ccgagtacaa ggccacgggg   1620
gggccagccg tgttccagaa gccggtcaag ttccaggttg atatcaccta cacggagggt   1680
ggggaggcgc agaaggagaa cggcatctac tccgtcacct tcaccctgct ctcaggcccc   1740
agccgtcgct tcaagagggt ggtggagacc atccaggccc agctgctgag cacacacgac   1800
ccgcctgcgg cccagcactt gtcagaaccc cccccaccag cgccaggact aagctggggt   1860
gctgggctta agggccagaa ggtggccacc agctacgaga gtagcctctg a           1911
```

```
<210> SEQ ID NO 5
<211> LENGTH: 636
<212> TYPE: PRT
<213> ORGANISM: Homo sapiens

<400> SEQUENCE: 5
```

```
Met Lys Val Glu Arg Glu Ile Ala Ile Leu Lys Leu Ile Glu His Pro
  1               5                  10                  15

His Val Leu Lys Leu His Asp Val Tyr Glu Asn Lys Lys Tyr Leu Tyr
             20                  25                  30

Leu Val Leu Glu His Val Ser Gly Gly Glu Leu Phe Asp Tyr Leu Val
         35                  40                  45

Lys Lys Gly Arg Leu Thr Pro Lys Glu Ala Arg Lys Phe Phe Arg Gln
     50                  55                  60

Ile Ile Ser Ala Leu Asp Phe Cys His Ser His Ser Ile Cys His Arg
 65                  70                  75                  80

Asp Leu Lys Pro Glu Asn Leu Leu Leu Asp Glu Lys Asn Asn Ile Arg
                 85                  90                  95

Ile Ala Asp Phe Gly Met Ala Ser Leu Gln Val Gly Asp Ser Leu Leu
            100                 105                 110

Glu Thr Ser Cys Gly Ser Pro His Tyr Ala Cys Pro Glu Val Ile Arg
        115                 120                 125

Gly Glu Lys Tyr Asp Gly Arg Lys Ala Asp Val Trp Ser Cys Gly Val
    130                 135                 140

Ile Leu Phe Ala Leu Leu Val Gly Ala Leu Pro Phe Asp Asp Asp Asn
145                 150                 155                 160

Leu Arg Gln Leu Leu Glu Lys Val Lys Arg Gly Val Phe His Met Pro
                165                 170                 175

His Phe Ile Pro Pro Asp Cys Gln Ser Leu Leu Arg Gly Met Ile Glu
            180                 185                 190

Val Asp Ala Ala Arg Arg Leu Thr Leu Glu His Ile Gln Lys His Ile
        195                 200                 205

Trp Tyr Ile Gly Gly Lys Asn Glu Pro Glu Pro Glu Gln Pro Ile Pro
```

```
            210                 215                 220
Arg Lys Val Gln Ile Arg Ser Leu Pro Ser Leu Glu Asp Ile Asp Pro
225                 230                 235                 240

Asp Val Leu Asp Ser Met His Ser Leu Gly Cys Phe Arg Asp Arg Asn
                245                 250                 255

Lys Leu Leu Gln Asp Leu Leu Ser Glu Glu Asn Gln Glu Lys Met
            260                 265                 270

Ile Tyr Phe Leu Leu Leu Asp Arg Lys Glu Arg Tyr Pro Ser Gln Glu
            275                 280                 285

Asp Glu Asp Leu Pro Pro Arg Asn Glu Ile Asp Pro Pro Arg Lys Arg
290                 295                 300

Val Asp Ser Pro Met Leu Asn Arg His Gly Lys Arg Pro Glu Arg
305                 310                 315                 320

Lys Ser Met Glu Val Leu Ser Val Thr Asp Gly Ser Pro Val Pro
                325                 330                 335

Ala Arg Arg Ala Ile Glu Met Ala Gln His Gly Gln Ser Lys Ala Met
            340                 345                 350

Phe Ser Lys Ser Leu Asp Ile Ala Glu Ala His Pro Gln Phe Ser Lys
            355                 360                 365

Glu Asp Arg Ser Arg Ser Ile Ser Gly Ala Ser Ser Gly Leu Ser Thr
370                 375                 380

Ser Pro Leu Ser Ser Pro Arg Val Thr Pro His Pro Ser Pro Arg Gly
385                 390                 395                 400

Ser Pro Leu Pro Thr Pro Lys Gly Thr Pro Val His Thr Pro Lys Glu
                405                 410                 415

Ser Pro Ala Gly Thr Pro Asn Pro Thr Pro Pro Ser Ser Pro Ser Val
            420                 425                 430

Gly Gly Val Pro Trp Arg Ala Arg Leu Asn Ser Ile Lys Asn Ser Phe
            435                 440                 445

Leu Gly Ser Pro Arg Phe His Arg Arg Lys Leu Gln Val Pro Thr Pro
450                 455                 460

Glu Glu Met Ser Asn Leu Thr Pro Glu Ser Ser Pro Glu Leu Ala Lys
465                 470                 475                 480

Lys Ser Trp Phe Gly Asn Phe Ile Ser Leu Glu Lys Glu Glu Gln Ile
            485                 490                 495

Phe Val Val Ile Lys Asp Lys Pro Leu Ser Ser Ile Lys Ala Asp Ile
            500                 505                 510

Val His Ala Phe Leu Ser Ile Pro Ser Leu Ser His Ser Val Ile Ser
            515                 520                 525

Gln Thr Ser Phe Arg Ala Glu Tyr Lys Ala Thr Gly Gly Pro Ala Val
530                 535                 540

Phe Gln Lys Pro Val Lys Phe Gln Val Asp Ile Thr Tyr Thr Glu Gly
545                 550                 555                 560

Gly Glu Ala Gln Lys Glu Asn Gly Ile Tyr Ser Val Thr Phe Thr Leu
            565                 570                 575

Leu Ser Gly Pro Ser Arg Arg Phe Lys Arg Val Val Glu Thr Ile Gln
            580                 585                 590

Ala Gln Leu Leu Ser Thr His Asp Pro Pro Ala Ala Gln His Leu Ser
            595                 600                 605

Glu Pro Pro Pro Pro Ala Pro Gly Leu Ser Trp Gly Ala Gly Leu Lys
            610                 615                 620

Gly Gln Lys Val Ala Thr Ser Tyr Glu Ser Ser Leu
625                 630                 635
```

-continued

```
<210> SEQ ID NO 6
<211> LENGTH: 26729
<212> TYPE: DNA
<213> ORGANISM: Homo sapiens
<220> FEATURE:
<221> NAME/KEY: misc_feature
<222> LOCATION: (1)...(26729)
<223> OTHER INFORMATION: n = A,T,C or G

<400> SEQUENCE: 6
```

| | | | | | |
|---|---|---|---|---|---|
| ttcagggaga | agcagctctt | cctccatgag | cacaccctgc | cgaggccacc | ccccacccct | 60 |
| ggcactgggc | tcccctctgt | gcccagcctg | tgtcactgcc | cggcctgcag | ctcccccctgc | 120 |
| ctctggggaa | gcccgcttct | tcggcaaggt | cctgggtccc | ccacccggcc | tgggctcacc | 180 |
| cagatccagg | cgtgacgcca | cacagatgaa | actgacggaa | agggcaaaat | aaagctaaaa | 240 |
| gccgatgggg | ccgggggaat | ggaggtttga | cgcgtgagac | aaaggattaa | tttcccaaaa | 300 |
| aaatcaaagg | gctcttgcaa | attggtaaga | aaatgcacac | atgtgcgtgc | accaggataa | 360 |
| aaacgagaac | aggaaaggag | cccagagcac | acccacacgg | tcagtaaaca | ccggtgacgt | 420 |
| cccgcgggtc | aacagggcga | ggccgagtct | gggtgaaatt | tgagcacagc | gcgtgcacgg | 480 |
| aaggatggcg | gccactaaag | cccagtggga | atgccagcca | ggatctgggt | gtctgggcgc | 540 |
| acctaggagt | ggggtcccct | gtgataacct | gggccggctc | tgcgtgtctg | ggggcaccta | 600 |
| ggagtggggt | ccctgtgat | aatatgggcc | ggctctgcgt | gtctggggc | acctaggagt | 660 |
| ggggtcccct | gtgataatat | gggccaggat | ctgcgtgtct | gggggcacct | aggagtgggg | 720 |
| tcccctgtga | taacctgggc | cggctctggg | tgtcggcgca | cccaggagtg | ggtcccctg | 780 |
| tgataacctg | gccggctct | gggtgtctgg | gggcacccag | gagtggggtc | ccctgtgata | 840 |
| acctgggccg | gctctgggtg | tctggggca | cccaggagtg | gggtcctctg | tgataacctg | 900 |
| ggccggctct | gggtgtctgg | gggcacctag | gagtggggtc | cccgtgataa | cctgggccgg | 960 |
| ctctgggtgt | ctgggcgcac | ctaggattgg | ggtccctgt | gataacctga | tccccccatg | 1020 |
| gttccaacat | gccccaacat | ggaatggcac | atgagtgcgc | ctgaggacct | ttgatggtag | 1080 |
| gaaagggcct | gggttgtggg | ctcctggggg | catctccagt | gtcaaggcca | cagctcaggc | 1140 |
| caggtggggc | tcagggtgt | ggccgggctg | tcctgggcag | gggcaagtat | ctggctgtga | 1200 |
| aaagagtggg | gagaggagaa | agggagggtg | ggccgaggcg | cggaggggga | ccgggaccgt | 1260 |
| gtgcccagcc | aaggcacatt | cccagagcac | cctgcctgcc | ttttaggtgg | gtctgggaag | 1320 |
| gaaggggctg | ccgggccgtg | gaggtctagg | gcagtgctgc | ctggggagct | acctggggcc | 1380 |
| cgtcctggtg | tcctggggtg | aacacagggc | cggggctcag | gtgcagagca | tctcagcaga | 1440 |
| ggagggggtgc | cggtgggggt | ctcagcggag | gaggggtgcc | ggtggatgtc | tcagcggagt | 1500 |
| agggtgccg | gtgggggtct | cagcggagga | ggggtgccgg | tggggtctc | ggcggaggag | 1560 |
| gggtgccggt | gggggtctcg | gcggaggagg | ggtgccggtg | ggggtctcgg | cggagggagg | 1620 |
| gtgccggtgg | ggtctcggc | ggaggagggg | tgccggtggg | ggtctcggcg | gaggagggt | 1680 |
| gccggttggg | gtctcggcgg | aggagggtt | gccggtgggg | gtctcggcgg | aagagaggtg | 1740 |
| tcggtagtgg | tctcggcgga | ggagggtcg | ctgtgggtgt | ctcggcggag | gaagtatgcc | 1800 |
| ggtgggggtc | tcggcggagg | aggggtgtcg | gtgggggtct | ccgcggaagg | ctgcgtctga | 1860 |
| ggtatctctg | cagaaggctg | caagttgggg | gtctcggcag | ggtgtgcgag | ggacagcctt | 1920 |
| cttgggccag | gcaggcacct | cgagggcacc | ctggctccca | gctgagggtg | gctgaagctg | 1980 |

-continued

```
aagggaggggg atttgggtcc cttggatggg gagaaggcaa gcgggcacag agactgagaa    2040
gcccaaccgg gcgtggagga agacacactt tcagccacgt gacccacact gactgtctga    2100
cacgaccagc ggcagggctc cctggaagcg gtggaccctg cttcagacgt ggaggctaca    2160
gctgagtcgt atatgtcaac tgttctgtgt aatgtatcgc tcaatcaaca catacaccga    2220
aataagttaa actggtccta atatactact aattatcgtc ctcatccgtt cgatggaact    2280
gcgnnnnnnn nnnnnnnnnn nnntctcggc ggagagggtg ccggtggggg tctcggcggt    2340 agagggtgc cggtgggggt ctcggcggag gagggtgtc ggtggggtc tcggcggagg      2400 aggggtgccg gtgggggtct cggcggagga ggggtgccgg tgggggtctc agcggaggag    2460
gggtgtcggt gggggtctcg gcggagggct gcggctgagg tatctctgca gaaggctgca    2520
ggtgggggtc tcggcagggt gtgcggggga cagccttctt gggccaggca ggcacctcga    2580 ggcaccctg gctcccagct gagggtggct gaaggctgaa gggagggat ttgggtgcct      2640 tgggatgggg agagggcgag gggggccaca gagacctgag aagcccaaag ggccggcgtg    2700
gagggaagac acagctttgc aggggcagcg tgacgccagc actgagctgt tctggacagc    2760
gacccaggcg ggcaggggcc tccggccctg gagcgggtgg gaccctgct gtccaggacg     2820 tgggaggagg ccccccaacct gcactgtccg gctgggtgct cgctgcaggc accctgggtg    2880
ggtctgagcg cggctgcttc tctcccgcag gtctggtgaa gctgggggtt cactgcgtca    2940
cctgccagaa ggtggccatc aagatcgtca accgtgagaa gctcagcgag tcggtgctga    3000
tgaaggtggg tggggccggg gagggaggcg gggccggcgg tggggtgggg cggggaatag    3060 cacagggtg ggagccaagg ttgtggggac ctgcggtgct ggatgcgggt gggggggcgg     3120
gcctgcaggc tcctgggccg ccacacccct gctggtcccc tggtagggtg cctttgctct    3180
tgctcctccc tccagccctg cccaccttc tcctgcctcc aagcagagtg ggcaccctg      3240 agggacagg ctgcagctgg gcagttcagt tgctgcagga cctgctgtgc tagcaggcgg     3300
ggcttcagtg ttcccagcta gaatggagag gagttccctg cctcagagca cccctctcct    3360
accagggcac agcttggcag agggagctg caccttcctc ttccactggg gcctggcctc     3420
cgtcggctcc atccggtggt gtctggtcac catggagacc aggcaggccc cctgggtgga    3480
gggtttctgg gctgtgaccc acctctcagt ggggagggg cggccccggc tgctgggaag     3540
cctgaccctg ggtgtagagg aagaggctgg ggctcccagc tgctccgggt cccacccaca    3600
gtgggacctg ggctggcagc gtgcgaccct cccagcactg gggccagtcg agccccctcc    3660
tctcccttcc tctccattcg ctccttggca tgcagggctg cgggtgggc aggacccggg     3720 gacgaggcca gtgggagtgg ccaagagagg ggaggcttgt ggaaggtgct aagggttggg    3780
gactgtgaca tgttgggcac cccccagctg ctggggtgtg gaggaattaa ccagactaaa    3840
ctggggaggc ctgggacccc tatggggagg tgggggtggg gttaagggct gctgagggct    3900
gcctggatgg ggctggcagg gtcccaccct gccttggagg agaaacagag gccctgggag    3960
tgatggggcc aggacagcgc ctggcagaga gatccagtgt gggcgtagc tggggagagt     4020 cccatgctga atttgggagg tgcctgtgag ccccgactaa aggagggcct ggggatgcgg    4080
gaaaggggag gtgtccctgt cacctgcagg cgctgtgcac agatgtccgc ctgggaggga    4140
aggacttggg gacaggctgg ccaactcgcc agggctggga ccccatcaca agactggccc    4200
tagctccaaa gcctggtcca cgctggctcc tgagggctgg accccaggc cgtggcctca     4260 ctggccccac cactgacacg gccacttctt tgtgctgggc ggagcaccag ctgcccgtgg    4320
ccaggcttgc atgtctgagg gaggggcccc tgccttacct cggagcagga ctgggtgtcc    4380
```

-continued

```
tgagtcaggt gccctctggg tcacttctgc ccctccctgg gccctcccca cttgggggac    4440
agtaccagct gggagcctgt ggatggggg cacgtgccct gcccacggcc tgcacaccta    4500
ctgtatgtcc cacacacaac aggatgcctg cccccacctc atggggccca cagaggcctg    4560
tcccggcccc tcctcctgtg aggcctccac cgtaaggaag ggcggagccc aggcacagcc    4620
tgcctggaag ggccctgcat ccgactggct gggagcctgg gaggccttat ctccaacagc    4680
tccaggcccc attcctgagg ctgggctcac agagaggccc aggctgcctg ccttcctggg    4740
cagtgtgggg aggggccctc ctgctccagg ggccccagt cctcagccct acaggctggt    4800
gtcagcccgg cggcctgggc tccctccact gaggcccctg ccctctgccc tctccaccag    4860
ccagggcccc agctgagcag cccacgtccc tgcatccccc acagctggca ccaaaggccc    4920
ctgcgtcccc cacagctggc accaaaggcc cctgcgtccc ccacagctgg caccaaaggc    4980
ccctgcgtcc cccacagctg gcaccaaagg cccctgcgtc cccacagct ggcaccaaag    5040 gcccctgcga ccccacagc tggcaccaaa ggcccctgcg accccacag ctggcaccaa    5100 aggcagtgtc tgtggggagc gatgcgtgcc ccagccctgt gagcgtgatg ttctctggcc    5160
tctcccatgc aggtggagcg ggagatcgcg atcctgaagc tcattgagca cccccacgtc    5220
ctaaagctgc acgacgttta tgaaaacaaa aatatttgt aggtattgct gggtctgaag    5280
agctggggtg gcggaggtgg cagctgtcgc tgcaggggtg ggtgtctggg gcttggggag    5340
cacaggggct ggaggccagg ggcgcctgct gcatcccagc agccctggcc ctgctagcat    5400
gaacacctgc ctgggtaggg tctcagccca ggctgctgtg gtctctgctt ctggaccaaa    5460
ccggagacct ggtctgtgga ggctcgcaga gccaccagcc tgaggctggc aaggggaac    5520 aggaccttct ggagggga taggagtttc agggcaaggg gcaggagcac ctggccctcc    5580
ccacatggcc acgctgagcc tcctggcctc tgcccaggac gtccccagcc ctgggcagtg    5640
agccatgtct ctatccctga ggctccctca cacgaggcac agccaccagg atcccgccct    5700
ggctggaccg tggctgagtg tggctgaaag tgtcacctcc gcagccgctg aggccagcag    5760
aaatccctac cctgtcccag gcatgcctgg ctgtgaaccc catcccccca gacccagcct    5820
cagggagctc ctgggaatgg gcacagtggt cactcacggc agtctcctct gtgtgctctg    5880
atggggcttt ctgacagatg aggcgctgct gcccaaggc tgtctggcct tgagcctcat    5940
ctgaccctcg ctggtcccag ggcggcggcg tgacctgcca ggtgatccta gccgggcatc    6000
tctgaggcat caggctctga gggagcaggg aacatacagg gctgggctgg gggctgccct    6060
cagggtgagc tggctgaggg cctggctgaa cccagcagct ccccttcccc cagcagcaac    6120
gtccacgctt gctctggcct gggtttctgc attctcgtgg ggagcatgtg caggtggcca    6180
gctcgtgtgt agctggggag aggaaaccca ggggtgggt gtggggagcc cgcctgcccc    6240
accatgagca ggggctcaga aactgtcacc agaggcctgg gggcgggg gtggtcctgg    6300 ccctgatgct ggcaaggtgg actgtgacaa ggggcatggc ttcctcatgg tgacacggtg    6360
ccggtgcagt gggtcctgg ggaggccttc tcggaggga gggcagggga gtgcgggggg    6420
gatgggcaca gcagccaagg cccaagaaca ggaaagagcc caggaggtgg gcatggccgg    6480
gctcgcggct tctcccgagg tctggccctg ggtgttgtcc caccccctct ggacaccatg    6540
tggcctatgc tgagccttgg gcctggccgc cccctgccc agaatcccac cctggccccc    6600
accaccttcc cctgccctga gggcttcaca ccttcctctg ccctgagggc ttcacacctt    6660 cccctgcccct ggggcttca caccctcccc tgccctgagg gcttcacacc ttcccctgcc    6720
```

```
ctgggggctt catatcttcc cctgccctgg gggcttcaca ccttcccctg ccctggggc      6780
ttcaccacaa cctctgctcc catccccaca ctgggcccct gactcctgcc aaaaccagct     6840
cctgggacag ccagtcatcc cagtccgcac ggcagtctg  agcatgcacc aaggtgccac     6900
ccccttggct gtacagcccc cctacatcac cacagccaca ccaggggcca ccaccctcac     6960
aggcctcccc cccgagctgg ttcagcctgg gtggagcggc cccaagcag  ctgcatgcag     7020
cgtcccacgg gcctctcacc aggaaccagc ccctcaggac cctccatgtg gctgagaccc     7080
cacggggtg  gtgctgggag cccaccaggg caggaagggg agggccaggc caacctttc     7140
ctcaccccct tccctggcc  ctcacacctc ctgttccccc cacagaggcc cagacagtcc     7200
ctgggcccct ggatgcggct gcgtggtctc cctgctcggt gcctgtgcca ctgaggacca     7260
cagggtgtga gggccagagc aggcagggca gagtcccgag gctaccccat gcaccgagcc     7320
ttggccccag cacccgccac actcagcctg tgggttccaa accctccctg gcggctgtgc     7380
ccccagaacc atcccttcac ctgtccctcc accctcaccc caccccaccc caacccaggc     7440
tccttgaaga ctcatttgag gtccacccc  aggagcccag atggtttgag atccaccata     7500
gtcagggctc ctctcagctg cccccccagc cagcaagagg atggggggcgg cctgcagaga     7560
ggctgggcca ggaggcggct gtgggaggcc ctgggatgag gaggggcggc gggcagccac     7620
agctgggcgc actggtggcc ccgtctcctg caggtacctg gtgctagaac acgtgtcagg     7680
tggtgagctc ttcgactacc tggtgaagaa ggggaggctg acgcctaagg aggctcggaa     7740
gttcttccgg cagatcatct ctgcgctgga cttctgccac agccactcca tatggtgagg     7800
ccccacccct ggtgccccc  actccccagg acccccaca  cccagtgcgc taccacagat     7860
gcccctgtg  ccccaaggac tacccccct  atggtgctat tccgaggtac annnnnnnnn     7920
nnnnnnnnnn nnnnnnnnnn nnnnnnnnnn nnnnnnnnnn nnnnnnnnnn nnnnnnnnnn     7980
nnnnnnnnnn nnnnnnnnnn nnnnnnnnnn nnnnnnnnnn nnnnnnnnnn nnnnnnnnnn     8040
nnnnnnnnnn nnnnnnnnnn nnnnnnnnnn nnnnnnnnnn nnnnnnnnnn nnnnnnnnnn     8100
nnnnnnnnnn nnnnnnnnnn nnnnnnnnnn nnnnnnnnnn nnnnnnnnnn nnnnnnnnnn     8160
nnnnnnnnnn nnnnnnnnnn nnnnnnnnnn nnnnnnnnnn nnnnnnnnnn nnnnnnnnnn     8220
nnnnnnnnnn nnnnnnnnnn nnnnnnnnnn nnnnnnnnnn nnnnnnnnnn nnnnnnnnnn     8280
nnnnnnnnnn nnnnnnnnnn nnnnnnnnnn nnnnnnnnnn nnnnnnnnnn nnnnnnnnnn     8340
nnnnnnnnnn nnnnnnnnnn nnnnnnnnnn nnnnnnnnnn nnnnnnnnnn nnnnnnnnnn     8400
nnnnnnnnnn nnnnnnnnnn nnnnnnnnnn nnnnnnnnnn nnnnnnnnnn nnnnnnnnnn     8460
nnnnnnnnnn nnnnnnnnnn nnnccccccc attaggctac ccctcaagtg caccgtccac     8520
cccattagct acccctcaag tgcaccgtcc cccattagc  taccccctcaa gtgcaccatc    8580
ccctcatta  gctaccccctc aggtgcatca tcccctcctc attagctgcc cctcaagtgc    8640
accgtccccc ccattagcta ccccctcaagt gcactgtccc ccccacccca ttagctacct    8700
ctcaagtgca ccatgtgcac caggtgcttc ccttttcccc ctgaggaccc cctgcacctc    8760
cccttttcccg agtgggcagt gtgtcgggaa gttttctgcc tggcacccac ccaagcactc    8820
tgggagcccc tcggccttcc caggggccat tgcttgcatc cctacgtgcc tgggggccct    8880
aggttggtct aggccagagc aggtgtgcta gggagcagga gggggcagga aggagcctgc    8940
cagggtgcag gagggcatgg caggagaaac agggatgcct gaccaaaggc cagagccaaa    9000
cggaccaggc aggcgacttc tgattggctg cctatgacat caccaggctg ggctgctatt    9060
ggcccttatg tgtgattggc gtttggagag gcagtgggct ctgggcaggg ggtctccagg   9120
```

```
gcggggaggc gctcaaggca gagactggcc ctgttcagcc tcaccaccct cctccccagc    9180
cacagggatc tgaaacctga aaacctcctg ctggacgaga agaacaacat ccgcatcgca    9240
gactttggca tggcgtccct gcaggttggc gacagcctgt tggagaccag ctgtgggtac    9300
gtggccctct gccctggaga gaggctgggg gacaggctgg gctgggggaa gaggagccag    9360
tggactgaga ggccccagc ctgcctgagc ctcccggcac cccacaggca ggcccccac      9420
aatgtgcctg agcctcccag taccccacag cctggtggtg gtggggagac aggcctcccg    9480
gcacagtaag ggtaggggta cagccctggc cctggcctgc ctgggagaga ggctgggacc    9540
cacttacatg cccctctcct ggggaccccc tggcccctgc ccagccgagt gggcagacag    9600
ctttgggcgc agcagagacc cagtgcccca ccttgatctc ctcccaaaag cccgcctggg    9660
gatgcaggga atgtgggggc gtctggcacc acagccctgg aggcctcctt gagggccctg    9720
cggtgcacca tcaccctggg gggagggcct ggcagcgccc ggagcccgc cgctgacctc     9780
tgcccttgcc cgcaggtccc cccactacgc ctgccccgag gtgatccggg tgagtcagcg    9840
ccgccgcgtg cagctctgtg gggcccaggt tggcggggac ctgaccctgg tgggaccccca   9900
gcctgccgca ccccaggtg ctgctaggct gcctgtcccc gggccgactc cctctgagcc     9960
caggccctcc aaggccccg ccctgccctg cgcccccaa cagcccgggc actgctgtcc     10020
acaggggag aagtatgacg gccggaaggc ggacgtgtgg agctgcggcg tcatcctgtt    10080
cgccttgctg gtggtgagac cctggccccc tcaaccctgc cctggcctct ccccaaacct    10140
gcccccccac gctgacccc acacccggcc gcccgcaggg ggctctgccc ttcgacgatg    10200
acaacttgcg acagctgctg gagaaggtga agcggggcgt gttccacatg ccgcacttta   10260
tcccgcccga ctgccagagt ctgctacggg gcatgatcga ggtggacgcc gcacgccgcc   10320
tcacggtgcg tgccctcgga gcggggcggc cccagagcgt ggcggggggc gcggggcgg    10380
gcgtgtgcct gtgtgtgcac aggtgtgtgc ccagacgtgt gggcacccag gtgtgtgggt   10440
cggtgcccag gtgtgtggac gtgtgcacag gtgtcggctt gtgttcaggt gtgggtgacc   10500
aaatgtgggc ccatggccgt gtgtgggtgc ccaggtgagt gttcaagtgt gtgtgcgcac   10560
ccaggtgtgg gagtgcccag gcgtgtgtgg gctcgtgttc aggtgtgtgg gtgcacaaat   10620
gtaggcacat gcccaggtgt gtgttcaagg gtgtgggggt acccaggcac atgcccaggt   10680
tcatgtgatt gggtgagggc gtaggtgtgg gcatgtgcac gtgtgggag gtgtgtccag    10740
gtgcttatga gcacttgtac cagtgtgggg tgtgcacagg tgtgggggc tgtgtgcaca     10800
tgtaggtgag acctggctat aagttacaca aaagcactgg tgcttcccca tcacggccat   10860
cctgcctcca gacgctgctg gggcaagctc caggcagcgt gaatagttct gctgagtgcc   10920
cccagcagct gtgggggcta gcaagagcca aggtagccc ccagctgctg gtcctgacct    10980
cctccagggc tgcctggtgt ggggaccgca cgtgtccact tgacagaagc aggtcacact   11040
ctgggctgac ccttccaggg tagcgttgac ctgttcccaa gtggccactg cctcacaccc   11100
cacgagctgt ccctgagtca gggtggagag aaggggccgt gtggctggcc ggccctccca   11160
gcctcctgcc tgcacctgca cccagccctg cccgccgca caggtgggcc gggttctcct    11220
ggcttcagct ccctcctggc tgctccctgc tctcctgcct tggttccttc ctagagccac   11280
ggaggggccc agcccaggca gcacaggcac ctggggctgc cctggctcca gcttccctcc   11340
ctcccccctct ccctccgctc cccaggcccc tgccctacc tggagcaccc cctccgactc   11400
cagctccccc gacttctctc ctccttgagg tgtgtgtttt cttctccact tgggagaggc   11460
```

```
aggagcaggg gtgctggcct tgagcctctg ggaacgcagc cccctcccta tcttcctccc    11520
caccttcccc ccactcactt gccctcaccc tctcctgctc tctccgtgct cccagcgccc    11580
ctgccttccc cctcacctcc taatgtgggc tctttccgtc cctcgtccgt actaactccc    11640
tgtttctctt tccttgtagc tagagcacat tcagaaacac atatggtata tgtaagtagc    11700
ttttccaccc actaatcgcc tgctttgcct gttgctgtgg cctggaggcc ctgctaggaa    11760 aggcggggg agggcgccgg cccagcgcag gtcctgccct gccttggccc tccgtggcct    11820
gcgctgggtg cggggtgcgg gcaggacgca ggaggcctcc ccgggctggg cacagggaga    11880
gtggcaggat gaagggcccc aggtgagggc gggcgtccca ccctcgcagc cgcccaggcc    11940
cggccggagc tgatgagcgg gtggcccgtc ctgtgtccac agaggggca agaatgagcc     12000 cgaaccagag cagcccattc ctcgcaaggt gcagatccgc tcgctgccca gcctggagga    12060
catcgacccc gacgtgctgg acagcatgca ctcactgggc tgcttccgag accgcaacaa    12120
gctgctgcag gacctgctgt ccgaggagtg cgtctgggc tgctcccggg tggggcacgg     12180
ggcctgaggt gggagcgctg ccccggagga ccggcggcc ccgtgtgcca gcgcgtctcg     12240
cgcctctcgc ccgctgtagg gagaaccagg agaagatgat ttacttcctc ctcctggacc    12300
ggaaagaaag gtacccgagc caggaggatg aggacctgcc cccccggaac gagataggta    12360
tgggtccagg ggtggcctcc agcccggcct gcactgcccc accggggtcc ggggctgtc     12420 tggcctgacc ttcgtctgta ctcagaccct cccccggaagc gtgtggactc cccgatgctg    12480
aaccggcacg gcaagcggcg gccagaacgc aaatccatgg aggtgctcag cgtgacggac    12540
ggcggctccc cggtgcctgc gcggcgggcc attgagatgg cccagcacgg ccagaggtgt    12600
gtgtgccccg aggctgctgg gcctccctcc ctgggcctg gctgcgcggc actgccgcct     12660
ggctcatcgc tacccattgg cctggggtct cggctgaggc cattgggtgg ggctgtatgg    12720
gctaaactgg gcttagctgg gcttggctgg gctgggctgg gcttagctgg gctgggctgg    12780
gctgggagct gagctgggct gggctgtgct ggactggact gggctaggct gagctgggct    12840
ggcctgggct gggctgggct ggtttgggct gggctagact gcacttggtt gagccgagct    12900
gggctgtact ggactgcgcg gctgagcagg gttgagttga attagggtgg gcgggctgg     12960 gctgagctgg gctgagctgg gctaggctgc actagaatgg gctgagacgg atttgactgg    13020
gctgagctgg gcagggctgg gctgagctgg gcagggctgg gctgggctaa actggatttg    13080
gctgagccga gccaggctgg gcagggctga gctgggctgg gctggcttga cccaagcttg    13140
gctgggctga gctgtgatat ggtcacacca tgctcagagc catcagccca gcaagcctgt    13200 cccctggtc ccagcaatgc tgggcccgtc tctgggtggc aagtgtggtg tgtgtggcca    13260
gggacatcac agaactcagc agtgatgagc agacctgtgg ccgaggaag ggcacccagc    13320 ccctctggag cctctgctgg gtgggggcag ggctgggctg cccgcacgag gccctcagca    13380
aatccttgga gccggtgcgg cctcttgggg atgagctcaa acgtccctca ccaggtggca    13440
gcttccaaca cttggggaca gcccttgcgc cagagagcac accaggaggt ccaggagccc    13500
gggcagcagt ctctggtctg ccctgtgatc tgggcctcag cacccaggg ccccctcctt     13560 gtactggaga tgtgggggt gggacaggcg tggcctgttc ctcgggaact tgggggaagc     13620
tgtggggaac tgcaaggtag cttggcagcc atcaggctaa acctgttcca gccccagccc    13680
tggccagagt actggtggtc ccagttctgg cagctcccag gccatggccc cctgggagtc    13740
ctaggccctc cccagggttt caggctggcc cagcttccaa cgtgggtcc cagccccag     13800 aacctccttc ccagggccca gtcagcgcag ccctgacgcc agtactaggg ggtagcaagg    13860
```

```
ggccctccta tctacattct actgtcctga ccttcagtgg cctgcatgtc atgggggcac   13920
cacaacctgt agcccaggtg cctgcctcct gcctgcgtgg ccacctcccc ggactccccg   13980
accctgcagg gcaggcccca ccaccccact gcctggcccc tccggtcagc ggcgtgggag   14040
gccgccctct tggcctctgc tgcaactccc aggcctggct gcctgggca ggtgtgggat   14100
gggccaggcc atggaccatt ccggggcctc tggaaggcca ctagtcctgg catgtcccag   14160
ccagattcca ctcctggtgg ggccacctgt gcagccagca gagacccagc tgcttggtgt   14220
tgggccacac agggctgctg actggggacg caggggtcct gggggctggg gtgggggcta   14280
ccaggccacc ctgcccagca gtcacacggt gcggggtgtg ctgtctggcc cagcctcctc   14340
tctcgccatc tttgtgcagc ggcctcagag ccacgtggag ttcttacccg gtgtggcccg   14400
ggccctgggg gccgacctgt gccgcgtgt ggccgtcagt aactgtgttt tctcgctctg   14460
ttctgctgta gtaaagcaat gttcagtaaa agcctggata tcgctgaggc ccatccccaa   14520
ttcagcaaag aagacaggta tacaccccga ccacccgtcc ccgcacctcc cagccccaga   14580
cacgctgtcc tgcctcaggc cgggcaggca catgggcggg tctggtggcg ggctgggctg   14640
cagggctcct gctgcggtga agccagccag caagccagga aagggcccgc gggccaggca   14700
gaggccgagg agggtgggg ctgctgaggc gtggcccacg cctgcctgtg agggaccacg   14760
caccatggct tacagggcct ggggctagag cccggcgtgg ctgcaggccg agccgctcct   14820
cctgccagcc cctgtgctgt gtccggtggg cctcggtggc cctgctgccc ctggggccgg   14880
ccagagttga agccgagcag ccgtcctgtg cccacctgca ggagctgagg agggcaggag   14940
gcgccgccgt caagaggggc ctctacctgg ggccagtttt gcgagcctgg gcgggtggcg   15000
ccgccccaa ggctgcagtg tgctggctgc cggtcgggt ccttctcttt gagccctggc   15060
cccgtgccta cctgggaccc tcacctgtgt gccctcactc tgcctgccct ggctgccctc   15120
agggctggcg ccgtctctcc tgcccctgcc ccagcaactg tagctcagtg ttcccagcag   15180
ctgcctggcc ggataggacc agggctcggc ccctccaccc cggggtttcc agcgcctctt   15240
ctgtcttcct cgtgcccagt cacgagctct ggcgggctc acaggaacc acaggtccag   15300
ggcctcactg gtggctgctg cccccatgag ggctgtccgc gctcccagct cagccctgaa   15360
agctctgggt ccagttccag ccctgggtgt catcctggcc cagacaggct gggttgtgca   15420
tggggtcccc gtcgcctccc tgccccttgg ctgtgtctgg tgagggagtt ggagggtcgt   15480
caccgtgggg accagccccc gggtgtccgg gagccaggtg tgtggccagc gtggcactct   15540
ccacggtccg gggcctgggc cgtggtgtgg actagcgagg cccctcgtgg ccggctggcg   15600
gtgggcaggc ctggtgggca gtgcaggccg ggcttttact cttctctgtc ctcttctctt   15660
cggcggctgc ctcggcccct ccctgcattt ccttcctcca aggatggcag ctgccactgt   15720
ctgggcacgt gggcgccggc tcgtccgtgc agtgtggtgg aacgacgcac agccgtcctg   15780
gtccctgcac gggggtggcg ccacacacc ggagtctcag ccgggcacgc cgggccaggg   15840
cctccctcct gctgtgtgca ggtctcaggc tgagtagggc agtggtggga caaggcccca   15900
ccgtccctgc cagcagctgc cccagcctgg cctgcccag gccctcctgg ttgtggacaa   15960
gggaagggcc ggccgctgac ccaggcatcc ctcacgggca tctagggaca tggaggacca   16020
ggctgcaggc cctgtgagag ctcagccagg ggggcttgg caggtgggag ctggagcca   16080
gcacgaggcc tggagcagaa ggggctgcat acaggaagct cccgtctgtc ccctcgtcct   16140
tccgtccacc cccacgctgg atggtccttt gccgcggctg tctgatgccg tatcctgtgc   16200
```

```
tgtgcctggg ctgctggcat ggggtggccc ccacacgtgg gctctgatgg gggccccagt    16260
ggggctgggc acagccaggc gccctgggcc ctcctgaatt gacagggtgt gcagcaggac    16320
ccagggcctc gaggctcttg gcccgggctc caggcctcct ggagggttta cctgggggga    16380
gcagagccca gcacctgctg ctccactgcc ccctggctga gcagtggccc tgtaccttgt    16440
gacctccagg tctcggtcca tcagcggtgc ctcctcaggc cttcccacca gcccactcag    16500 cagccccgg gtgagtgacc cccgccccc acccagctcg gatgcacaga ggccccaacc    16560
ctcccagtca gcgtgtgcca gggtggggc agcctcgtgg accctgggaa gcagccccag    16620
gcgcccccca tgcccacgct cctgtggcgg ctgctgctct gtggcgcagg ctgctctgct    16680
aactgcacgc tcttttgttt tgttttgttt gttttcttgt gtgtcacttg ttttcttttg    16740
tggctaatcc tcctgcccat gcctgcctgc ctccccaccc tcccgctccc gcctgtttct    16800
ttctggtcct cctgtgccgt gtgcatgcgg gggactgggg tgcatgtgcc gcgcggctgc    16860 cccaccccg ctcgctccct gcgcctcccc gtagcctatt aggaagcttg tcctgccccc    16920 accgccccc gagccgccct tcgtggcccg ccccctggcc acctccacgg agcccgaagc    16980
ttgtgggagc gcctcgaggc ctggacacgt cctccctctg caggccgccc tgcggcccga    17040
ccccaagacc cagaccttgc cgtgcaaggc caagctgacc gacaagcctc tgcagggcac    17100
caagtccaac cccttcccgg ccagcacccc agcccgccct cccgccactg gcctttgtcc    17160
ccagctggca ccaccctgg gcccgcctgc cctgcgggtg cccccccggc ccccacccgc    17220
cgggattgaa ccaaacacca aatctgtccc caccatacag gtgacccctc acccctcacc    17280 aagggggcagt cccctcccca cccccaaggg gacacctgtc cacacgccaa aggagagccc    17340
ggctggcacg cccaacccca cgcccccgtc cagccccagc gtcggagggg tgccctggag    17400
ggcgcggctc aactccatca agaacagctt tctgggctca ccccgcttcc accgccggaa    17460
actgcaaggt gagtgtctgc ccggaggcgc cagagtgggg ctgggagaga gcagaggctg    17520
ccttggggag ggccccgccc ggcagtgcca gaccagtccg agggggcctgt agctgcaggg    17580 gtggcctggg cctgcccacg tctcactgtc ccgaaagcgc ccagcagcag cctgtgtcct    17640
acctgtcgca caggctggta tcccctccag acattctgtg ttcctgagtc tacccactct    17700
gtgtcctggg gccaggcaca cagcaaggag agctggccac cgaggggcca ctgccagtca    17760
ggaggcccca tgtgtggggc accaagggcc agccagtgct gctggagaag gcacagccga    17820
cttcagcacc agaggcgggg acagctcccc ttagcctggg gggcgccact gccagtgggc    17880
ctctaaggtg gccgggagct ggggtggacc agtgcccctg ggggctgtc ccagtgtgtg    17940 tgggtggact cctgatgacc ctgacctcgg cgcaaggtgg ccaggcagg ggaaggatgg    18000 agcggtcacc acgcctttcc tcctgttcat cctgtgtgca cagttccgac gccggaggag    18060
atgtccaacc tgacaccaga gtcgtcccca gagtaagtgg ccctgctgg aggcctcctg    18120 gtacctgaca ccaggctggc cgggagaggg gcatggaacc cttcccctat ggccaacggg    18180
gtgctccttc tccacgtggc cccacctccc actgcaggca ggcccgtctc ggccactgag    18240
tctctgaagt tcgaattccc ggctgtgagg ggaaggccag ccagggggagg agcccccagc    18300 cctgttgaga agcttcaggc cttgggagag cctaggttg gctggaggcg agcagggggt    18360
acactgggca gagtctcccc agggcctgag ctcgccaagg gcagagaccg ggtcgctcag    18420
gtctcaagga gaaagcagcc cgtgttaaga acaaaggggc agcaggcctg gtgggaacac    18480
gtgtgcaggg gcggagcgga gcagccaagc cgaggtctgg ccccgccgcc tttctgagcc    18540
gtgagaggtg ccactgcaga gactctacag cgcccaggtg ctgagatgcc ctgggggccg    18600
```

-continued

```
ctgtgactgg tgtctggaca aagatgtccc cagagagacc ccttcccagc gcccaggccc   18660
tctccctcct ctccacgatg gcctcagtca ctgggcagtg tctcggagac caggcgactg   18720
gcggtgtaca catatgagcc tgcagcgtga ccccaggcca ggcagcggca gagagcggcg   18780
gtcaggctgg agtcacttca caggagaccc cgggaaatga agatgtggcc agctgtggac   18840
tgagtaagac gagaaccttc gtcctgctgc tggcttttaaa ccaggggccc ctgtggaaac   18900
tgctcagtgc taagccccag gagcagcatc tgcagcctgt gccaggattc cacccagtgg   18960
cctttctgcg ccgatcaggt ggcccttcca gctgggtgcc caggtcggag gtgtgtaggt   19020
attgtcgcaa gcccagatgc acagggctca gcagacttgg gaaccttccg cctaggccct   19080
gacattgccg tttctgctgc taccaaaagc tttcatgaac agactcataa ttatcttcct   19140
cagagaaggt ggaaaacatc aaagccgaga aggtggcttt gatgccactg tggctgcctg   19200
cgcttctccc ctcccccatc ttgagatggc ctggaggccc tgacccctct caagggtccg   19260
gcacggatgc ctcccacagc cccacccaag ggcccggcac agacacccct tcccaagggt   19320
ccagcacaga tgcctcctac agctccaccc aagggcccgg cacagatgcc tgcgacagcc   19380
gttcccgagg gtccagcaca gacacctccc acagccccac ccaagggccc ggcacagatg   19440
cctgtgacag cccttattga gggtcctgca cagacgcctt ggacgagggt ccagcacgga   19500
tgcctcccac agtccctctt tggcgacaac tcgcttgctg gggacctgag ataaccccca   19560
gcccagctg ctgccagccc catgtcaacc aggcacccca gaggaacagc accaaggggag   19620
gcagctggct tcaggaaggg atgcatgcgg ttgtctggga cactcagggc tgatgtcctt   19680
gagtctgaag tgctagctgg aagcccaggc agtttccagg ttgcagcctc gagggcgtt   19740
cttctccccag gaagaccgaa cctggcggat gcacccaccc tgtgaggaag ggtccccgc   19800
cagactcaac aggcgactga tttaagttcg tctcatctaa aaatagcttc atagcaacac   19860
ccagactagt gtccggccag gctgtgcact gcccaccacg tgggtgctgg agtcacagtg   19920
caggcccctc acccctcgtc ggcctggcct ccctgggccg tcaggcatct ttcacacatg   19980
ggactatttt tgccaaatgc tgcacccctg ggccgcaaag cagagagtca cgtttgtacc   20040
atctgtcctg tctcttcatc gggcagaaca tcgaccatgt agaaactcac ctgtgcttcc   20100
agaactgcca ggctgctttg tgcacttcct ggctccaggc cctggcatgg ggctggggta   20160
aggtcagggc cagtggtggc cctcggagtt ttgaacccag aacagacagc cgccgagacc   20220
ggcaggacac tgaggaggcg tcgaggggct gagtgagggt tggacctggt ccccgtgctt   20280
gtccggcagg actcccaggc cgcacagtgg ccgaggaggc agctccagga atgggcaagg   20340
gaaaggggag ttgtgaggcc gctgggaggg gcctcagaat cagtcgggag agggcaccac   20400
tgagccccag ccctgctggc ccctcctccc gtccctgcc tctgcctctc agcacacctg   20460
gttccacctc caggcagcaa cggcagggga gccagcaga gcgtgccacc tctgaacagc   20520
cacccaggcg cgctctgcct gagtctcggg ctgtgctaga ggcgcctctg gccatggtcc   20580
tctcacggct gggcttcctg gccccgcgc tggtgggtgg ggttcgggtg ctcttgagct   20640
ggagagcaga gggcctctgc atgttggggt gagcctgcca gcaagacagg agtagccttc   20700
tgtggcctca gaagcgcctc cccactctcc tgttggaagc gagttgcagg ccccgcctgc   20760
tcctgggggt gggggggcaca gctgacttca ggagcccagc ttgagccacc tctcacagcg   20820
gccttggtga ggggggggctc acctgtgggg ggctcacctg tggggggctc acctgtggag   20880
gggcatcccc agacttggga gtgggtggca tatgggccag ggtcagggcg ttagggcttg   20940
```

```
gagaaaggtt agggttgggg ttggggttag agccacggtg atggtcaggg catatgggct    21000
agggttaggg cgttggggtc agggccatgg gttctggcta gcactgtgga gacagccgtt    21060
tctatcacga agcgatggaa gattccgccg ttccaacccc agattcgagg gaggcagggg    21120
tgtggacggt gccacacctc aatcctcaca gcctctgtct cccactgccc aggctggcga    21180
agaagtcctg gtttgggaac ttcatcagcc tggagaagga ggagcagatc ttcgtggtca    21240
tcaaagacaa acctctgagc tccatcaagg ctgacatcgt gcacgccttc ctgtcggtga    21300
ggccacaggg cgctggggga ggcgggcagc cctcccaacc ccacacggcc cagcccgag    21360 aatccagcct cctcacgtag acaggacatg tccacgcgca cagcacggac gtccgctcac    21420
ccgtgggcct gcctggccgc cttcactgga caggcgctct ctcctgccca ccctcgtgag    21480
ggaggggtca ctgcccatct ggggtgcttg gcctgcggag ggagtcaggg ctttgctcac    21540
tggtccccag cagccctagg tgtgtgccgg acaggcctgg gcagctggca cgtggggcag    21600
aaggaaggct ccagctgggt gggtctcaga ggggacatt tccatcagac tcggggagaa    21660
gcccttgtga ggccatggcc ctagggaccg gtggggctct gctggccctc agtggacagc    21720
cccagccctc agtgtctca gtttccctgg tctcaccctg ccctcggagg ccgggtggct    21780
ctccacagag tggtcgcgct cggggtcttg ggtgggcttc atttgtcttt gctgggcatc    21840
tttgggttag gaggagcaga aaggccctaa aagcctcaaa tggagaaagt ttattgccag    21900
gactccagca cccagtccca tcaggacgcc ccttccttgc cggccctgcc ccaccctgtg    21960
ctgcacccag cgcccaggca tcacagggc tgcccccac ccgcctcccc caccgccccc    22020
agcctgcctc cccagggctg ctgtcctgcc ctgtgctcac cactgcccgg gcgccctccc    22080
tggccccagg gtcttggcaa gatcaggccg tggttcgctt cggcagcctc tctagctagg    22140
gactggcccc caccccacca tatgctctgc ccccgggcac tcaggccact gctgccctgg    22200
ctgcagctga gcttccctta cgctgtgggg acagcttgga gccctgcag aaggctccag    22260 ggccaggaga gcccagcgct gggcagggca ggcctcagac tgcacttgga ccctggcctc    22320
aggggtcctc agcgtcccg tccccgtccc cacaggctgc tcacttcctc ggcctcctcc    22380
ctcaccacat cccttcatgc tgcccctggt tgccacggct aacctcagac tcagcccctc    22440
cccatgccgg cccagtgag gcggctgtgt gccagcctgg gccctgtgcg ctgggtggcc    22500
ctgagttctg cttcctgcag ctgcccctc ggtactgtga agcccaccca gccagtgccc    22560
agcaccatag gtcccgcaac cagtgggagt cccaggaagc cccagcagga gggcacagcc    22620
ccagccccgc ccttgcacct ccctctcagt ggcagctccc agacccccca cctcccactc    22680
agctccaccc tggaccccca cctcaggctg caggggtcac cttccacctc catctttgcc    22740
cttaaggctc ctctgtaagg tcctggtcat cctgtgctgt ggctgcctga gaaaagcccg    22800 gcagggctt agctgtgccc gctaagtgga ccaaagcttt ggagggtggg ggctggaaac    22860 gccctcccc ctgctccagc cgtctccaac cgcactgtgc ccctcacgga agcagaggtg    22920
cctgggtgct cacaatgtgt gcacggtggg gctggctcgc cccagggctg cctccccaga    22980 gggcagggt gggacctgcc aggccagcca cgctcacgct gctctctctc cacagattcc    23040
cagtctcagc cacagcgtca tctcccaaac gagcttccgg gccgagtaca aggccacggg    23100
ggggccagcc gtgttccaga agccggtcaa gttccaggtt gatatcacct acacggaggg    23160 tgggaggcg cagaaggaga acggcatcta ctccgtcacc ttcaccctgc tctcaggtga    23220
gctggcgccc ccagggcggc tccgggccca ggccgtcca gggcataacc ccctgtctcc    23280
cctaggcccc agccgtcgct tcaagagggt ggtggagacc atccaggccc agctgctgag    23340
```

```
cacacacgac ccgcctgcgg cccagcactt gtcaggtgag gcgggctcag ctccggccaa    23400
cctgcggcct gcgagtgggg cgtggccagc tggtgctgcg cggacgggag gcgtgaggac    23460
ccgggcgcag cctcctggcc cctcttgacg gacgccccca cctccctgcc ccgagctgtg    23520
gctgcacccc tcagggagca gagcccctcc ctggcctggc gggaccaccc gcctcgcctc    23580
tgcacgccag ggacataggg cgcagccgca ccacactgaa aggcgcctct tgtccaccgt    23640
agaacccccc ccaccagcgc caggactaag ctggggtgct gggcttaagg gccagaaggt    23700
ggccaccagc tacgagagta gcctctgacg ctggcaggta aggcgcccgg cctgtgctgg    23760
ggcggggagg ggctgcgggc aggtcctcgg cggagccagg ctggccctga gcagggccct    23820
ccatgcccac ccacaggtct cggccctgga caggccaagc atgccccggg cggcccatct    23880
gctagggcag cctgcacagg acctgggaga gcagtgacaa ggccctgccc tcgggactcc    23940
ccgccatggc acctaggag ggccgcgggc tgcctgacgg gctgtgactt ctcatctctc    24000
catacttcct gacagcccag ggccatgcct ccagcagggc agaggggctt gagcccagcc    24060
agagcggggg cttcaccaca gcctgatggg ctcacacagg ggagggttgc cccagcctgg    24120
aaccaccagg gtctaggacc cgagggtccg tgccactcgg catacggcag ggagggctcc    24180
ccccactccc ctgggcccat gtgtggtggg ggcagggcgg agcactgggc acatgcatgg    24240
gcctggtctg tcagcaaggg ggtgtgggtg tgcctctgaa cgctggtacg gcgtggggc    24300 gctgggcgtc gtgggggagc acccggctgg accctggggg tccctctcc cagcctgcat    24360 ctcagcagct ccgtggcatg ctagggtcac ctcctgtgtt tccatgtggg gtcctggaag    24420
ccaaagaggg ccccactgcc cctccccatg acatcctcat tccatcatca tgccatcacc    24480
tgtgggagcc ccccagagt gtgcttcacc ttgctgcggg ctgggggctg aggtccccaa    24540
cagccctggc cctaaccgaa gccccagtgg gtggaggagt agccccttc tcctgatttt    24600 gggagccagg ctggcacagc gggtaaggag gagcagggtt ccaggtgctc ggccccgcag    24660
gtacacgtgg cgcttcccta cagcggaggc catgccgtcg gccggcagca gcctctggct    24720
ctctgagcct tgaaagcctt catcttagga agggaaaccg aggccaggga acgacagggc    24780
agccacctag gccagggatg gacagggctt gtctggtagg gcaagcagaa acgggccccg    24840
gggtactgcc caggtgtcc ccgcacctga gcagccatct gggtgcctca gtcgagcgct    24900
cctgcgtggg ctgtaggcaa agctccccca gcctggcccc ttaaagtgtg gtaccgcctg    24960
tcagcacgca gcactcccct ggagccaact ccaagcccct ctccattcct gccccggacc    25020
ctgacctcag tggagcccac tgcagaggct cttgggggtc tattctgggc cccatctatc    25080
tccctgtgga cttggggagc ccagcctatc cccgtgatct cgctacgccc agcccttccc    25140
agccctgccc ccctcccaca ctggatgctt ttgtccagtg agcccagctc caaggatgtg    25200
tggaaggtgg ctagccagca gggggcctcc tcagacactg cccacccccc cagagactgc    25260
ggccgaggga ggggaggctg agagccccca gtgagcaggc acaggcagac cagggcgtgt    25320
gtccaccctg tgcaggcgcc agtgagggcc ttgagggagt agcccctccc agggccttgc    25380
tcccacccca gtcctggact ggcagcacca acatccccag gcccagcagt agggaagagg    25440
gccgaggaag agggtgcctg ccttgagttg aagggcagcc agaagccaca gggccctgga    25500
gctgctgagt ggcacagtga ggatgcaggc cacggccagg gcagagttgt cagcccaggg    25560 gagggggctag gcccacccag ggcaccggcc atatccaggc tcaggctcag gctgctggag    25620
gtccggctgc tgcccaggtg gctccgcctt gttccctgcc tccgcagccc cgcctcactc    25680
```

```
caggccctgc ccctgcactg ccccttataa gccccgcccc ctctggctct ggcccccca      25740
gtattcccca cccatgcctc tgggccccta cccactcctg gctccacccc ctccccatcg      25800
aggctgtggg cgtccagcca gaaggcccag acagccttt cactcactcc ctccctcctc      25860
tctccattct gtactccaga caccactaac tgtatggaaa tgatgacggg gcggctttcc      25920
aaatgtggta agaatccccc acgctcacct ggcacctcca cctgccactt caccgctcac      25980
cctcagcccg ctgtggccgc cacctgccgc ccgggttgtc ccggcctccc tgtgtagatg      26040
taggcaccca gcagcccaga tgtccccggc cccatcctct accaggagca gcccccgtcg      26100
ctcccctacc acagcaagcc caggcggggt tcctggccag actcacctct gccaggccct      26160
aggatcaggg caggcccaag aagggctcc caaggcctga agccagtgag gtcccgctg       26220
gtcccactgg tgcaggctgt ggcctagggg aggggccggt gcccatccct ctgtccactg     26280
gaggctgtgc ctggcaggga gcggaggggc ccacagctca gggctcaggt gggggttagg     26340
cttaggaagt gggattgagg ggcctccatc gacacacctg gcagtgagc acagggcccc     26400
aagaagggtg ggctccccat ttccgcccct cttctcagga ctgcccccat cccagggacc     26460
cgggacatga ctctagctgc ttgccccag cccccagcc tgcctccac atccaccct        26520
ccatgcttgt ccacccatct gttcatctgt ctgtctgctg ctaaactgtg tccaagctgg     26580
ccaggggtcg ggcttcaggc ctctctgggg aggtgtggtg ggcacaccct ctccctgtca     26640
tccactgggc ctcatgcagt ggggccagca gctgccccca gggtcctgcg aggcttcaga    26700
gctcccagca ggcccttgtc tttacgctg                                       26729
```

<210> SEQ ID NO 7
<211> LENGTH: 674
<212> TYPE: PRT
<213> ORGANISM: Homo sapiens

<400> SEQUENCE: 7

```
Met Thr Ser Thr Gly Lys Asp Gly Gly Ala Gln His Ala Gln Tyr Val
 1               5                   10                  15

Gly Pro Tyr Arg Leu Glu Lys Thr Leu Gly Lys Gly Gln Thr Gly Leu
            20                  25                  30

Val Lys Leu Gly Val His Cys Val Thr Cys Gln Lys Val Ala Ile Lys
        35                  40                  45

Ile Val Asn Arg Glu Lys Leu Ser Glu Ser Val Leu Met Lys Val Glu
    50                  55                  60

Arg Glu Ile Ala Ile Leu Lys Leu Ile Glu His Pro His Val Leu Lys
65                  70                  75                  80

Leu His Asp Val Tyr Glu Asn Lys Lys Tyr Leu Tyr Leu Val Leu Glu
                85                  90                  95

His Val Ser Gly Gly Glu Leu Phe Asp Tyr Leu Val Lys Lys Gly Arg
            100                 105                 110

Leu Thr Pro Lys Glu Ala Arg Lys Phe Phe Arg Gln Ile Ile Ser Ala
        115                 120                 125

Leu Asp Phe Cys His Ser His Ser Ile Cys His Arg Asp Leu Lys Pro
    130                 135                 140

Glu Asn Leu Leu Leu Asp Glu Lys Asn Asn Ile Arg Ile Ala Asp Phe
145                 150                 155                 160

Gly Met Ala Ser Leu Gln Val Gly Asp Ser Leu Leu Glu Thr Ser Cys
                165                 170                 175

Gly Ser Pro His Tyr Ala Cys Pro Glu Val Ile Arg Gly Glu Lys Tyr
            180                 185                 190
```

-continued

```
Asp Gly Arg Lys Ala Asp Val Trp Ser Cys Gly Val Ile Leu Phe Ala
            195                 200                 205
Leu Leu Val Gly Ala Leu Pro Phe Asp Asp Asn Leu Arg Gln Leu
        210                 215                 220
Leu Glu Lys Val Lys Arg Gly Val Phe His Met Pro His Phe Ile Pro
225                 230                 235                 240
Pro Asp Cys Gln Ser Leu Leu Arg Gly Met Ser Glu Val Asp Ala Ala
                245                 250                 255
Arg Arg Leu Thr Leu Glu His Ile Gln Lys His Ile Trp Tyr Ile Gly
            260                 265                 270
Gly Lys Asn Glu Pro Glu Pro Glu Gln Pro Ile Pro Arg Lys Val Gln
        275                 280                 285
Ile Arg Ser Leu Pro Ser Leu Glu Asp Ile Asp Pro Asp Val Leu Asp
290                 295                 300
Ser Met His Ser Leu Gly Cys Phe Arg Asp Arg Asn Lys Leu Leu Gln
305                 310                 315                 320
Asp Leu Leu Ser Glu Glu Asn Gln Glu Lys Met Ile Tyr Phe Leu
            325                 330                 335
Leu Leu Asp Arg Lys Glu Arg Tyr Pro Ser Gln Glu Asp Glu Asp Leu
            340                 345                 350
Pro Pro Arg Asn Glu Ile Asp Pro Pro Arg Lys Arg Val Asp Ser Pro
            355                 360                 365
Met Leu Asn Arg His Gly Lys Arg Arg Pro Glu Arg Lys Ser Met Glu
370                 375                 380
Val Leu Ser Val Thr Asp Gly Gly Ser Pro Val Pro Ala Arg Arg Ala
385                 390                 395                 400
Ile Glu Met Ala Gln His Gly Gln Arg Ser Arg Ser Ile Ser Gly Ala
                405                 410                 415
Ser Ser Gly Leu Ser Thr Ser Pro Leu Ser Ser Pro Arg Val Thr Pro
            420                 425                 430
His Pro Ser Pro Arg Gly Ser Pro Leu Pro Thr Pro Lys Gly Thr Pro
            435                 440                 445
Val His Thr Pro Lys Glu Ser Pro Ala Gly Thr Pro Asn Pro Thr Pro
450                 455                 460
Pro Ser Ser Pro Ser Val Gly Gly Val Pro Trp Arg Ala Arg Leu Asn
465                 470                 475                 480
Ser Ile Lys Asn Ser Phe Leu Gly Ser Pro Arg Phe His Arg Arg Lys
            485                 490                 495
Leu Gln Val Pro Thr Pro Glu Glu Met Ser Asn Leu Thr Pro Glu Ser
            500                 505                 510
Ser Pro Glu Leu Ala Lys Lys Ser Trp Phe Gly Asn Phe Ile Ser Leu
            515                 520                 525
Glu Lys Glu Glu Gln Ile Phe Val Val Ile Lys Asp Lys Pro Leu Ser
            530                 535                 540
Ser Ile Lys Ala Asp Ile Val His Ala Phe Leu Ser Ile Pro Ser Leu
545                 550                 555                 560
Ser His Ser Val Ile Ser Gln Thr Ser Phe Arg Ala Glu Tyr Lys Ala
                565                 570                 575
Thr Gly Gly Pro Ala Val Phe Gln Lys Pro Val Lys Phe Gln Val Asp
            580                 585                 590
Ile Thr Tyr Thr Glu Gly Gly Glu Ala Gln Lys Glu Asn Gly Ile Tyr
            595                 600                 605
```

-continued

```
Ser Val Thr Phe Thr Leu Leu Ser Gly Pro Ser Arg Arg Phe Lys Arg
    610                 615                 620
Val Val Glu Thr Ile Gln Ala Gln Leu Leu Ser Thr His Asp Pro Pro
625                 630                 635                 640
Ala Ala Gln His Leu Ser Glu Pro Pro Pro Ala Pro Gly Leu Ser
                645                 650                 655
Trp Gly Ala Gly Leu Lys Gly Gln Lys Val Ala Thr Ser Tyr Glu Ser
                660                 665                 670
Ser Leu

<210> SEQ ID NO 8
<211> LENGTH: 674
<212> TYPE: PRT
<213> ORGANISM: Homo sapiens

<400> SEQUENCE: 8

Met Thr Ser Thr Gly Lys Asp Gly Gly Ala Gln His Ala Gln Tyr Val
  1               5                  10                  15
Gly Pro Tyr Arg Leu Glu Lys Thr Leu Gly Lys Gly Gln Thr Gly Leu
                 20                  25                  30
Val Lys Leu Gly Val His Cys Val Thr Cys Gln Lys Val Ala Ile Lys
             35                  40                  45
Ile Val Asn Arg Glu Lys Leu Ser Glu Ser Val Leu Met Lys Val Glu
 50                  55                  60
Arg Glu Ile Ala Ile Leu Lys Leu Ile Glu His Pro His Val Leu Lys
 65                  70                  75                  80
Leu His Asp Val Tyr Glu Asn Lys Lys Tyr Leu Tyr Leu Val Leu Glu
                 85                  90                  95
His Val Ser Gly Gly Glu Leu Phe Asp Tyr Leu Val Lys Lys Gly Arg
            100                 105                 110
Leu Thr Pro Lys Glu Ala Arg Lys Phe Phe Arg Gln Ile Ile Ser Ala
            115                 120                 125
Leu Asp Phe Cys His Ser His Ser Ile Cys His Arg Asp Leu Lys Pro
        130                 135                 140
Glu Asn Leu Leu Leu Asp Glu Lys Asn Asn Ile Arg Ile Ala Asp Phe
145                 150                 155                 160
Gly Met Ala Ser Leu Gln Val Gly Asp Ser Leu Leu Glu Thr Ser Cys
                165                 170                 175
Gly Ser Pro His Tyr Ala Cys Pro Glu Val Ile Arg Gly Glu Lys Tyr
            180                 185                 190
Asp Gly Arg Lys Ala Asp Val Trp Ser Cys Gly Val Ile Leu Phe Ala
        195                 200                 205
Leu Leu Val Gly Ala Leu Pro Phe Asp Asp Asp Asn Leu Arg Gln Leu
    210                 215                 220
Leu Glu Lys Val Lys Arg Gly Val Phe His Met Pro His Phe Ile Pro
225                 230                 235                 240
Pro Asp Cys Gln Ser Leu Leu Arg Gly Met Ser Glu Val Asp Ala Ala
                245                 250                 255
Arg Arg Leu Thr Leu Glu His Ile Gln Lys His Ile Trp Tyr Ile Gly
            260                 265                 270
Gly Lys Asn Glu Pro Glu Pro Glu Gln Pro Ile Pro Arg Lys Val Gln
        275                 280                 285
Ile Arg Ser Leu Pro Ser Leu Glu Asp Ile Asp Pro Asp Val Leu Asp
    290                 295                 300
```

```
Ser Met His Ser Leu Gly Cys Phe Arg Asp Arg Asn Lys Leu Leu Gln
305                 310                 315                 320

Asp Leu Leu Ser Glu Glu Asn Gln Glu Lys Met Ile Tyr Phe Leu
            325                 330                 335

Leu Leu Asp Arg Lys Glu Arg Tyr Pro Ser Gln Glu Asp Glu Asp Leu
            340                 345                 350

Pro Pro Arg Asn Glu Ile Asp Pro Arg Lys Arg Val Asp Ser Pro
            355                 360                 365

Met Leu Asn Arg His Gly Lys Arg Arg Pro Glu Arg Lys Ser Met Glu
            370                 375                 380

Val Leu Ser Val Thr Asp Gly Gly Ser Pro Val Pro Ala Arg Arg Ala
385                 390                 395                 400

Ile Glu Met Ala Gln His Gly Gln Arg Ser Arg Ser Ile Ser Gly Ala
                405                 410                 415

Ser Ser Gly Leu Ser Thr Ser Pro Leu Ser Ser Pro Arg Val Thr Pro
                420                 425                 430

His Pro Ser Pro Arg Gly Ser Pro Leu Pro Thr Pro Lys Gly Thr Pro
            435                 440                 445

Val His Thr Pro Lys Glu Ser Pro Ala Gly Thr Pro Asn Pro Thr Pro
450                 455                 460

Pro Ser Ser Pro Ser Val Gly Gly Val Pro Trp Arg Ala Arg Leu Asn
465                 470                 475                 480

Ser Ile Lys Asn Ser Phe Leu Gly Ser Pro Arg Phe His Arg Arg Lys
                485                 490                 495

Leu Gln Val Pro Thr Pro Glu Glu Met Ser Asn Leu Thr Pro Glu Ser
            500                 505                 510

Ser Pro Glu Leu Ala Lys Lys Ser Trp Phe Gly Asn Phe Ile Ser Leu
            515                 520                 525

Glu Lys Glu Glu Gln Ile Phe Val Val Ile Lys Asp Lys Pro Leu Ser
530                 535                 540

Ser Ile Lys Ala Asp Ile Val His Ala Phe Leu Ser Ile Pro Ser Leu
545                 550                 555                 560

Ser His Ser Val Ile Ser Gln Thr Ser Phe Arg Ala Glu Tyr Lys Ala
                565                 570                 575

Thr Gly Gly Pro Ala Val Phe Gln Lys Pro Val Lys Phe Gln Val Asp
            580                 585                 590

Ile Thr Tyr Thr Glu Gly Gly Glu Ala Gln Lys Glu Asn Gly Ile Tyr
            595                 600                 605

Ser Val Thr Phe Thr Leu Leu Ser Gly Pro Ser Arg Arg Phe Lys Arg
            610                 615                 620

Val Val Glu Thr Ile Gln Ala Gln Leu Leu Ser Thr His Asp Pro Pro
625                 630                 635                 640

Ala Ala Gln His Leu Ser Glu Pro Pro Pro Ala Pro Gly Leu Ser
                645                 650                 655

Trp Gly Ala Gly Leu Lys Gly Gln Lys Val Ala Thr Ser Tyr Glu Ser
            660                 665                 670

Ser Leu
```

<210> SEQ ID NO 9
<211> LENGTH: 614
<212> TYPE: PRT
<213> ORGANISM: Homo sapiens

<400> SEQUENCE: 9

```
Met Lys Val Glu Arg Glu Ile Ala Ile Leu Lys Leu Ile Glu His Pro
 1               5                  10                  15

His Val Leu Lys Leu His Asp Val Tyr Glu Asn Lys Lys Tyr Leu Tyr
            20                  25                  30

Leu Val Leu Glu His Val Ser Gly Glu Leu Phe Asp Tyr Leu Val
            35                  40                  45

Lys Lys Gly Arg Leu Thr Pro Lys Glu Ala Arg Lys Phe Phe Arg Gln
50                      55                  60

Ile Ile Ser Ala Leu Asp Phe Cys His Ser His Ser Ile Cys His Arg
65                  70                  75                  80

Asp Leu Lys Pro Glu Asn Leu Leu Leu Asp Glu Lys Asn Asn Ile Arg
                85                  90                  95

Ile Ala Asp Phe Gly Met Ala Ser Leu Gln Val Gly Asp Ser Leu Leu
                100                 105                 110

Glu Thr Ser Cys Gly Ser Pro His Tyr Ala Cys Pro Glu Val Ile Arg
            115                 120                 125

Gly Glu Lys Tyr Asp Gly Arg Lys Ala Asp Val Trp Ser Cys Gly Val
            130                 135                 140

Ile Leu Phe Ala Leu Leu Val Gly Ala Leu Pro Phe Asp Asp Asp Asn
145                 150                 155                 160

Leu Arg Gln Leu Leu Glu Lys Val Lys Arg Gly Val Phe His Met Pro
                165                 170                 175

His Phe Ile Pro Pro Asp Cys Gln Ser Leu Leu Arg Gly Met Ser Glu
            180                 185                 190

Val Asp Ala Ala Arg Arg Leu Thr Leu Glu His Ile Gln Lys His Ile
            195                 200                 205

Trp Tyr Ile Gly Gly Lys Asn Glu Pro Glu Pro Glu Gln Pro Ile Pro
210                 215                 220

Arg Lys Val Gln Ile Arg Ser Leu Pro Ser Leu Glu Asp Ile Asp Pro
225                 230                 235                 240

Asp Val Leu Asp Ser Met His Ser Leu Gly Cys Phe Arg Asp Arg Asn
                245                 250                 255

Lys Leu Leu Gln Asp Leu Leu Ser Glu Glu Asn Gln Glu Lys Met
                260                 265                 270

Ile Tyr Phe Leu Leu Leu Asp Arg Lys Glu Arg Tyr Pro Ser Gln Glu
            275                 280                 285

Asp Glu Asp Leu Pro Pro Arg Asn Glu Ile Asp Pro Pro Arg Lys Arg
            290                 295                 300

Val Asp Ser Pro Met Leu Asn Arg His Gly Lys Arg Arg Pro Glu Arg
305                 310                 315                 320

Lys Ser Met Glu Val Leu Ser Val Thr Asp Gly Gly Ser Pro Val Pro
                325                 330                 335

Ala Arg Arg Ala Ile Glu Met Ala Gln His Gly Gln Arg Ser Arg Ser
            340                 345                 350

Ile Ser Gly Ala Ser Ser Gly Leu Ser Thr Ser Pro Leu Ser Ser Pro
            355                 360                 365

Arg Val Thr Pro His Pro Ser Pro Arg Gly Ser Pro Leu Pro Thr Pro
            370                 375                 380

Lys Gly Thr Pro Val His Thr Pro Lys Glu Ser Pro Ala Gly Thr Pro
385                 390                 395                 400

Asn Pro Thr Pro Pro Ser Ser Pro Ser Val Gly Gly Val Pro Trp Arg
                405                 410                 415

Ala Arg Leu Asn Ser Ile Lys Asn Ser Phe Leu Gly Ser Pro Arg Phe
```

```
                   420                 425                 430
His Arg Arg Lys Leu Gln Val Pro Thr Pro Glu Glu Met Ser Asn Leu
            435                 440                 445

Thr Pro Glu Ser Ser Pro Glu Leu Ala Lys Lys Ser Trp Phe Gly Asn
    450                 455                 460

Phe Ile Ser Leu Glu Lys Glu Gln Ile Phe Val Ile Lys Asp
465                 470                 475                 480

Lys Pro Leu Ser Ser Ile Lys Ala Asp Ile Val His Ala Phe Leu Ser
                485                 490                 495

Ile Pro Ser Leu Ser His Ser Val Ile Ser Gln Thr Ser Phe Arg Ala
            500                 505                 510

Glu Tyr Lys Ala Thr Gly Gly Pro Ala Val Phe Gln Lys Pro Val Lys
            515                 520                 525

Phe Gln Val Asp Ile Thr Tyr Thr Glu Gly Gly Glu Ala Gln Lys Glu
    530                 535                 540

Asn Gly Ile Tyr Ser Val Thr Phe Thr Leu Leu Ser Gly Pro Ser Arg
545                 550                 555                 560

Arg Phe Lys Arg Val Val Glu Thr Ile Gln Ala Gln Leu Leu Ser Thr
                565                 570                 575

His Asp Pro Pro Ala Ala Gln His Leu Ser Glu Pro Pro Pro Pro Ala
            580                 585                 590

Pro Gly Leu Ser Trp Gly Ala Gly Leu Lys Gly Gln Lys Val Ala Thr
        595                 600                 605

Ser Tyr Glu Ser Ser Leu
        610

<210> SEQ ID NO 10
<211> LENGTH: 614
<212> TYPE: PRT
<213> ORGANISM: Homo sapiens

<400> SEQUENCE: 10

Met Lys Val Glu Arg Glu Ile Ala Ile Leu Lys Leu Ile Glu His Pro
1               5                   10                  15

His Val Leu Lys Leu His Asp Val Tyr Glu Asn Lys Lys Tyr Leu Tyr
            20                  25                  30

Leu Val Leu Glu His Val Ser Gly Gly Glu Leu Phe Asp Tyr Leu Val
        35                  40                  45

Lys Lys Gly Arg Leu Thr Pro Lys Glu Ala Arg Lys Phe Phe Arg Gln
    50                  55                  60

Ile Ile Ser Ala Leu Asp Phe Cys His Ser His Ser Ile Cys His Arg
65                  70                  75                  80

Asp Leu Lys Pro Glu Asn Leu Leu Leu Asp Glu Lys Asn Asn Ile Arg
                85                  90                  95

Ile Ala Asp Phe Gly Met Ala Ser Leu Gln Val Gly Asp Ser Leu Leu
            100                 105                 110

Glu Thr Ser Cys Gly Ser Pro His Tyr Ala Cys Pro Glu Val Ile Arg
        115                 120                 125

Gly Glu Lys Tyr Asp Gly Arg Lys Ala Asp Val Trp Ser Cys Gly Val
    130                 135                 140

Ile Leu Phe Ala Leu Leu Val Gly Ala Leu Pro Phe Asp Asp Asp Asn
145                 150                 155                 160

Leu Arg Gln Leu Leu Glu Lys Val Lys Arg Gly Val Phe His Met Pro
                165                 170                 175
```

```
His Phe Ile Pro Pro Asp Cys Gln Ser Leu Leu Arg Gly Met Ser Glu
            180                 185                 190

Val Asp Ala Ala Arg Arg Leu Thr Leu Glu His Ile Gln Lys His Ile
        195                 200                 205

Trp Tyr Ile Gly Gly Lys Asn Glu Pro Glu Pro Glu Gln Pro Ile Pro
    210                 215                 220

Arg Lys Val Gln Ile Arg Ser Leu Pro Ser Leu Glu Asp Ile Asp Pro
225                 230                 235                 240

Asp Val Leu Asp Ser Met His Ser Leu Gly Cys Phe Arg Asp Arg Asn
                245                 250                 255

Lys Leu Leu Gln Asp Leu Leu Ser Glu Glu Asn Gln Glu Lys Met
                260                 265                 270

Ile Tyr Phe Leu Leu Leu Asp Arg Lys Glu Arg Tyr Pro Ser Gln Glu
                275                 280                 285

Asp Glu Asp Leu Pro Pro Arg Asn Glu Ile Asp Pro Pro Arg Lys Arg
        290                 295                 300

Val Asp Ser Pro Met Leu Asn Arg His Gly Lys Arg Pro Glu Arg
305                 310                 315                 320

Lys Ser Met Glu Val Leu Ser Val Thr Asp Gly Gly Ser Pro Val Pro
                325                 330                 335

Ala Arg Arg Ala Ile Glu Met Ala Gln His Gly Gln Arg Ser Arg Ser
            340                 345                 350

Ile Ser Gly Ala Ser Ser Gly Leu Ser Thr Ser Pro Leu Ser Ser Pro
        355                 360                 365

Arg Val Thr Pro His Pro Ser Pro Arg Gly Ser Pro Leu Pro Thr Pro
    370                 375                 380

Lys Gly Thr Pro Val His Thr Pro Lys Glu Ser Pro Ala Gly Thr Pro
385                 390                 395                 400

Asn Pro Thr Pro Pro Ser Ser Pro Ser Val Gly Gly Val Pro Trp Arg
                405                 410                 415

Ala Arg Leu Asn Ser Ile Lys Asn Ser Phe Leu Gly Ser Pro Arg Phe
            420                 425                 430

His Arg Arg Lys Leu Gln Val Pro Thr Pro Glu Glu Met Ser Asn Leu
        435                 440                 445

Thr Pro Glu Ser Ser Pro Glu Leu Ala Lys Lys Ser Trp Phe Gly Asn
    450                 455                 460

Phe Ile Ser Leu Glu Lys Glu Glu Gln Ile Phe Val Val Ile Lys Asp
465                 470                 475                 480

Lys Pro Leu Ser Ser Ile Lys Ala Asp Ile Val His Ala Phe Leu Ser
                485                 490                 495

Ile Pro Ser Leu Ser His Ser Val Ile Ser Gln Thr Ser Phe Arg Ala
            500                 505                 510

Glu Tyr Lys Ala Thr Gly Gly Pro Ala Val Phe Gln Lys Pro Val Lys
        515                 520                 525

Phe Gln Val Asp Ile Thr Tyr Thr Glu Gly Gly Glu Ala Gln Lys Glu
    530                 535                 540

Asn Gly Ile Tyr Ser Val Thr Phe Thr Leu Leu Ser Gly Pro Ser Arg
545                 550                 555                 560

Arg Phe Lys Arg Val Val Glu Thr Ile Gln Ala Gln Leu Leu Ser Thr
                565                 570                 575

His Asp Pro Pro Ala Ala Gln His Leu Ser Glu Pro Pro Pro Ala
            580                 585                 590
```

```
                                       -continued
Pro Gly Leu Ser Trp Gly Ala Gly Leu Lys Gly Gln Lys Val Ala Thr
        595                 600                 605
Ser Tyr Glu Ser Ser Leu
    610
```

US 6,919,191 B2

ISOLATED HUMAN KINASE PROTEINS, NUCLEIC ACID MOLECULES ENCODING HUMAN KINASE PROTEINS, AND USES THEREOF

This application claims priority to U.S. Provisional application No. 60/330,756 filed Oct. 30, 2001.

FIELD OF THE INVENTION

The present invention is in the field of kinase proteins that are related to the serine/threonine kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks NK (1992) *Annu. Rev. Cell. Biol.* 8:463–93). Regulation of PTK activity may therefore be an important strategy in controlling some types of cancer.

Serine/Threonine Kinases

The novel human protein, and encoding gene, provided by the present invention is related to the serine/threonine kinase subfamily. The protein of the present invention is expressed in numerous types of cancerous tissue, such as germ cell tumors, liver adenocarcinoma, epid tumors, and lung small cell carcinoma, thus suggesting that the protein/gene is an important therapeutic/diagnostic target for a wide variety of cancers. Serine/threonine kinases are also important as maternally localized cytoplasmic determinants, which play important roles in embryogenesis, particularly in determining cell fates and in establishing the embryonic axis (Sasakura et al., *Mech Dev* 1998 Aug;76(1–2):161–3), and thus may also be important therapeutic/diagnostic targets for developmental disorders. Stanchi et al. (*Yeast* 2001 Jan 15;18(1):69–80) also describes a serine/threonine kinase.

Kinase proteins, particularly members of the serine/threonine kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the serine/threonine kinase subfamily.

SUMMARY OF THE INVENTION

The present invention is based in part on the identification of amino acid sequences of human kinase peptides and proteins that are related to the serine/threonine kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in the brain (including medulla, anaplastic oligodendroglioma, glioblastoma, and fetal brain), eye (retinoblastoma), liver (adenocarcinoma), germ cell tumors, epid tumor, and lung (small cell carcinoma).

DESCRIPTION OF THE FIGURE SHEETS

FIG. 1A through FIG. 1D provides the nucleotide sequence of cDNA molecules or transcript sequences of two kinase splice forms, indicated as "splice form 1" (SEQ ID NO: 1) and "splice form 2" (SEQ ID NO: 4). In addition, structure and functional information is provided for each splice form, such as ATG start, stop and tissue distribution, where available, that allows one to readily determine specific uses of the inventions based on these molecular sequences. Experimental data as provided in FIG. 1 indicates expression in the brain (including medulla, anaplastic oligodendroglioma, glioblastoma, and fetal brain), eye (retinoblastoma), liver (adenocarcinoma), germ cell tumors, epid tumor, and lung (small cell carcinoma).

FIG. 2A through FIG. 2I provides the predicted amino acid sequence of two kinase splice forms, indicated as "splice form 1" (SEQ ID NO: 2) and "splice form 2" (SEQ ID NO: 5). In addition, structure and functional information such as protein family, function, and modification sites is provided where available, allowing one to readily determine specific uses of the inventions based on these molecular sequences.

FIG. 3-1 through FIG. 3-66 provides genomic sequences (SEQ ID NOS:3 and 6) that span the gene encoding the kinase proteins of the present invention. In addition, structure and functional information, such as intron/exon structure, promoter location, etc., is provided where available, allowing one to readily determine specific uses of inventions based on this molecular sequence. FIG. 3 provides information on SNPs identified in the gene encoding the kinase proteins of the present invention.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the serine/threonine kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the serine/threonine kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the serine/threonine kinase subfamily and the expression pattern observed. Experimental data as provided in FIG. 1 indicates expression in the brain (including medulla, anaplastic oligodendroglioma, glioblastoma, and fetal brain), eye (retinoblastoma), liver (adenocarcinoma), germ cell tumors, epid tumor, and lung (small cell carcinoma). The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known serine/threonine kinase family or subfamily of kinase proteins.

Specific Embodiments

Peptide Molecules

The present invention provides nucleic acid sequences that encode protein molecules that have been identified as being members of the kinase family of proteins and are related to the serine/threonine kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in the brain (including medulla, anaplastic oligodendroglioma, glioblastoma, and fetal brain), eye (retinoblastoma), liver (adenocarcinoma), germ cell tumors, epid tumor, and lung (small cell carcinoma). For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NOS:2 and 5), for example, proteins encoded by the transcript/cDNA nucleic acid sequences shown in FIG. 1 (SEQ ID NOS:1 and 4) and the genomic sequences provided in FIG. 3 (SEQ ID NOS:3 and 6). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NOS:2 and 5), for example, proteins encoded by the transcript/cDNA nucleic acid sequences shown in FIG. 1 (SEQ ID NOS:1 and 4) and the genomic sequences provided in FIG. 3 (SEQ ID NOS:3 and 6). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NOS:2 and 5), for example, proteins encoded by the transcript/cDNA nucleic acid sequences shown in FIG. 1 (SEQ ID NOS:1 and 4) and the genomic sequences provided in FIG. 3 (SEQ ID NOS:3 and 6). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48): 444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1): 387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol.*

*Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17): 3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. As indicated by the data presented in FIG. 3, the map position was determined to be on human chromosome 11.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. As indicated by the data presented in FIG. 3, the map position was determined to be on human chromosome 11. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in the gene encoding the kinase proteins of the present invention, including a non-synonymous coding SNP that results in a change in the encoded amino acid sequence. The change in the amino acid sequence caused by this SNP is indicated in FIG. 3 and can readily be determined using the universal genetic code and the protein sequence provided in FIG. 2 as a reference.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in the brain (including medulla, anaplastic oligodendroglioma, glioblastoma, and fetal brain), eye (retinoblastoma), liver (adenocarcinoma), germ cell tumors, epid tumor, and lung (small cell carcinoma), as indicated by virtual northern blot analysis. A large percentage of pharmaceutical agents are being developed that modulate the activity of kinase proteins, particularly members of the serine/threonine kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the brain (including medulla, anaplastic oligodendroglioma, glioblastoma, and fetal brain), eye (retinoblastoma), liver (adenocarcinoma), germ cell tumors, epid tumor, and lung (small cell carcinoma). Such uses can readily be determined using the information provided herein, that which is known in the art, and routine experimentation.

The proteins of the present invention (including variants and fragments that may have been disclosed prior to the present invention) are useful for biological assays related to kinases that are related to members of the serine/threonine kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in the brain (including medulla, anaplastic oligodendroglioma, glioblastoma, and fetal brain), eye (retinoblastoma), liver (adenocarcinoma), germ cell tumors, epid tumor, and lung (small cell carcinoma), as indicated by virtual northern blot analysis.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in the brain (including medulla, anaplastic oligodendroglioma, glioblastoma, and fetal brain), eye (retinoblastoma), liver (adenocarcinoma), germ cell tumors, epid tumor, and lung (small cell carcinoma). In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete, for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in the brain (including medulla, anaplastic oligodendroglioma, glioblastoma, and fetal brain), eye (retinoblastoma), liver (adenocarcinoma), germ cell tumors, epid tumor, and lung (small cell carcinoma), as indicated by virtual northern blot analysis.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in the brain (including medulla, anaplastic oligodendroglioma, glioblastoma, and fetal brain), eye (retinoblastoma), liver (adenocarcinoma), germ cell tumors, epid tumor, and lung (small cell carcinoma). These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the brain (including medulla, anaplastic oligodendroglioma, glioblastoma, and fetal brain), eye (retinoblastoma), liver (adenocarcinoma), germ cell tumors, epid tumor, and lung (small cell carcinoma). The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Pharmacol. Physiol. 23(10–11):983–985 (1996)), and Linder, M. W. (Clin. Chem. 43(2):254–266 (1997). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the brain (including medulla, anaplastic oligodendroglioma, glioblastoma, and fetal brain), eye (retinoblastoma), liver (adenocarcinoma), germ cell tumors, epid tumor, and lung (small cell carcinoma). Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in the brain (including medulla, anaplastic oligodendroglioma, glioblastoma, and fetal brain), eye (retinoblastoma), liver (adenocarcinoma), germ cell tumors, epid tumor, and lung (small cell carcinoma), as indicated by virtual northern blot analysis. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the brain (including medulla, anaplastic oligodendroglioma, glioblastoma, and fetal brain), eye (retinoblastoma), liver (adenocarcinoma), germ cell tumors, epid tumor, and lung (small cell carcinoma). If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the brain (including medulla, anaplastic oligodendroglioma, glioblastoma, and fetal brain), eye (retinoblastoma), liver (adenocarcinoma), germ cell tumors, epid tumor, and lung (small cell carcinoma). The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the brain (including medulla, anaplastic oligodendroglioma, glioblastoma, and fetal brain), eye (retinoblastoma), liver (adenocarcinoma), germ cell tumors, epid tumor, and lung (small cell carcinoma). Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NOS:1 and 4, transcript sequence and SEQ ID NOS:3 and 6, genomic sequence), or any nucleic acid molecule that encodes the protein provided in FIG. 2, SEQ ID NOS:2 and 5. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NOS:1 and 4, transcript sequence and SEQ ID NOS:3 and 6, genomic sequence), or any nucleic acid molecule that encodes the protein provided in FIG. 2, SEQ ID NOS:2 and 5. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NOS:1 and 4, transcript sequence and SEQ ID NOS:3 and 6, genomic sequence), or any nucleic acid molecule that encodes the protein provided in FIG. 2, SEQ ID NOS:2 and 5. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically-comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on human chromosome 11.

FIG. 3 provides information on SNPs that have been found in the gene encoding the kinase proteins of the present invention, including a non-synonymous coding SNP that results in a change in the encoded amino acid sequence. The change in the amino acid sequence caused by this SNP is indicated in FIG. 3 and can readily be determined using the universal genetic code and the protein sequence provided in FIG. 2 as a reference.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. FIG. 3 provides information on SNPs identified in the gene encoding the kinase proteins of the present invention.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on human chromosome 11.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in the brain (including medulla, anaplastic oligodendroglioma, glioblastoma, and fetal brain), eye (retinoblastoma), liver (adenocarcinoma), germ cell tumors, epid tumor, and lung (small cell carcinoma), as indicated by virtual northern blot analysis. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in the brain (including medulla, anaplastic oligodendroglioma, glioblastoma, and fetal brain), eye (retinoblastoma), liver (adenocarcinoma), germ cell tumors, epid tumor, and lung (small cell carcinoma), as indicated by virtual northern blot analysis.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in the brain (including medulla, anaplastic oligodendroglioma, glioblastoma, and fetal brain), eye (retinoblastoma), liver (adenocarcinoma), germ cell tumors, epid tumor, and lung (small cell carcinoma). The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free, systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in the brain (including medulla, anaplastic oligodendroglioma, glioblastoma, and fetal brain), eye (retinoblastoma), liver (adenocarcinoma), germ cell tumors, epid tumor, and lung (small cell carcinoma), as indicated by virtual northern blot analysis. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in the brain (including medulla, anaplastic oligodendroglioma, glioblastoma, and fetal brain), eye (retinoblastoma), liver (adenocarcinoma), germ cell tumors, epid tumor, and lung (small cell carcinoma).

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in the gene encoding the kinase proteins of the present invention, including a non-synonymous coding SNP that results in a change in the encoded amino acid sequence. The change in the amino acid sequence caused by this SNP is indicated in FIG. 3 and can readily be determined using the universal genetic code and the protein sequence provided in FIG. 2 as a reference. As indicated by the data presented in FIG. 3, the map position was determined to be on human chromosome 11. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) Biotechniques 19:448), including sequencing by mass spectrometry (see, e.g., PCT International Publication No. WO 94/16101; Cohen et al., Adv. Chromatogr. 36:127–162 (1996); and Griffin et al., Appl. Biochem. Biotechnol. 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286–295 (1992)), electrophoretic mobility of mutant and wild type nucleic acid is compared (Orita et al., PNAS 86:2766 (1989); Cotton et al., Mutat. Res. 285:125–144 (1993); and Hayashi et al., Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in the gene encoding the kinase proteins of the present invention, including a non-synonymous coding SNP that results in a change in the encoded amino acid sequence. The change in the amino acid sequence caused by this SNP is indicated in FIG. 3 and can readily be determined using the universal genetic code and the protein sequence provided in FIG. 2 as a reference.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in the brain (including medulla, anaplastic oligodendroglioma, glioblastoma, and fetal brain), eye (retinoblastoma), liver (adenocarcinoma), germ cell tumors, epid tumor, and lung (small cell carcinoma), as indicated by virtual northern blot analysis. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1, 3, 4, and 6).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in the gene encoding the kinase proteins of the present invention, including a non-synonymous coding SNP that results in a change in the encoded amino acid sequence. The change in the amino acid sequence caused by this SNP is indicated in FIG. 3 and can readily be determined using the universal genetic code and the protein sequence provided in FIG. 2 as a reference.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate-containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kuijan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufmnan et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell- free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule, wherein the nucleotide sequence of said nucleic acid molecule consists of a nucleotide sequence selected from the group consisting of:
   (a) a nucleotide sequence that encodes a polypeptide having an amino acid sequence comprising SEQ ID NO:2;
   (b) SEQ ID NO:1;
   (c) SEQ ID NO:3;
   (d) nucleotides 2258–67382 of SEQ ID NO:3; and
   (e) a nucleotide sequence that is completely complementaiy to the nucleotide sequence of (a), (b), (c), or (d).

2. An isolated nucleic acid molecule comprising a nucleotide sequence selected from the group consisting of:
   (a) a transcript or cDNA sequence that encodes a polypeptide having an amino acid sequence comprising SEQ ID NO:2;
   (b) SEQ ID NO:1; and
   (c) a nucleotide sequence that is completely complementary to the nucleotide sequence of (a) or (b).

3. An isolated nucleic acid molecule, wherein the nucleotide sequence of said nucleic acid molecule consists of SEQ ID NO:1 or the complete complement thereof.

4. An isolated nucleic acid molecule, wherein the nucleotide sequence of said nucleic acid molecule comprises SEQ ID NO:1 or the complete complement thereof.

5. An isolated nucleic acid molecule, wherein the nucleotide sequence of said nucleic acid molecule consists of SEQ ID NO:3 or the complete complement thereof.

6. An isolated nucleic acid molecule, wherein the nucleotide sequence of said nucleic acid molecule consists of nueleotides 2258–67382 of SEQ ID NO:3, or the complete complement thereof.

7. An isolated nucleic acid molecule, wherein the nucleotide sequence of said nucleic acid molecule consists of a nucleotide sequence that encodes a polypeptide comprising SEQ ID NO:2, or the complete complement of said nucleotide sequence.

8. An isolated transcript or cDNA nucleic acid molecule comprising a nucleotide sequence that encodes a polypeptide comprising SEQ ID NO:2, or the complete complement of said nucleotide sequence.

9. A nucleic acid construct comprising the nucleic acid molecule of claim 1 or 2 fused to a heterologous nucleotide sequence.

10. The nucleic acid construct of claim 9, wherein the heterologous nucleotide sequence encodes a heterologous amino acid sequence.

11. A vector comprising the nucleic acid molecule of claim 1 or 2.

12. An isolated host cell containing the vector of claim 11.

13. A process for producing a polypeptide, the process comprising culturing the host cell of claim 12 under conditions sufficient for the production of said polypeptide, and recovering said polypeptide.

14. The vector of claim 11, wherein said vector is selected from the group consisting of a plasmid, a virus, and a bacteriophage.

15. The vector of claim 11, wherein said nucleic acid molecule is inserted into said vector in proper orientation and correct reading frame such that a polypeptide comprising SEQ ID NO:2 is expressed by a cell transformed with said vector.

16. The vector of claim 15, wherein said isolated nucleic acid molecule is operatively linked to a promoter sequence.

\* \* \* \* \*